US012496327B2

(12) United States Patent
Eggan et al.

(10) Patent No.: US 12,496,327 B2
(45) Date of Patent: Dec. 16, 2025

(54) METHODS AND COMPOSITIONS FOR RESTORING STMN2 LEVELS

(71) Applicant: President and Fellows of Harvard College, Cambridge, MA (US)

(72) Inventors: Kevin C. Eggan, Boston, MA (US); Joseph Robert Klim, Boston, MA (US); Francesco Limone, Cambridge, MA (US); Irune Guerra San Juan, Cambridge, MA (US); Luis Williams, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1130 days.

(21) Appl. No.: 17/423,104

(22) PCT Filed: Jan. 14, 2020

(86) PCT No.: PCT/US2020/013581

§ 371 (c)(1),
(2) Date: Jul. 14, 2021

(87) PCT Pub. No.: WO2020/150290

PCT Pub. Date: Jul. 23, 2020

(65) Prior Publication Data

US 2022/0133848 A1 May 5, 2022

Related U.S. Application Data

(60) Provisional application No. 62/792,276, filed on Jan. 14, 2019.

(51) Int. Cl.

| | |
|---|---|
| ***C07H 21/02*** | (2006.01) |
| ***A61K 31/7088*** | (2006.01) |
| ***A61K 38/17*** | (2006.01) |
| ***A61K 48/00*** | (2006.01) |
| ***A61P 25/28*** | (2006.01) |
| ***C12Q 1/6851*** | (2018.01) |
| ***G01N 33/50*** | (2006.01) |
| ***G01N 33/68*** | (2006.01) |

(52) U.S. Cl.

CPC ...... *A61K 38/1703* (2013.01); *A61K 31/7088* (2013.01); *A61K 48/00* (2013.01); *A61P 25/28* (2018.01); *C12Q 1/6851* (2013.01); *G01N 33/5058* (2013.01); *G01N 33/6896* (2013.01); *G01N 2800/28* (2013.01)

(58) Field of Classification Search

CPC ........................ C12Q 2600/178; C12N 15/113
See application file for complete search history.

(56) References Cited

U.S. PATENT DOCUMENTS

| | | | |
|---|---|---|---|
| 9,486,541 B2 | 11/2016 | Hutton et al. |
| 2009/0253622 A1 | 10/2009 | Van Noort et al. |
| 2016/0291037 A1 | 10/2016 | Sierks et al. |
| 2024/0011027 A1 | 1/2024 | Eggan et al. |

FOREIGN PATENT DOCUMENTS

| | | |
|---|---|---|
| EP | 3976010 A2 | 4/2022 |
| WO | WO-2013/169793 A2 | 11/2013 |
| WO | WO-2018/154337 A1 | 8/2018 |
| WO | WO-2019/241648 A1 | 12/2019 |
| WO | WO-2020/247419 A2 | 12/2020 |

OTHER PUBLICATIONS

Gonzalez et al. (Harvard Library 2015), pp. 1-24.*
Ling et al. (Science, 2015, 49, 6248, 650-655).*
Chen, et al., "Modulation of Nuclear REST by Alternative Splicing: A Potential Therapeutic Target for Huntington's Disease," *J. Cell. Mol. Med.*, 21(11):2974-2984, (May 19, 2017).
Klim, "TDP-43—The Key to Unlocking ALS Through Pluripotent Stem Cell Disease Modeling," Stem Cell and Regenerative Medicine Center, University of Wisconsin-Madison, Oct. 9, 2018. Retrieved from the internet <https://stemcells.wics.edu/even/j-carter-ralphe-associate-professor-pediatic-cardiology-2018-10-09/> pp. 1-3.
Klim, et al., "ALS Implicated Protein TDP-43 Sustains Levels of STMN2 a Mediator of Motor Neuron Growth and Repair," *Nat. Neurosci.*, 22(2):167-179, (Feb. 2019).
Lee, et al., "STMN2 is a Novel Target of ß-catenin/TCF-mediated Transcription in Human Hepatoma Cells," *Biochemical and Biophysical Research Communications*, 345:1059-1067, (May 11, 2006).
Ooi, et al., "BRG1 Chromatin Remodeling Activity is Required for Efficient Chromatin Binding by the Transcriptional Repressor Rest and Facilitates Rest-Mediated Repression," *J. Biol. Chem.*, 281(51):38974-38980, (Dec. 22, 2006).
Eggan, et al., Abstract "Generation and Characterization of Amyotrophic Lateral Sclerosis," National Institutes of Health Grant No. NS078736 (Funding Start Date: Jul. 1, 2012).
Eggan, et al., Abstract "Generation and Characterization of Amyotrophic Lateral Sclerosis iPS Cells," National Institutes of Health Grant No. NS069395 (Funding Start Date: Sep. 30, 2009).
International Search Report from PCT/US2020/013581, dated Jul. 16, 2020.
Melamed, et al., "Premature Polyadenylation-Mediated Loss of Stathmin-2 is a Hallmark of TDP-43-Dependent Nurodegeneration," *Nature Neuroscience*, 22(2):180-190, (2014).
Shin, et al., "SCG10 is a JNK Target in the Axonal Degeneration Pathway," *Proceedings of the National Academy of Sciences*, 109(25):E3696-E3705, (Nov. 27, 2012).

(Continued)

*Primary Examiner* — Amy Rose Hudson
(74) *Attorney, Agent, or Firm* — Morse, Barnes-Brown & Pendleton, P.C.; Lisa M. Warren, Esq.; Erin E. Bryan, Esq.

(57) ABSTRACT

The disclosure relates to compositions and methods for treating a disease or condition associated with a TDP-pathology or a decline in TDP-43 functionality in neuronal cells in a subject, and for identifying candidate agents to restore expression of a normal full-length or protein coding STMN2 RNA.

17 Claims, 141 Drawing Sheets
(135 of 141 Drawing Sheet(s) Filed in Color)

Specification includes a Sequence Listing.

(56) References Cited

OTHER PUBLICATIONS

Melamed, et al., "Premature polyadenylation-mediated loss of stathmin-2 is a hallmark of TDP-43-dependent neurodegeneration," Nature Neuroscience 22.2 (2019): 180-190.
International Search Report from PCT/US2021/024254, dated Oct. 4, 2021.
Watts, et al., Abstract, "Next-generation antisense therapeutics for ALS and frontotemporal dementia," National Institutes of Health Grant No. NS111990 (Funding Start Date: May 15, 2019).
Ling, et al., "TDP-43 repression of nonconserved cryptic exons is compromised in ALS-FTD," Science 349.6248 (2015): 650-655.

* cited by examiner

FIG. 4E
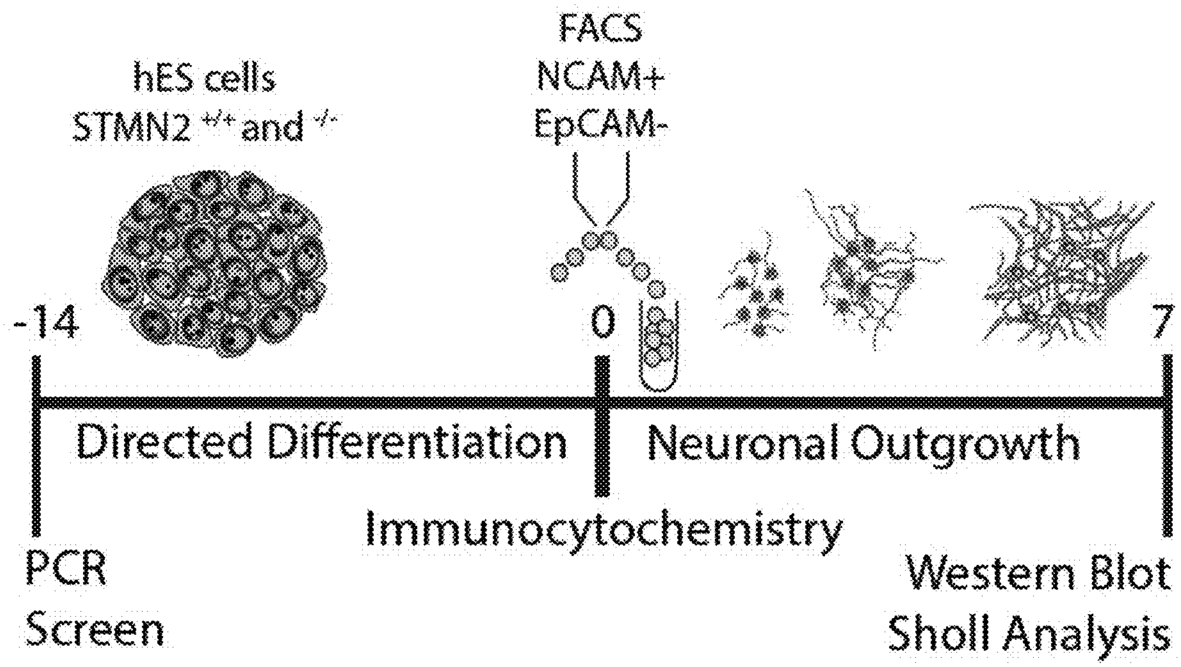
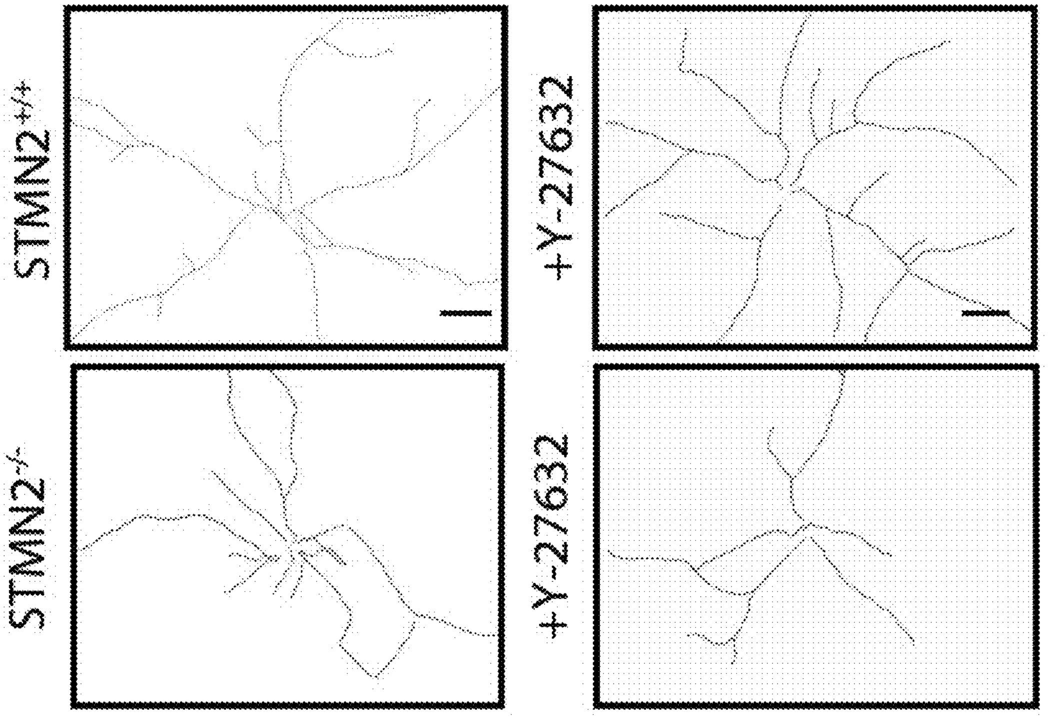
FIG. 4F

FIG. 4G
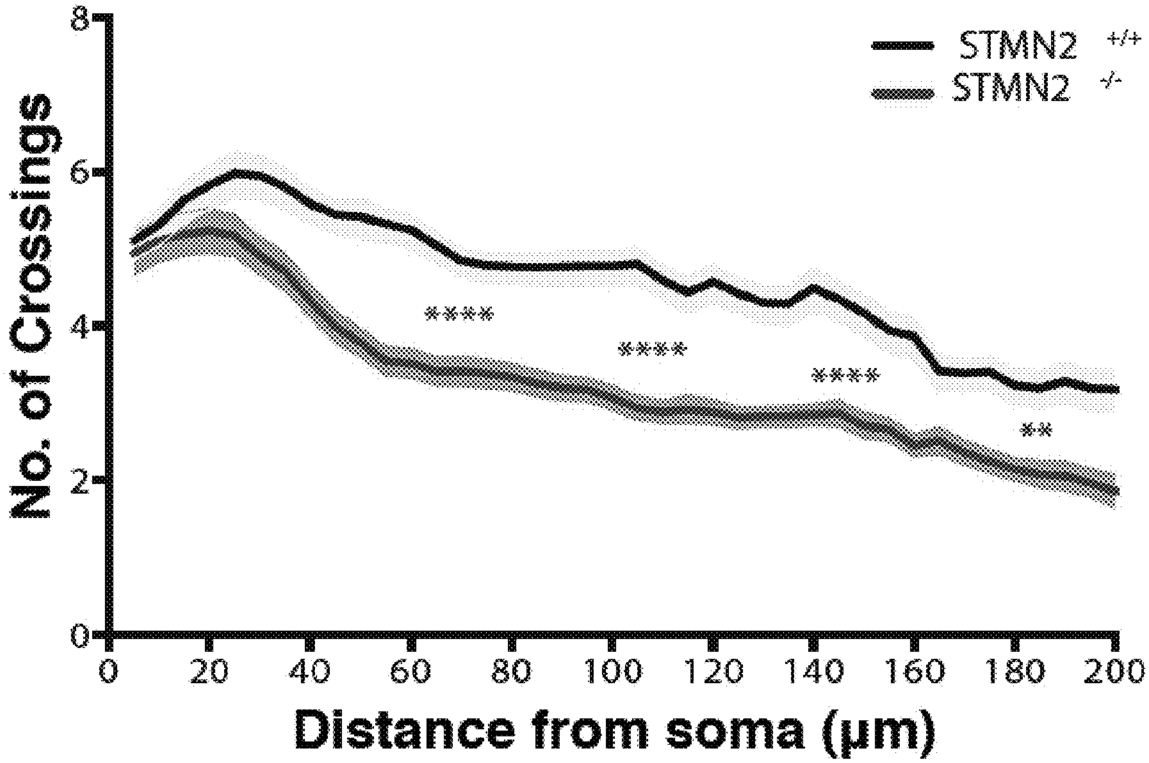
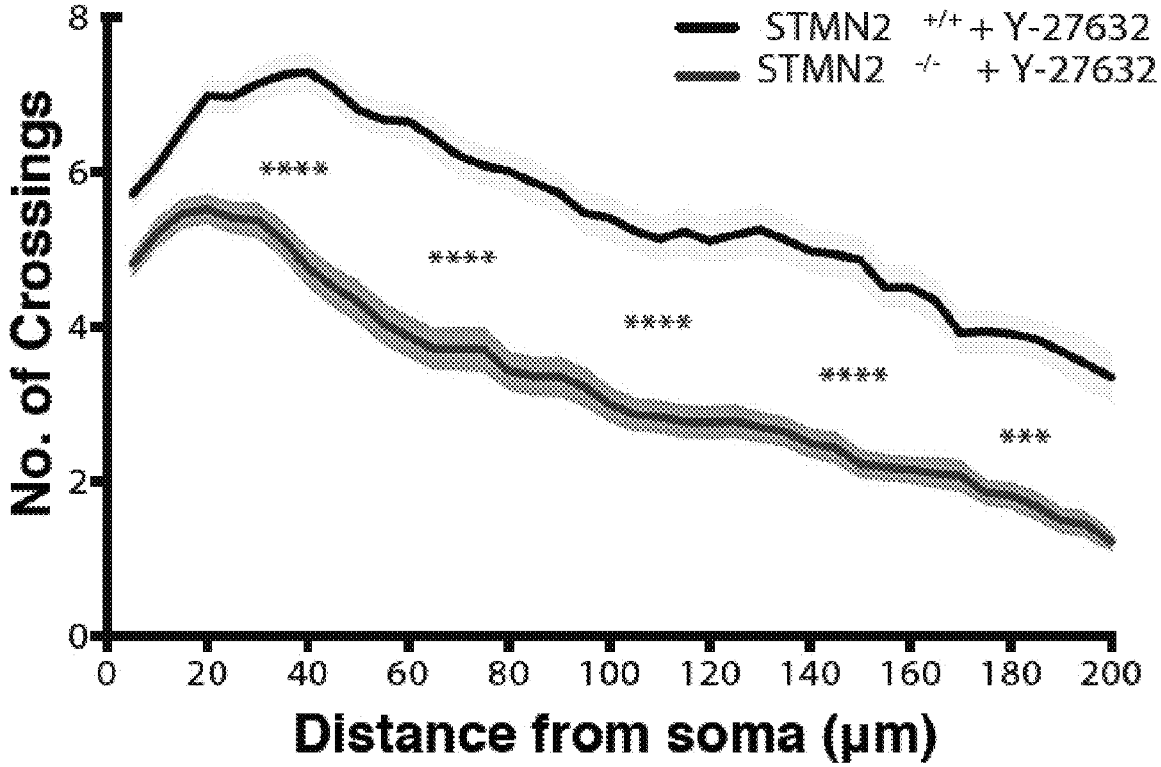
FIG. 4H

FIG. 4I
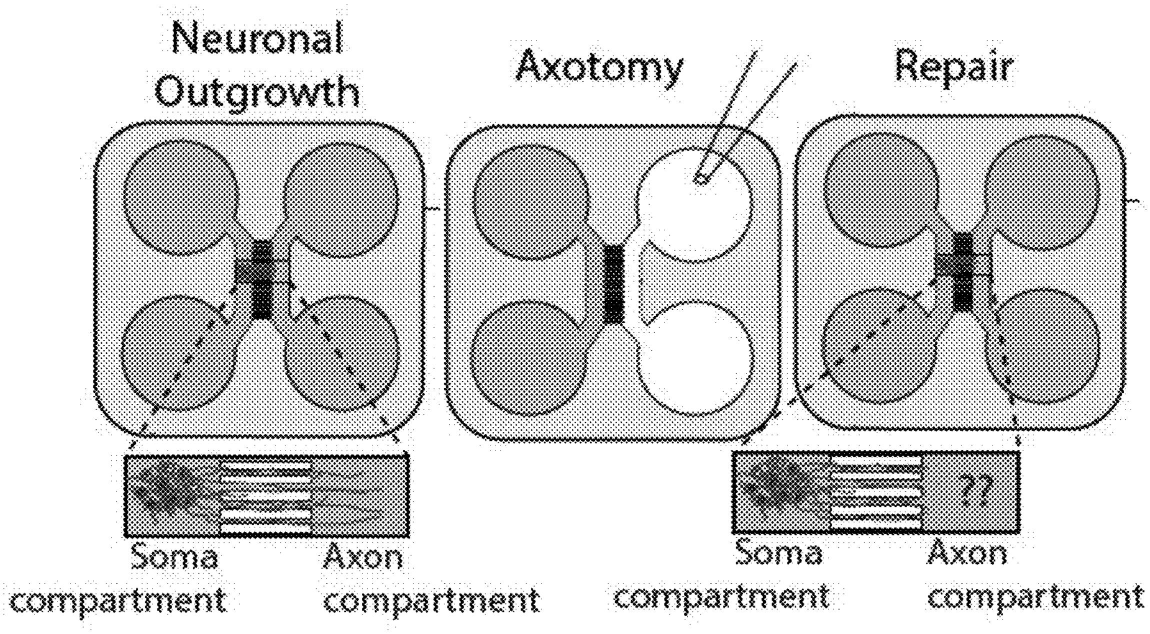
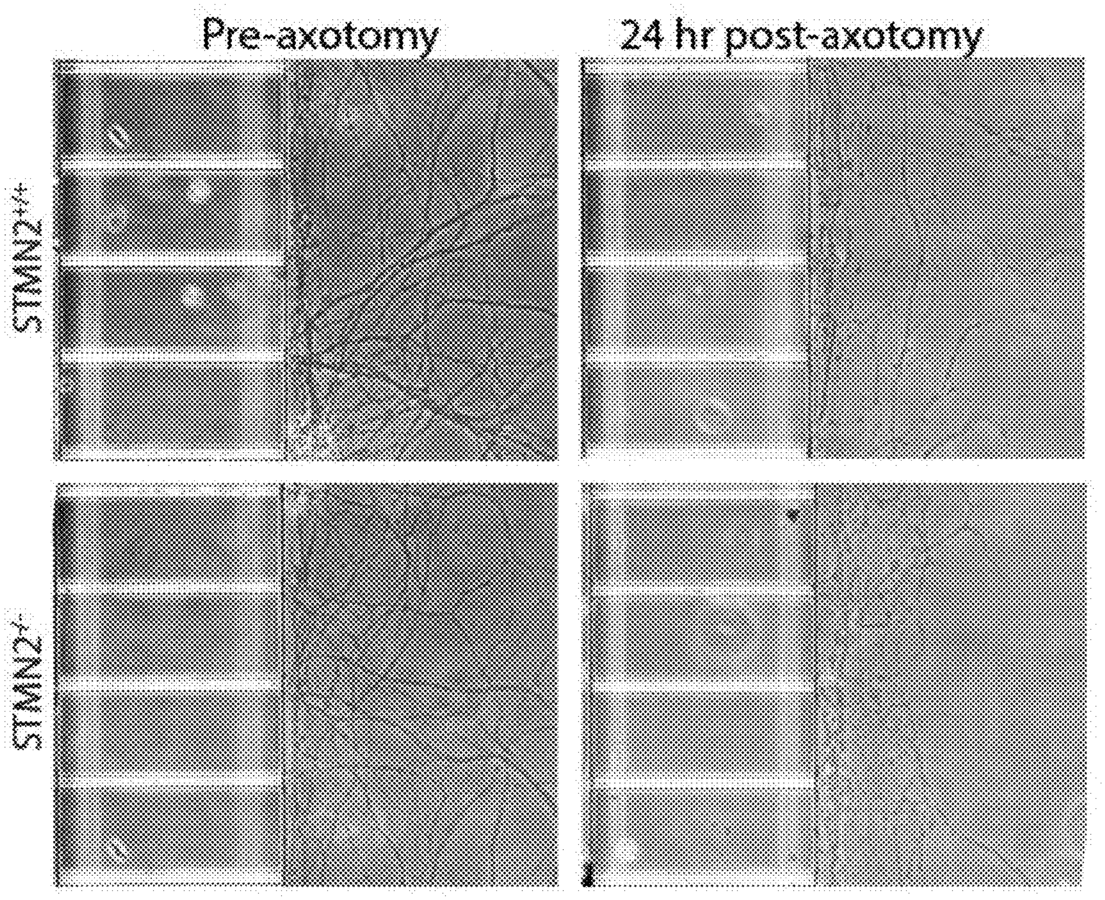
FIG. 4J

FIG. 13E
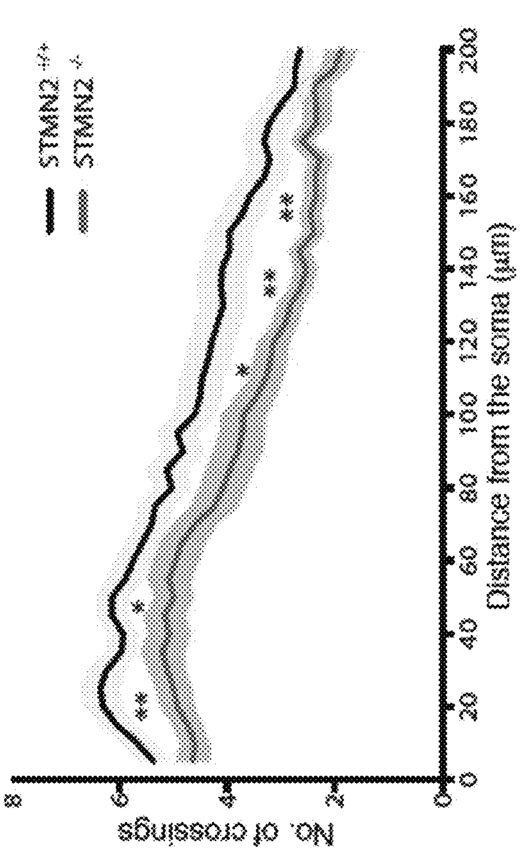
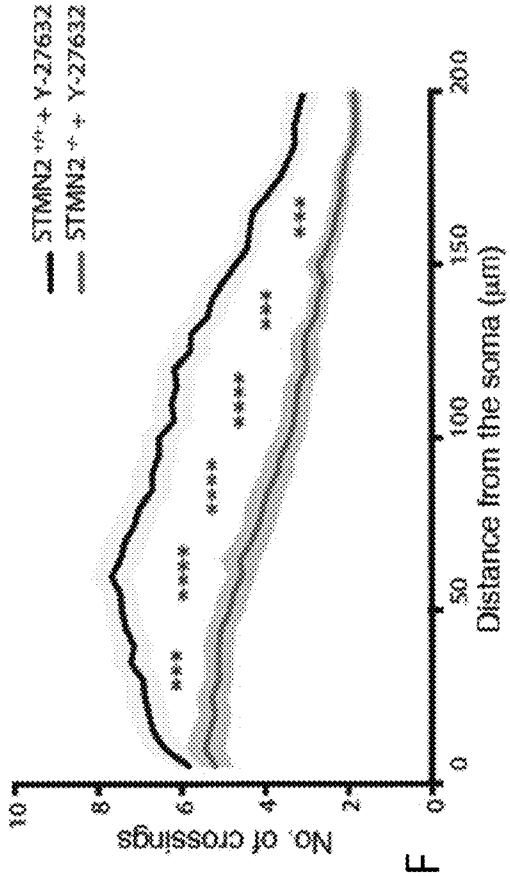
FIG. 13F
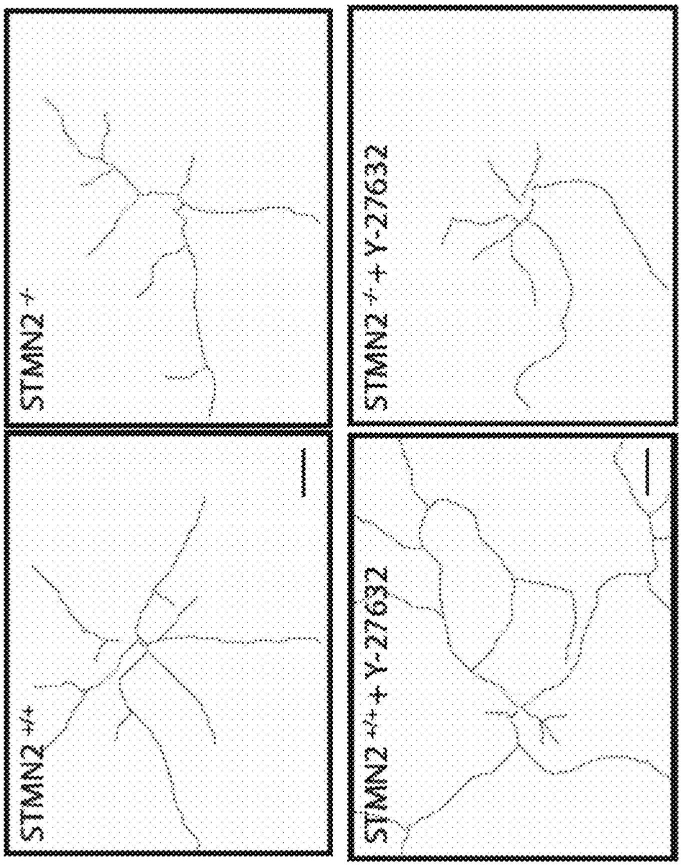
FIG. 13D

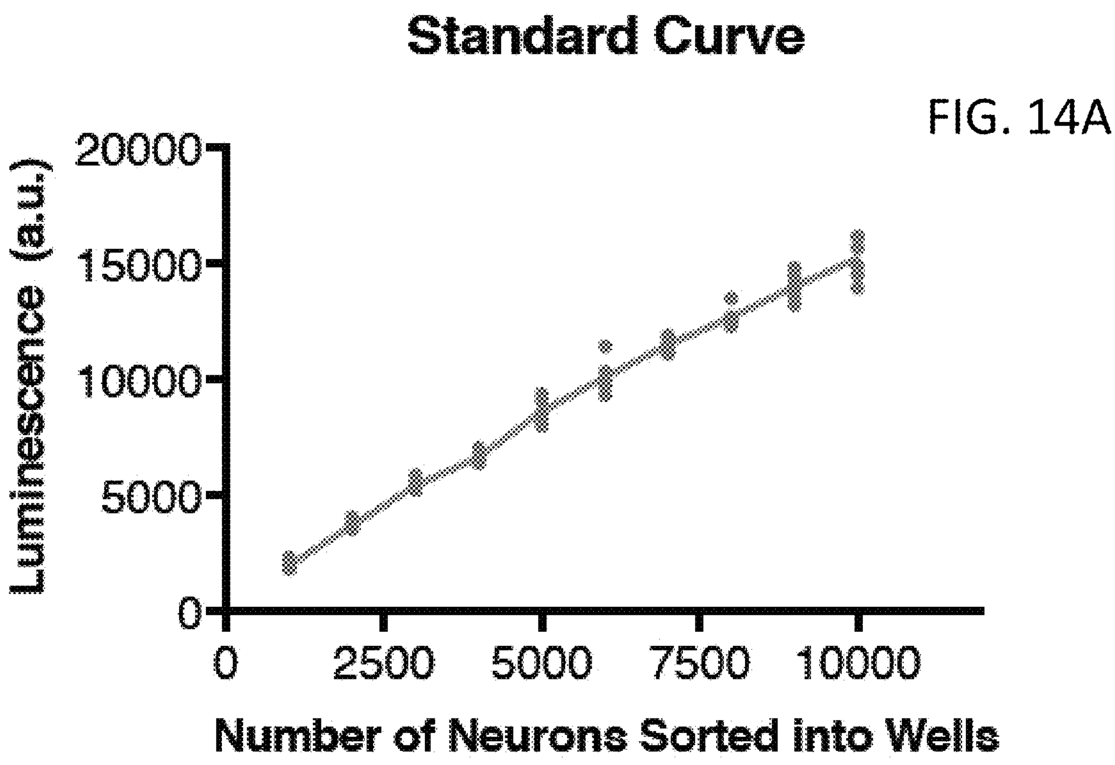
FIG. 14A
FIG. 14B
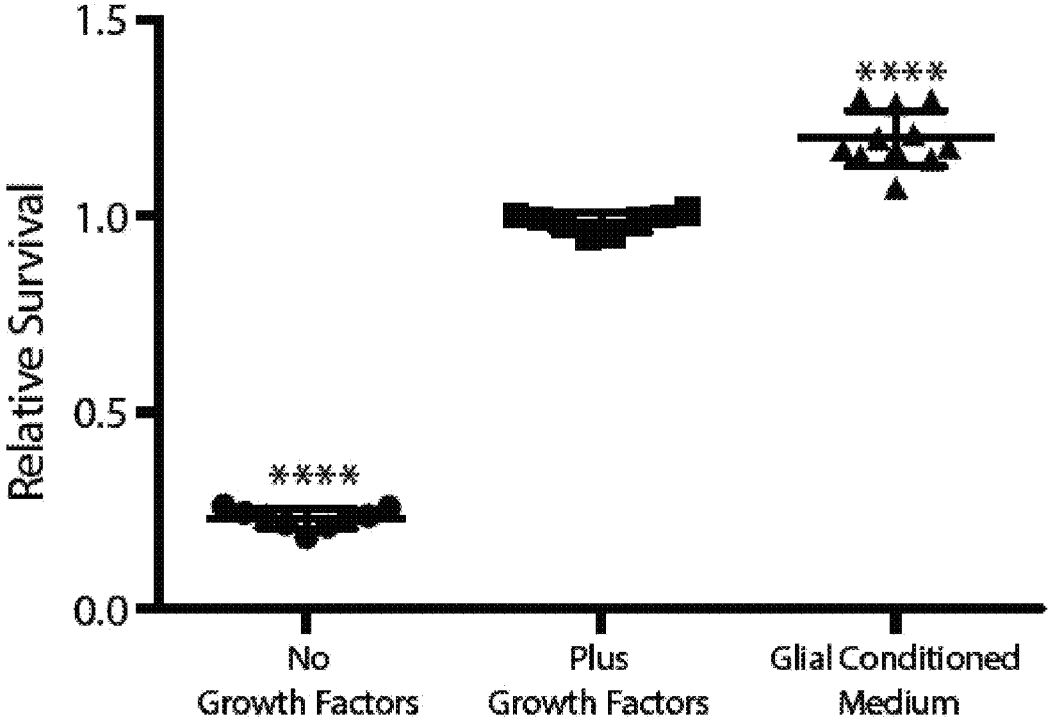

* Patient is alive
Data not available

* Patient is alive
\# Data not available

Alsultan et al. *Degenerative Neurological and Neuromuscular Disease*. 2016, *6*, 49-64.

Buratti and Baralle *Trends in Biochem. Sci.*. 2012, *6*, 237-247.

Klim et al. *Nature Neuroscience* vol. 22, pages 167–179 (2019)

J. Eun Shin et al. *PNAS* 2012, *109*, E3696-3705.

*See* Klim et al. *Nature Neuroscience* vol. 22, pages 167–179 (2019).

| Gene | Locus | Inheritance | Level of evidence[a] | Mutation frequency | | | | | | | TDP-43 pathology | Implicated disease pathway |
|---|---|---|---|---|---|---|---|---|---|---|---|---|
| | | | | Overall ALS (%) | Familial ALS (%) | Sporadic ALS (%) | Overall FTD (%) | Familial FTD (%) | Sporadic FTD (%) | ALS-FTD (%) | | |
| *TBK1*[b] | 12q14.2 | AD[c] | Established | 1.3 | 3 | <1 | <1 | 2 | 1 | 3–4 | + | Autophagy, inflammation |
| *CHCHD10* | 22q11.23 | AD | Established | <1 | 2 | <1 | <1 | <1 | <1 | <1 | + | Mitochondrial dysfunction, synaptic integrity |
| *TUBA4A* | 2q35 | AD | To be validated | <1 | 1 | <1 | <1 | <1 | – | – | + | Cytoskeletal dynamics, axonal transport |
| *MATR3* | 5q31.2 | AD | Established | <1 | 1–2 | 1 | – | – | – | – | + | RNA metabolism |
| *CCNF* | 16p13.3 | AD | Established | <1 | 0.6–3.3 | <1 | 4[d] | – | – | – | + | Proteostasis |
| *NEK1*[b] | 4q33 | n.d.[c] | To be validated | 1 | 1–2 | <1 | – | – | – | – | n.d. | DNA damage responses, cell cycle control, cytoskeletal organization, mitochondrial membrane regulation |
| *C21orf2*[b] | 21q22.3 | n.d. | To be validated | <1 | – | – | – | – | – | – | n.d. | DNA damage response, cytoskeletal organization |
| *ANXA11* | 10q22.3 | AD | To be validated | 1.1 | 1 | 1.7 | – | – | – | – | + | Proteostasis |
| *TIA1* | 2p13.3 | AD | To be validated | <1 | 2.2 | <1 | – | – | – | <1 | + | RNA metabolism |

-Nguyen, et al., Trends in Genetics, 2018

FIG. 41

--Hansen, et al., Nature Reviews Molecular Cell Biology. 2018

| | WT | Delta |
|---|---|---|
| 1) F1+R1 | 1.2kb | - |
| 2) F2+R2 | 961bp | - |
| 3) F1+R2 | - | 955bp |

| Mouse ID and sex | Guide Target Site? | PCR Band Analysis | | | Sequence analysis | | Comments |
|---|---|---|---|---|---|---|---|
| | | WT band | Band shift or no band | 13 Kb deletion? | % of WT Sequence | % Indel Frequency | |
| 1 - M | Exon 2 | Y | | | 18 | 27 (-6 nt)<br>21 (-3 nt)<br>7 (-1 nt) | |
| | Exon 4 | Y | | | 0 | 28 (-14 nt)<br>28 (-12 nt)<br>40 (-8 nt) | |
| 2 - M | Exon 2 | Y | | | 0 | 84 (+1 nt) | |
| | Exon 4 | Y | | | 0 | 92 (-12 nt) | |
| 3 - M | Exon 2 | N | Y | | failed | failed | |
| | Exon 4 | Y | | | failed | failed | |
| 4 - M | Exon 2 | Y | | | 20 | 4 (-27 nt)22 (-8 nt) | |
| | Exon 4 | Y | | | 0 | 96 (-12 nt) | |
| 5 - M | Exon 2 | N | Y | Y | 0 | | |
| | Exon 4 | Y | | | 0 | 97 (-1 nt) | |
| 6 - M | Exon 2 | Y | | Y | 0 | 94 (-17 nt) | |
| | Exon 4 | Y | | | 0 | 97 (-12 nt) | |
| 7 - M | Exon 2 | N | Y | Y | failed | failed | |
| | Exon 4 | Y | | | failed | failed | |
| 8 - M | Exon 2 | Y | Y | | 0 | 58 (-28 nt)<br>11 (-22 nt)<br>3 (-3 nt)<br>8 (+26 nt) | |
| | Exon 4 | Y | | | 0 | 95 (-11 nt) | |
| 9 - M | Exon 2 | Y | | | 5.3 | 85 (+1 nt) | |
| | Exon 4 | Y | | | 0 | 38 (-12 nt)<br>38 (-11 nt)<br>20 (-9 nt) | |
| 10 - M | Exon 2 | N | Y | | ? | ? | |
| | Exon 4 | N | Y | | ? | ? | |
| 11 - M | Exon 2 | N | Y | Y | | | |
| | Exon 4 | N | Y | | | | |
| 12 - F | Exon 2 | N | Y | Y | | | |
| | Exon 4 | N | Y | | | | |
| 13 - F | Exon 2 | Y | Y | | 23 | 72 (+1 nt) | |
| | Exon 4 | N | Y | | 0 | 98 (-12 nt) | |
| 14 - F | Exon 2 | N | Y | | 0 | 55 (-28 nt)23 (-10 nt)23 (+1 nt) | |
| | Exon 4 | Y | | | | | |
| 15 - F | Exon 2 | Y | | | 0 | 95 (+1 nt) | |
| | Exon 4 | Y | | | 0 | 98 (-12 nt) | |
| 16 - F | Exon 2 | Y | | | 4 | Mixed | |
| | Exon 4 | Y | | | 0 | 93 (-11 nt) | |
| 17 - F | Exon 2 | N | Y | | | | |
| | Exon 4 | N | Y | | | | |
| 18 - | Exon 2 | Y | | Y | 97 - | | |
| | Exon 4 | N | | | | | |
| 19 - | Exon 2 | Y | | | 30 | 56 (+1 nt) | |
| | Exon 4 | Y | | | 0 | 96 (-1 nt) | |
| 20 - | Exon 2 | Y | | Y | 0 | 97 (+2 nt) | |
| | Exon 4 | Y | | | 0 | 96 (-11 nt) | |
| 21 - | Exon 2 | Y | | Y | 0 | 95 (-8 nt) | |
| | Exon 4 | Y | | | 0 | 95 (-11 nt) | |
| 22 - | Exon 2 | Y | | Y | 0 | 96 (-3 nt) | |
| | Exon 4 | N | | | | | |

FIG. 47C

*Each individual dot is the average from 2 technical replicates/mouse

METHODS AND COMPOSITIONS FOR RESTORING STMN2 LEVELS

RELATED APPLICATION(S)

This application is a national stage filing under 35 U.S.C. 371 of International Application No. PCT/US2020/013581, filed Jan. 14, 2020, which claims the benefit of U.S. Provisional Application No. 62/792,276, filed on Jan. 14, 2019. The entire teachings of the above applications are incorporated herein by reference. International Application No. PCT/US2020/013581 was published under PCT Article 21 (2) in English.

GOVERNMENT SUPPORT

This invention was made with government support under NS069395, NS078736, and NS089742 awarded by the National Institutes of Health. The government has certain rights in the invention.

BACKGROUND OF THE INVENTION

Amyotrophic lateral sclerosis (ALS) is a fatal neurodegenerative disease characterized by the selective loss of both upper and lower motor neurons (1). Patients with ALS experience progressive paralysis and develop difficulties in speaking, swallowing, and eventually breathing (2, 3) and usually succumb to the disease after 1-5 years from the time of diagnosis. Aside from two FDA approved drugs which modestly alter disease progression (4), treatment for ALS is limited to supportive care. ALS is now recognized to be on the same clinical and pathological spectrum as frontotemporal dementia (FTD), the most common cause of pre-senile dementia. FTD is characterized by behavioral changes, language impairment, and loss of executive functions (5) for which there is no effective treatment. Although the etiology of most ALS and FTD cases remains unknown, pathological findings and family-based linkage studies have demonstrated that there is overlap in molecular pathways involved in both diseases (1, 6).

SUMMARY OF THE INVENTION

TDP-43 is a predominantly nuclear DNA/RNA-binding protein with functional roles in transcriptional regulation, splicing, pre-microRNA processing, stress granule formation, and messenger RNA transport and stability. TDP-43 has been found to be a major constituent of inclusions in many sporadic cases of ALS and FTD. In response to aberrant expression of TDP-43, a decrease in STMN2 levels is seen. STMN2, also known as SCG10, is a regulator of microtubule stability and has been shown to encode a protein necessary for normal human motor neuron outgrowth and repair. Described herein are methods and compositions for restoring or increasing STMN2 levels.

In some aspects, the invention is directed to methods of treating or reducing the likelihood of a disease or condition associated with a decline in TAR DNA-binding protein 43 (TDP-43) functionality in neuronal cells in a subject in need thereof. The method comprises contacting the neuronal cells with an agent that corrects reduced levels of STMN2 protein.

In some aspects, the invention is directed to methods of treating or reducing the likelihood of a disease or condition associated with a decline in TAR DNA-binding protein 43 (TDP-43) functionality in neuronal cells in a subject in need thereof. In some embodiments the method comprises contacting the neuronal cells with an agent that suppresses or prevents inclusion of a cryptic exon in STMN2 RNA.

In some embodiments, the agent specifically binds an STMN2 RNA, pre-RNA, or nascent RNA transcript. In some embodiments, the agent specifically binds an abortive STMN2 RNA, pre-RNA, or nascent RNA transcript. In some embodiments, the agent specifically binds an STMN2 RNA, pre-RNA, or nascent RNA sequence coding for a cryptic exon. In some embodiments, the agent is designed to target a 5' splice site, a 3' splice site, a normal binding site, or a polyadenylation site in said transcript. In some embodiments, the agent is designed to target one or more splice sites in said transcript. In some embodiments, the agent is a small molecule or an oligonucleotide (e.g., an antisense oligonucleotide). In some embodiments the agent is not an antisense oligonucleotide.

In some embodiments, the agent restores normal length or protein coding of STMN2 pre-mRNA or mRNA. In some embodiments, the agent is a JNK inhibitor (e.g., a small molecule inhibitor of JNK, an oligonucleotide designed to reduce expression of a JNK, or a gene therapy designed to inhibit JNK).

In some embodiments, the subject exhibits improved neuronal outgrowth and repair as a result of administration of the agent. In some embodiments, the disease or condition is a neurodegenerative disease (e.g., is selected from the group consisting of amyotrophic lateral sclerosis (ALS), frontotemporal dementia (FTD), inclusion body myositis (IBM), Parkinson's disease, and Alzheimer's disease). In some embodiments, the disease or condition is a traumatic brain injury (TBI) or is associated with a traumatic brain injury. In some embodiments, the disease or condition is a proteasome-inhibitor-induced neuropathy. In some embodiments, the disease or condition is associated with mislocalized TDP-43 or mutant or reduced levels of TDP-43 in neuronal cells.

In some embodiments, the methods described herein further comprise administering an effective amount of a second agent to the subject. In some aspects, the second agent is administered to treat a neurodegenerative disease, a TBI, and/or a proteasome-inhibitor induced neuropathy. In some embodiments, the second agent is STMN2 (e.g., administered as a gene therapy). In some embodiments, the second agent is a JNK inhibitor. In some embodiments, the second agent is a second oligonucleotide (e.g., antisense oligonucleotide).

In some aspects, the invention is directed to an agent that specifically binds an STMN2 mRNA, pre-mRNA, or nascent RNA sequence coding for a cryptic exon, thereby suppressing or preventing inclusion of a cryptic exon in STMN2 RNA.

In some aspects, the invention is directed to an agent that binds to an abortive or altered STMN2 RNA sequence that occurs and increases in abundance when TDP-43 function declines or TDP-pathology occurs, thereby restoring expression of a normal full-length or protein coding STMN2 RNA.

In some embodiments, the agent is an oligonucleotide, protein or small molecule. In some embodiments, the agent is an antisense oligonucleotide. In some embodiments, the agent is an antisense oligonucleotide comprising a sequence of SEQ ID NO: 11. In some embodiments, the agent is designed to target a 5' splice site, a 3' splice site, a normal binding site, or a polyadenylation site in the STMN2 transcript. In some embodiments, the agent is designed to target one or more splice sites. In some embodiments the agent does not target or bind to a polyadenylation site in the transcript.

In some aspects, the invention is directed to a pharmaceutical composition comprising an agent, wherein the agent prevents degradation of STMN2 protein. In some embodiments, the agent is an oligonucleotide, protein or small molecule. In some embodiments, the agent is an antisense oligonucleotide (e.g., an antisense oligonucleotide comprising the sequence of SEQ ID NO: 11). In some embodiments, the agent is designed to target a 5' splice site, a 3' splice site, a normal binding site, or a polyadenylation site. In some embodiments, the agent is designed to target one or more splice sites.

In some aspects, the invention is directed to a pharmaceutical composition comprising an oligonucleotide. The oligonucleotide may specifically bind an STMN2 mRNA, pre-mRNA, or nascent RNA sequence coding for a cryptic exon. In some embodiments, the oligonucleotide is an antisense oligonucleotide (e.g., comprising the sequence of SEQ ID NO: 11).

In some embodiments, the oligonucleotide suppresses or prevents inclusion of a cryptic exon in STMN2 RNA and/or suppresses cryptic splicing. In some embodiments, the oligonucleotide targets a 5' splice site, a 3' splice site, a normal protein binding site, e.g., for TDP-43, or a polyadenylation site. In some embodiments, the oligonucleotide targets one or more splice sites. In some embodiments, the oligonucleotide restores expression of a normal full-length or protein coding STMN2 RNA.

In some embodiments, the pharmaceutical composition further comprises an agent for treating a neurodegenerative disease, a traumatic brain injury, or a proteasome-inhibitor induced neuropathy. In some embodiments, the pharmaceutical composition further comprises STMN2 as a gene therapy. In some embodiments, the pharmaceutical composition further comprises a JNK inhibitor.

In some aspects, the invention is directed to methods of screening one or more test agents to identify candidate agents for treating or reducing the likelihood of a disease or condition associated with a decline in TDP-43 functionality in neuronal cells in a subject. The methods comprise providing a neuronal cell having mislocalized TDP-43 or reduced or mutant TDP-43 levels; contacting the cell with the one or more test agents; determining if the contacted cell has an increased level of STMN2 protein; and identifying the test agent as a candidate agent if the contacted cell has an increased level of STMN2 protein.

In some embodiments, the step of determining if the contacted cell has increased level of STMN2 protein comprises measuring STMN2 protein levels in the contacted cell. The measuring of the STMN2 protein levels in the contacted cell may comprise using an ELISA assay. In some embodiments, the step of determining if the contacted cell has increased level of STMN2 protein comprises assessing the morphology or function of the contacted cell. The morphology or function of the contacted cell may be assessed using immunoblotting and/or immunocytochemistry.

In some embodiments, the disease or condition is a neurodegenerative disease. For example, the disease or condition may be selected from the group consisting of amyotrophic lateral sclerosis (ALS), frontotemporal dementia (FTD), inclusion body myositis (IBM), Parkinson's disease, and Alzheimer's disease. In some embodiments, the disease or condition is a traumatic brain injury. In some embodiments, the disease or condition is a proteasome-inhibitor induced neuropathy.

In some aspects, the invention is directed to methods of screening one or more test agents to identify candidate agents for treating or reducing the likelihood of a disease or condition associated with a decline in TDP-43 functionality in neuronal cells in a subject. The methods comprise providing a neuronal cell having mislocalized TDP-43 or mutant or reduced TDP-43 levels; contacting the cell with the one or more test agents; determining if the contacted cell has cryptic exons in STMN2 RNA; and identifying the test agent as a candidate agent if the contacted cell has a decreased level of cryptic exons in STMN2 RNA.

In some embodiments, the step of determining if the contacted cell has cryptic exons in STMN2 RNA comprises assessing the contacted cell using RT-PCR, qPCR, or RNA Seq to identify whether the contacted cell has cryptic exons in STMN2 RNA.

In some embodiments, the disease or condition is a neurodegenerative disease. For example, the disease or condition may be selected from the group consisting of amyotrophic lateral sclerosis (ALS), frontotemporal dementia (FTD), inclusion body myositis (IBM), Parkinson's disease, and Alzheimer's disease. In some embodiments, the disease or condition is a TBI or is associated with a TBI. In some embodiments, the disease or condition is a proteasome-inhibitor induced neuropathy.

In some aspects, the invention is directed to methods of screening one or more test agents to identify candidate agents for treating or reducing the likelihood of a disease or condition associated with a decline in TDP-43 functionality in neuronal cells in a subject. The methods comprise providing a neuronal cell having mislocalized TDP-43 or mutant or reduced TDP-43 levels; contacting the cell with the one or more test agents; determining if the contacted cell expresses normal full-length or protein coding STMN2 RNA; and identifying the test agent as a candidate agent if the contacted cell expresses normal full-length or protein coding STMN2 RNA.

In some aspects, the invention is directed to methods of detecting altered levels of STMN2 protein in a subject. The methods comprise obtaining a sample from the subject; and detecting whether the STMN2 protein levels are altered.

In some embodiments, the subject has amyotrophic lateral sclerosis. In some embodiments, the detection of whether the STMN2 levels are altered comprises determining if the STMN2 levels are decreased (e.g., using an ELISA). In some embodiments, the sample is a biofluid sample (e.g., a CSF sample).

In some aspects, the invention is directed to an assay for detecting STMN2 cryptic exon in a sample. The assay comprises obtaining a biofluid sample; extracting exosome RNA from the biofluid sample; converting the extracted exosome RNA into cDNA; and assaying the cDNA, wherein the assay detects the presence or absence of the STMN2 cryptic exon transcript. In some embodiments, the assay is a qPCR assay.

In some aspects, the invention is directed to a method of processing a sample. The method comprises obtaining a biofluid sample; extracting exosome RNA from the biofluid sample; and converting the extracted exosome RNA into cDNA.

In some embodiments, the method further comprises assessing the cDNA using an assay (e.g., a qPCR assay). In some embodiments, the biofluid sample is a cerebral spinal fluid sample.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A provides a schematic showing hMN differentiation, purification, and RNAi strategy for TDP-43 knockdown in cultured MNs. FIG. 1B provides multidimensional scaling analysis for RNA-Seq data sets obtained from two biologically independent MN differentiation and siRNA transfection experiments based on 500 most differentially expressed genes. FIG. 1C provides a volcano plot showing statistically misregulated genes in hMNs treated with siTDP-43 compared to those treated with scrambled controls. Genes identified as significant (Benjamini-Hochberg adjusted P value cutoff of 0.05 and a log fold-change ratio cutoff of 0) after differential expression analysis are highlighted in yellow (for up-regulated/increased abundance genes) and in blue (for down-regulated/decreased abundance genes). FIG. 1D provides a scatter plot comparing TPM values for all genes expressed in MNs treated with control siRNAs versus the fold change in expression for those genes in cells treated with siTDP-43. FIGS. 1E and 1F show a subset of 11 genes initially identified as 'hits' (significantly up-regulated (FIG. 1E) or down-regulated (FIG. 1F)) in the TDP43 knockdown experiment were selected for validation by qRT-PCR. A total of 9 out 11 of these genes (including TDP-43) exhibited the predicted response to TDP-43 depletion when their expression was assayed by qRT-PCR (Unpaired t test, P value <0.05).

FIG. 2A provides a schematic of a strategy for assessing gene expression in iPS cell-derived hMNs expressing mutant TDP-43. FIG. 2B provides micrographs showing the morphology of neurons cultured for 10 days derived from the iPS cells of healthy controls (11a, 18a, 20b, 17a) and patients with mutations in TARDP (+/Q343R, +/G298S, +/A315T, and +/M337V). FIGS. 2C-2H provide qRT-PCR analysis of the genes consistently downregulated (FIGS. 2D-2F) or upregulated (FIG. 2C) after TDP-43 knockdown in neurons differentiated from the controls or TDP-43 patients. (Unpaired t test, P value <0.05). FIG. 2I provides representative micrographs of control and patient neurons immunostained for TDP-43 (red), β-III tubulin (green) and counterstained with DAPI (blue). Scale bar, 100 μm. FIG. 2J provides Pearson's correlation analysis for TDP-43 immunostaining and DAPI fluorescence comparing control neurons to neurons with TDP-43 mutations. Dots represent individual cells. (Unpaired t test, P value <0.05).

FIG. 3A provides qRT-PCR analysis for the STMN2 transcript in independent experiments using two different sets of primer pairs. (Unpaired t test, P value <0.05). FIG. 3B provides immunoblot analysis for TDP-43 and STMN2 protein levels following partial depletion of TDP-43 by siRNA knockdown. Protein levels were normalized to GAPDH and are expressed relative to the levels in MNs treated with the siRED control. FIG. 3C provides qRT-PCR analysis for STMN2 transcript analysis in Hb9::GFP+MNs treated with siRNAs targeting three ALS-linked genes (TDP-43, FUS, and C9ORF72). (Dunnett's multiple comparison test, Alpha value <0.05). FIGS. 3D-3F show formaldehyde RNA immunoprecipitation was used to identify transcripts bound to TDP-43. After TDP-43 immunoprecipitation (FIG. 3D), qRT-PCR analysis was used to test for enrichment of TDP-43 transcripts (FIG. 3E) and STMN2 transcripts (FIG. 3F) relative to the sample input. FIG. 3G provides micrographs of Hb9::GFP+MNs immunostained for TDP-43 (red), β-III tubulin (green) and counterstained with DAPI (blue). FIG. 3H provides micrographs of Hb9::GFP+MNs co-cultured on glia immunostained for STMN2 (red) and MAP2 green and GOLGIN97 (green). FIG. 3I provides a micrograph of Hb9::GFP+MNs day 3 after sorting immunostained for STMN2 (red), MAP2 (green) and counterstained with F-actin-binding protein phalloidin (white). Scale bar, 5 μm.

FIGS. 4A-4K demonstrate STMN2 Knockout. FIG. 4A provides a schematic of the knockout strategy using guide RNAs (gRNAs) targeting two constitutive exons, Exon 2 and 4, of the human STMN2 gene. The intervening DNA segment (~18 Kb) is targeted and deleted as a result of NHEJ (Non-homologous end joining) repair of the two double strand breaks (DSBs) introduced by the Cas9/gRNA nuclease complex. FIGS. 4B-4D show STMN2 knockout was confirmed in the HUES3 Hb9::GFP line by RT-PCR analysis of genomic DNA (FIG. 4B), by immunoblot analysis (FIG. 4C), and by immunofluorescence (FIG. 4D). FIG. 4E provides an experimental strategy used to assess the cellular effect of lacking STMN2 in hMNs. FIGS. 4F-4H show Sholl analysis of hMNs with and without STMN2 and in the absence (FIG. 4G) or presence (FIG. 4H) of a ROCK inhibitor (Y-27632, 10 μM) to stimulate neurite outgrowth. (Unpaired t test, P value <0.05). FIG. 4I provides an experimental strategy used to assess the cellular effect of lacking STMN2 in hMNs after axonal injury. FIGS. 4J-4K show axonal regrowth after injury. Representative micrographs of hMNs in the microfluidics device prior to and after axotomy (FIG. 4J). Measurements of axonal regeneration after axotomy. (Unpaired t test, P value <0.05).

FIG. 5A provides an experimental strategy used to assess the effect of proteasome inhibition on TDP-43 localization in human motor neurons. FIG. 5B shows Pearson's correlation analysis for TDP-43 immunostaining and DAPI fluorescence of cells treated with MG-132 (1 μM). (Dunnett's multiple comparison test, Alpha value <0.05). FIG. 5C provides micrographs of HUES3 motor neurons untreated or treated with MG-132 and immunostained for TDP-43 (red), β-III tubulin (green) and counterstained with DAPI (blue). Scale bar, 100 μm. FIG. 5D provides immunoblot analysis of TDP-43 in detergent soluble (RIPA) and detergent-insoluble (UREA) fractions in neurons treated with MG-132 (Unpaired t test, P value <0.05). FIG. 5E provides qRT-PCR analysis of STMN2 expression for motor neurons treated with MG-132 at the indicated concentrations and durations relative to DMSO control (Unpaired t test, P value <0.05). FIG. 5F provides a diagram of RT-PCR detection strategy for STMN2 cryptic exon. FIG. 5G provides a tapestation analysis for the STMN2 cryptic exon in hMNs control cells treated with MG-132 (1 μM).

FIGS. 6A-6C provides histologic analysis of human adult lumbar spinal cord from post-mortem samples collected from a subject with no evidence of spinal cord disease (control) (FIG. 6A) or two patients diagnosed with sporadic ALS (FIGS. 6B-6C). Immunoreactivity to STMN2 was detected in the perinuclear region (indicated by arrows) of spinal motor neurons but not in the surrounding glial cells. STMN2 immunoreactivity in lumbar spinal motor neurons from control and ALS cases was scored as 'strong' [as indicated by arrows in control (FIG. 6A) and sporadic ALS (FIG. 6B)]

or as 'absent' [as indicated by arrowheads in sporadic ALS (FIG. 6C)]. Scale bars, 50 μm. FIG. 6D show the percentage of lumbar spinal motor neurons with strong STMN2 immunoreactivity was significantly lower in ALS tissue samples (n=3 controls and 3 ALS cases; approximately 40 MNs were scored for each subject; Two-tailed t-test, P value <0.05). FIGS. 6E-6G show gene expression analysis for STMN2 from previously published data sets, Rabin et al 2009 (FIG. 6E), Highley et al 2014 (FIG. 6F), and D'Erchia et al. 2017 (Two-tailed t-test, P value <0.05). FIG. 6H provides a molecular model of ALS pathogenesis.

FIG. 7A shows hMN differentiation, purification, and culture strategy. FIG. 7B provides flow-cytometric analysis of differentiated HUES3 Hb9::GFP cells. Cells not treated with the RA and SHH pathway agonist were used as negative control for the gating of GFP expression. FIGS. 7C-7F provides micrographs and quantification of purified Hb9::GFP+ cells immunostained for HB9 and counterstained with DAPI (FIG. 7C) (Scale bar=10 μm) or immunostained for ISL1 and the neuronal markers β-III tubulin and MAP2 (FIG. 7E) (Scale bar=20 μm). FIGS. 7G-7J show differentiated MNs are electrophysiologically active as determined by whole-cell patch-clamp recordings. FIG. 7G show upon depolarization in voltage-clamp mode, cells exhibited fast inward currents followed slow outward currents, indicating the expression and opening of voltage-activated sodium and potassium channels, respectively. FIG. 7H shows in current-clamp mode, depolarization elicited repetitive action potential firing. FIG. 7I shows response to Kainate is consistent with the expression of functional receptors for excitatory glutamatergic transmitters.

FIG. 8A provides RNAi strategy for TDP-43 knockdown in cultured MNs. FIG. 8B shows phase and red fluorescence micrographs of cultured hMNs 4 days after treatment with different siRNAs including scrambled siRNA conjugated to Alexa Fluor 555. FIG. 8C provides flow-cytometric analysis of hMNs after treatment with different siRNAs. FIG. 8D shows relative levels of TDP-43 mRNA in MNs exposed to different siRNAs for 2, 4 or 6 days. Levels for each sample were normalized to GAPDH and expressed relative to the no transfection control. FIG. 8E provides immunoblot analysis of hMNs after RNAi treated with the indicated siRNAs. Each sample was normalized using GAPDH, and TDP-43 protein levels were calculated relative to the siSCR_555-treated control sample.

FIG. 9A shows global transcriptional analysis of motor neurons treated as indicated represented as a heat map. Unsupervised clustering of expression profiles revealed that the samples segregated based on the batch on motor neuron production and analysis. FIG. 9B provides analysis of TDP-43 transcript abundance after RNA-Sequencing validated the knockdown (Benjamini-Hochberg adjusted P value cutoff of 0.05). FIG. 9C shows alteration in the splicing pattern of the POLDIP3 gene was detected as result of TDP-43 knockdown, with siTDP43-treated cells showing significant reduction of isoform 1 and increased levels of spliced variant 2 (which lacks Exon3) (false discovery rate 'FDR'>0.05).

FIG. 11A shows using a cell surface marker screen, antibodies enriched on GFP+ motor neurons (Quadrant 1) and GFP− cells (Quadrant 3) were identified. FIG. 11B shows after sorting for NCAM+ and EpCAM− cells, high content imaging was used to determine if the sorting method can deplete the cultures of mitotic cells (EdU+) and significantly enrich for motor neurons (Isl1+) and neurons (MAP2+). N=6 different iPS cell lines. Statistical analysis was performed using a two-tailed Student's t test. FIGS. 11C-11D provides qRT-PCR analysis of cultures after sorting for the motor neuron marker ISL1 (FIG. 11C) and the neuronal marker βIII-tubulin (FIG. 11D) revealed enrichment and more homogenous cultures compared to unsorted cultures. FIG. 11E provides flow-cytometric analysis with phycoerythrin (PE)-conjugated antibodies to EpCAM (anti-epCAM-PE) and Alexa Fluor 700-conjugated antibodies to NCAM (anti-NCAM-AF700) of cultures differentiated from the indicated healthy controls (grey) and TDP-43 mutant lines (red). FIG. 11F shows the percentage of NCAM+ cells for the indicated lines from 4-6 independent differentiations. No significant difference was observed between mutant and control lines in terms of their ability to generate NCAM+ cells. Statistical analysis was performed using a two-tailed Student's t test, P value <0.05.

FIGS. 12A-12C provide qRT-PCR validation of the downregulation of ALS genes upon siRNA treatments. Expression of TDP-43 (FIG. 12A), FUS (FIG. 12B), and C9ORF72 (FIG. 12C) was assessed for all the controls and each siRNA used (Unpaired t test, P value <0.05). FIG. 12D provides a western blot analysis of STMN2 protein in different cell types along the motor neuron differentiation. FIG. 12E shows RNA-Seq expression levels for the Stathmin family in motor neurons treated with either siSCR (−) or siTDP-43 (+) oligos. Only STMN2 levels were altered after TDP-43 knockdown.

FIGS. 12F-12G shows TDP-43 binding sites within the Stathmin family of genes (FIG. 12F) normalized to gene length (FIG. 12G). STMN2 has the greatest number of binding motifs.

FIGS. 13A-13H demonstrate STMN2 regulates neuronal outgrowth. CRISPR-mediated STMN2 knockout in the WA01 line was confirmed by RT-PCR analysis of genomic DNA (FIG. 13A), by immunoblot analysis (FIG. 13B), and by immunofluorescence (FIG. 13C). FIGS. 13D-13F provide Sholl analysis of hMNs with and without STMN2 and in the presence of a Y-27632 (10 μM), a ROCK inhibitor (FIG. 13F) (Unpaired t test, P value <0.05). FIGS. 13G-13H shows axonal regrowth after injury. Representative micrographs of hMNs in the microfluidics device prior to and after axotomy (FIG. 13G). Analysis of axonal regrowth after axotomy (Unpaired t test, P value <0.05) (FIG. 13H).

FIGS. 14A-14E demonstrate cell survival and proteasome activity assays. FIGS. 14A-14C shows Cell Titer Glo uses ATP from metabolically active cells to generate light. (FIG. 14A) shows a direct relationship exists between luminescence and the number of cell in culture over several orders of magnitude. FIG. 14B shows the assay can detect differences in neuronal survival in the absence of growth factors. N=6 separate wells of neurons. (Unpaired t test, P value <0.05). FIG. 14C shows MG-132 neuronal survival experimental outline. FIG. 14D shows dose response curve for motor neurons cultured with indicated concentrations of MG-132 for the indicated times. N=triplicate wells. Cells are viable after 1 day of treatment at all the concentrations tested and lower concentrations are tolerated for more extended periods of time. FIG. 14E shows following cleavage by the proteasome, the substrate for luciferase is liberated, which allows for quantitative measurement of proteasome activity.

Neurons treated with MG-132 show significantly decreased proteasome activity. N=4 separate wells of neurons (Unpaired t test, P value <0.05).

Figure 15B:
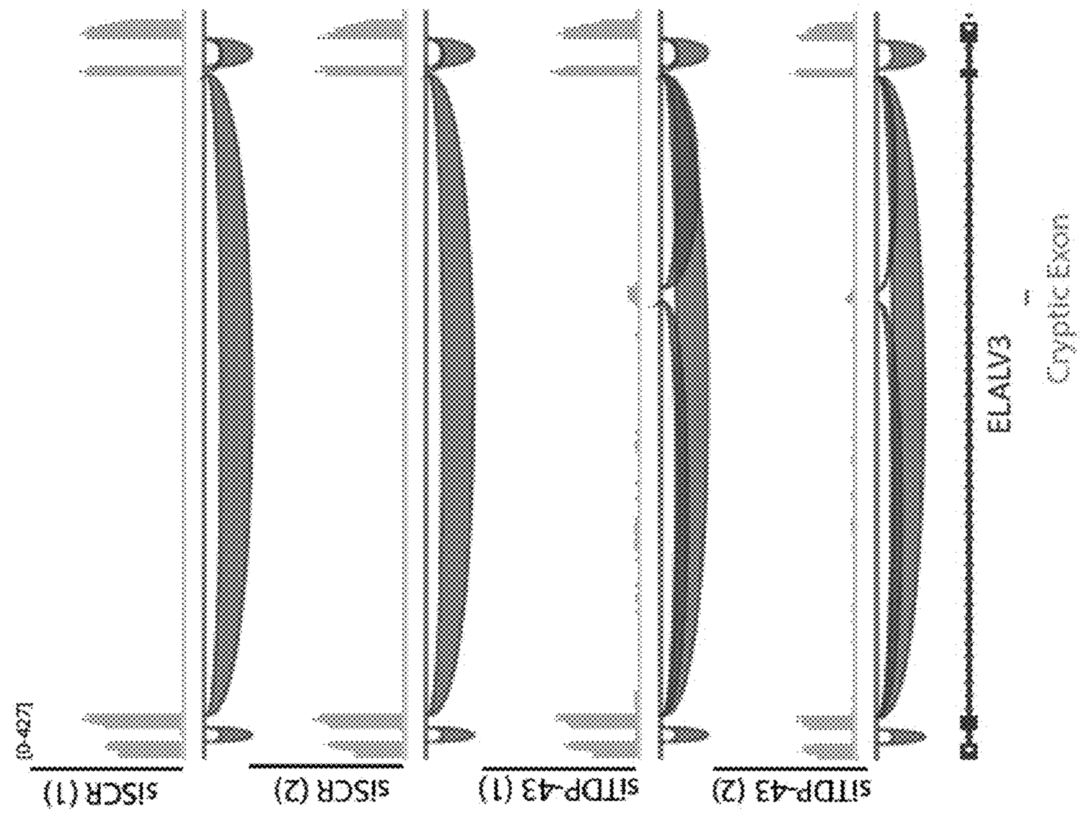
Figure 15A:
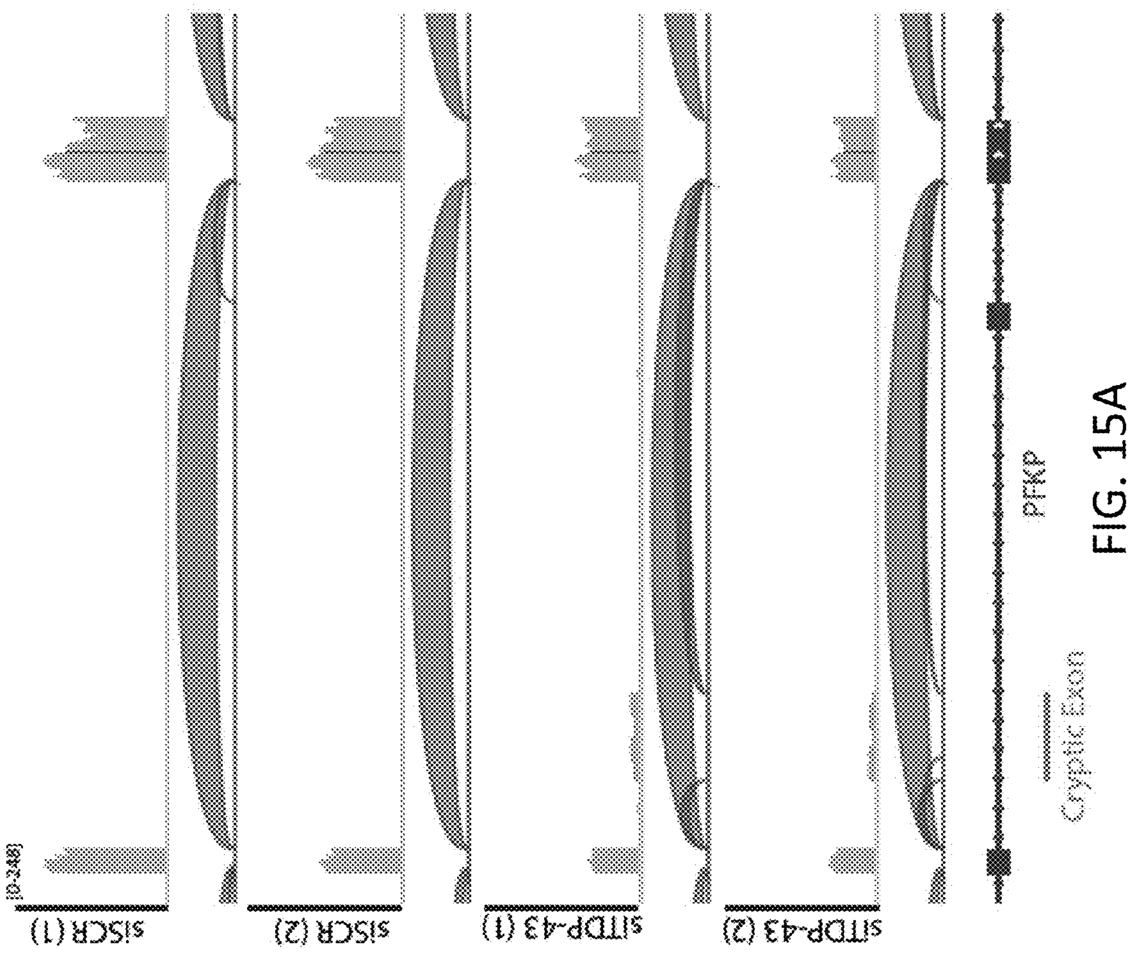
Figure 15C:
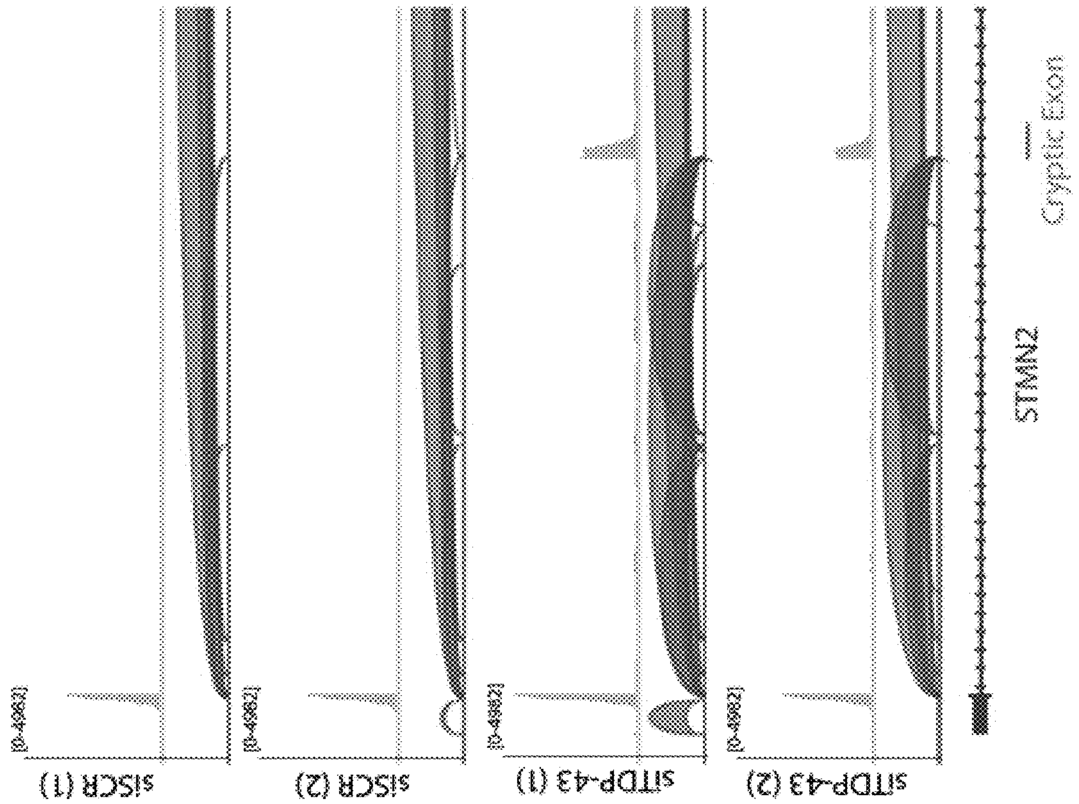
Figure 15D:
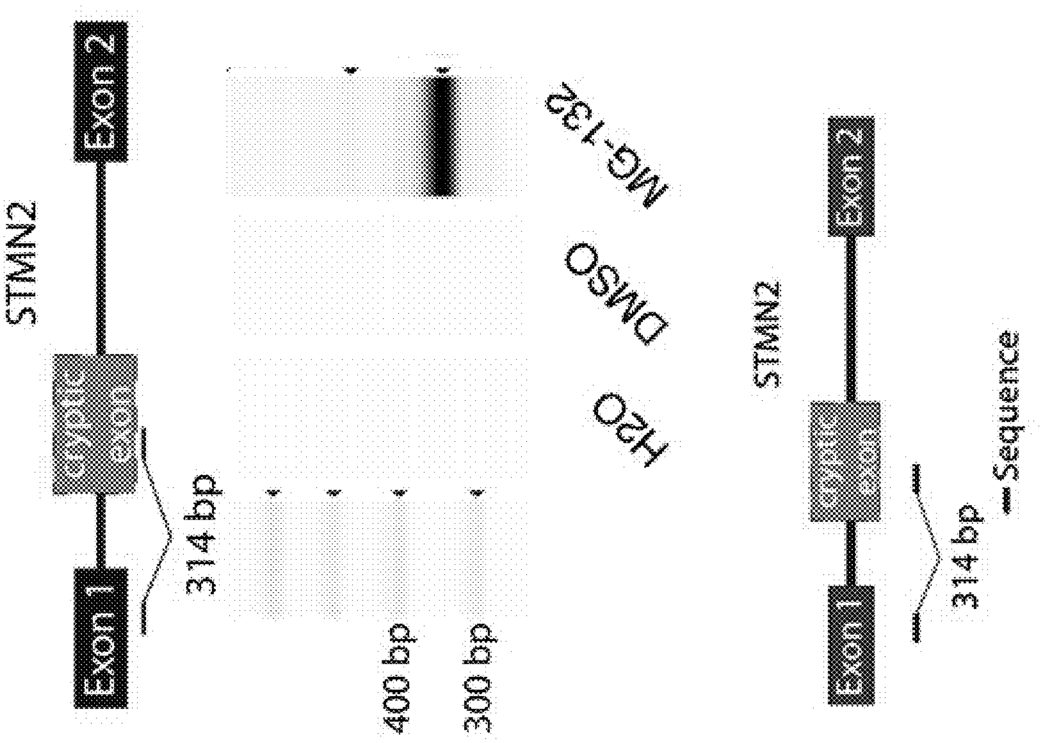
Figure 15E:
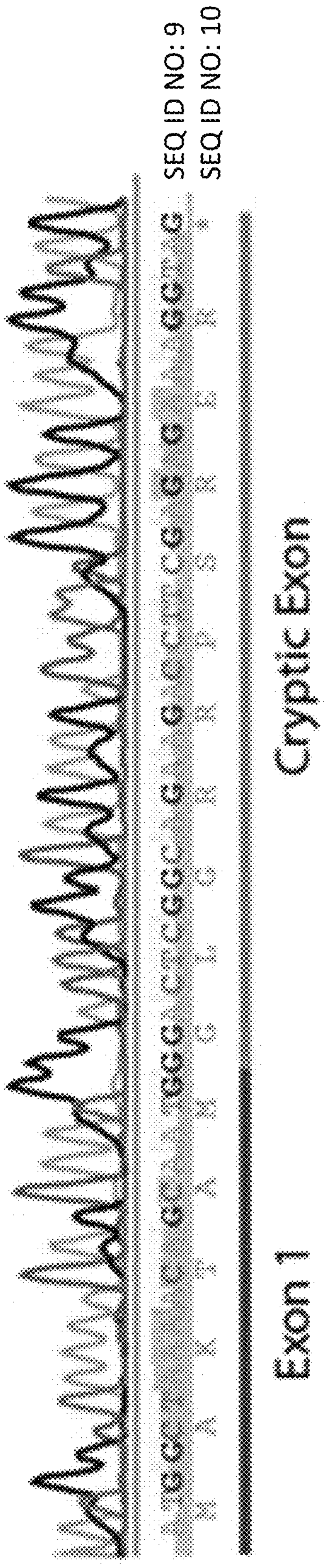

FIGS. 15A-15E demonstrate TDP-43 regulates cryptic exon splicing in hMNs (FIGS. 15A-15C). Visualization of the cryptic exons for PFKP (FIG. 15A), ELAVL3 (FIG. 15B), and STMN2 (FIG. 15C) for the cells treated with scrambled siRNAs or siRNAs targeting TDP-43 transcript. Read coverage and splice junctions are shown for alignment to the human HG19 genome. FIGS. 15D-15E provides diagram of RT-PCR detection strategy for STMN2 cryptic exon (FIG. 15D), and Sanger sequencing of the PCR product confirmed the splicing of STMN2 Exon 1 with the cryptic exon (FIG. 15E).

Figure 16A:
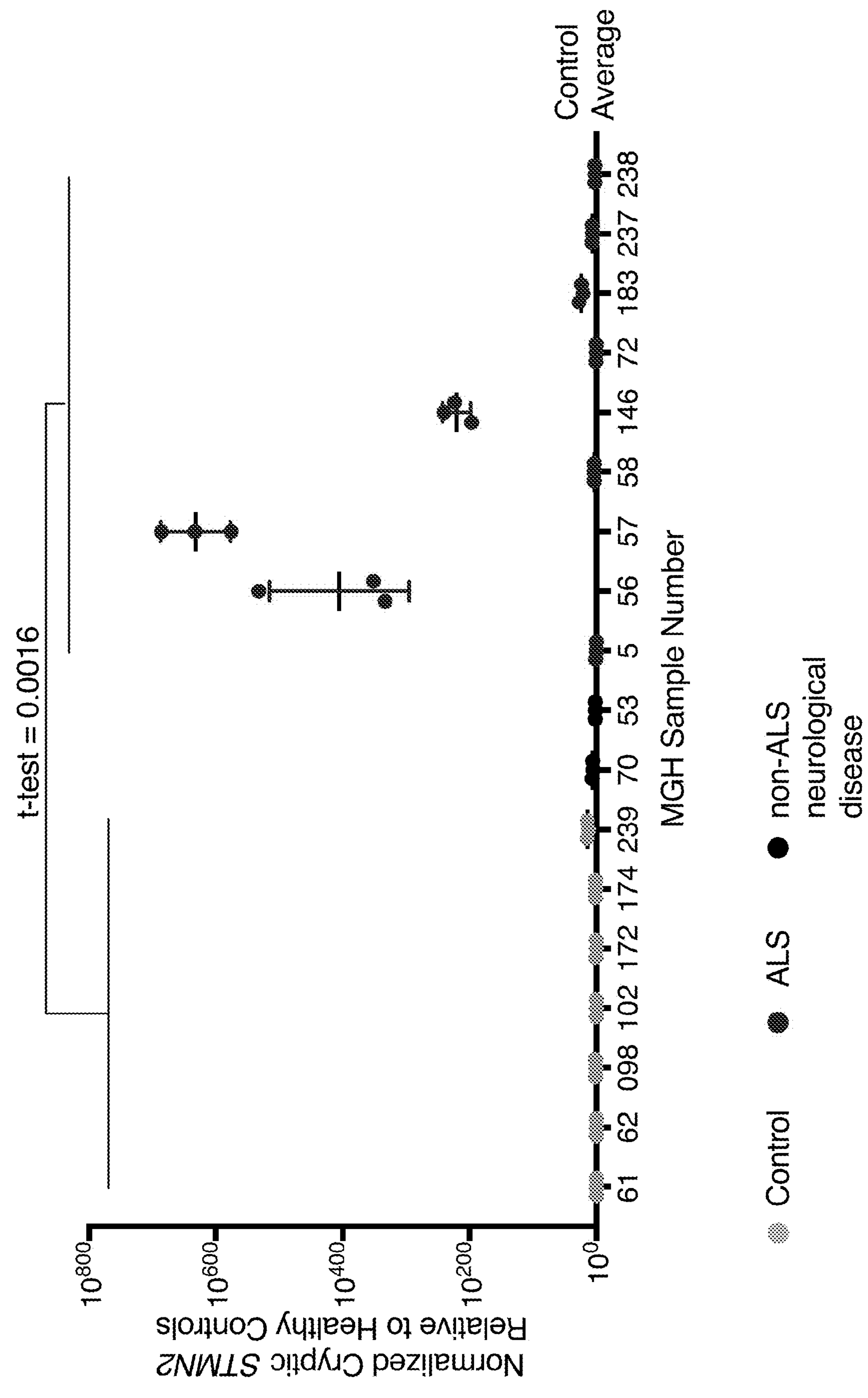
Figure 16B:
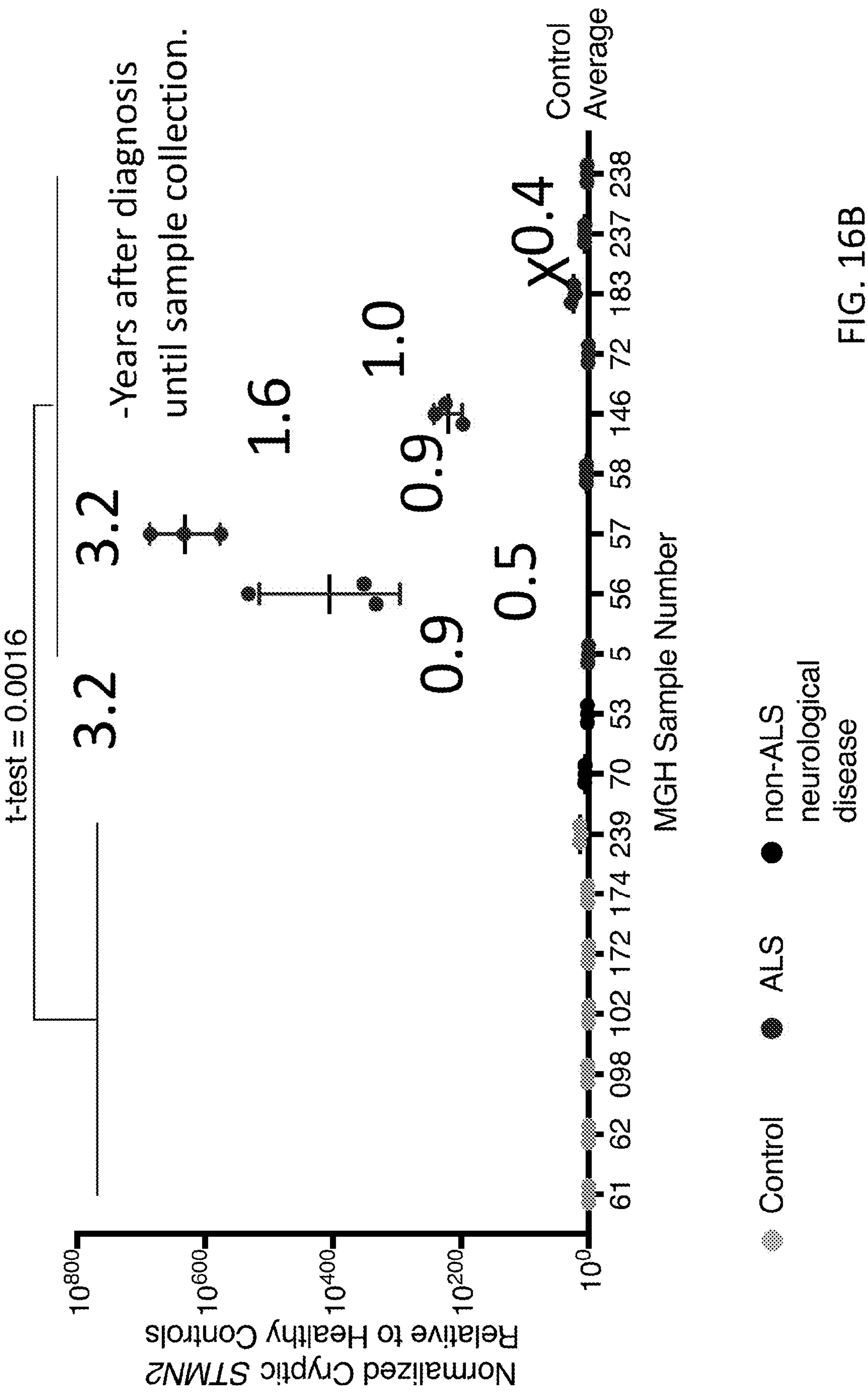
Figure 16C:
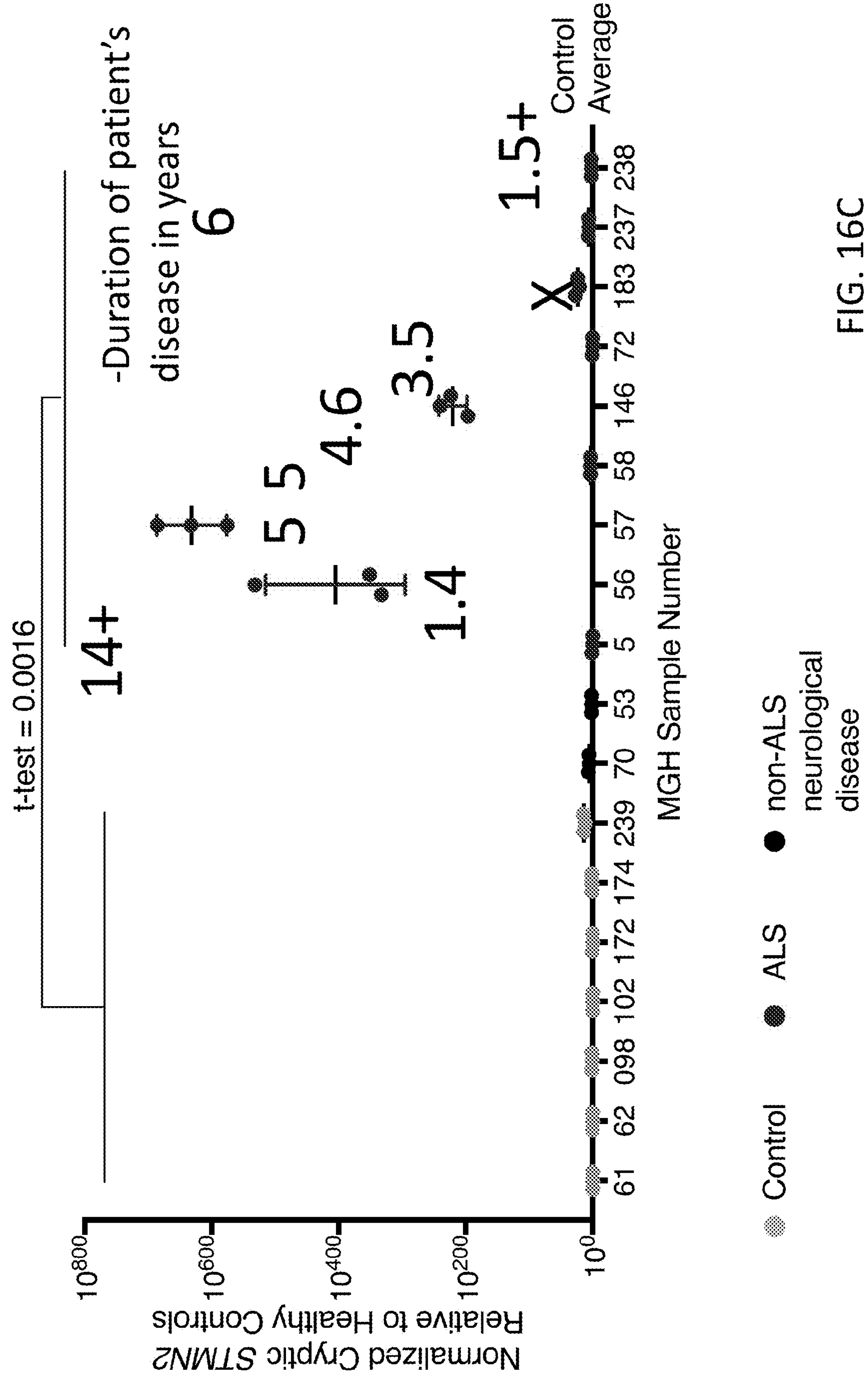
Figure 16D:
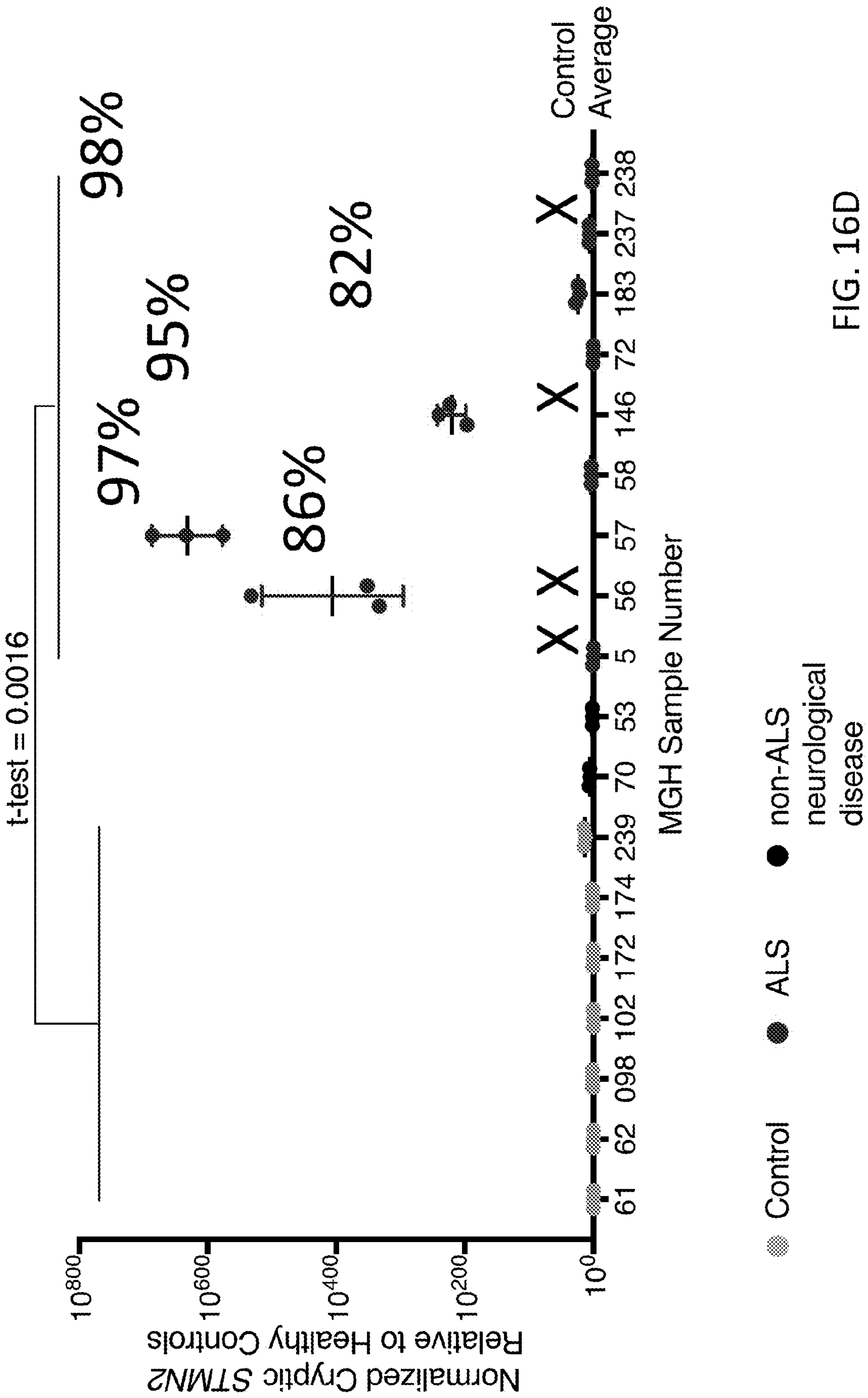
Figure 16E:
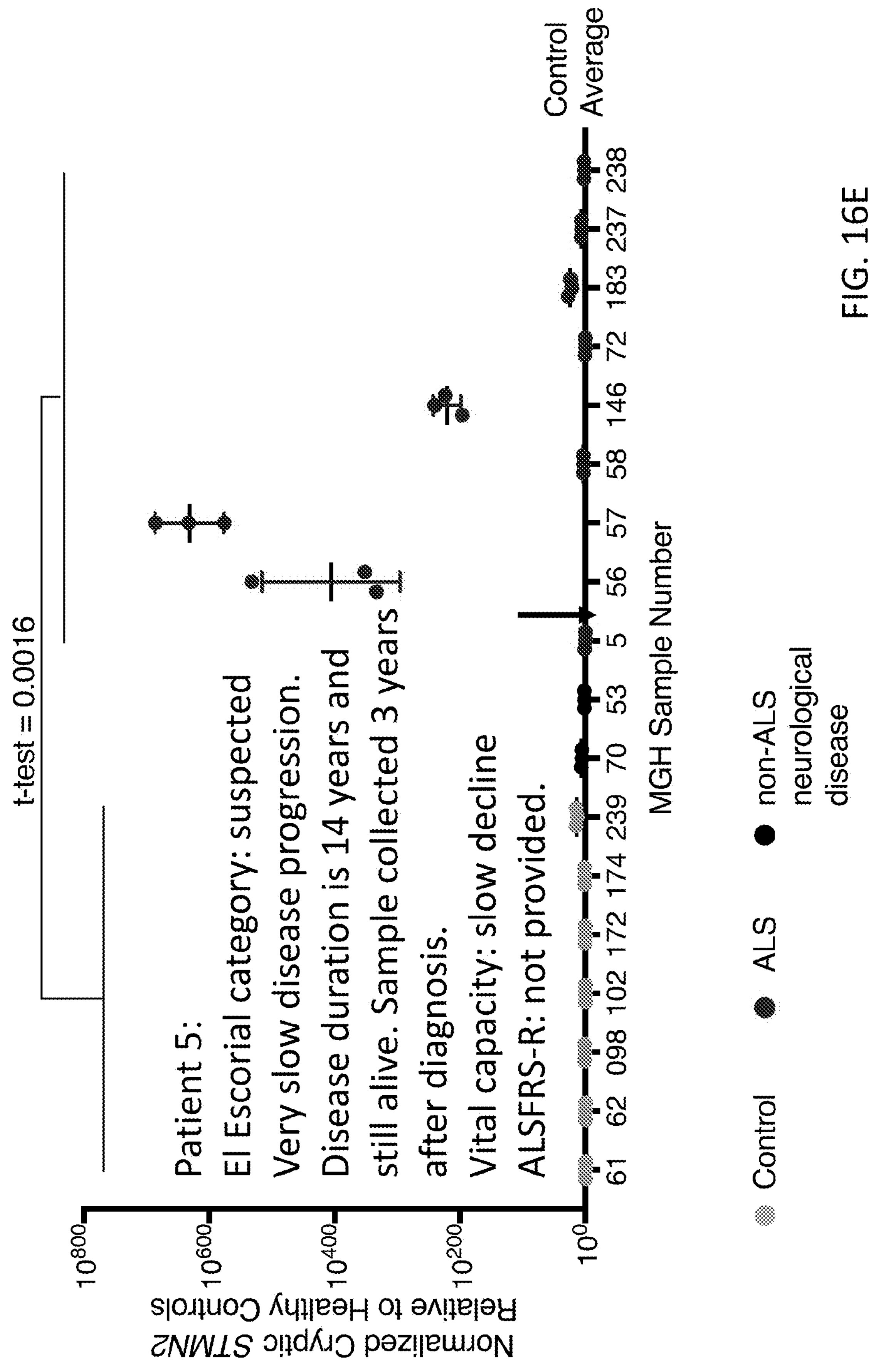
Figure 16F:
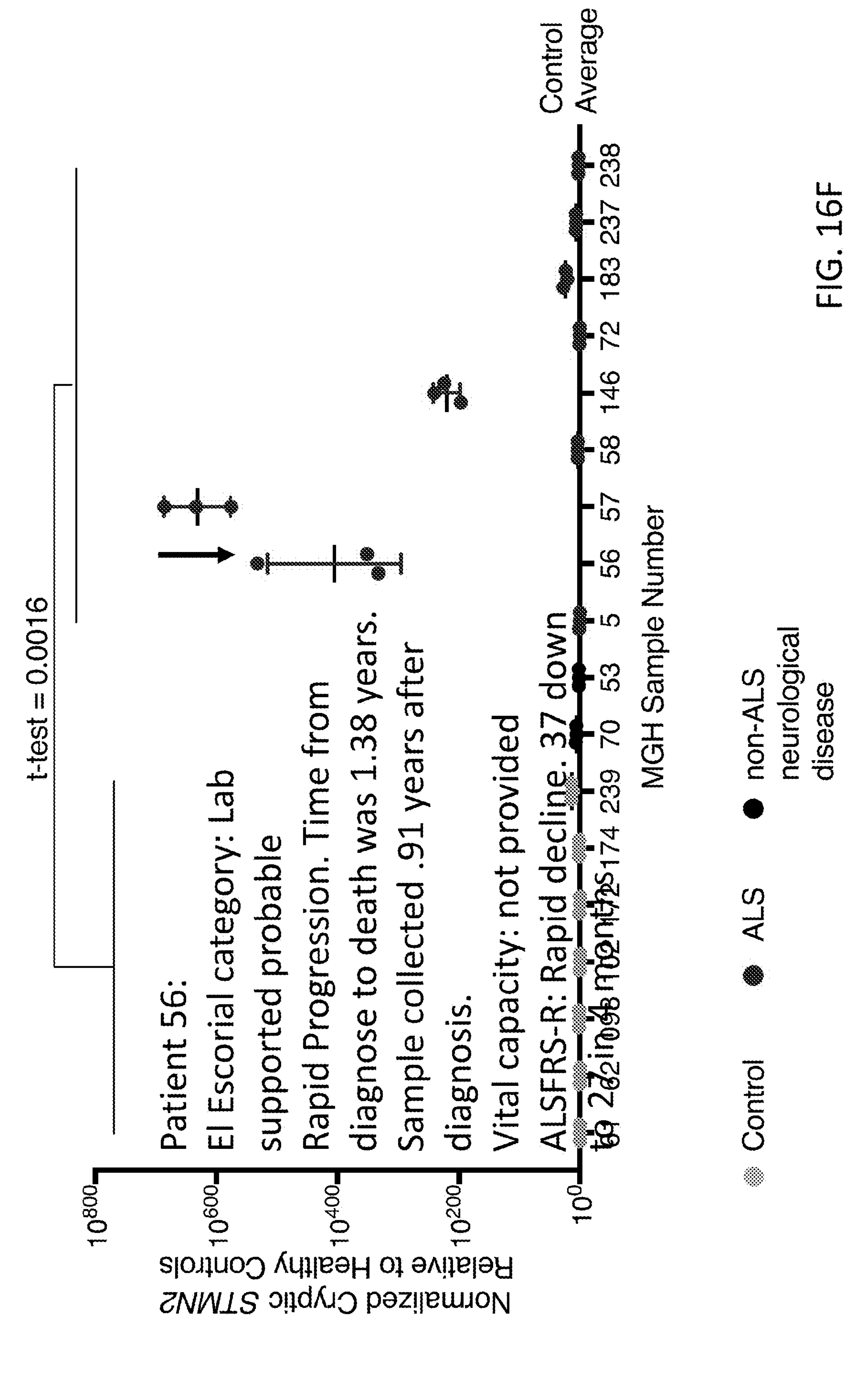
Figure 16G:
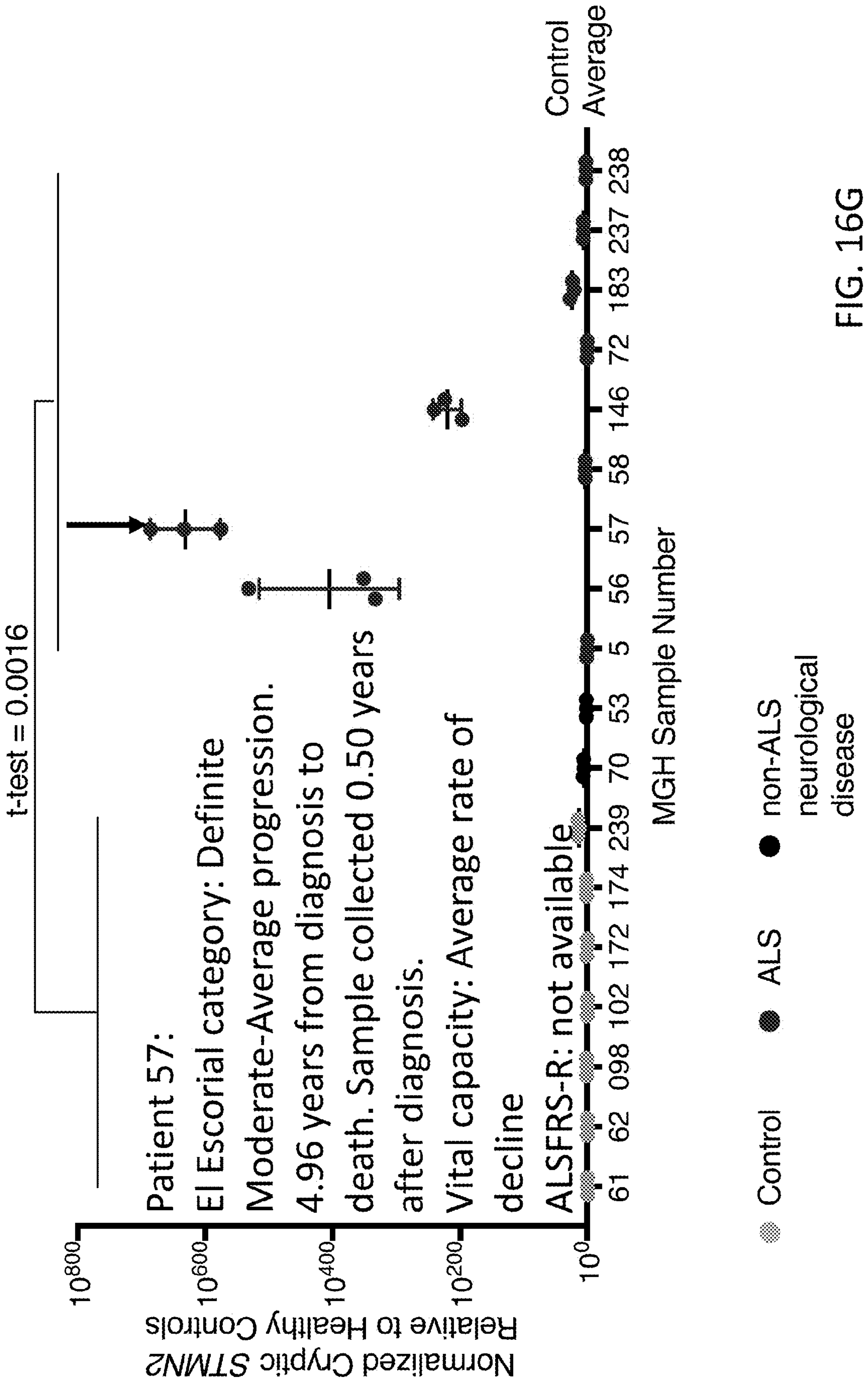
Figure 16H:
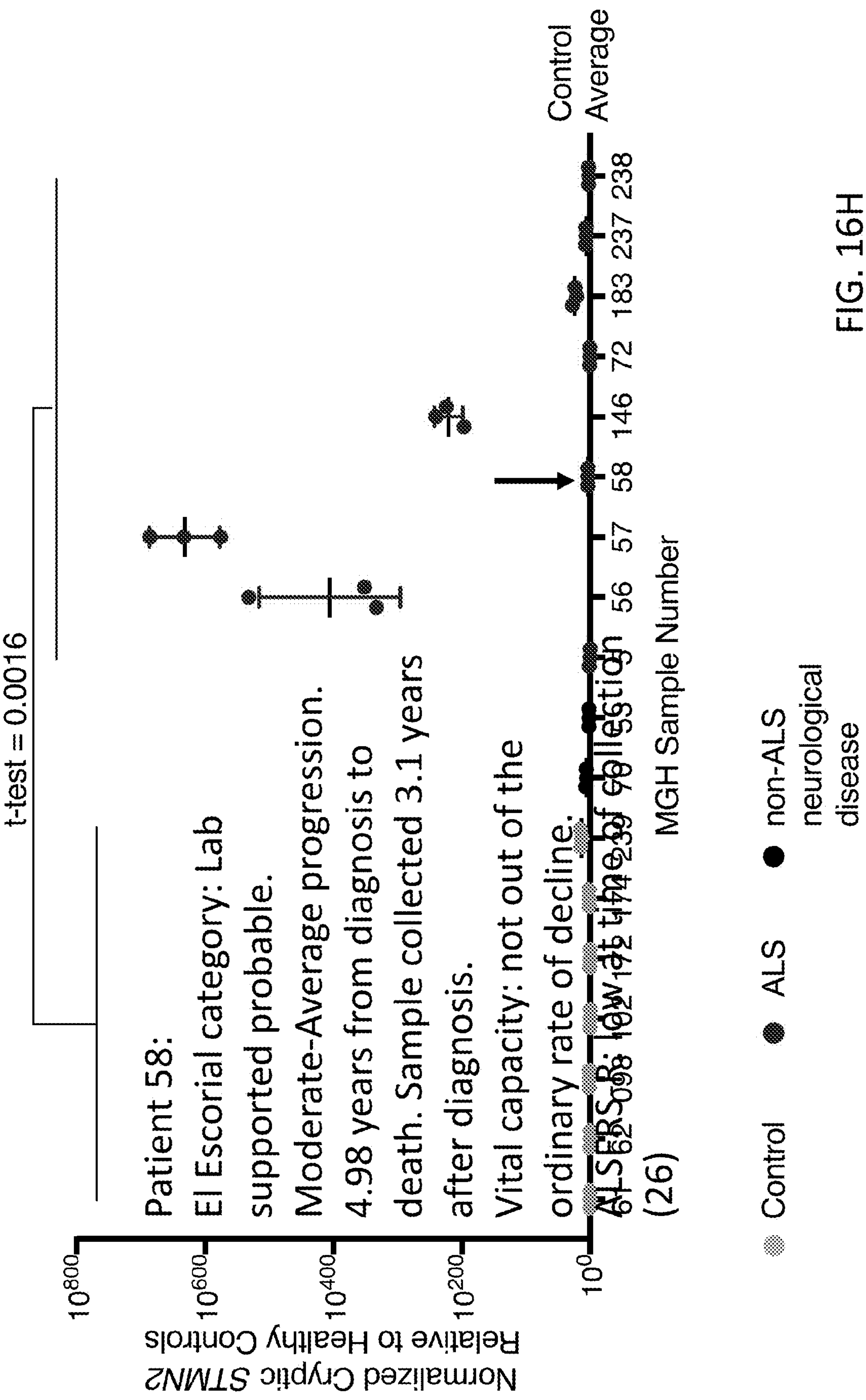
Figure 16I:
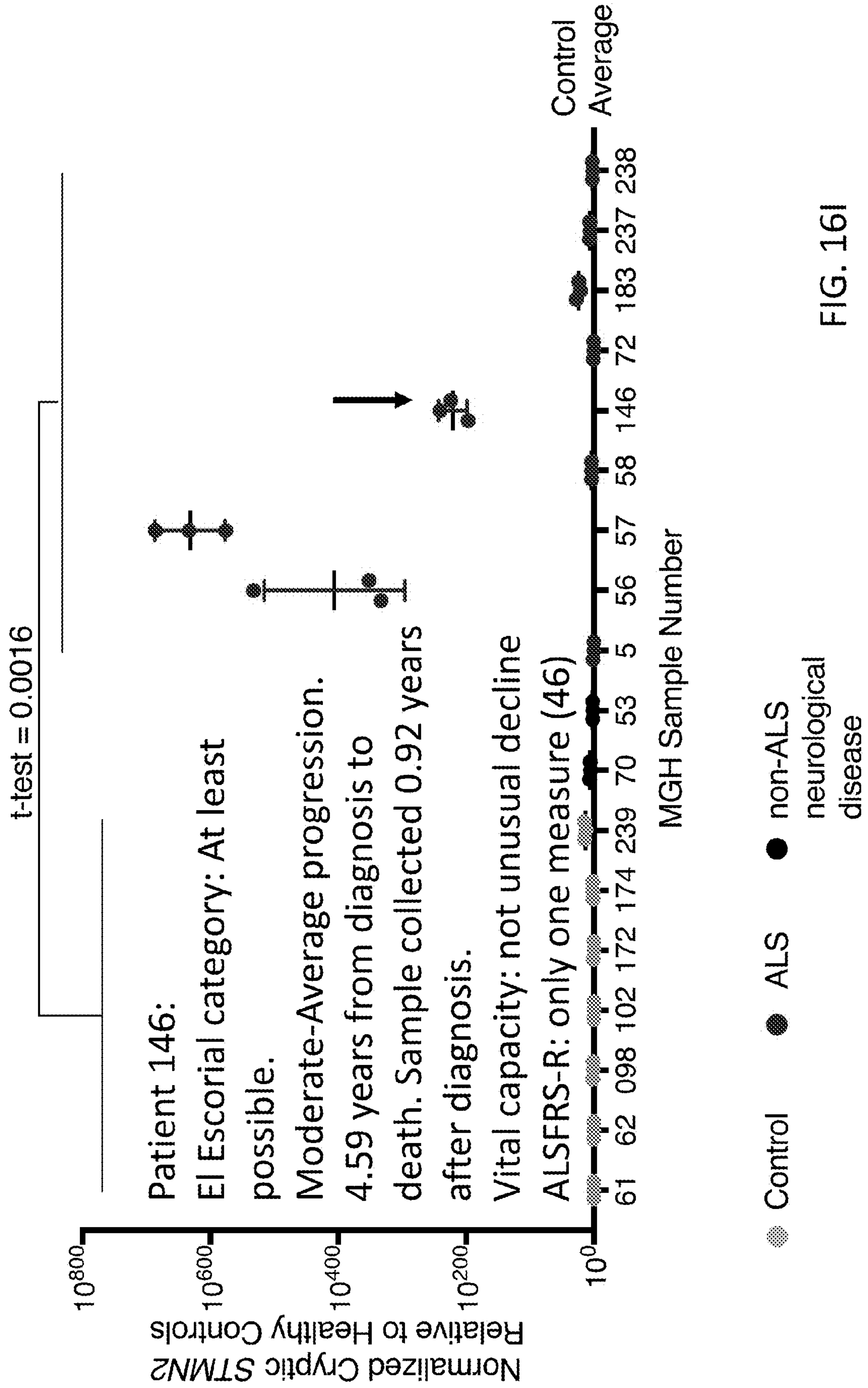
Figure 16J:
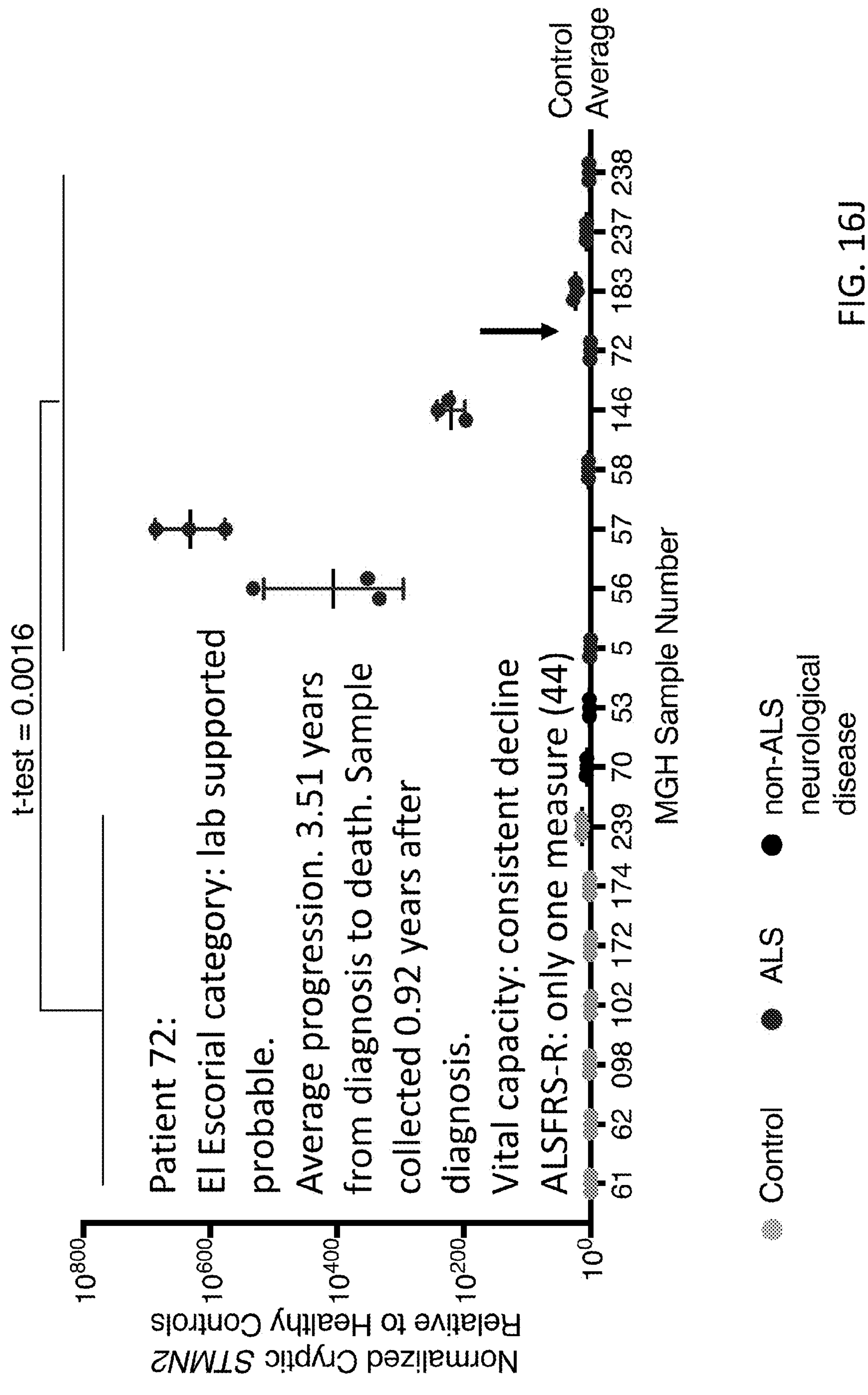
Figure 16K:
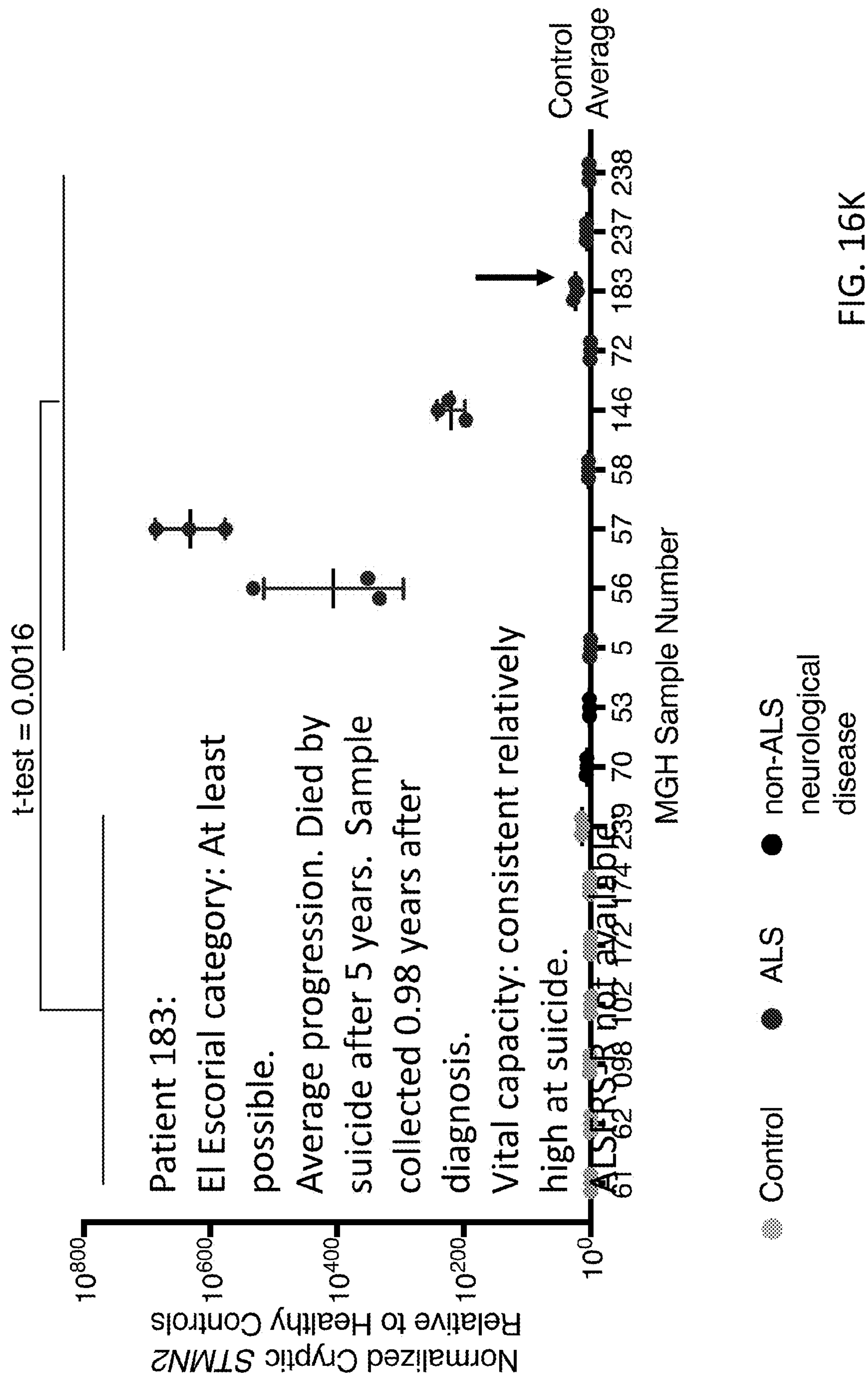
Figure 16L:
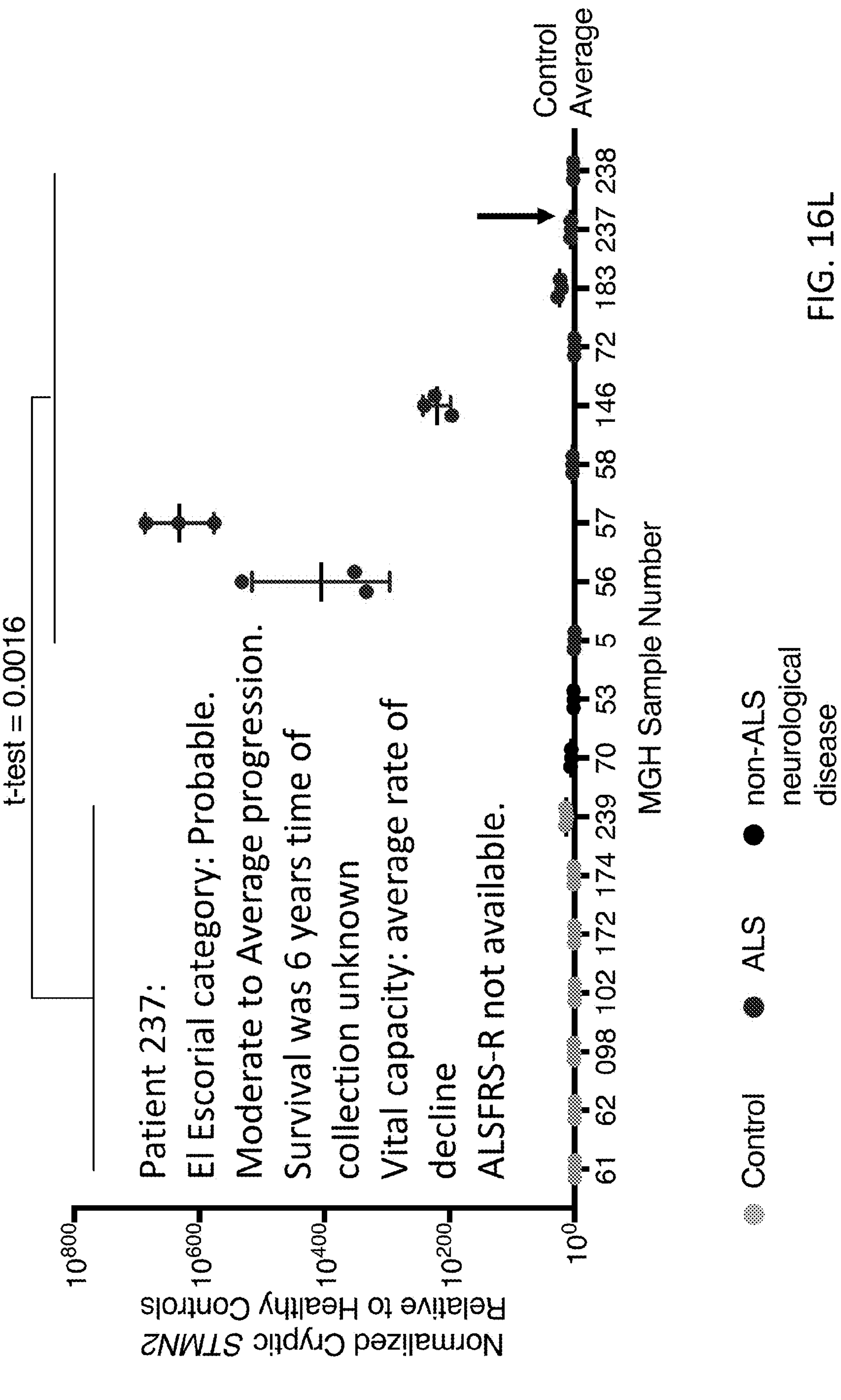
Figure 16M:
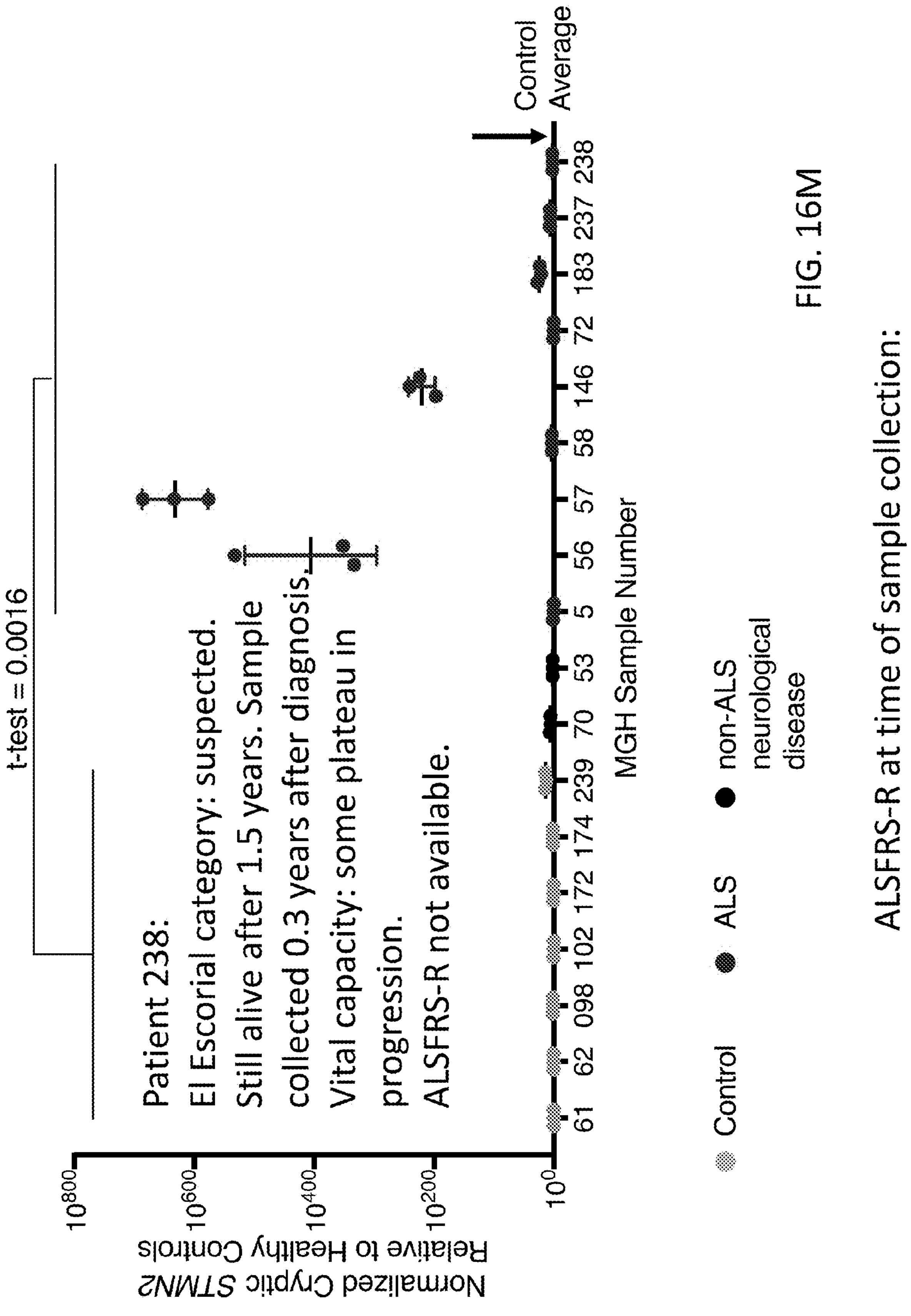
Figure 16N:
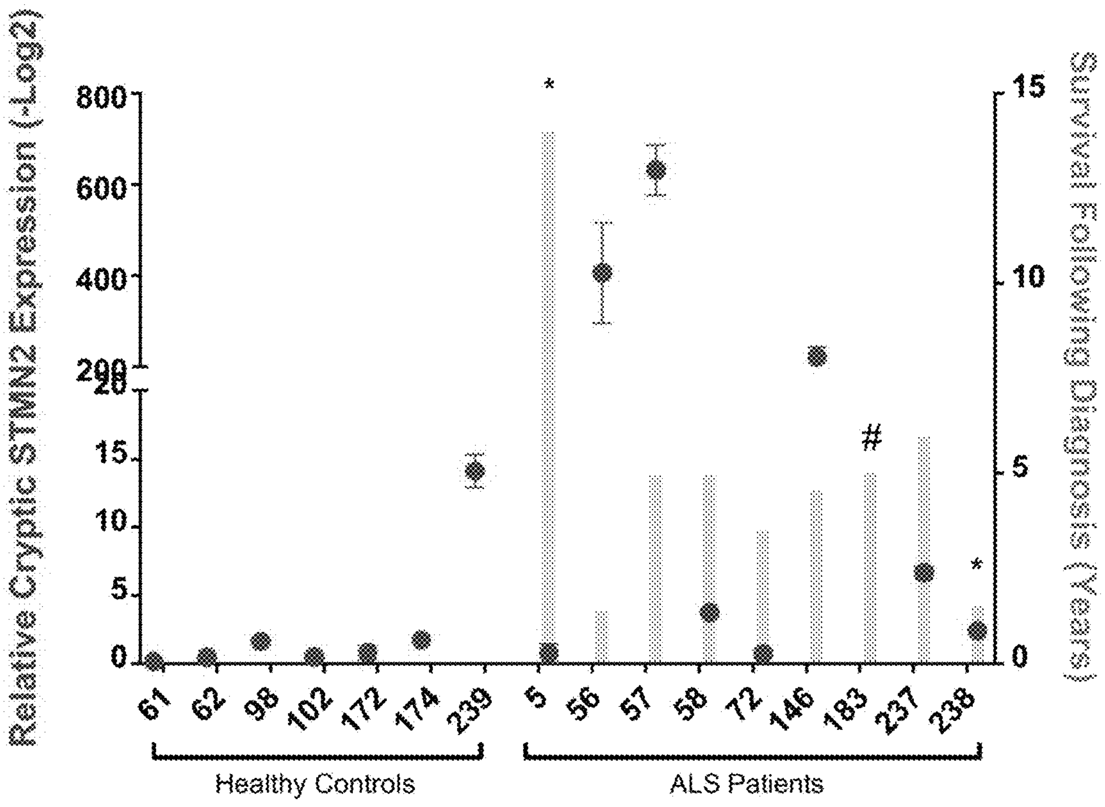
Figure 16O:
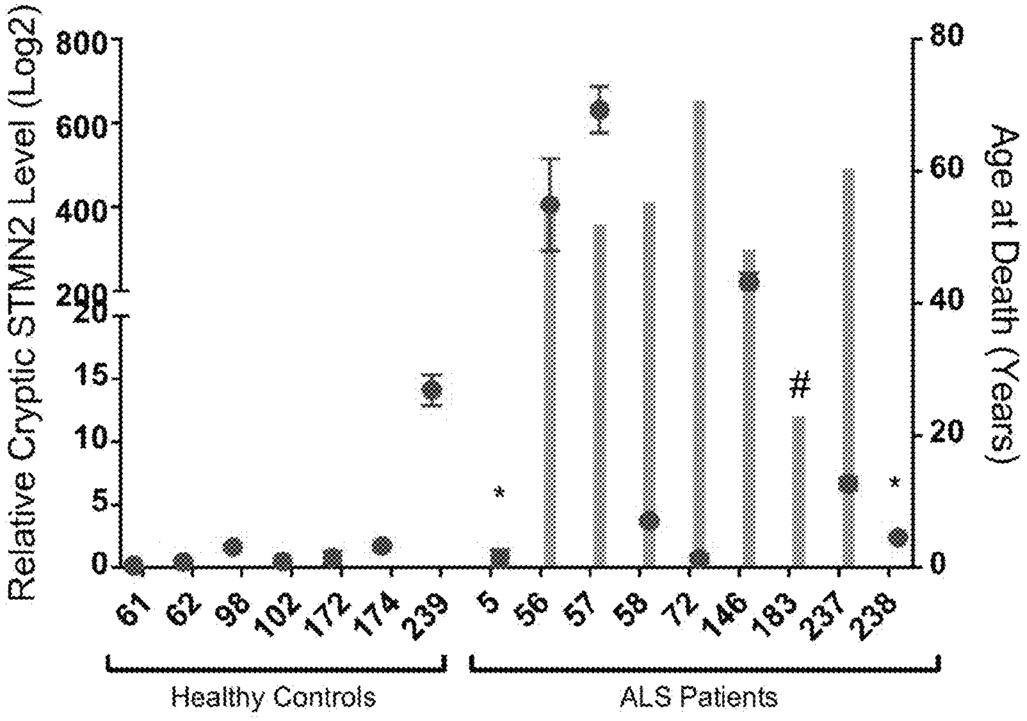
Figure 16P:
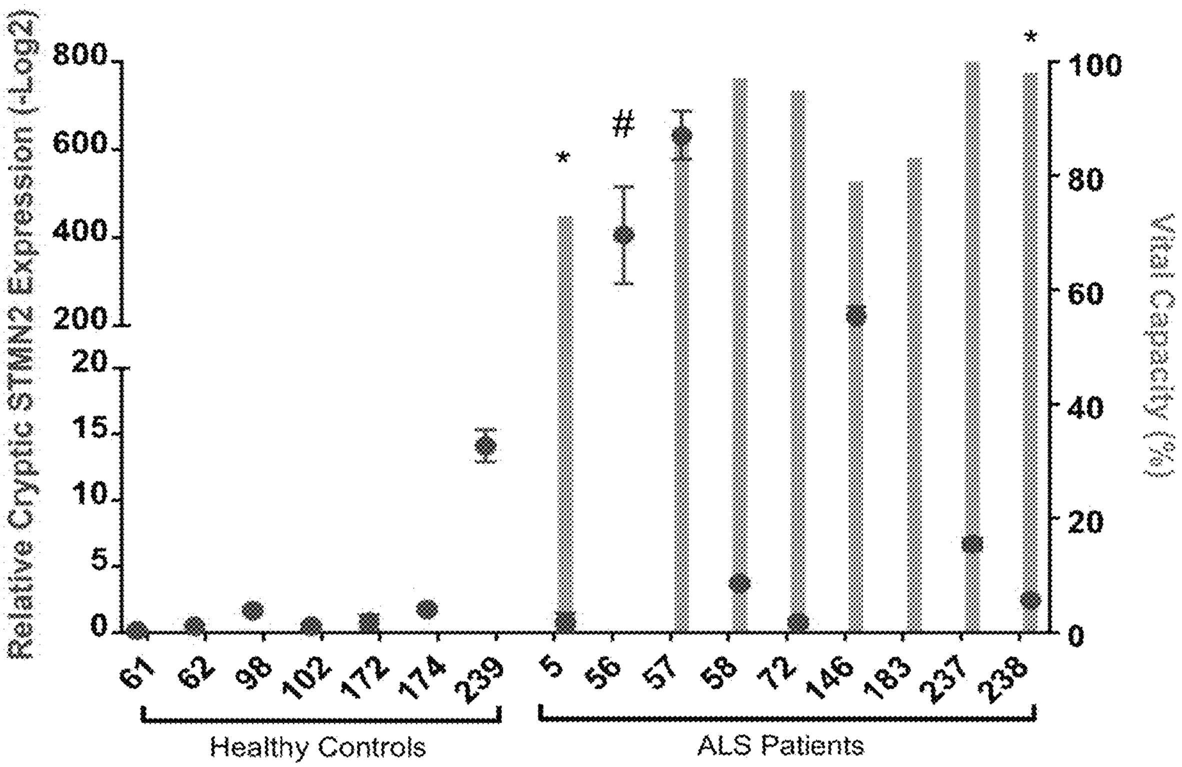

FIGS. 16A-16P provide cryptic STMN2 transcript qPCR data from patient cerebral spinal fluid (CSF) samples. FIGS. 16A-16D provide graphs summarizing the patient sample data of normalized cryptic STMN2 relative to healthy controls. FIGS. 16E-16M provide graphs providing details regarding individual patient samples. FIG. 16N provides a graph demonstrating survival duration following diagnosis. FIG. 16O provides a graph demonstrating age at death. FIG. 16P provides a graph demonstrating vital capacity.

Figure 17A:
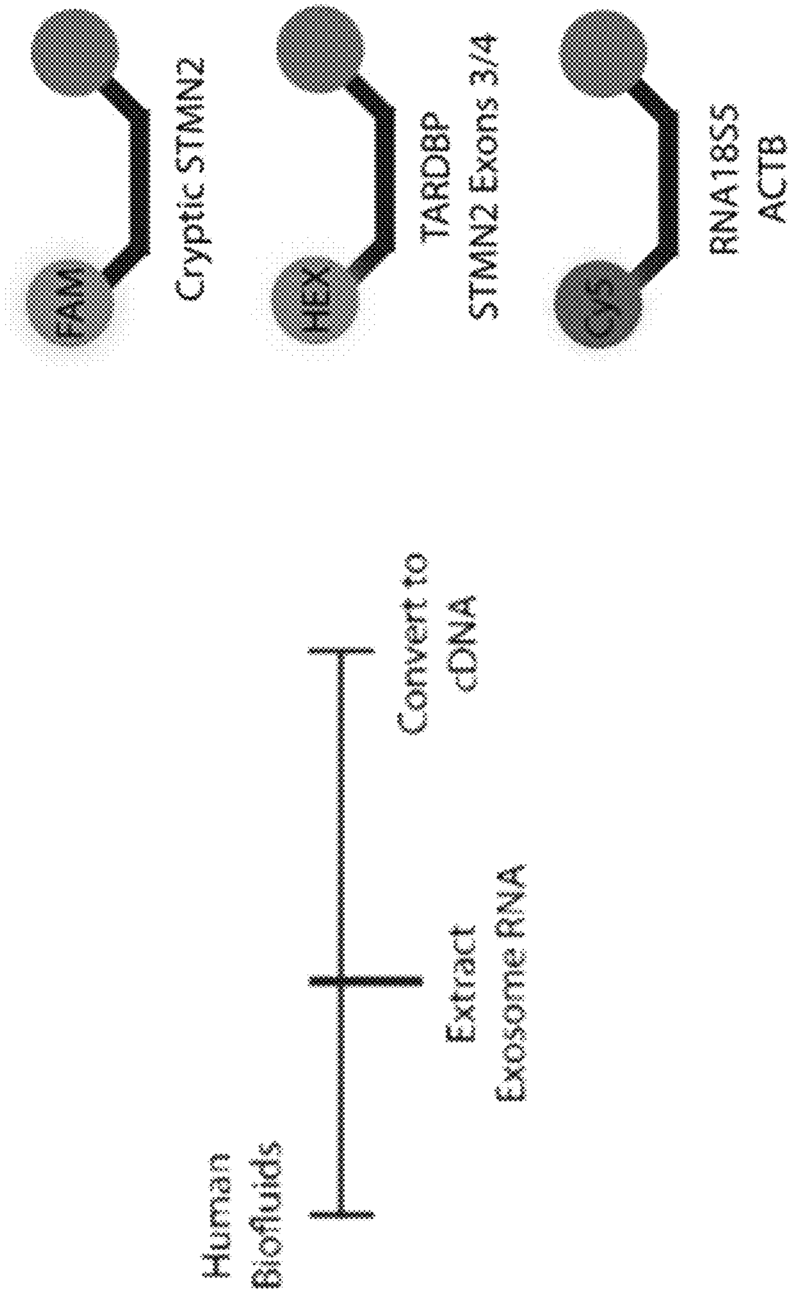
Figure 17B:
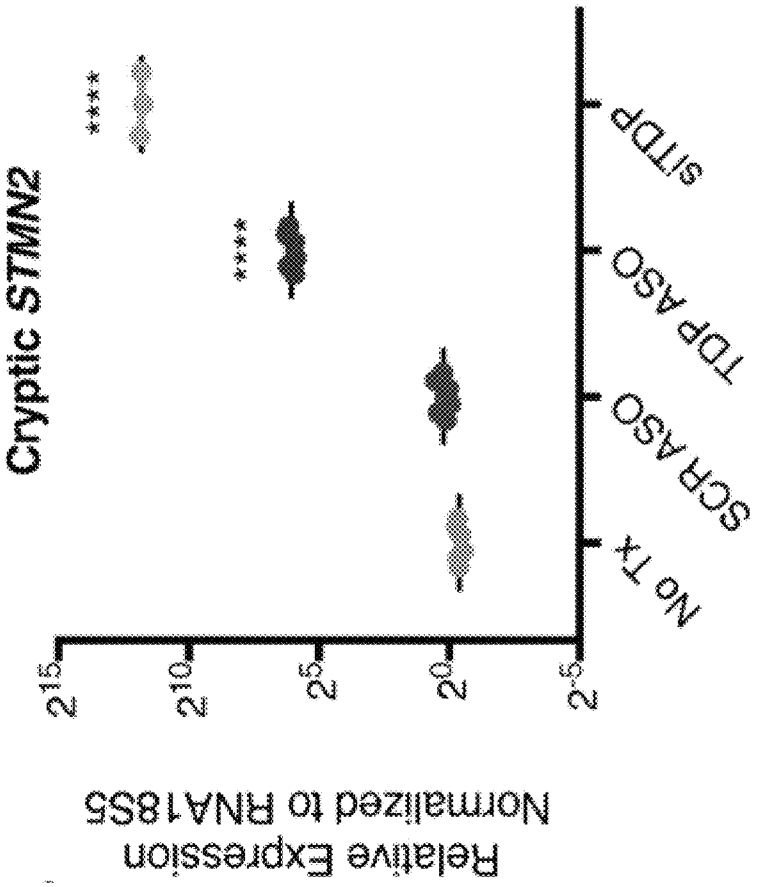
Figure 17C:
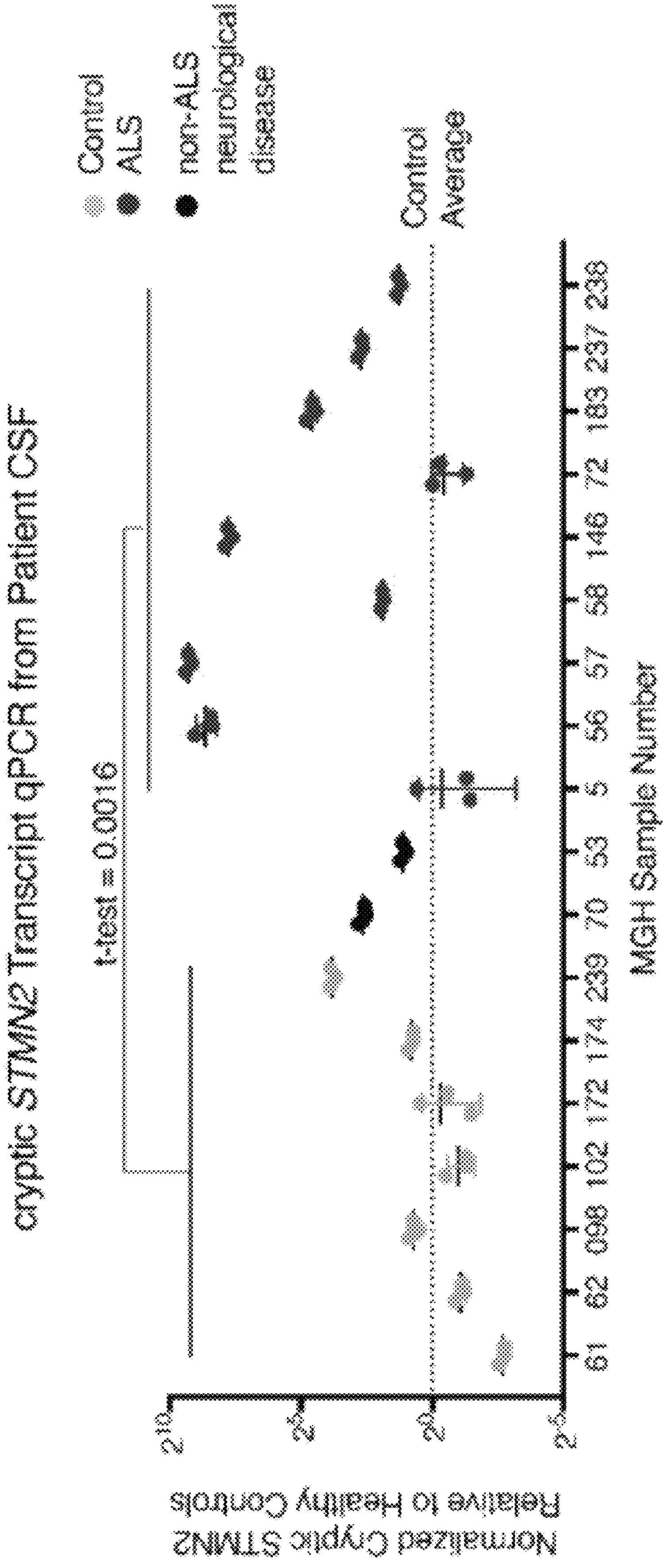

FIGS. 17A-17C demonstrate an STMN2 multiplexed qPCR Assay. FIG. 17A shows Q-RT PCT assay for STMN2 in fluids. Experimental schemes are provided and STMN2 multiplexed TaqMan assay is shown to simultaneously detect cryptic STMN2, normal STMN2 transcript, and the housekeeping gene RNA18S5. RNA can be collected from CSF-derived exosomes and then converted into cDNA to assay for full and cryptic STMN2 transcripts, as well as control RNAs for normalization. FIG. 17B shows in vitro validation of the multiplexed assay in cells where TDP-43 levels were reduced using either an ASO or using siRNA. FIG. 17C shows the STMN2 multiplexed qPCR assay was used to probe cryptic STMN2 transcript levels in the cDNA samples generated from the MGH CSF samples. STMN2 cryptic splicing is significantly induced in ALS patients.

Figure 18A:
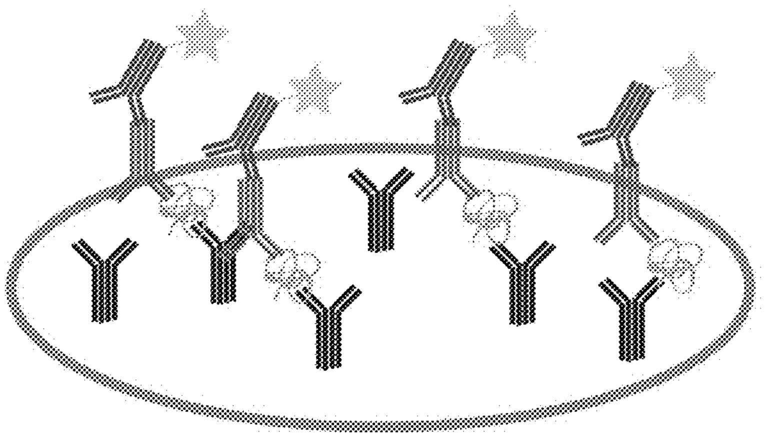
Figure 18B:
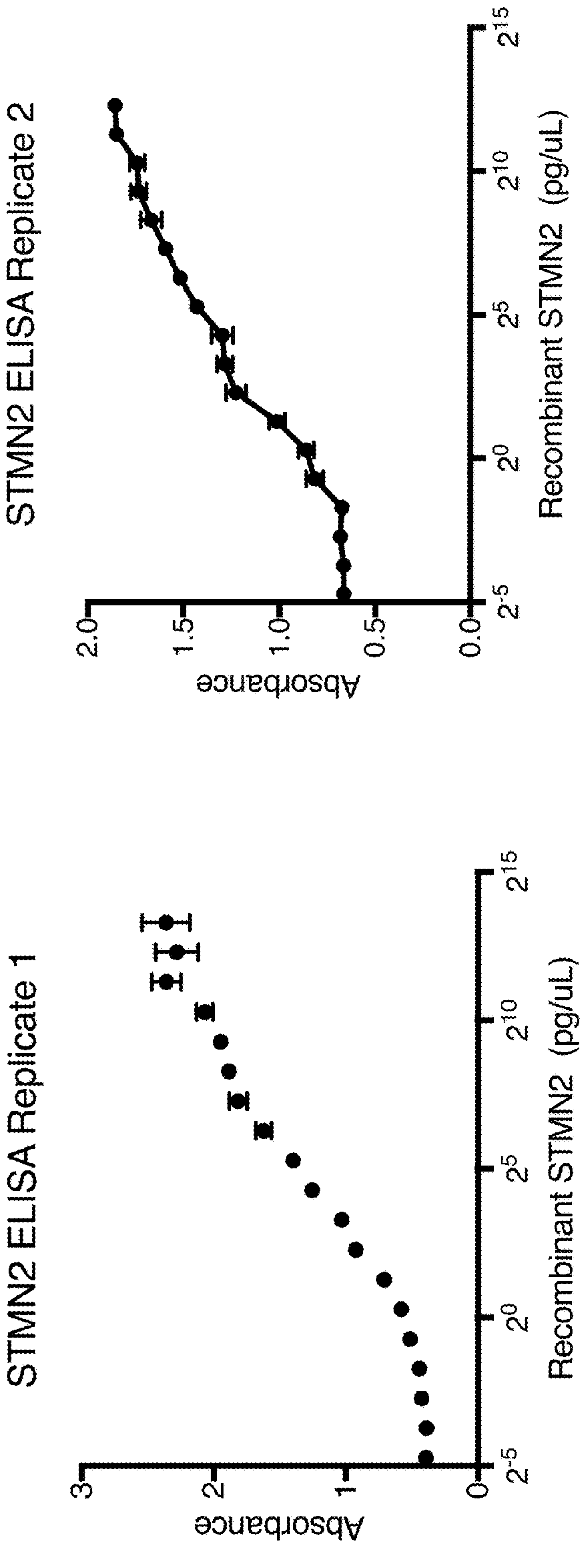
Figure 18C:
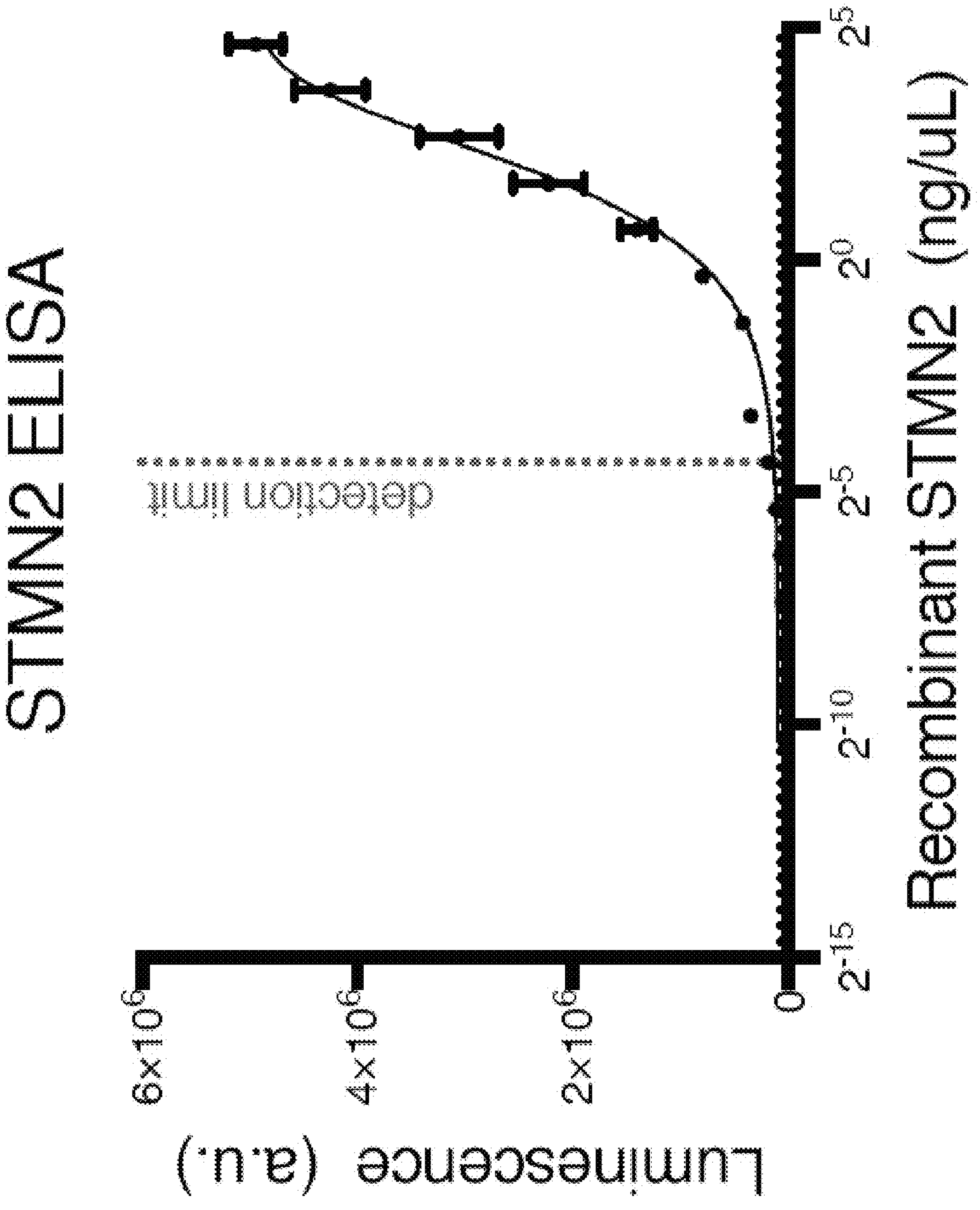
Figure 18D:
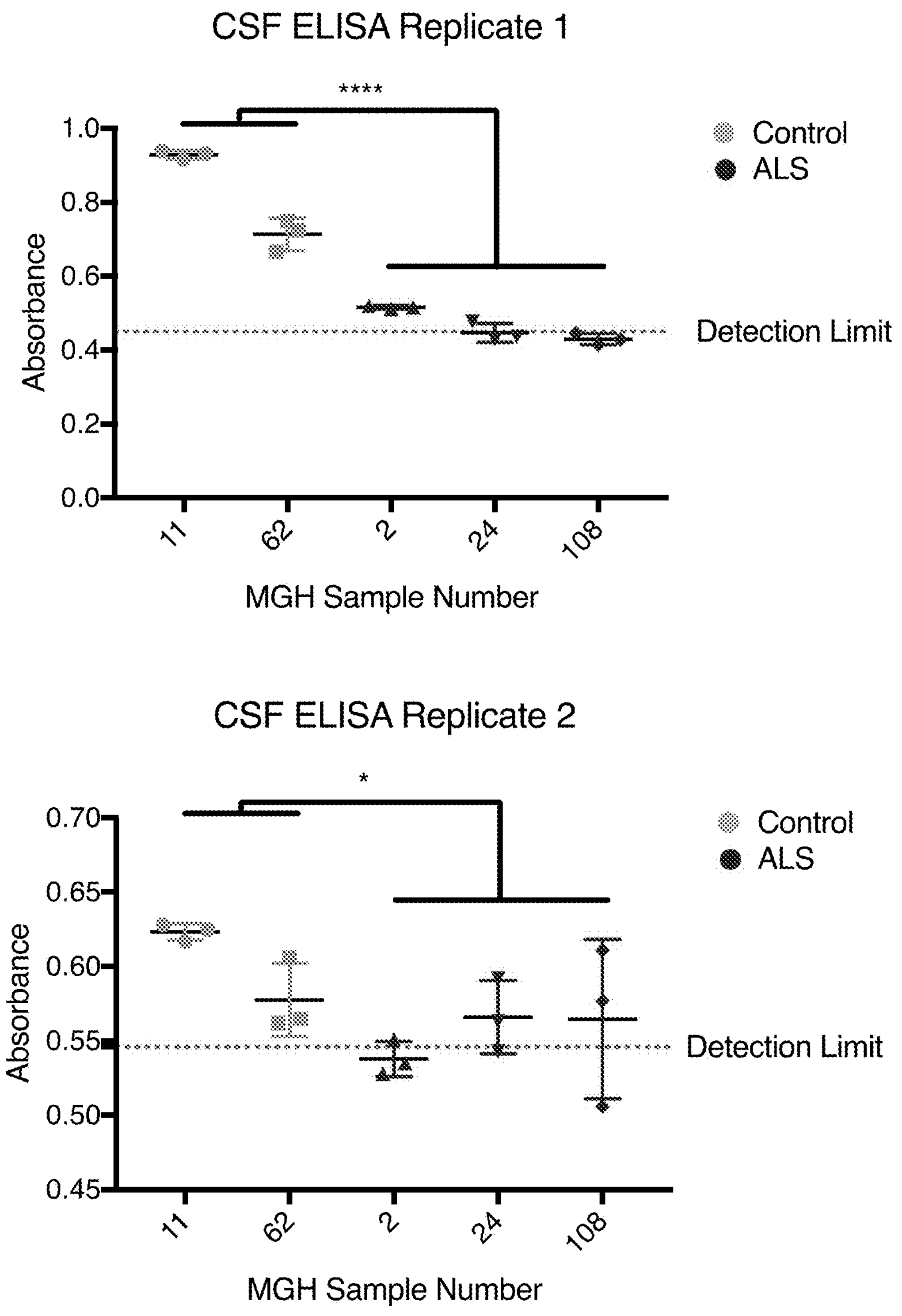

FIGS. 18A-18D demonstrate a sandwich ELISA for detecting STMN2 protein. FIG. 18A provides a schematic of the STMN2 sandwich ELISA. FIG. 18B demonstrates the sensitivity of the STMN2 ELISA to picogram quantities. FIG. 18C shows the sandwich ELISA was validated using recombinant STMN2 protein and is capable of detecting picogram levels of STMN2. FIG. 18D shows STMN2 levels are reduced in patient cerebral spinal fluid (CSF) when assessed using the STMN2 ELISA.

Figure 19:
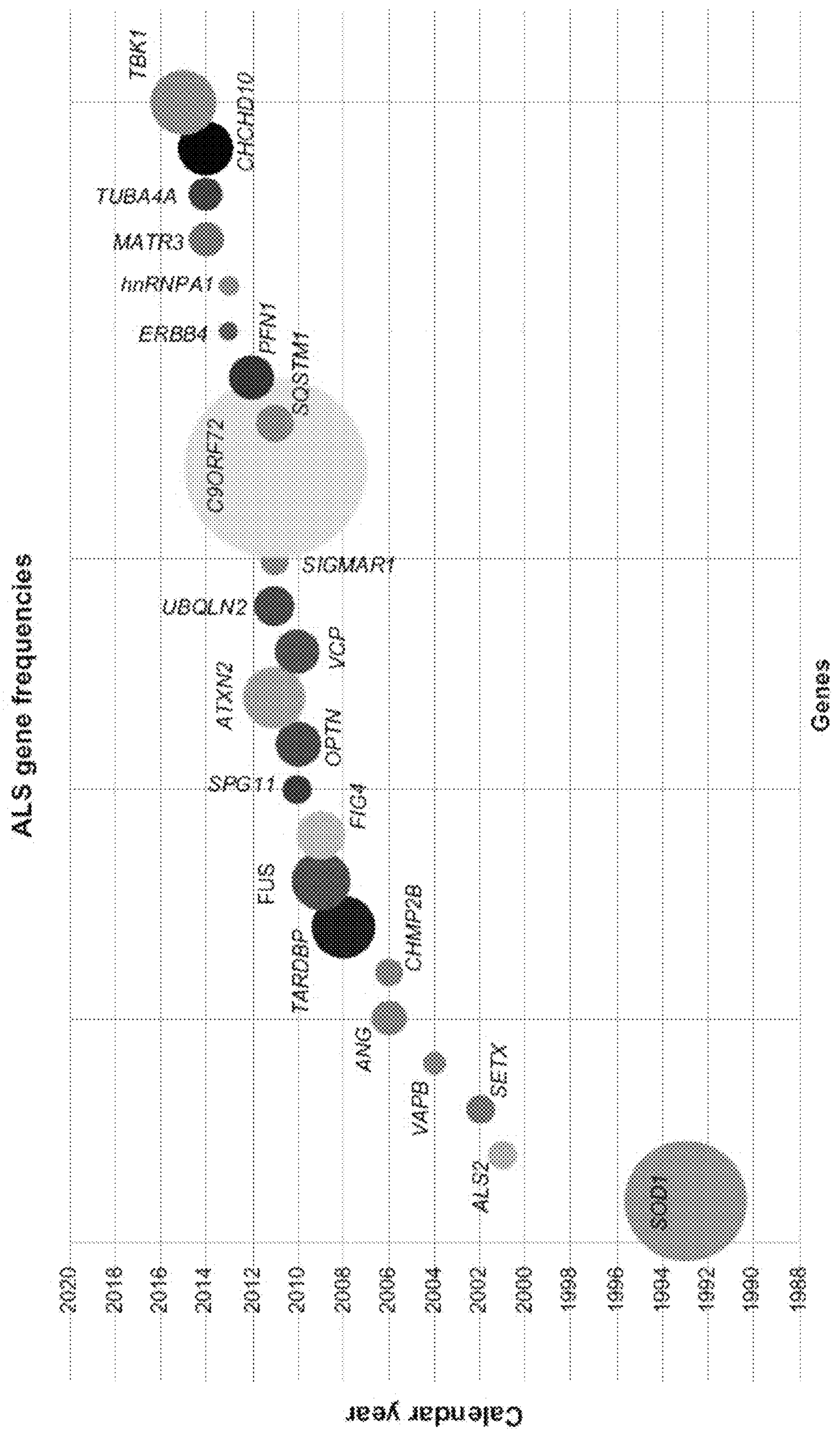

FIG. 19 provides a chart demonstrating the genetics of ALS, with each gene being plotted against the year it was discovered. See Alsultan et al. Degenerative Neurological and Neuromuscular Disease. 2016, 6, 49-64.

Figure 20:
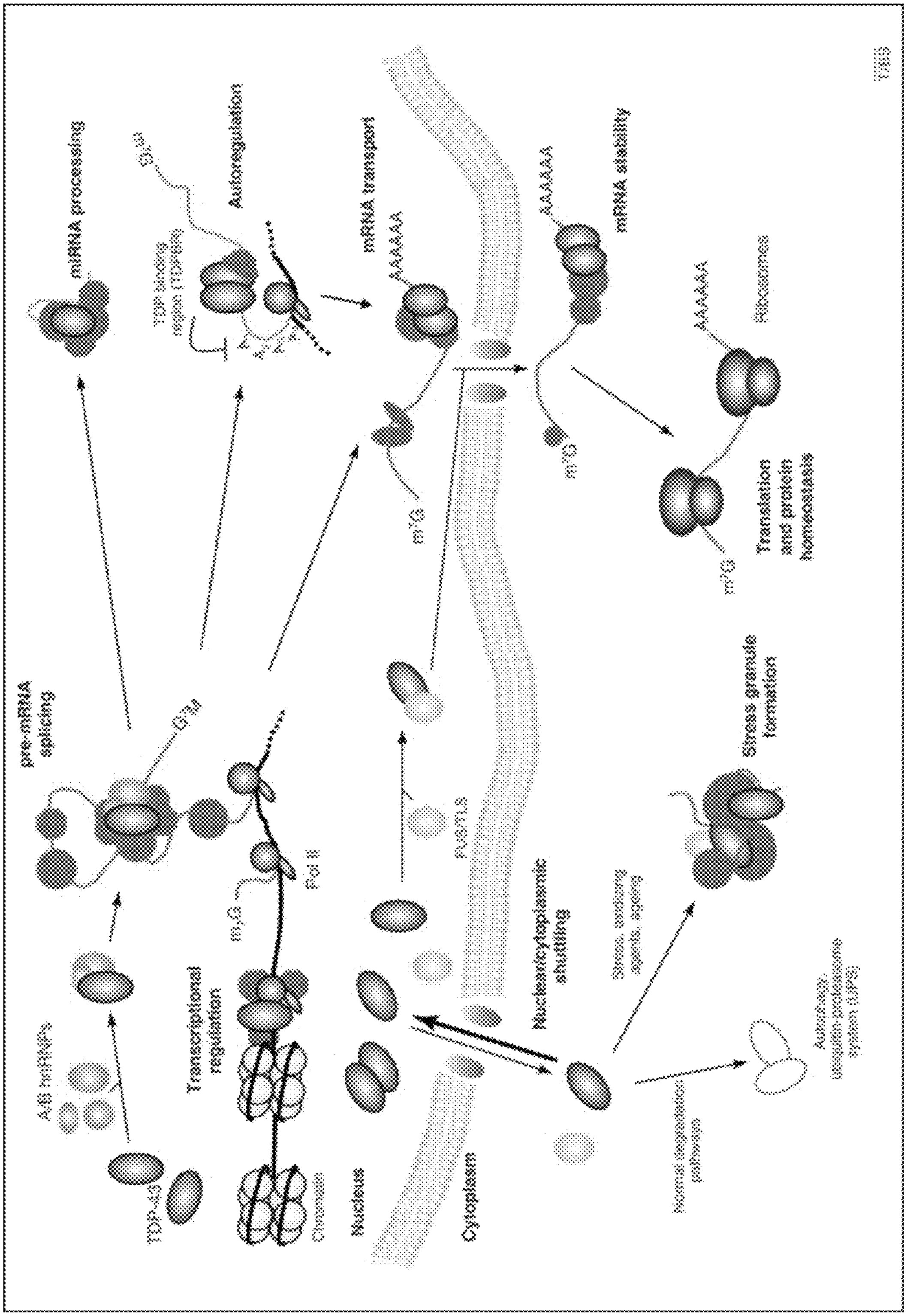

FIG. 20 demonstrates that TDP-43 is a multifunctional nucleic acid-binding protein. TDP-43 has been shown to play a role in various functions including RNA splicing, miRNA processing, autoregulation of its own transcript, RNA transport and stability, and stress granule formation. The transcripts TDP-43 regulates are highly species and cell type dependent. See Buratti and Baralle *Trends in Biochem. Sci.* 2012, 6, 237-247.

Figure 21:
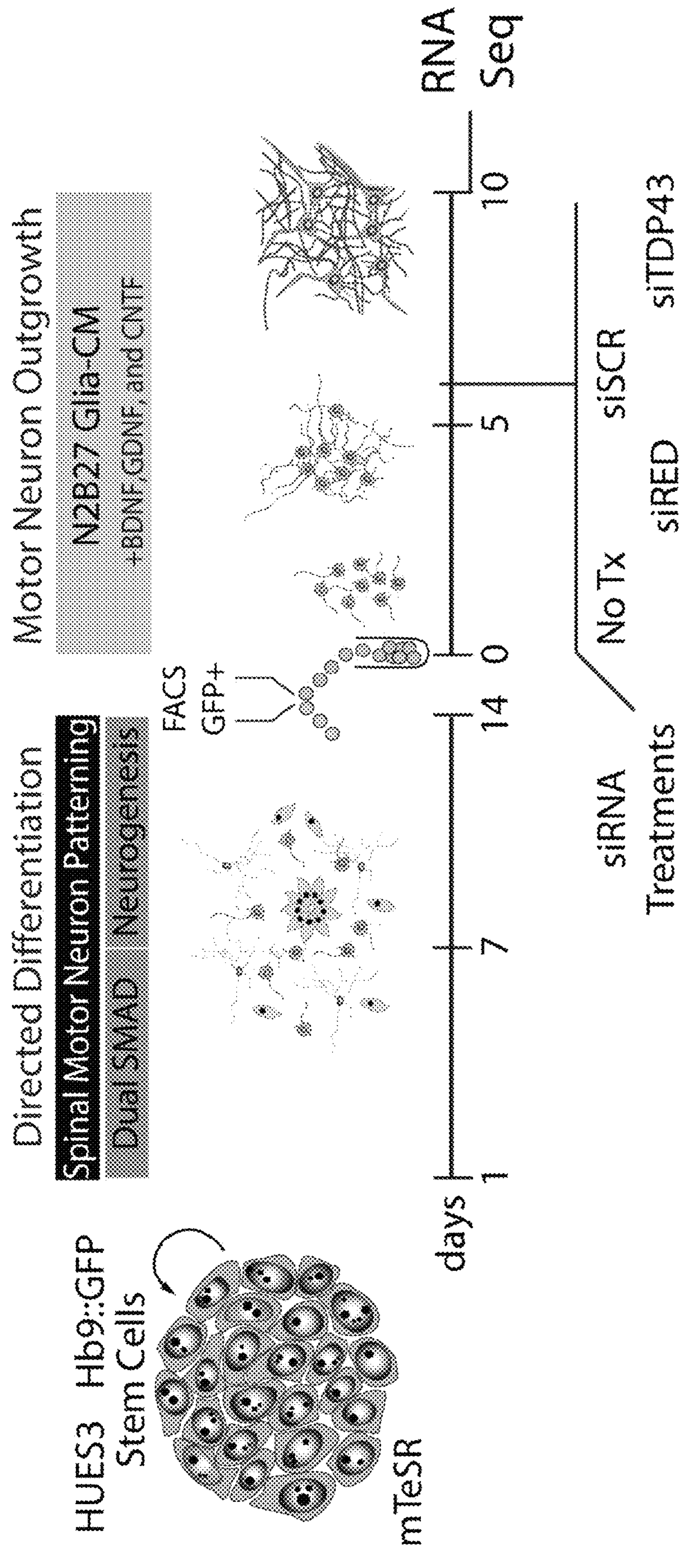

FIG. 21 provides a strategy for measuring transcriptional effects of TDP-43 depletion. The schematic demonstrates hMN differentiation, purification, and culture strategy. The strategy uses small molecules that mimic early development to convert stem cells into postmitotic neurons in 2 weeks. Various methods were developed to sort and study the neurons. siRNA technology combined with RNA sequencing was used to identify transcripts regulated by TDP-43.

Figure 22:
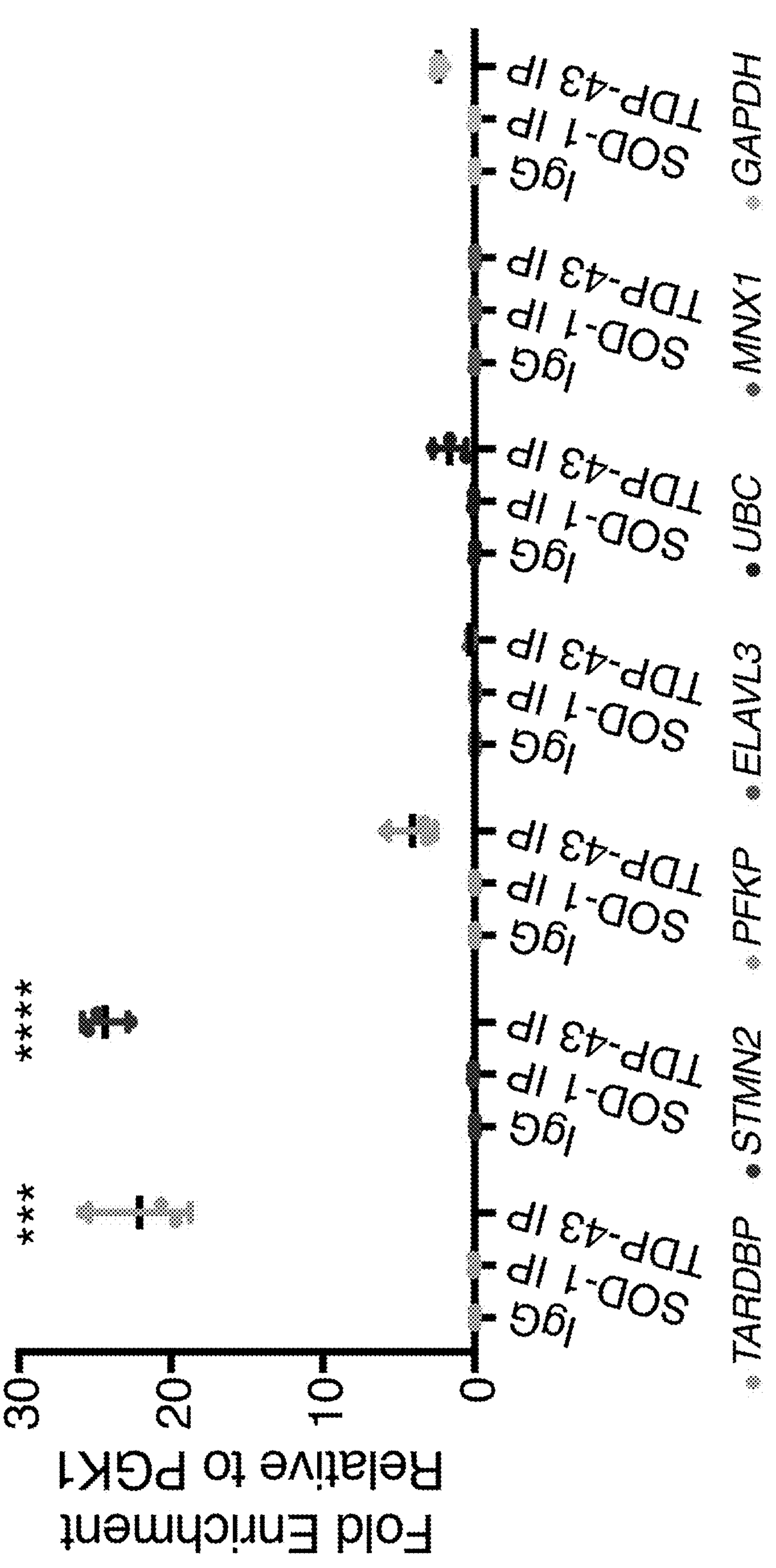

FIG. 22 demonstrates TDP-43 binds to STMN2. ALS patient spinal cords were stained for STMN2 and decreased STMN2 protein in ALS patients was observed based on fold enrichment relative to PGK1 (fRIP). See Klim et al. *Nature Neuroscience* vol. 22, pages 167-179 (2019).

Figure 23:
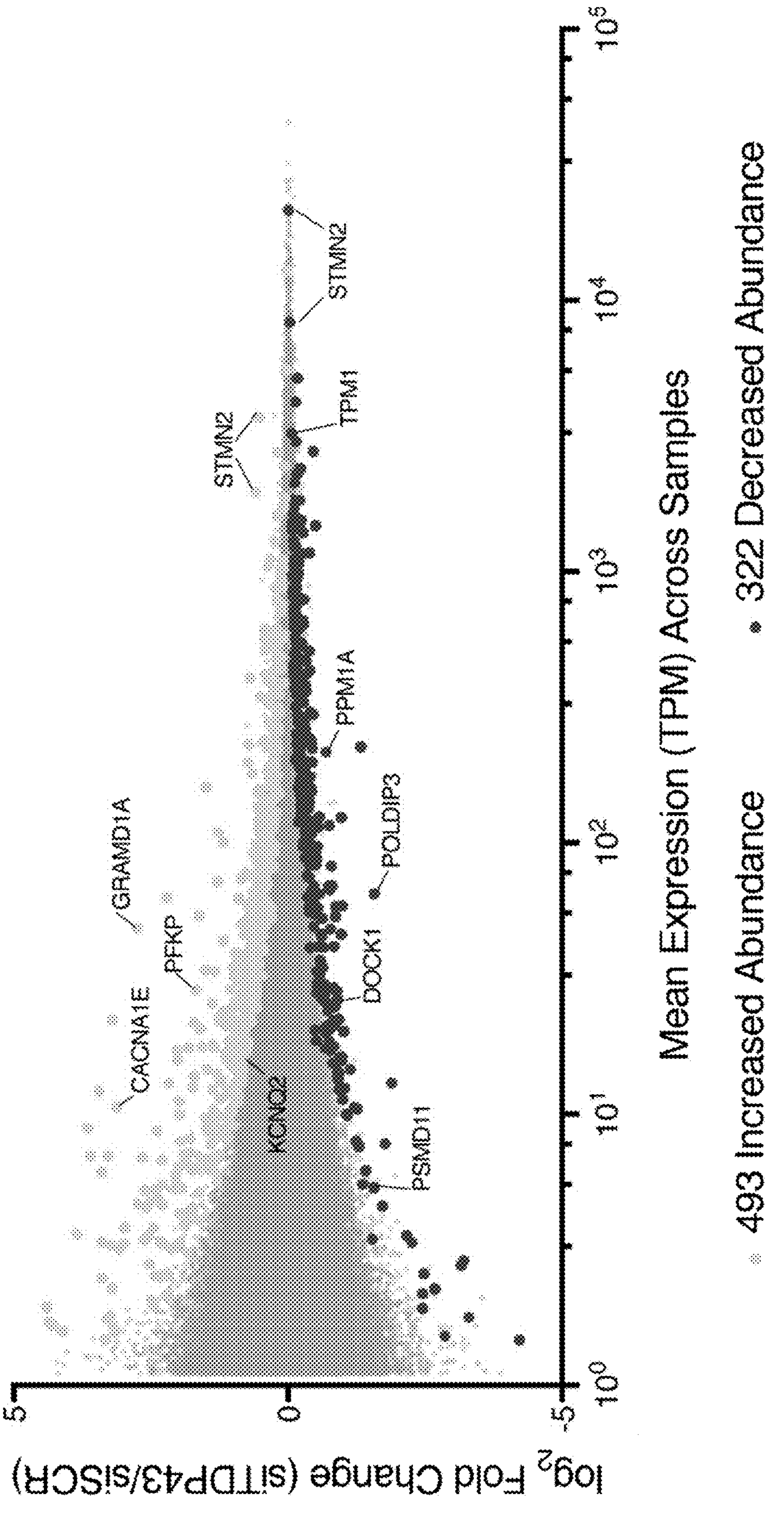

FIG. 23 shows splicing alterations after TDP-43 depletion. Differential exon usage analysis was performed on RNA-seq samples from motor neurons treated with siTDP. Splicing changes were observed in STMN2.

Figure 24:
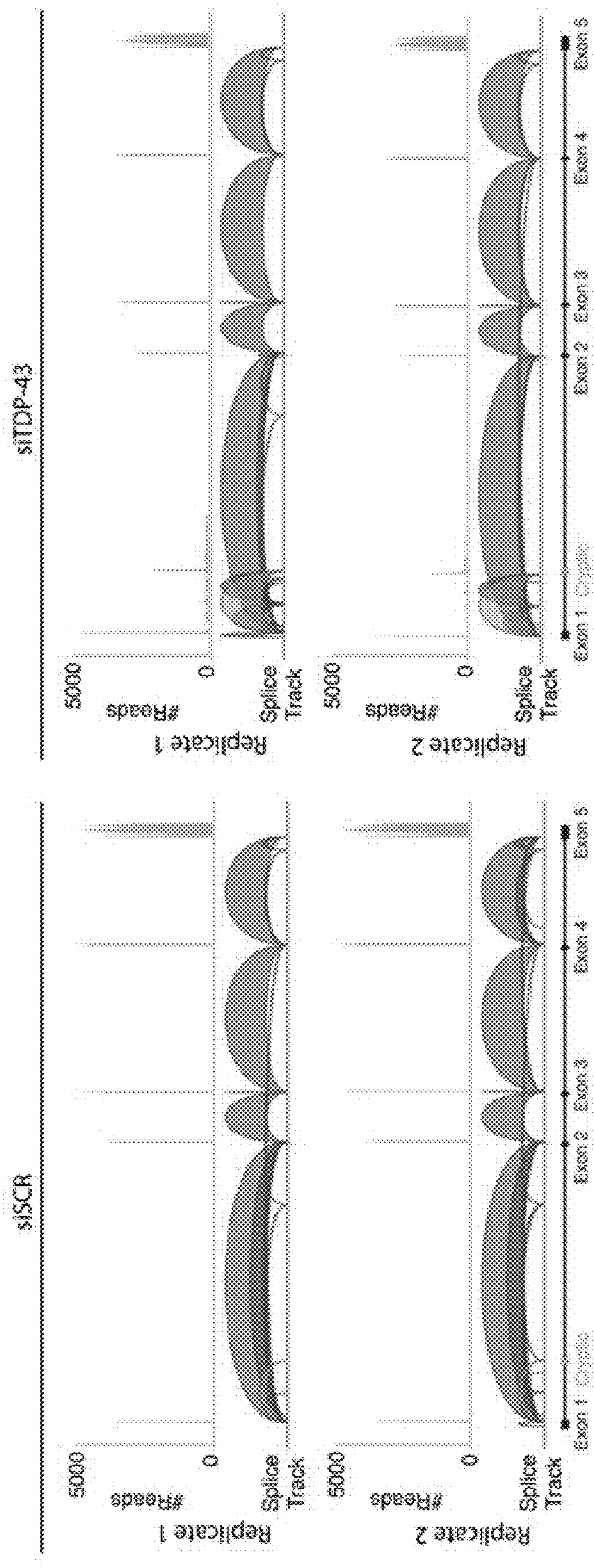

FIG. 24 demonstrates TDP-43 suppresses a cryptic exon in STMN2. The integrated genome viewer was used to look at where RNA seq reads were mapped to the human genome (top graph # of reads) and how the reads reconnected between the exons (splice track). The graphs show the number of reads mapped to areas of a gene.

Figure 25:
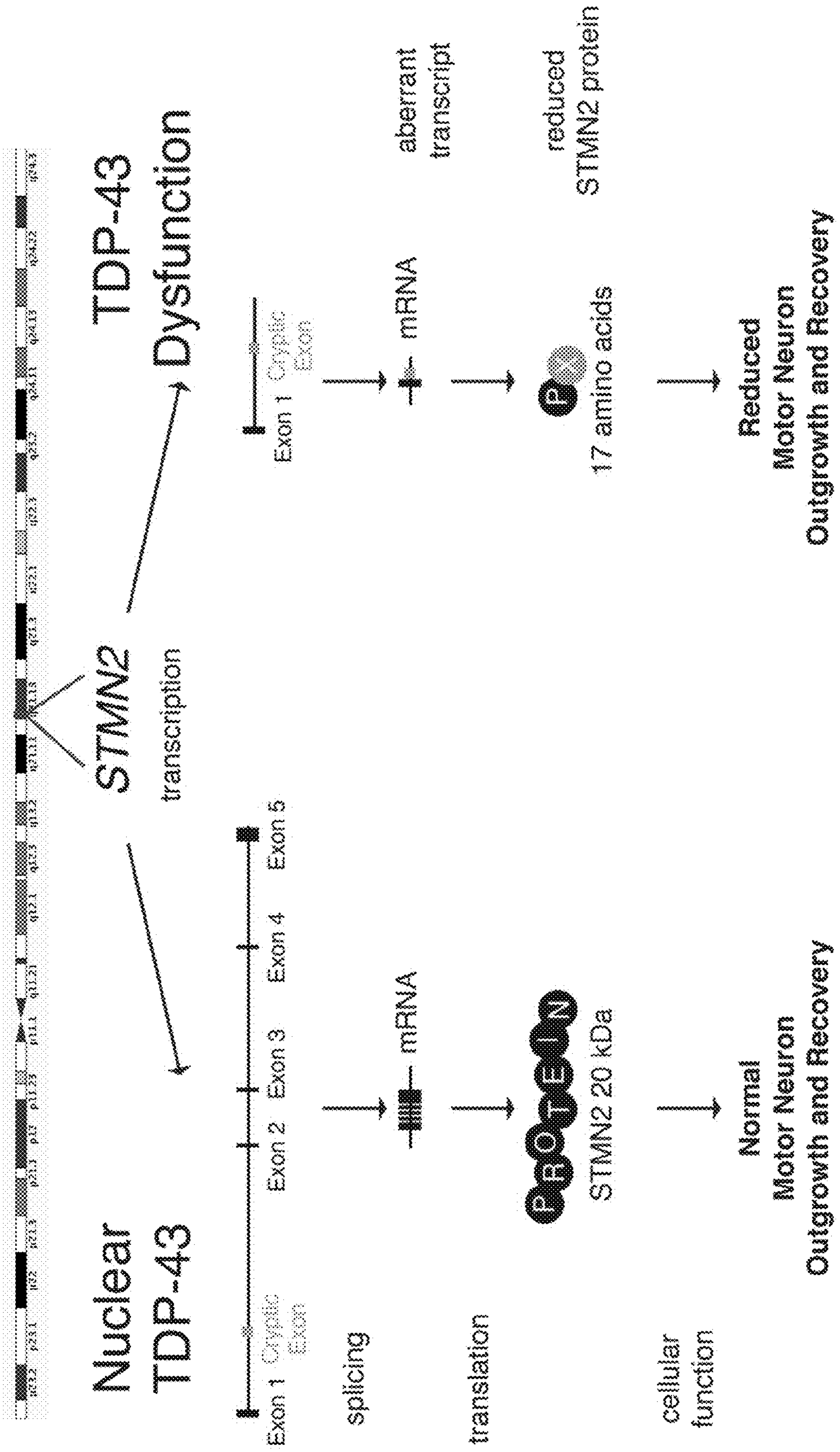

FIG. 25 provides a STMN2 splicing defect summary. Under normal conditions STMN2 is transcribed with all 5 exons leading to an mRNA that is translated into a 20 kDa STMN2 protein. After TDP-43 perturbations, the cryptic exon intercepts the transcript so that only a 17 amino acid polypeptide could be translated.

Figure 26:
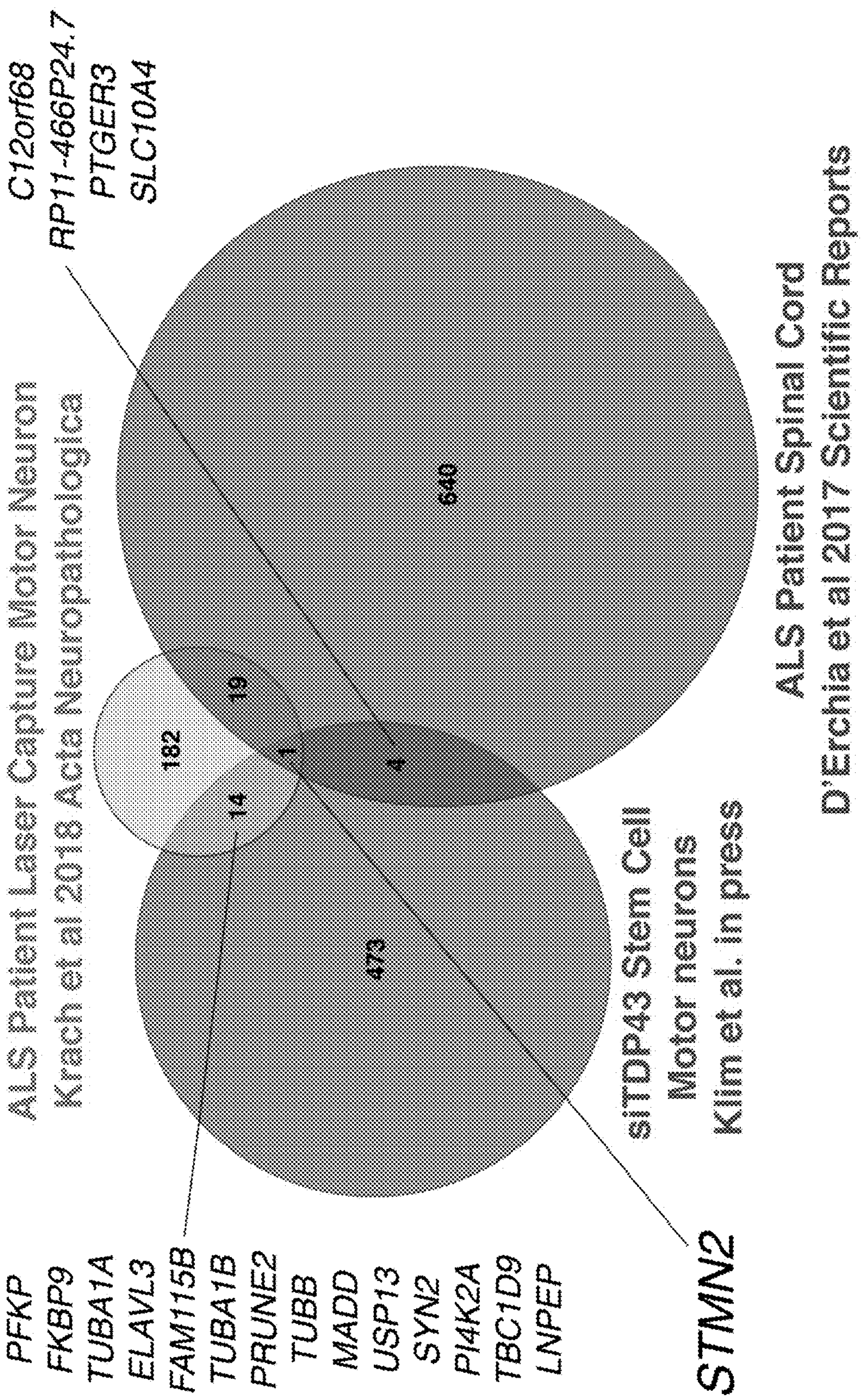

FIG. 26 shows STMN2 is consistently decreased. The overlap of decreased transcripts down in 3 human RNA seq data sets (ALS patient data sets and siTDP43 stem cell motor neuron data set) were compared and STMN2 is the only transcript down in all three data sets.

Figure 27:
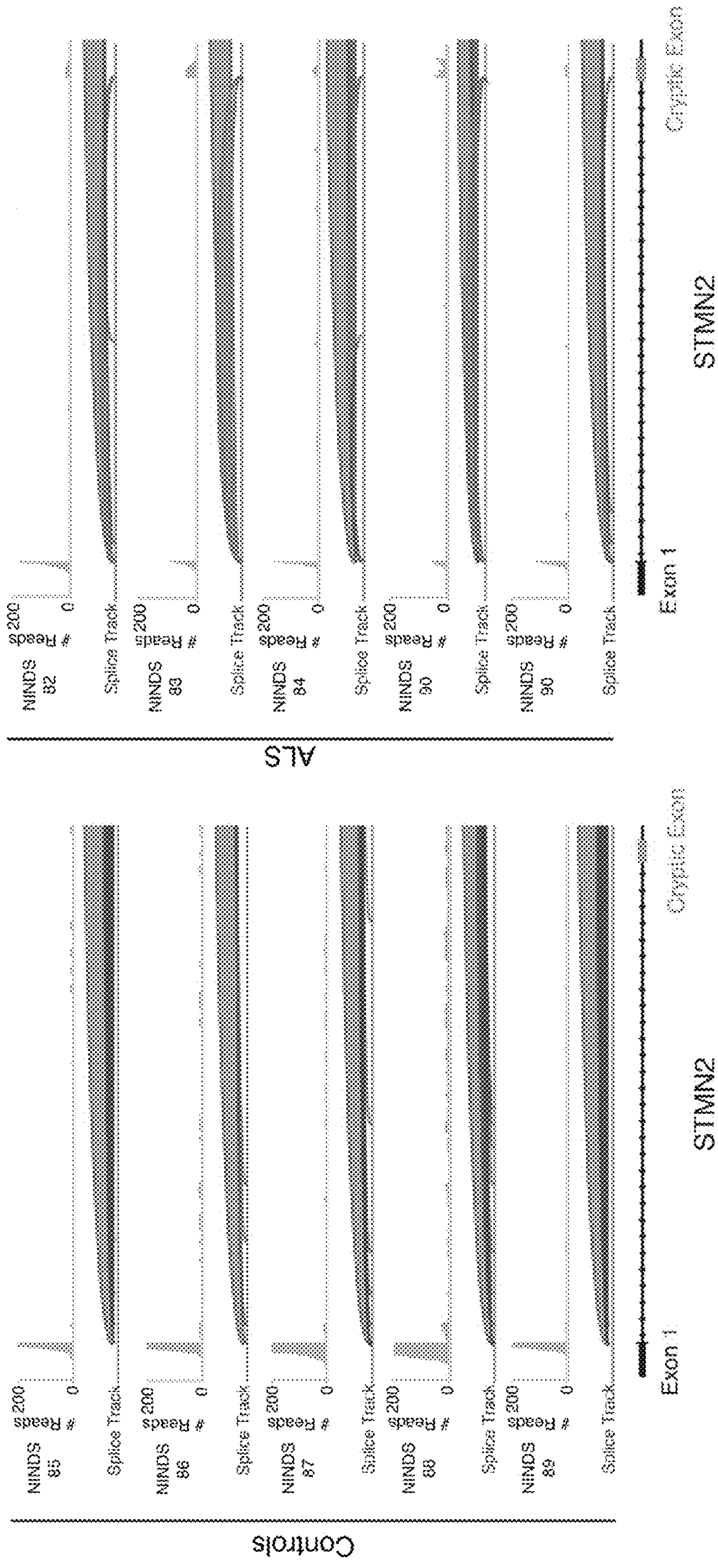

FIG. 27 shows the STMN2 cryptic exon is present in ALS patient spinal cords. Read coverage and splice junctions are shown for alignment to the human HG19 genome. The reads mapped to the human genome in ALS patients was observed, and for 5 out of 6 patients reads mapped to and splicing went into the cryptic exon and none of the controls.

Figure 28:
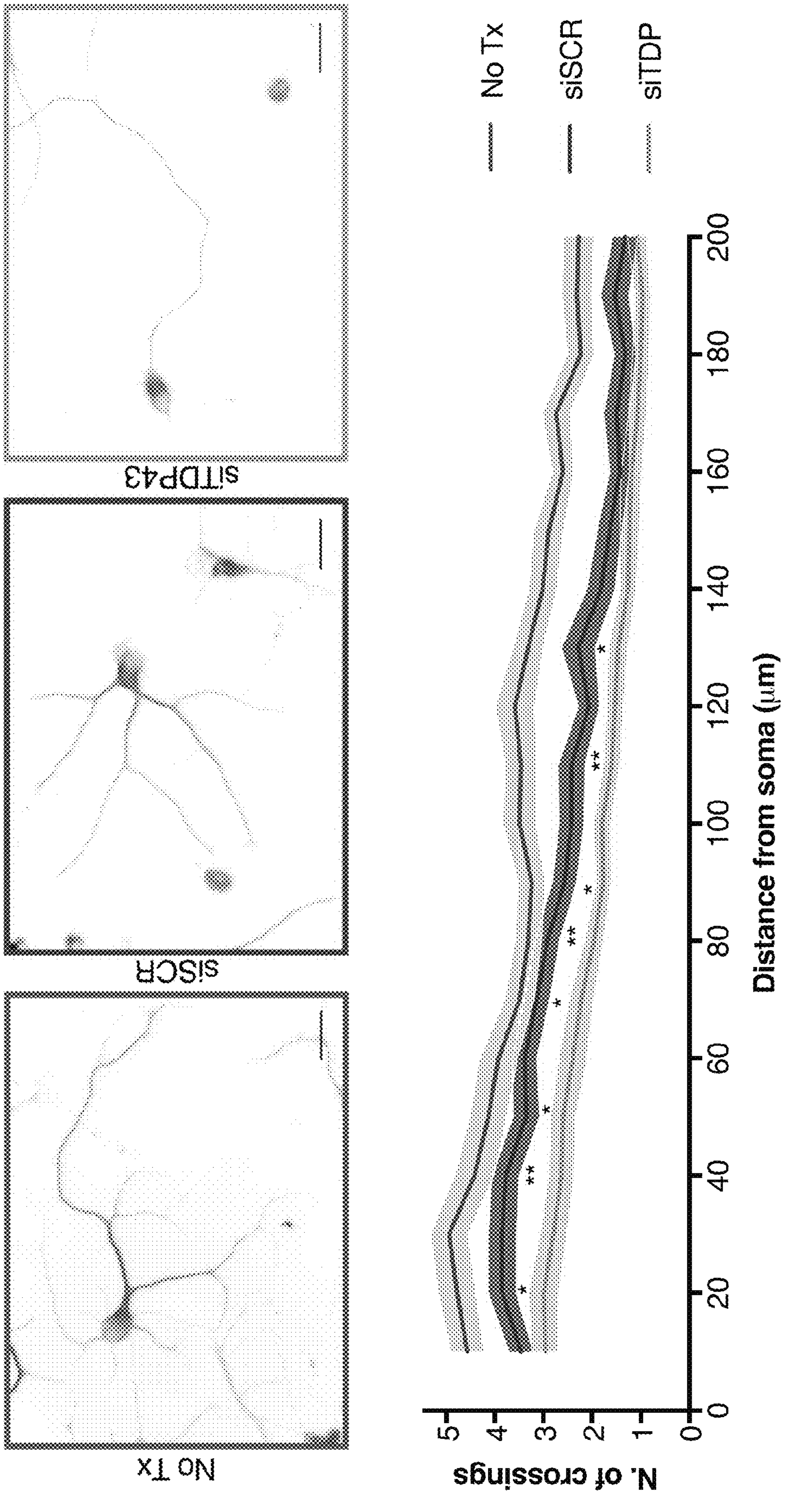

FIG. 28 shows TDP-43 depletion leads to neurite outgrowth and axonal regrowth defects. Representative micrographs of hMNs treated with indicated siRNAs and immunostained for β-III tubulin to perform Sholl analysis are provided. A Sholl analysis of hMNs after siRNA treatment is provided. Lines represent sample means and shading represents the s.e.m. with unpaired t-test between siTDP43 and siSCR, two sided, P<0.05.

Figure 29:
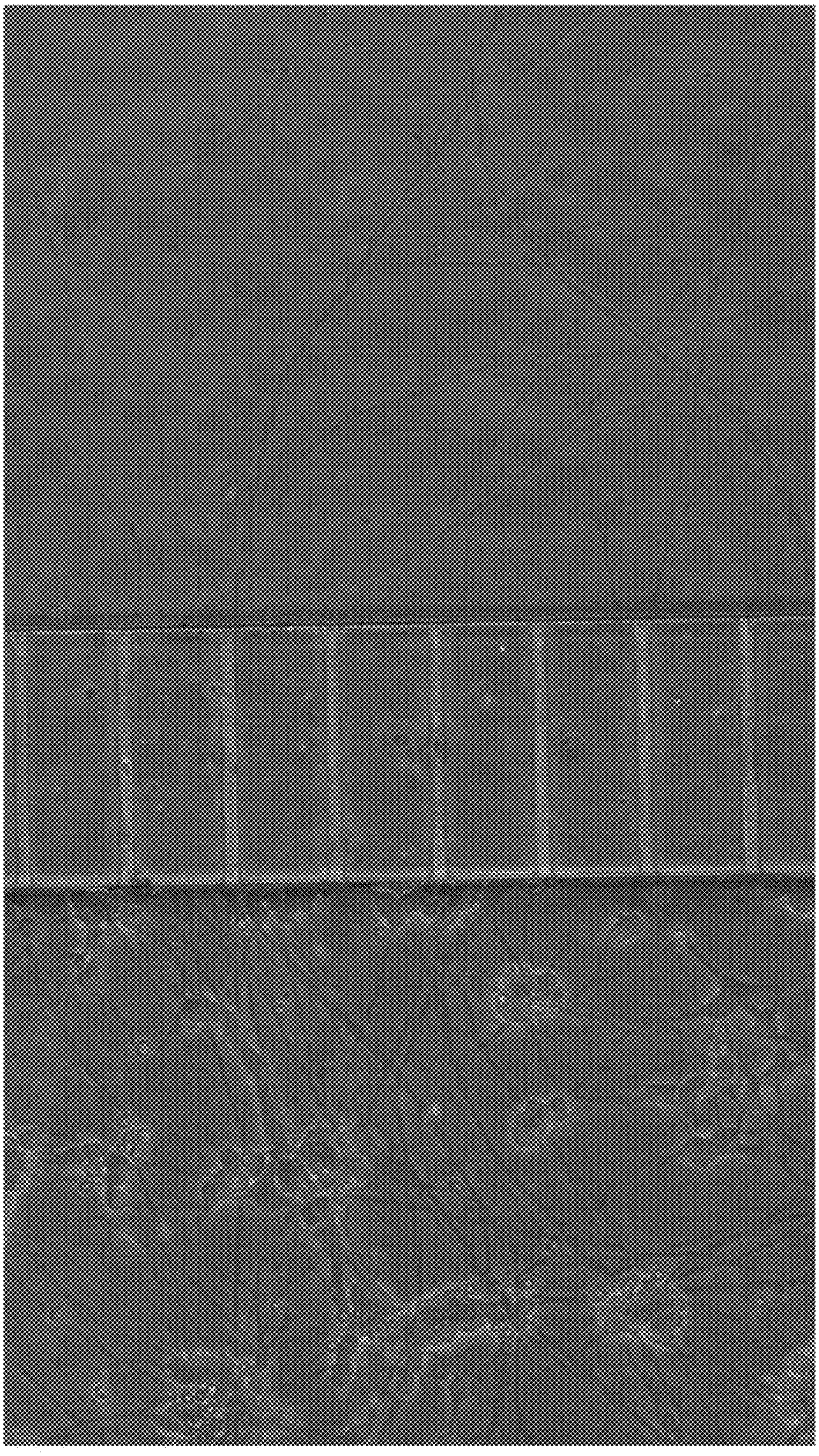

FIG. 29 shows microfluidic devices for investigating axon regeneration. The microfluidic device includes a soma compartment (left panel) and axon compartment (right panel).

Figure 30A:
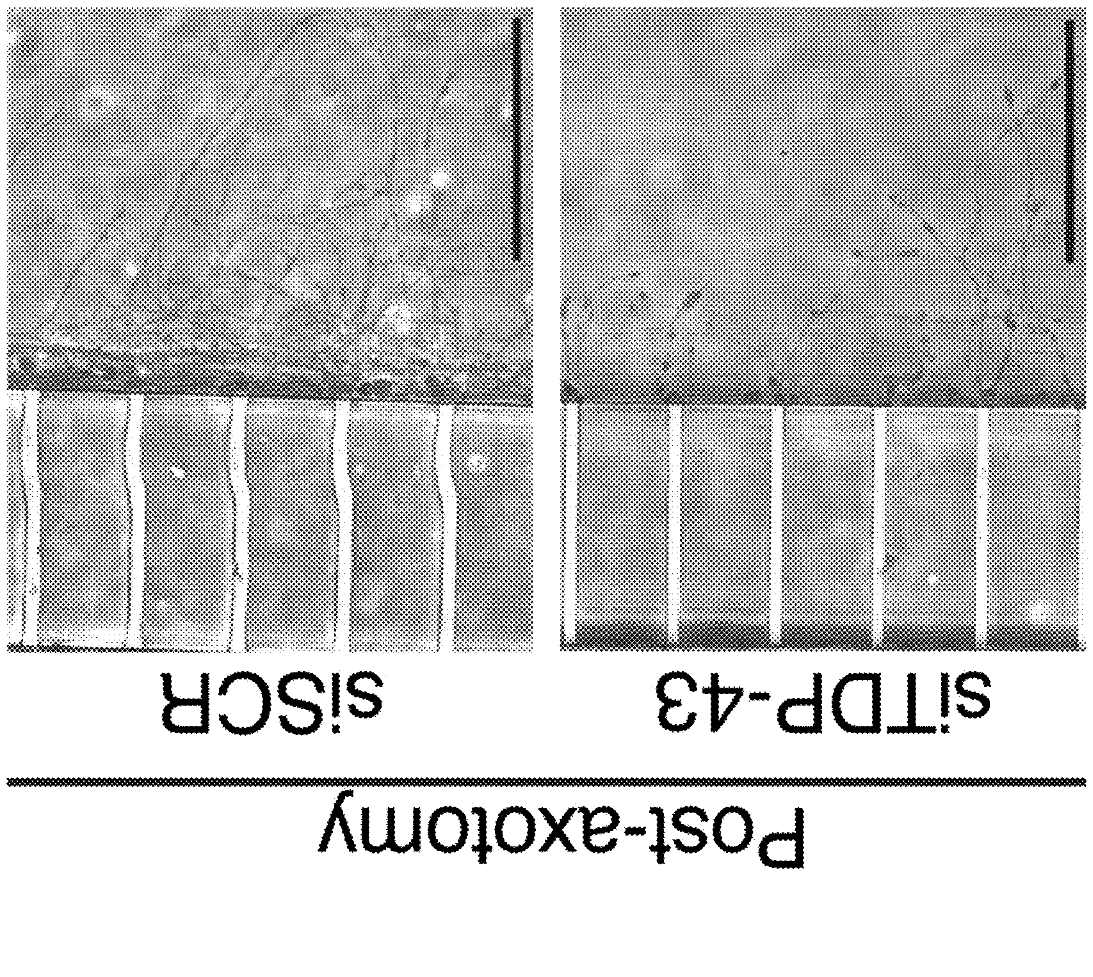
Figure 30B:
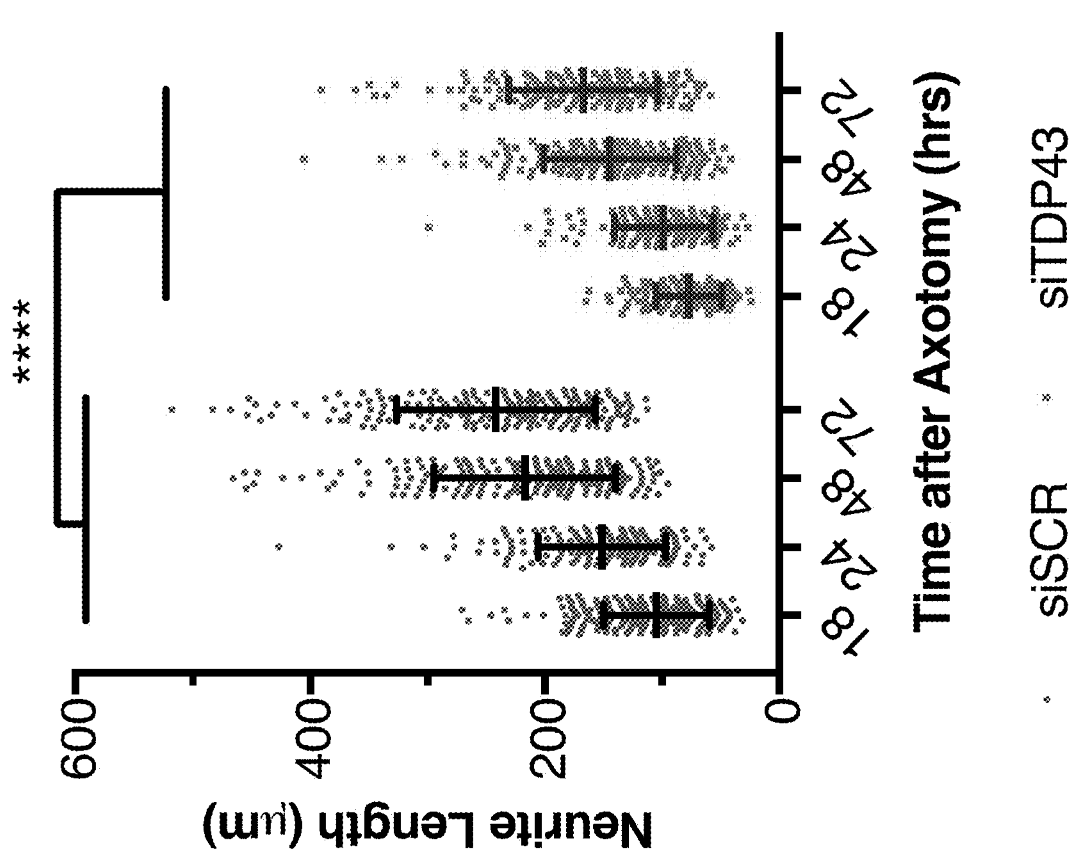

FIGS. 30A-30B demonstrate TDP-43 depletion leads to neurite outgrowth and axonal regrowth defects. FIG. 30A provides representative micrographs of hMNs in the microfluidics device after axotomy. Scale bars, 150 μM. FIG. 30B provides measurements of axonal regrowth and regeneration after axotomy (Unpaired t test, two sided, P value ≤0.05 18 h≤0.0001, 24 h≤0.0001, 48≤0.0001 and 72≤0.0001).

Figure 31:
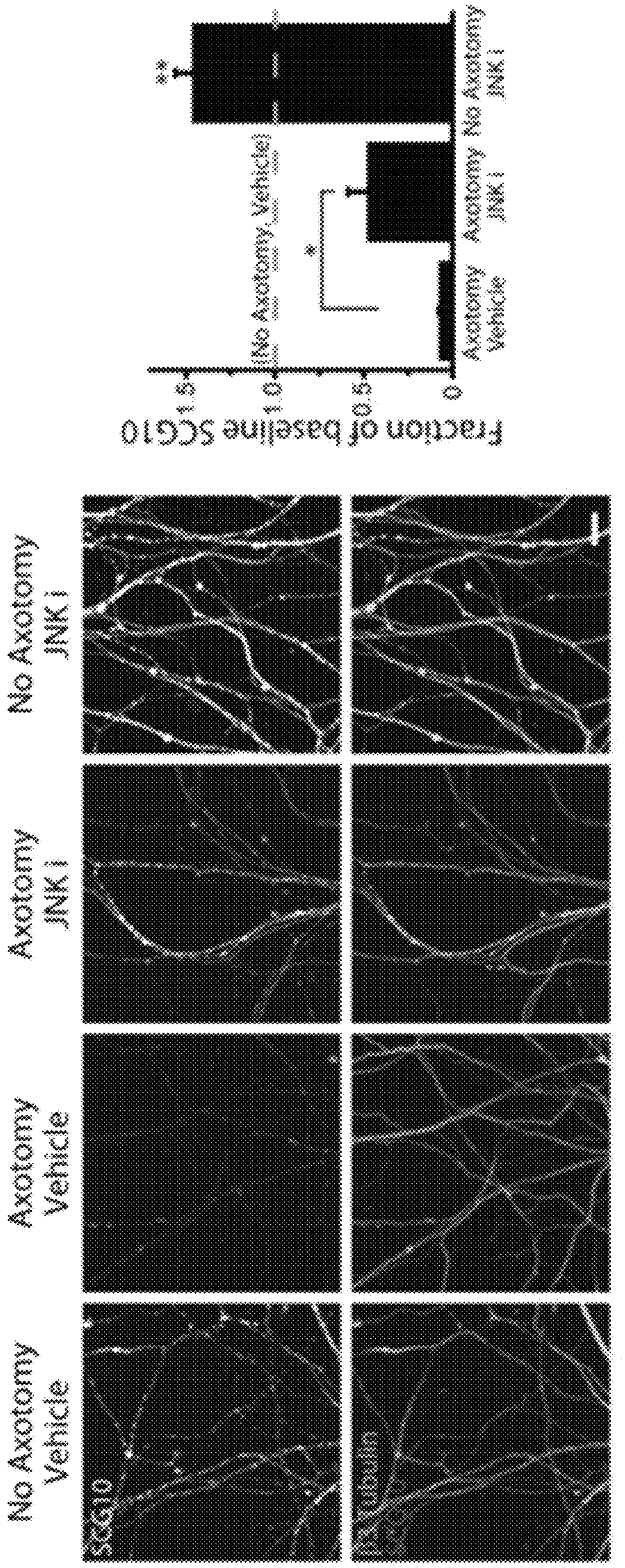

FIG. 31 demonstrates STMN2 is a JNK target in the axonal degeneration pathway. JNK1 is shown to bind to and phosphorylate STMN2, and phosphorylated STMN2 is rapidly degraded. See J. Eun Shin et al. *PNAS* 2012, 109, E3696-3705.

Figure 32:
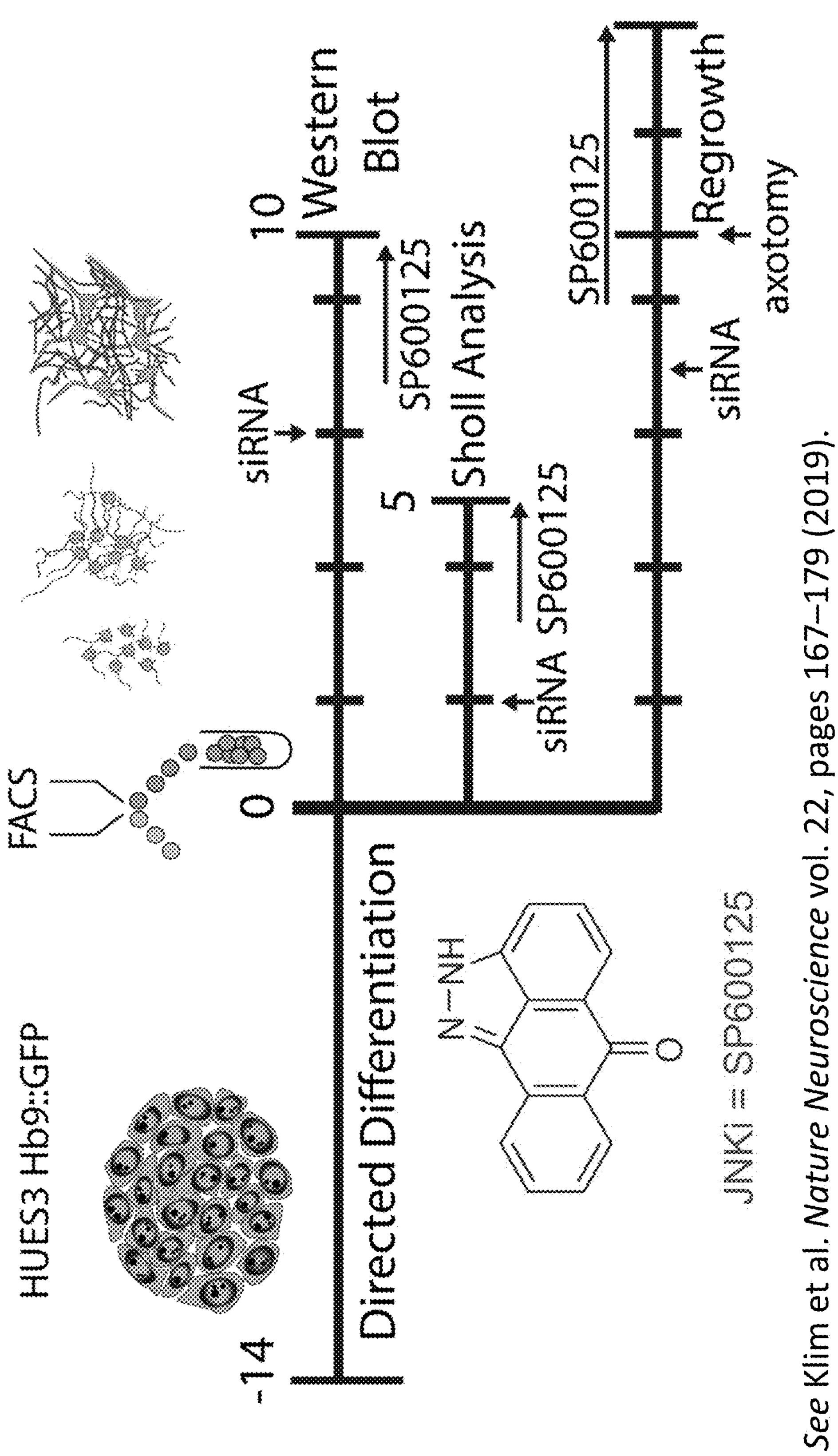

FIG. 32 provides a strategy to determine if JNKi can rescue siTDP43 phenotypes. See Klim et al. *Nature Neuroscience vol.* 22, pages 167-179 (2019).

Figure 33:
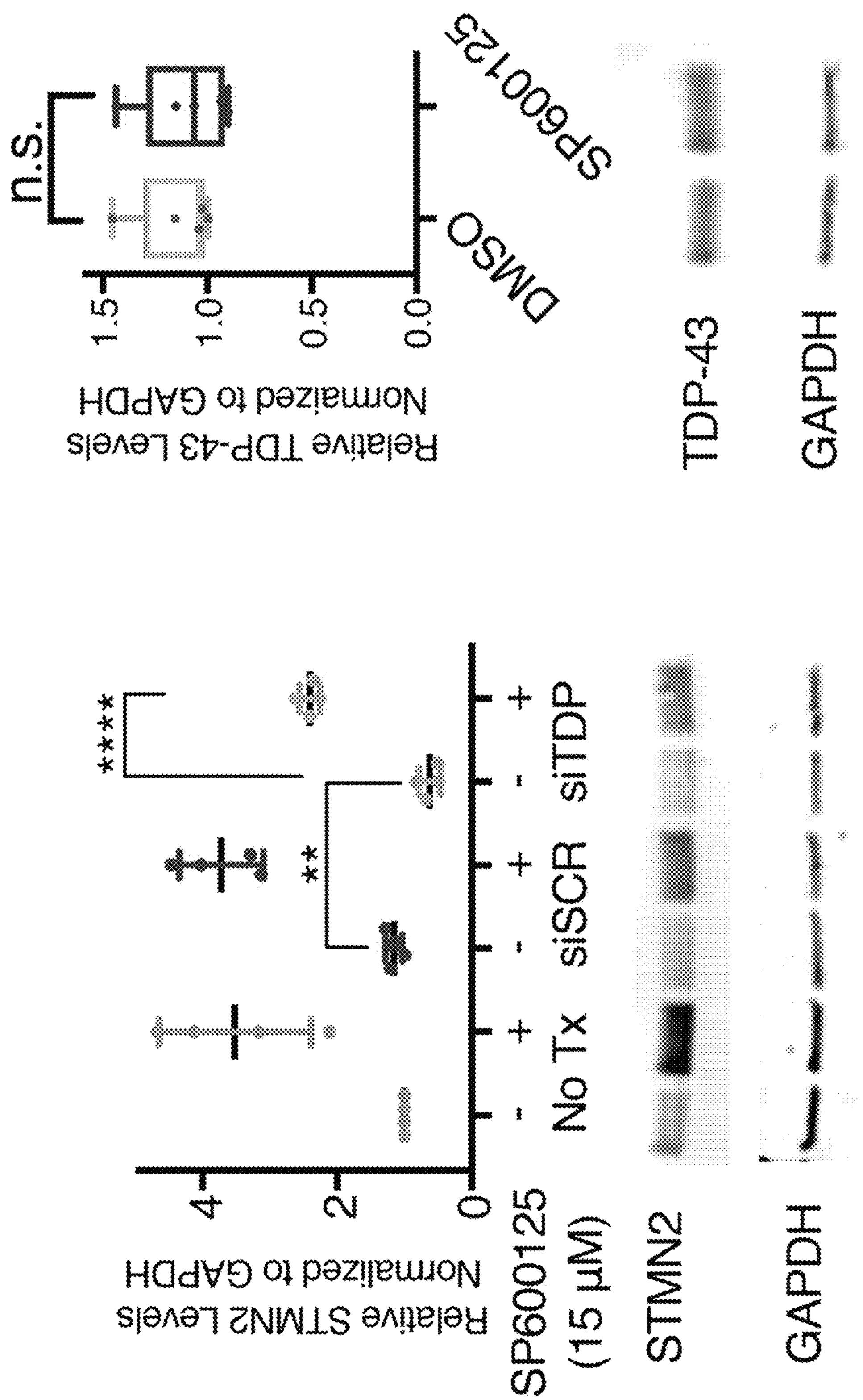

FIG. 33 shows a JNK inhibitor (SP600125) boosts STMN2 levels. STMN2 protein levels increased in neurons treated with JNKi and lower levels observed in cells treated with siTDP43 could be rescued.

Figure 34:
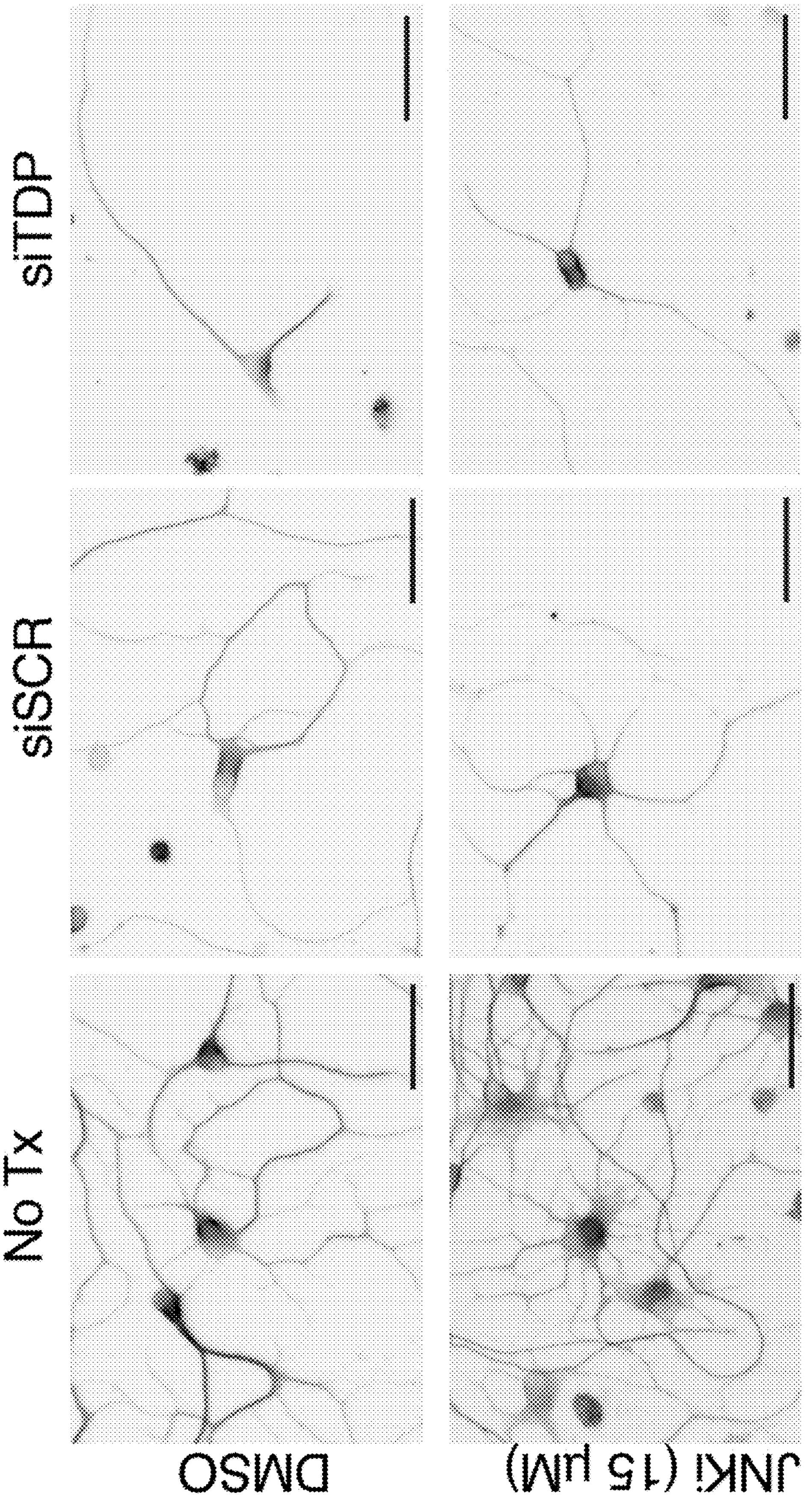

FIG. 34 shows JNKi (SP600125) increases neurite outgrowth. Cells treated with JNKi exhibited increased neurite branching.

Figure 35:
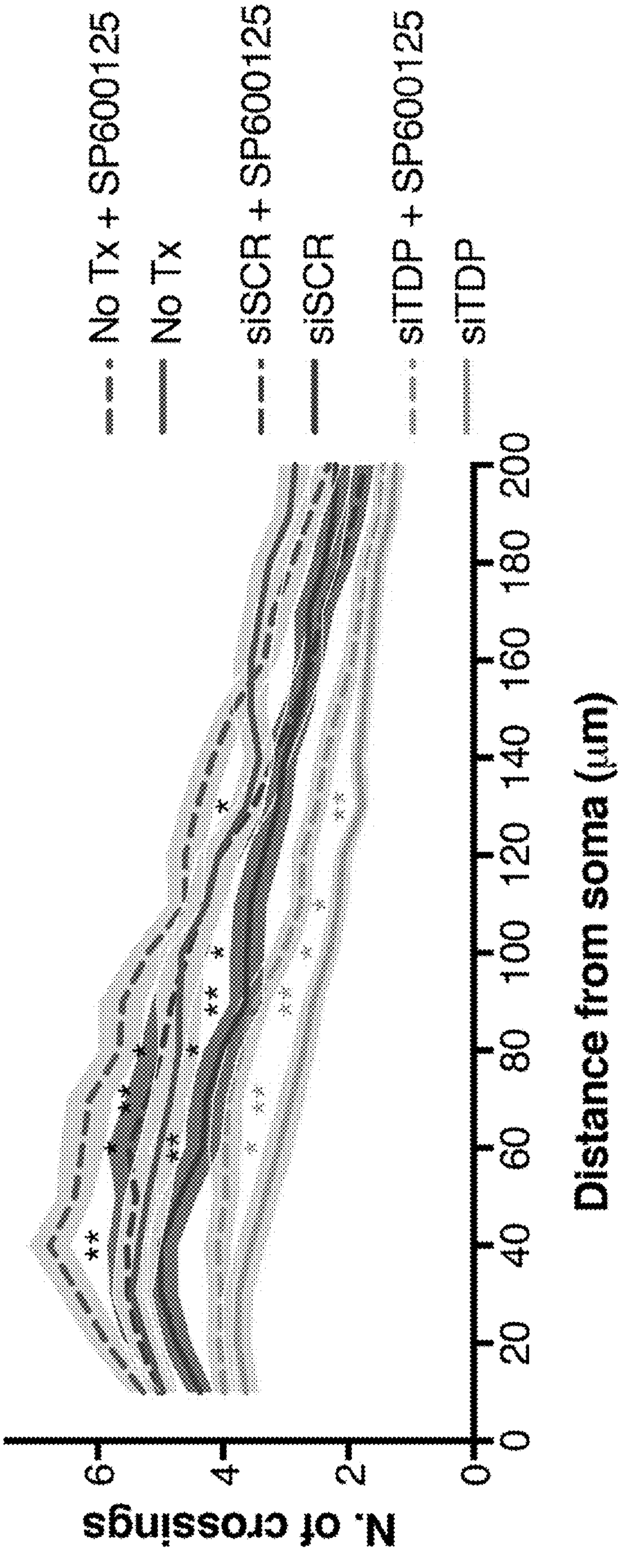

FIG. 35 shows JNKi (SP600125) increases neurite outgrowth. Sholl analysis confirmed that under all conditions JNKi increased neurite branching and regrowth following injury.

Figure 36:
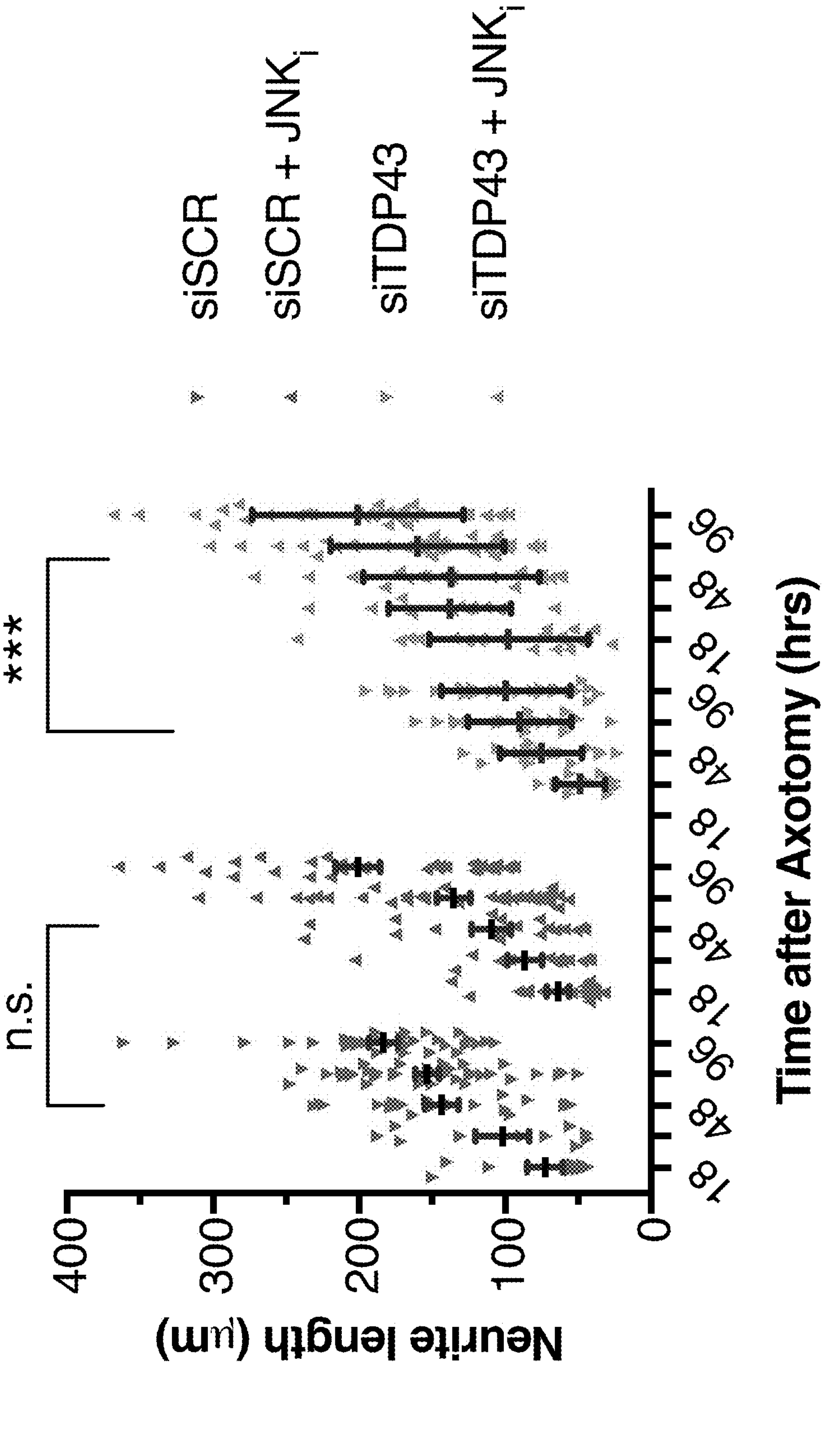

FIG. 36 shows JNKi increases axon regeneration. Microfluidic devices confirmed that under all conditions JNKi increased neurite branching and regrowth following injury.

Figure 37:
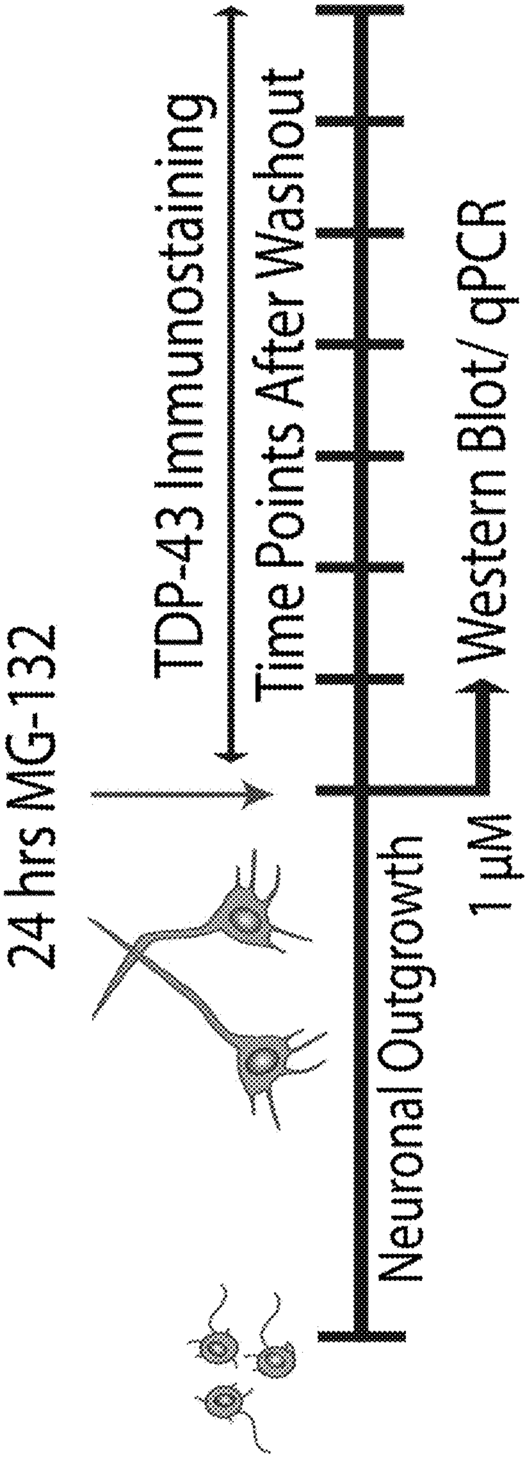

FIG. 37 provides a model for proteasome inhibition. Disruptions to protein homeostasis lead to TDP-43 mislocalization and altered STMN2 levels, which disrupts axon biology.

Figure 38A:
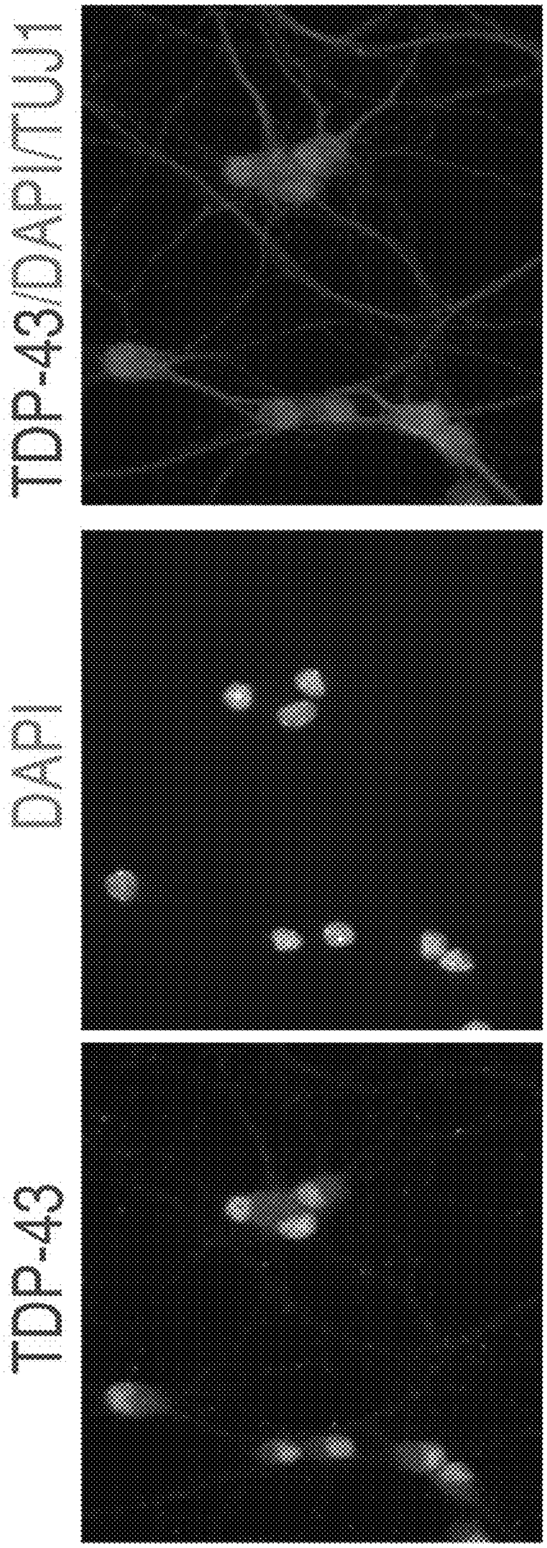
Figure 38B:
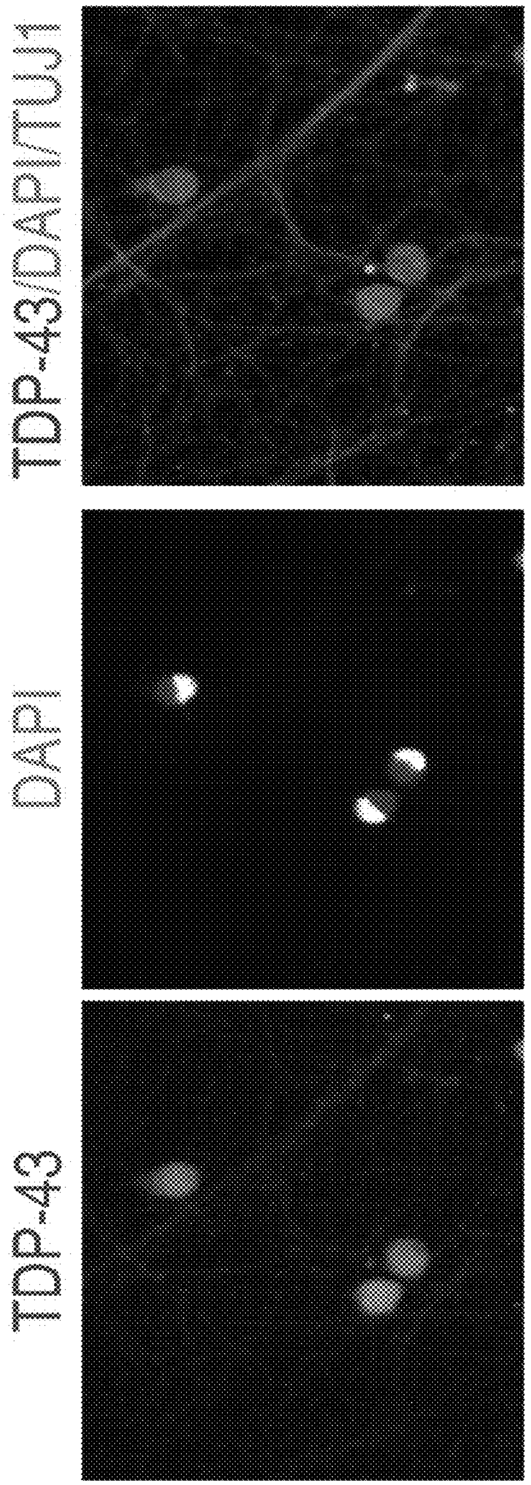

FIGS. 38A-38B shows TDP-43 localization. TDP-43 is normally nuclear (FIG. 38A), but after compound washout, a loss of distinct nuclear TDP-43 staining was observed (FIG. 38B). No cytoplasmic aggregation was observed, only loss of nuclear TDP-43.

Figure 39:
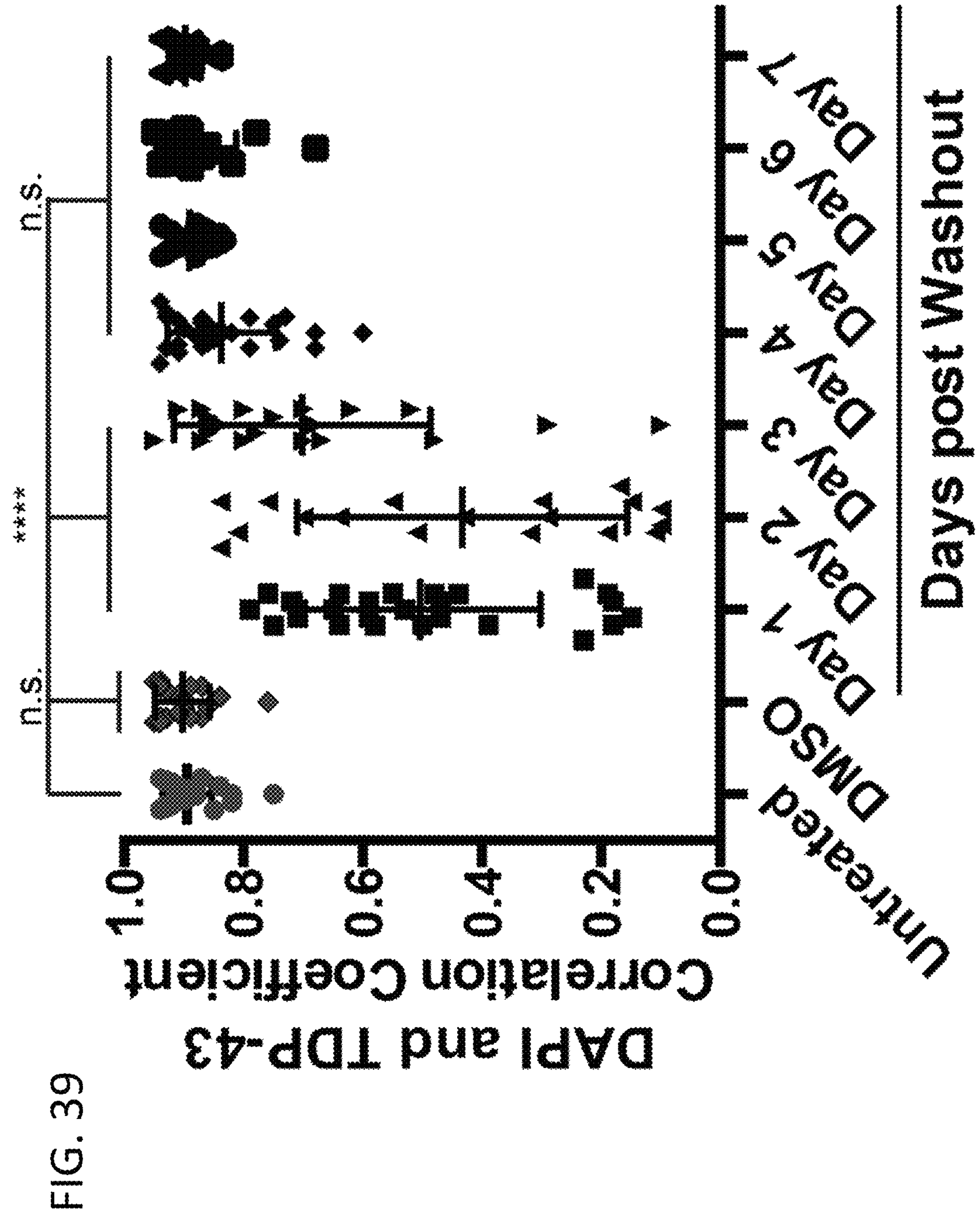

FIG. 39 shows TDP-43 mislocalization is reversible.

Figure 40:
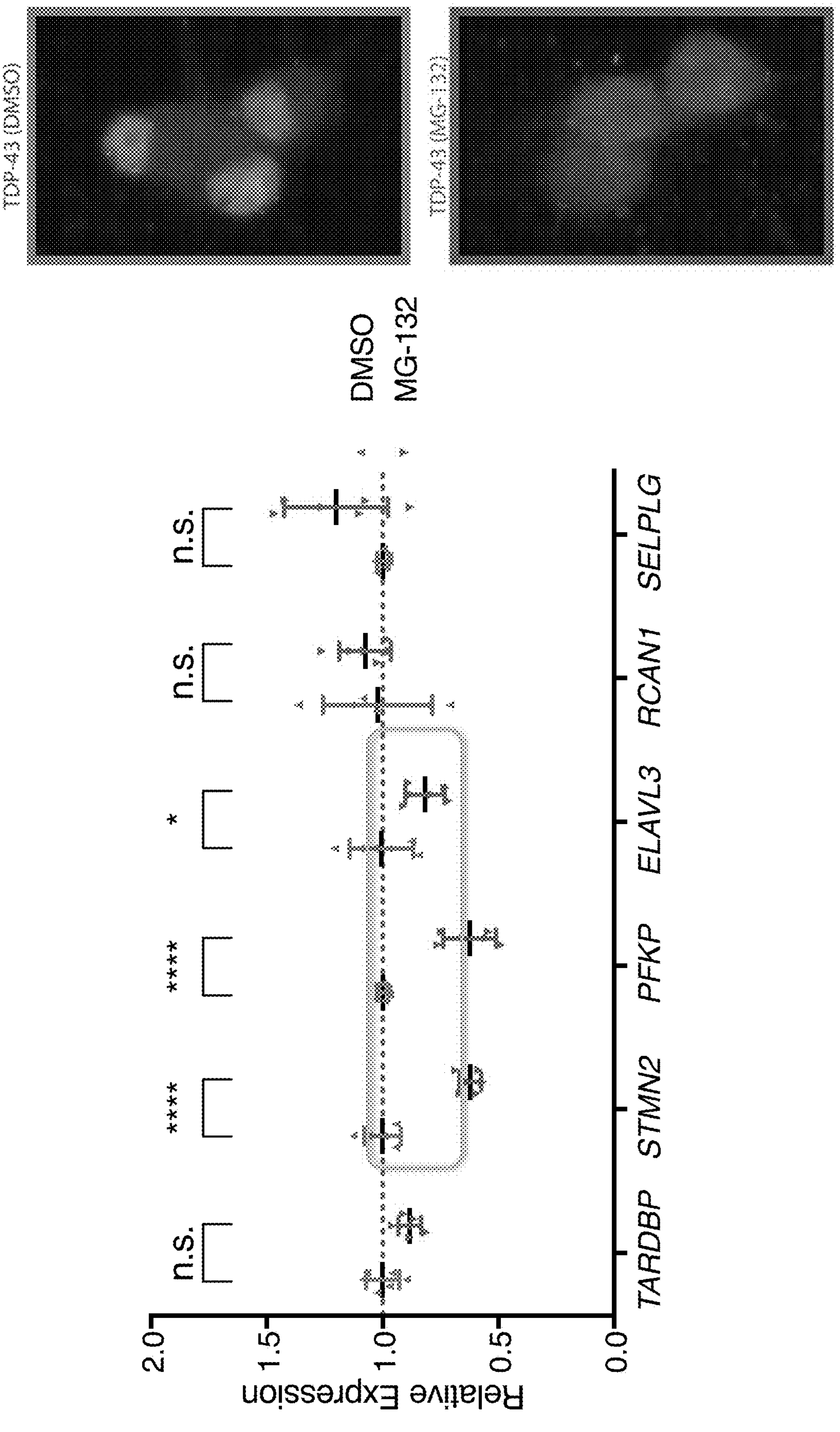

FIG. 40 shows STMN2 transcripts decreased after TDP-43 mislocalization. The decrease for STMN2 was even more pronounced than in cells expressing mutant TDP-43.

FIG. 41 provides a table summarizing recent ALS genes with their relative mutation frequencies in different ALS and FTD cohorts and associated pathways. Advances in WGS and WES have led to identification of genes carrying rare causal variants: TBK1, CHCHD10, TUBA4A, MATR3, CCNF, NEK1, C21orf2, ANXA11, and TIA1. TBK1 is shown as having the highest mutation frequencies of ALS-FTD (3-4%) in different cohorts. See Nguyen, et al., *Trends in Genetics,* 2018.

Figure 42:
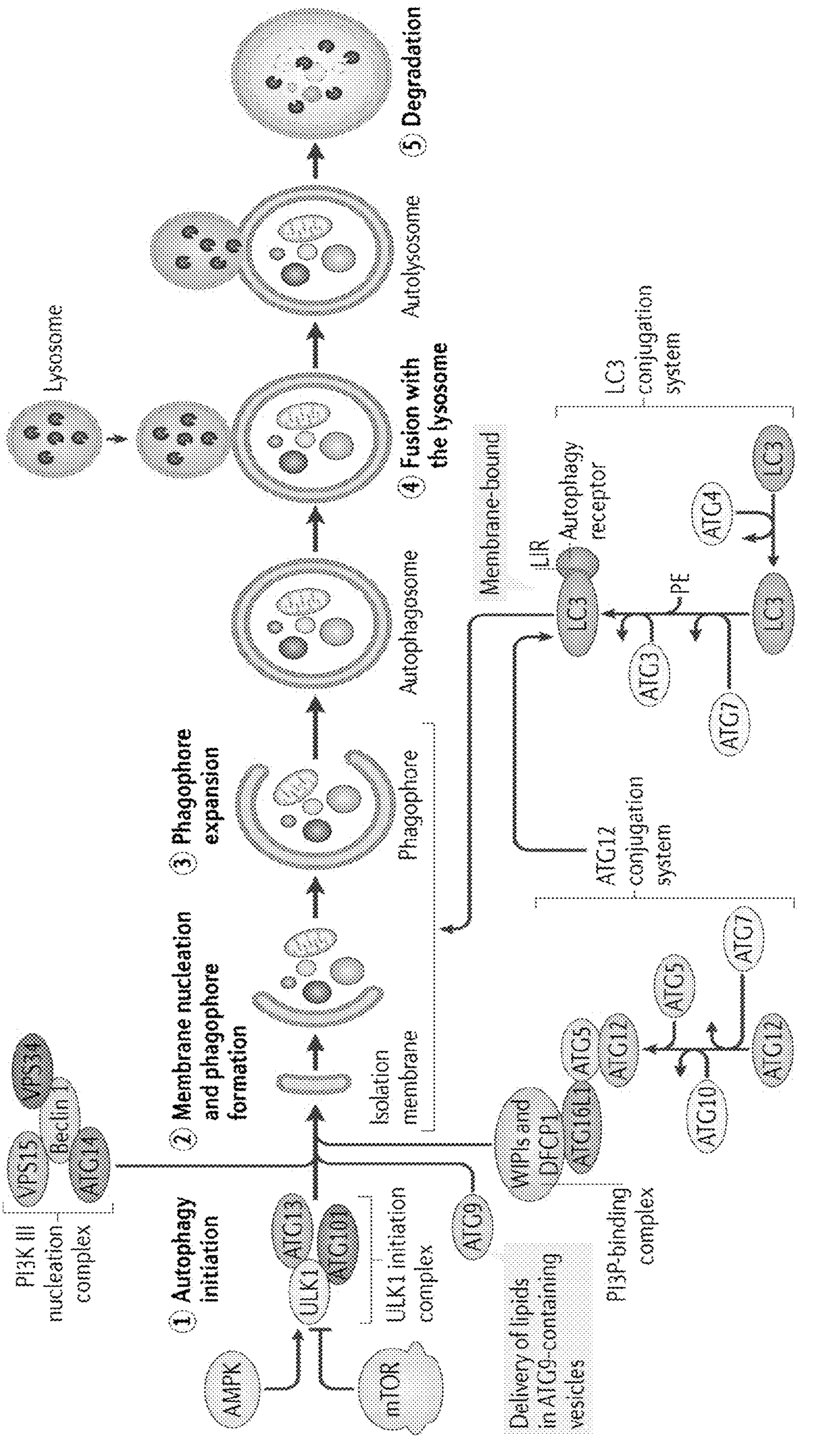

FIG. 42 shows Atg7 and TBK1 act at distinct times in autophagy. See Hansen, et, al., *Nature Reviews Molecular Cell Biology.* 2018

Figure 43:
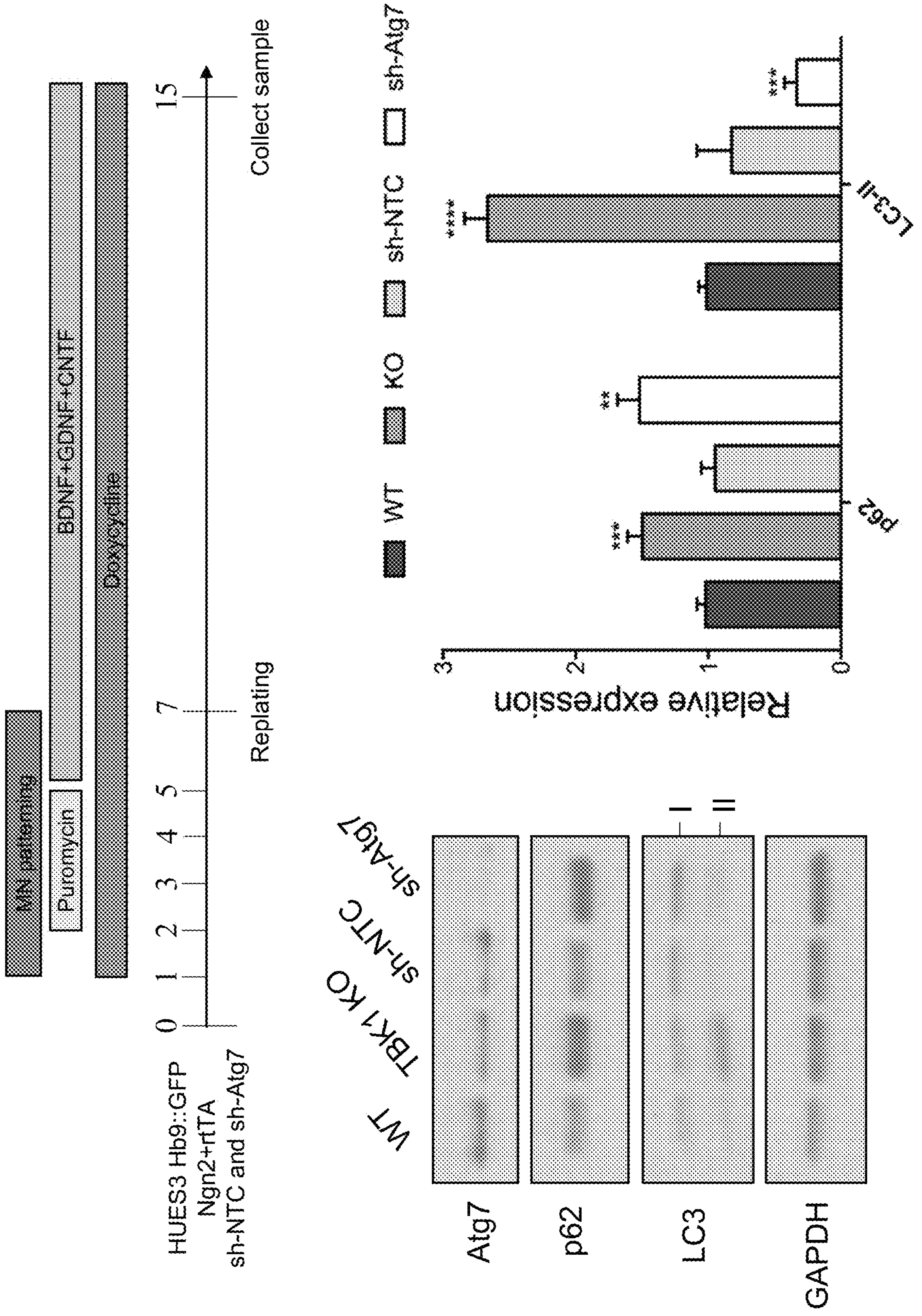

FIG. 43 shows eliminating TBK1 shares similarities with, but is distinct from, blocking autophagy initiation.

Figure 44:
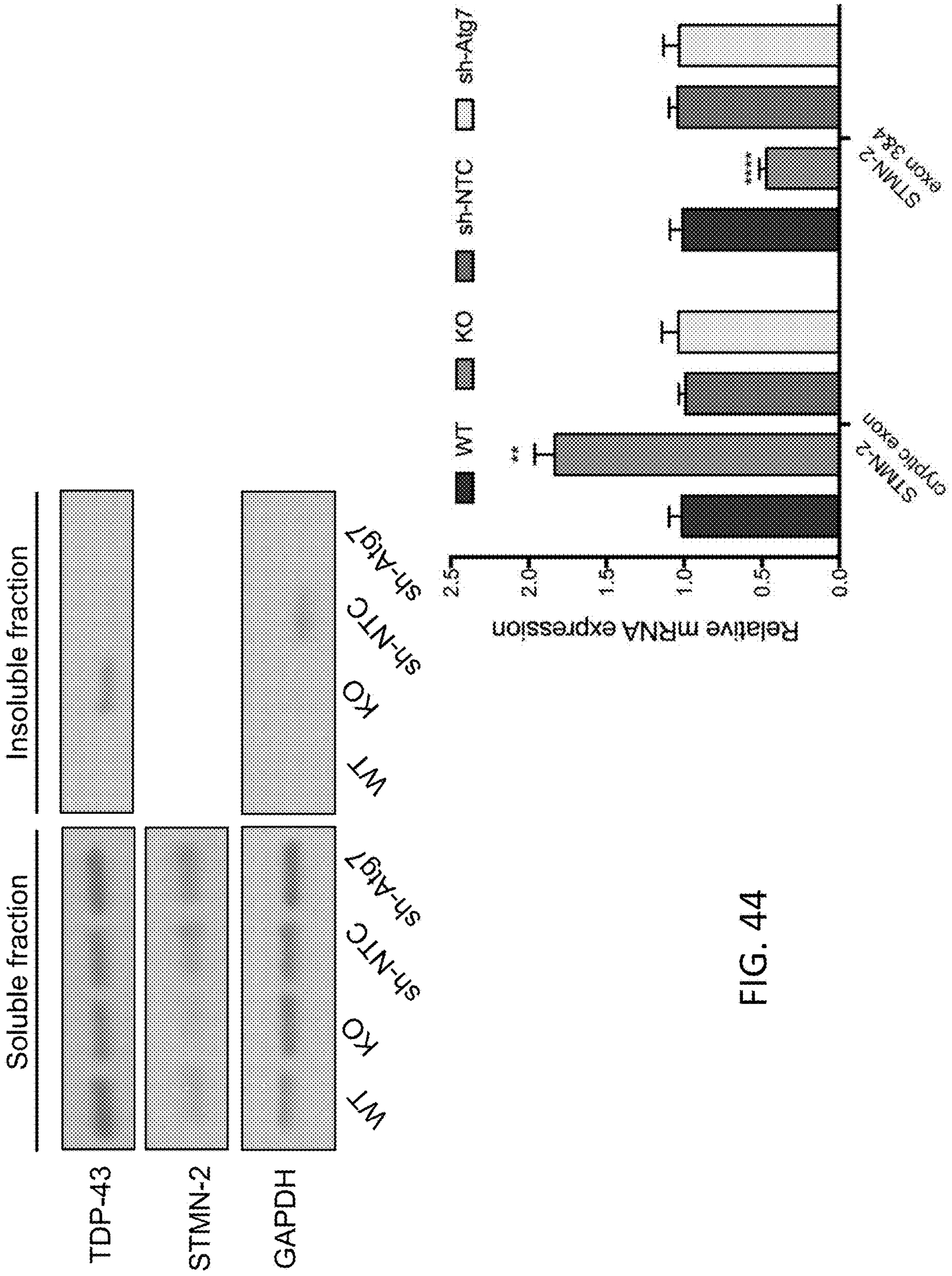

FIG. 44 shows TBK1 knock out decreases functional TDP-43 and STMN2 levels while eliminating ATG7 has no effect. Loss of TBK1 induces TDP-43 pathology in motor neurons through autophagy-independent mechanisms.

Figure 45:
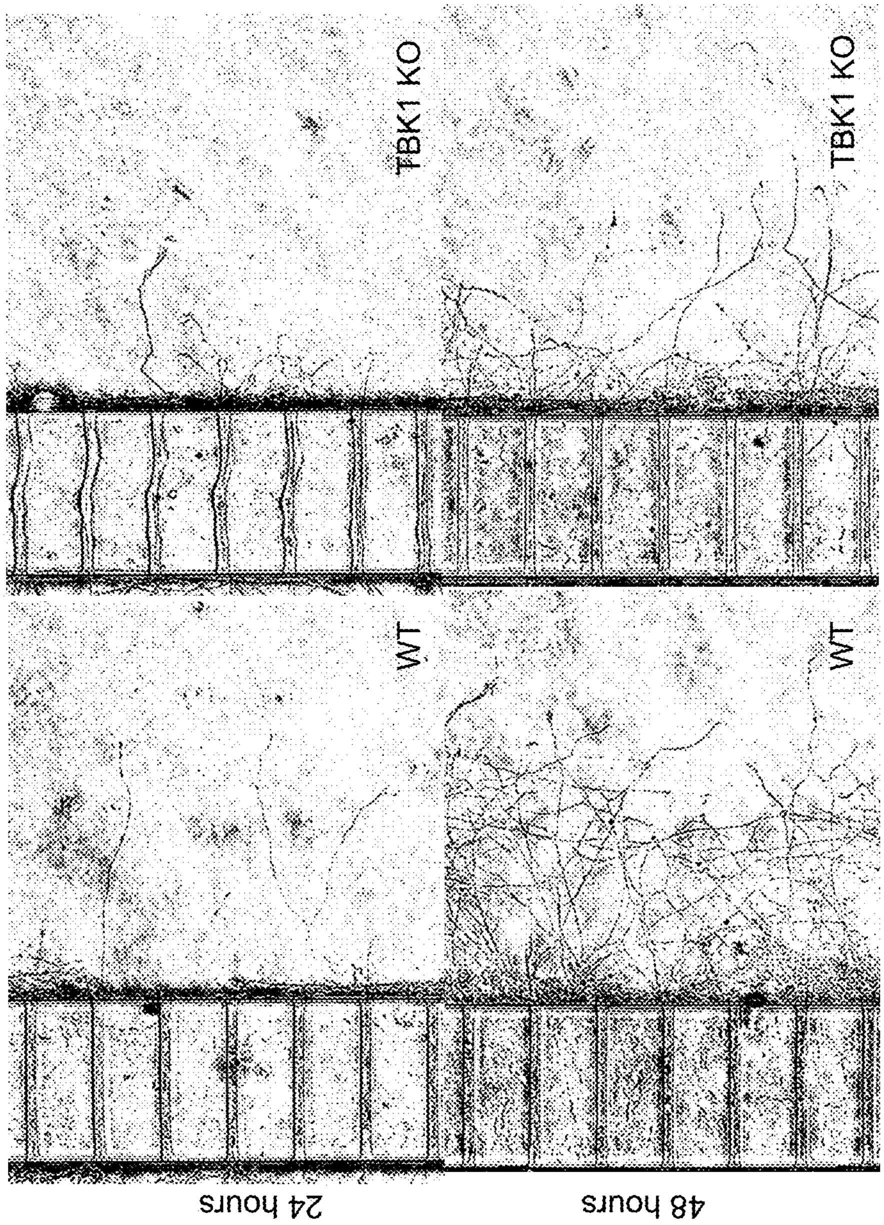

FIG. 45 shows loss of TBK1 shows impaired axon regeneration after axon injury.

Figure 46:
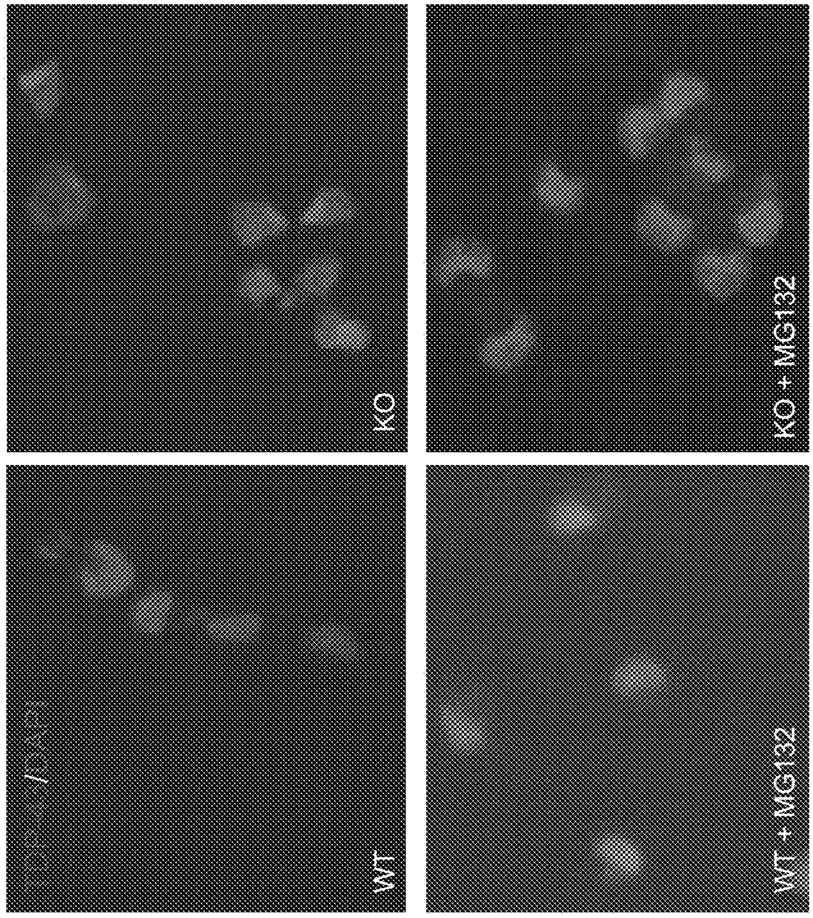
Figure 46:
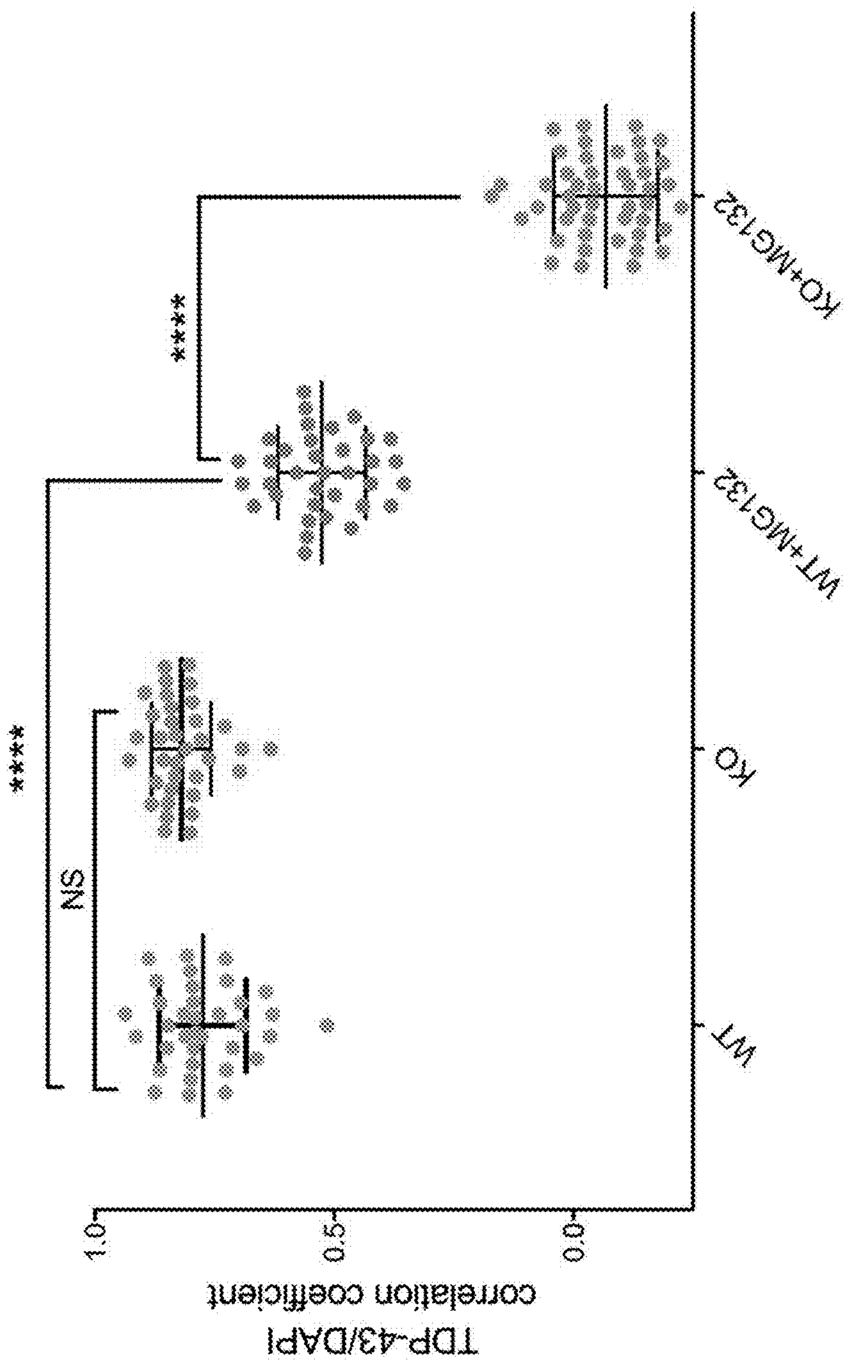

FIG. 46 shows proteasome inhibition induced TDP-43 mislocalization in TBK1 mutant motor neurons.

Figure 47A:
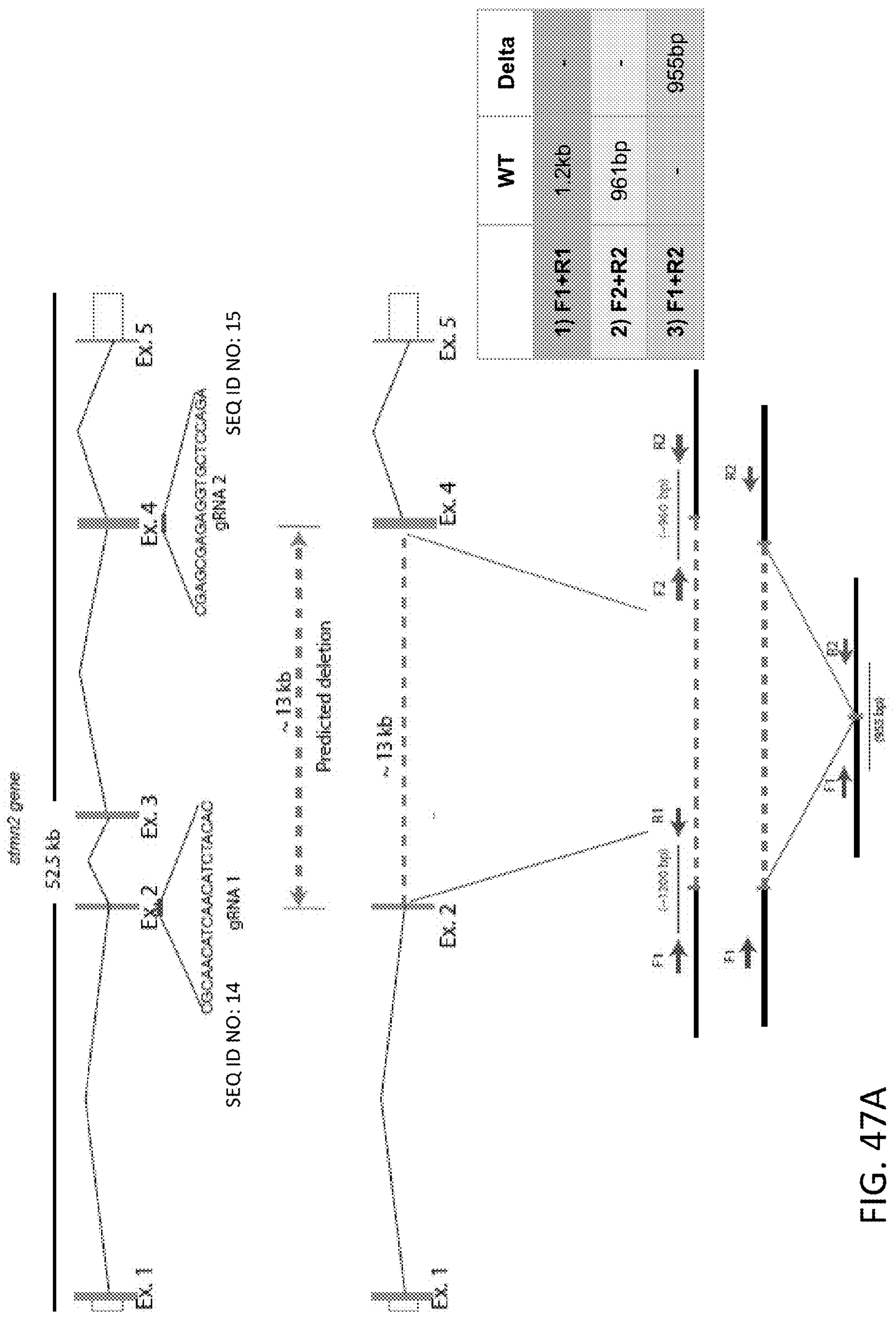
Figure 47B:
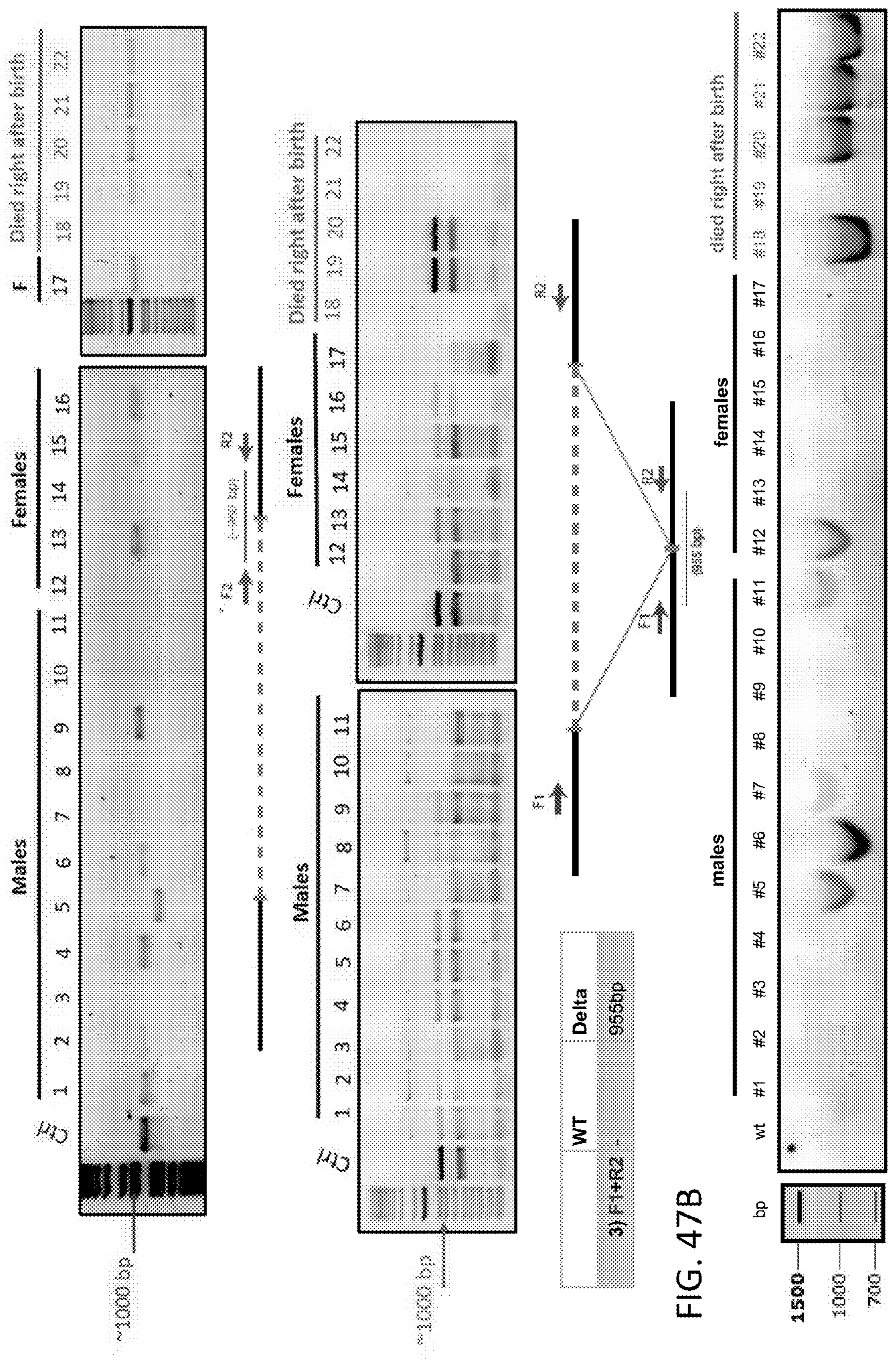

FIGS. 47A-47C demonstrate targeting STMN2 intron using CRISPR. A CRISPR strategy for targeting STMN2 is provided, as well as genotyping for STMN2 (FIGS. 47A-47B). FIG. 47C provides a table summarizing the CRISPR targeting strategy and genotyping for STMN2.

Figure 48:
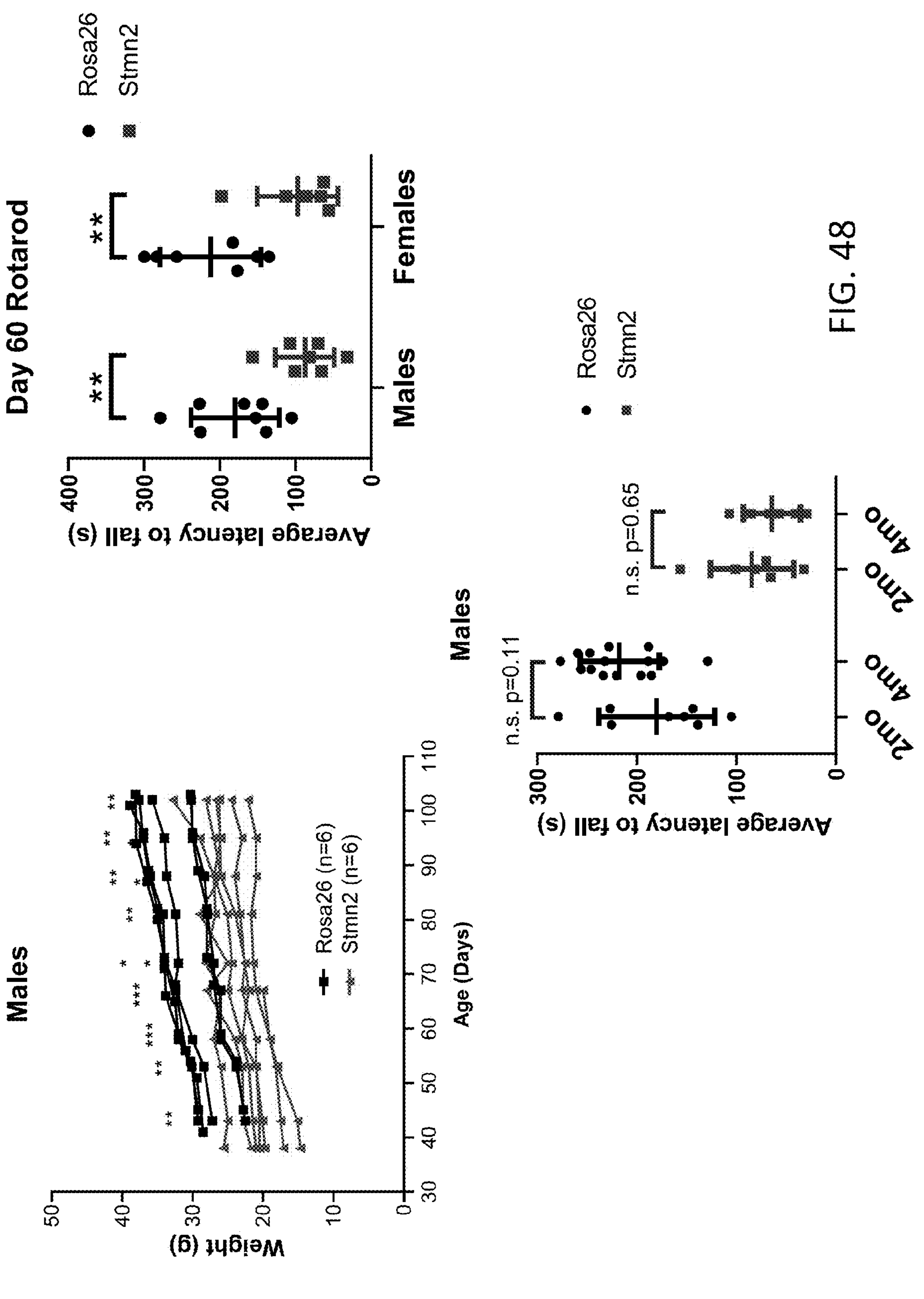
Figure 48:
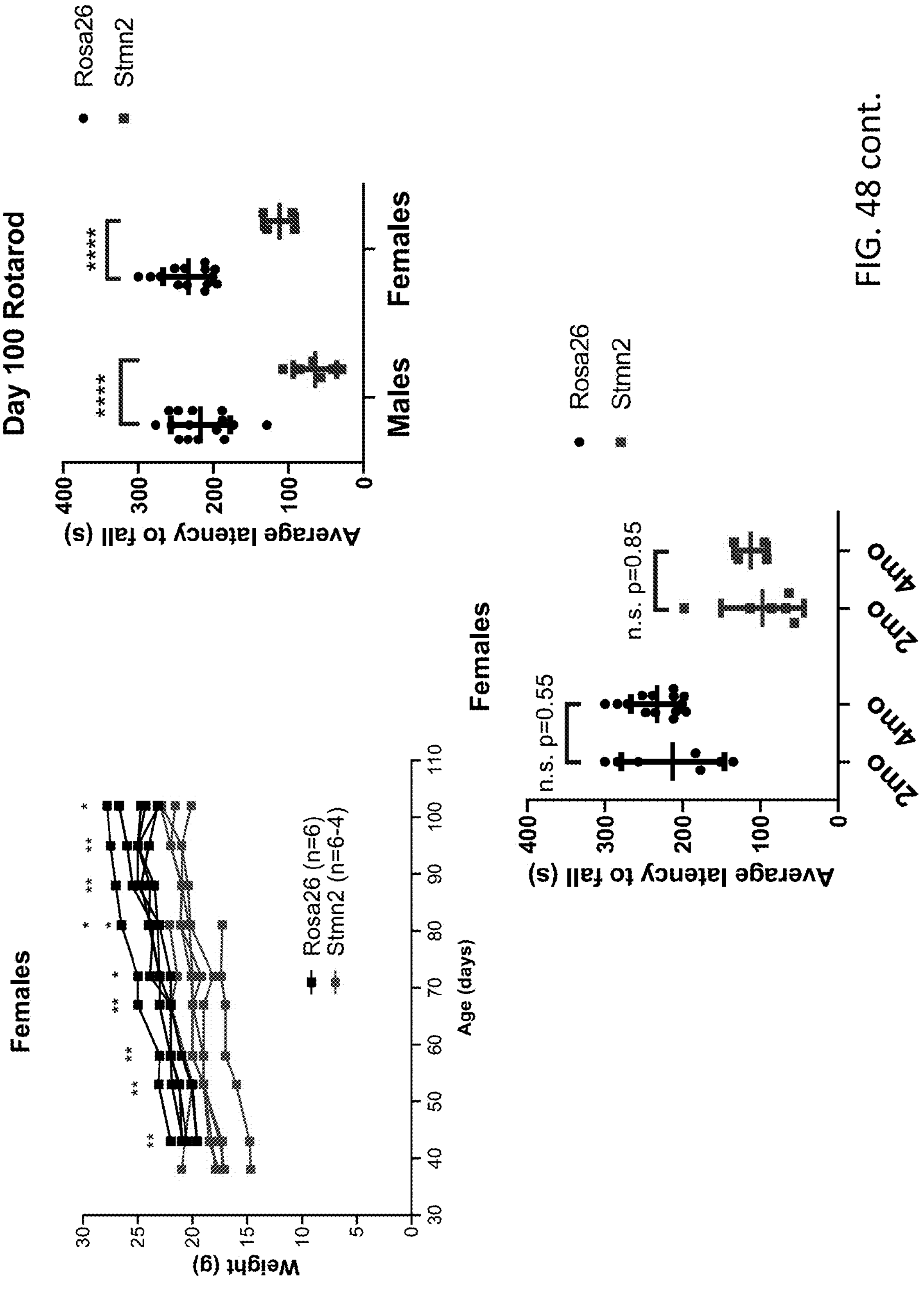

FIG. 48 demonstrates STMN2 mice are significantly smaller than Rosa26 control mice and show deficiencies in motor performance tasks with no signs of progression of these deficits over time.

Figure 49:
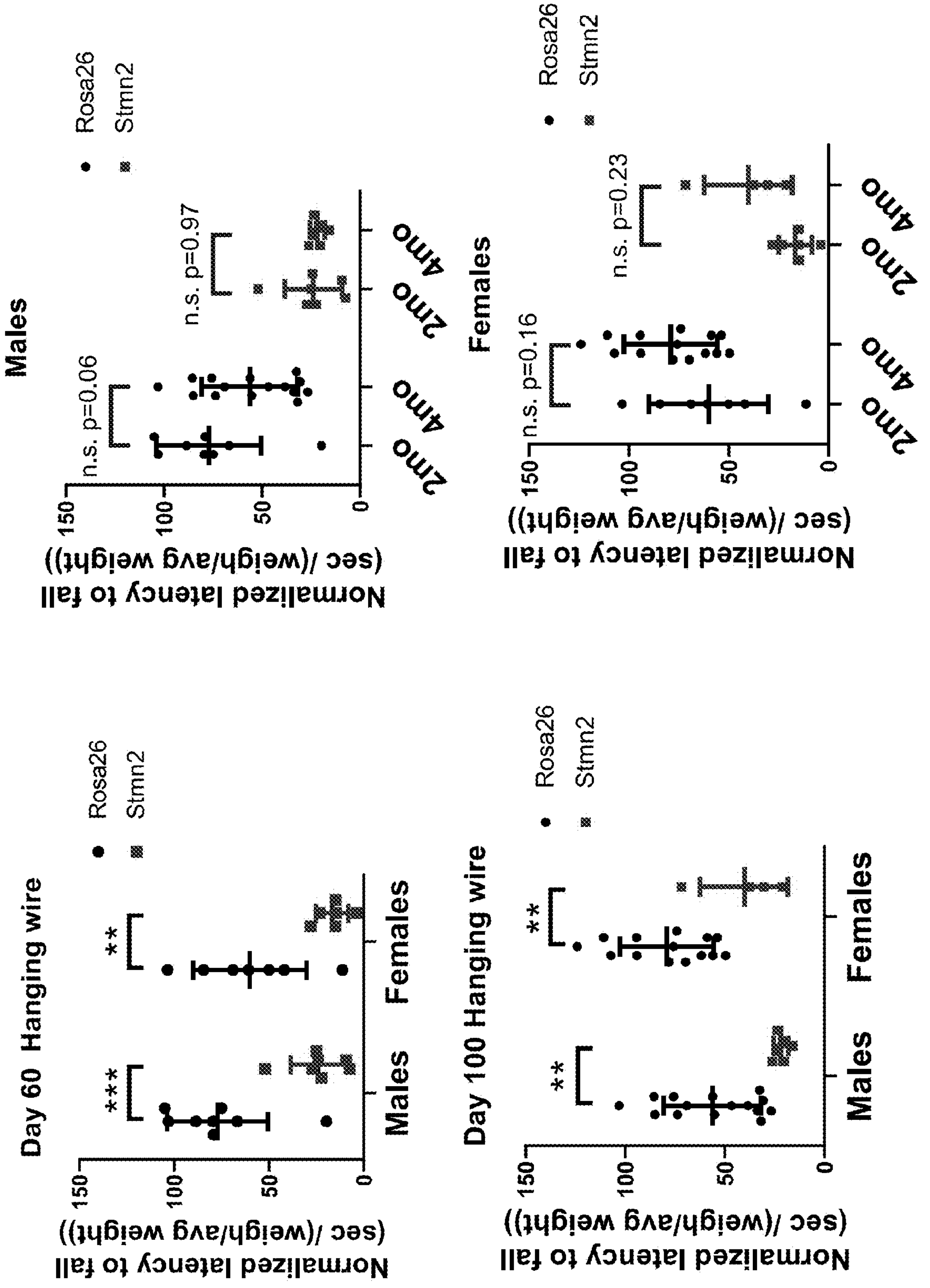
Figure 49:
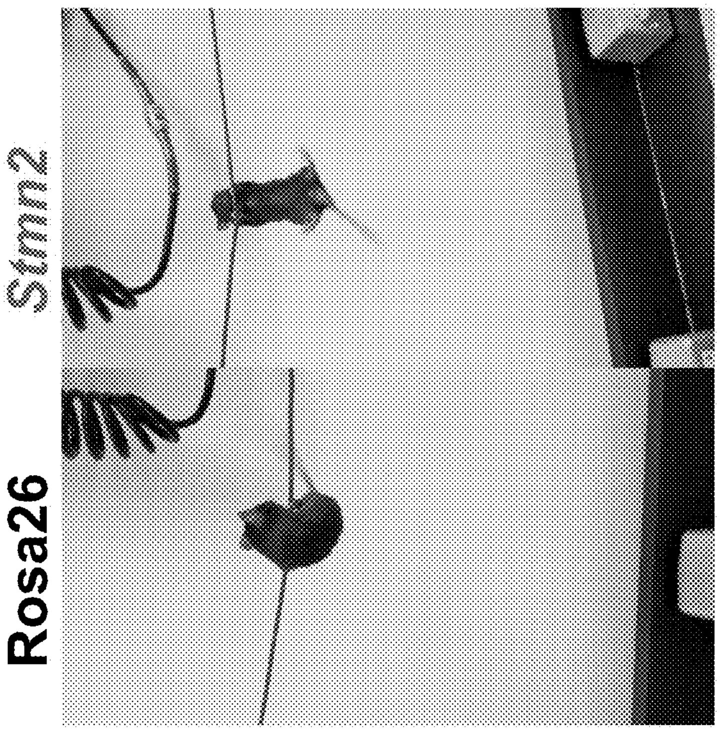

FIG. 49 demonstrates STMN2 mice are significantly smaller than Rosa26 control mice and show deficiencies in motor performance tasks with no signs of progression of these deficits over time.

Figure 50:
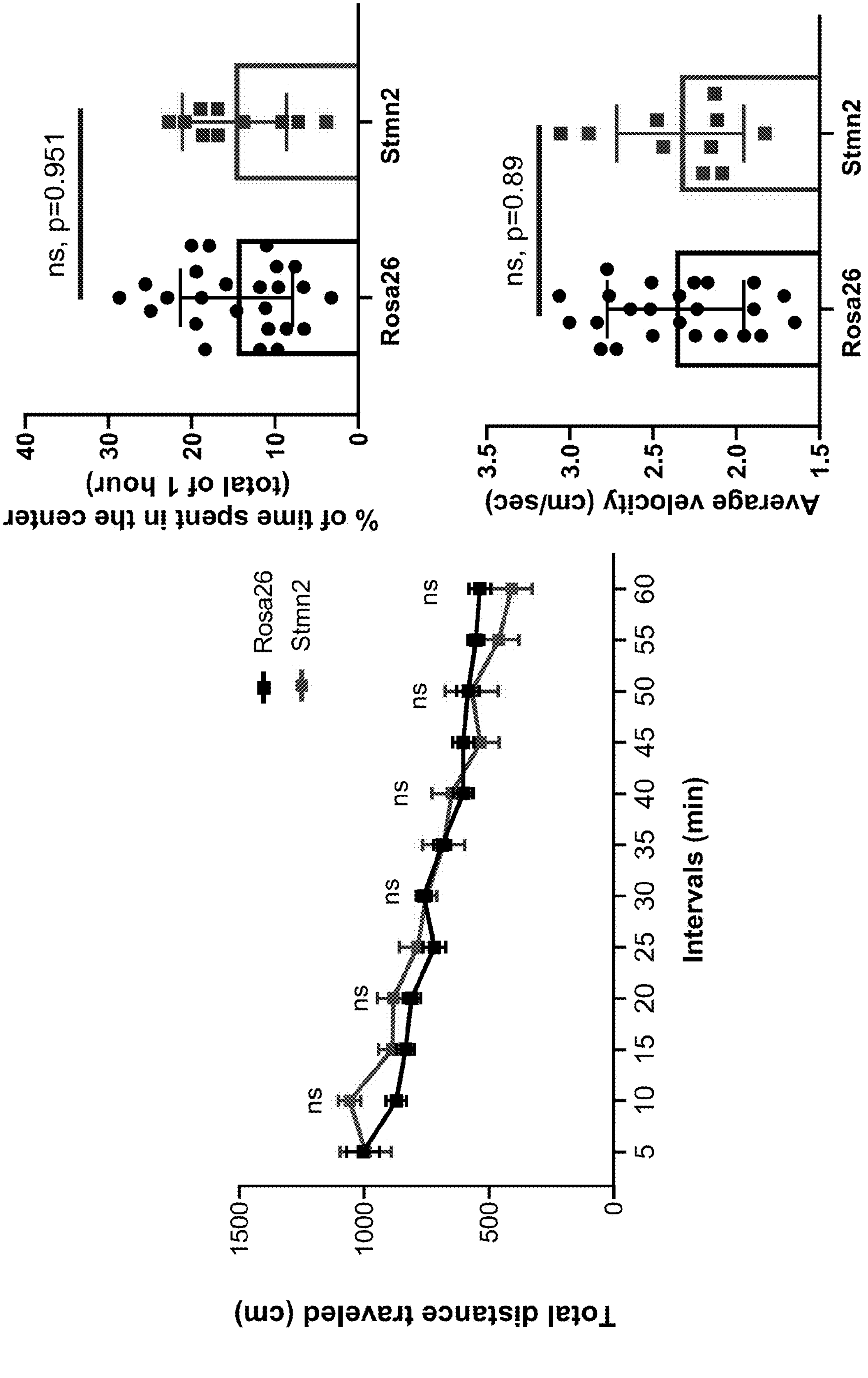

FIG. 50 demonstrates behavioral outcomes, as well as the total distance traveled in open field assays, appear to be similar between two mice cohorts.

Figure 51:
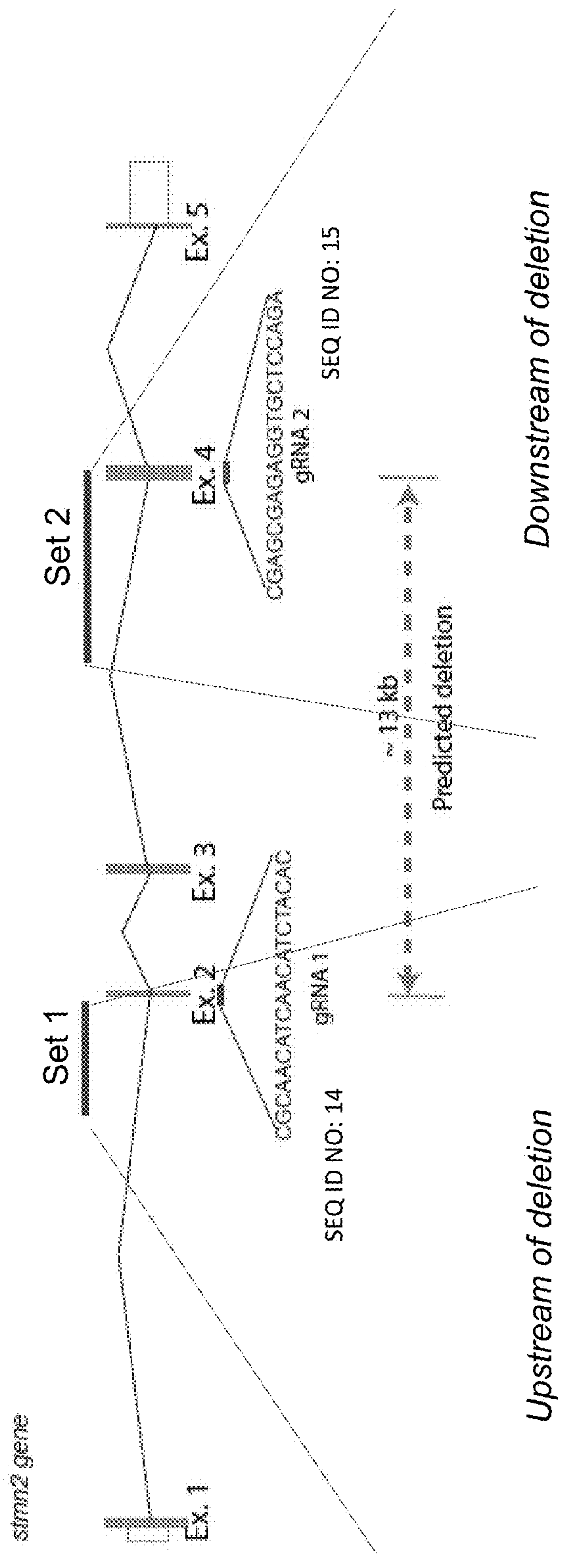
Figure 51:
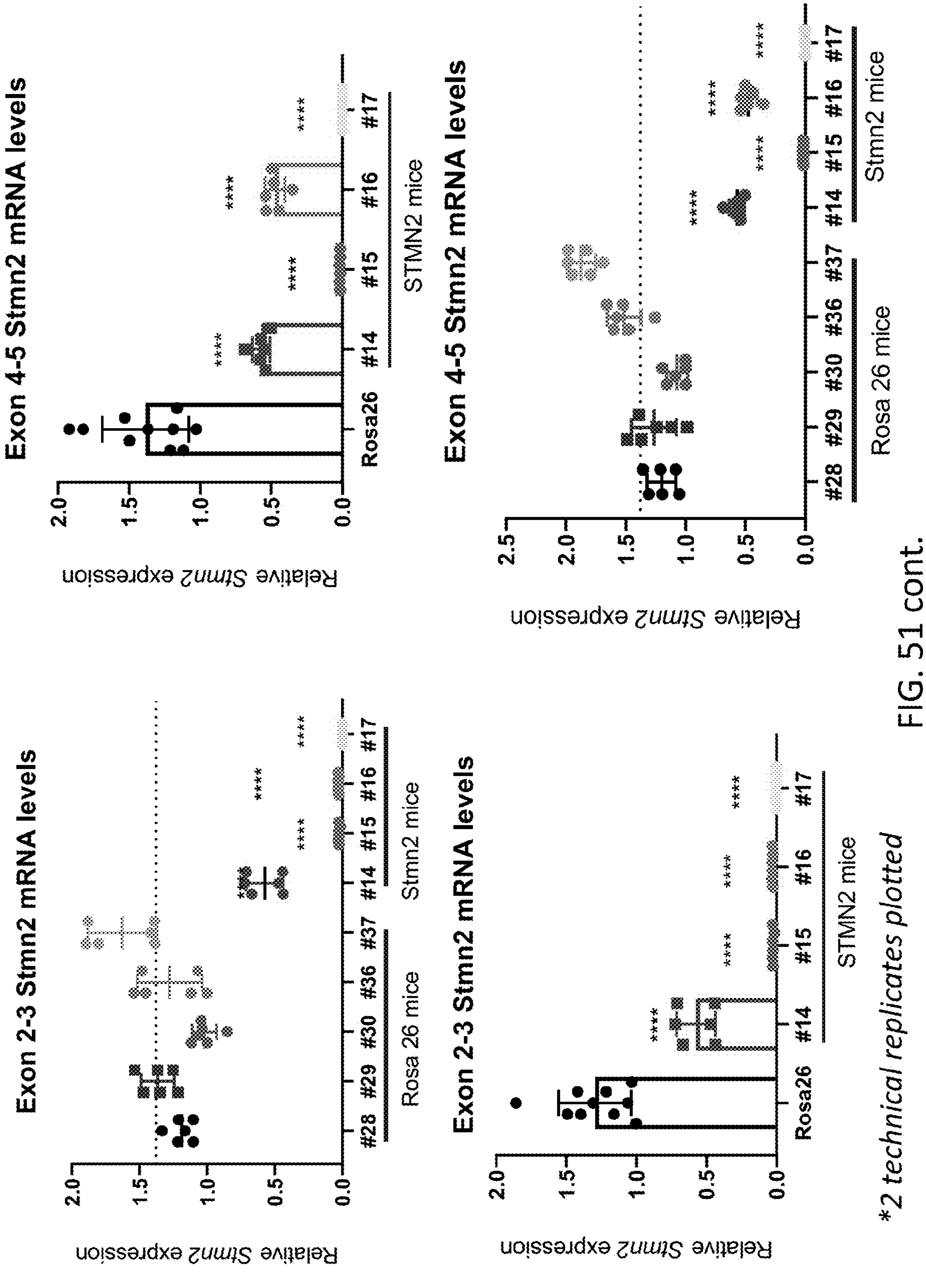

FIG. 51 demonstrates STMN2 transcript levels are significantly reduced or no transcript is present in brain tissue from mutant cohort.

Figure 52:
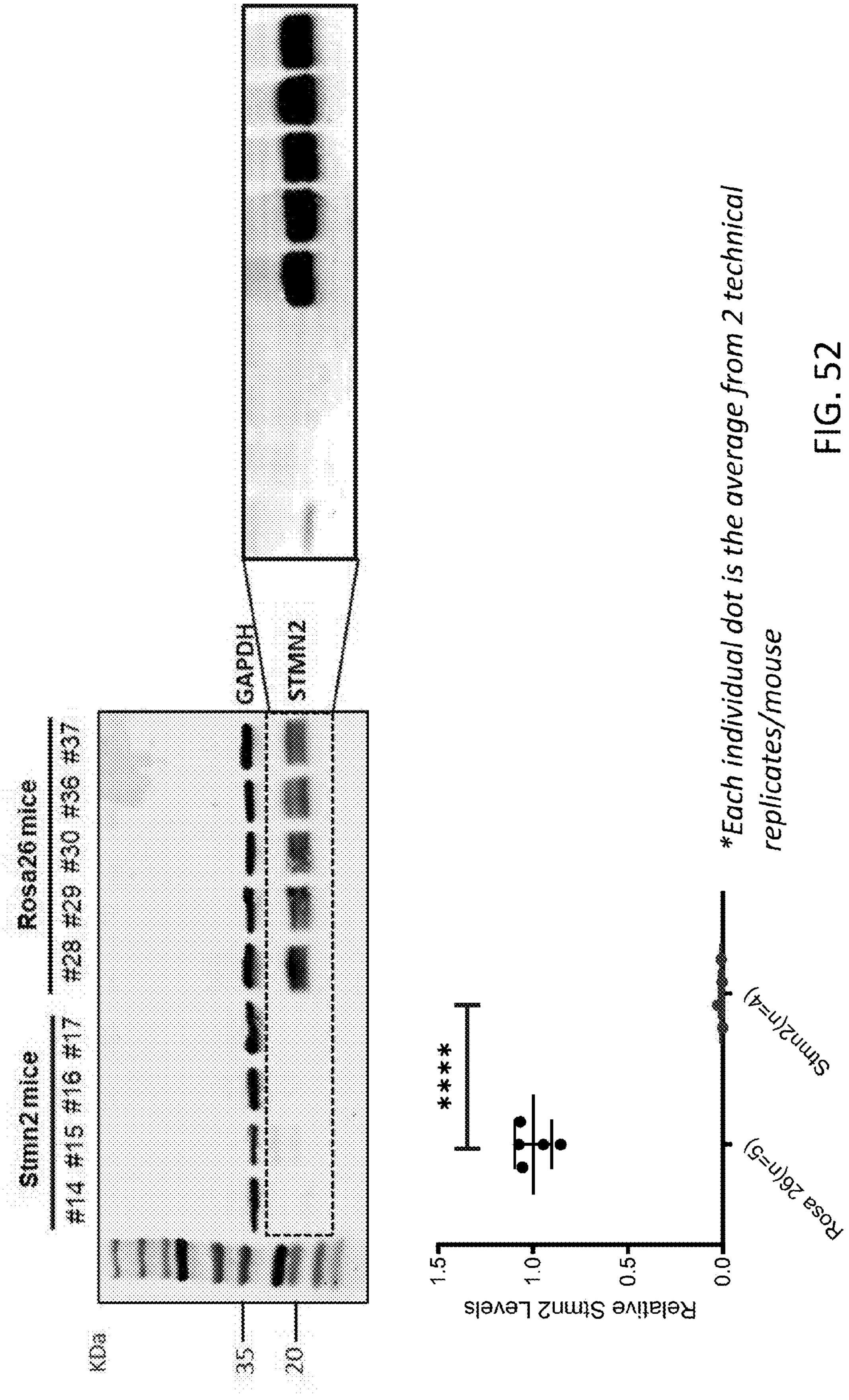

FIG. 52 provides Western Blot of brain tissue validating loss or significant reduction of STMN2 protein in mutant mice cohort.

Figure 53:
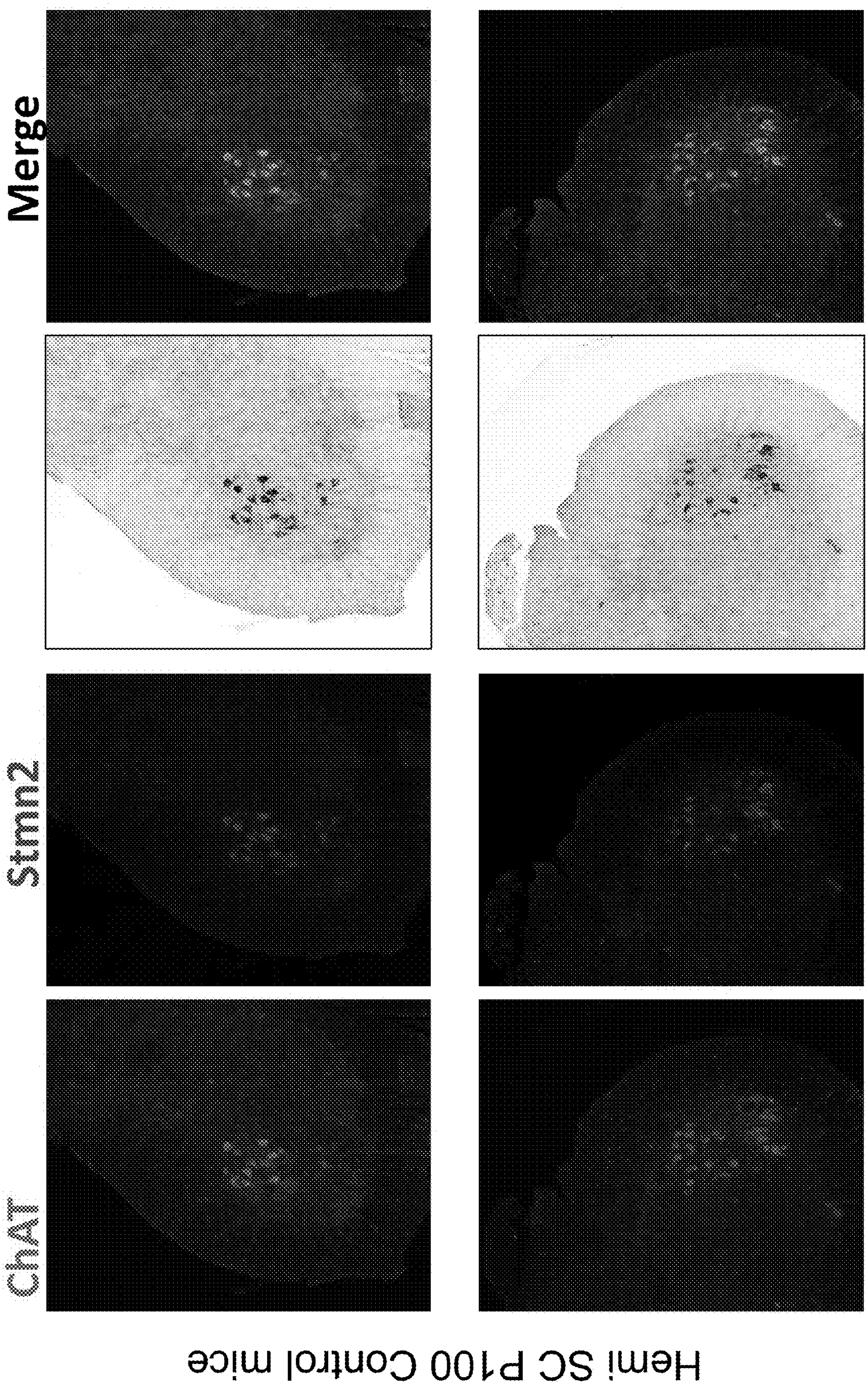

FIG. 53 demonstrates STMN2 primarily localizes to ChAT+ motor neurons in the ventral horn of adult mice spinal cords.

Figure 54:
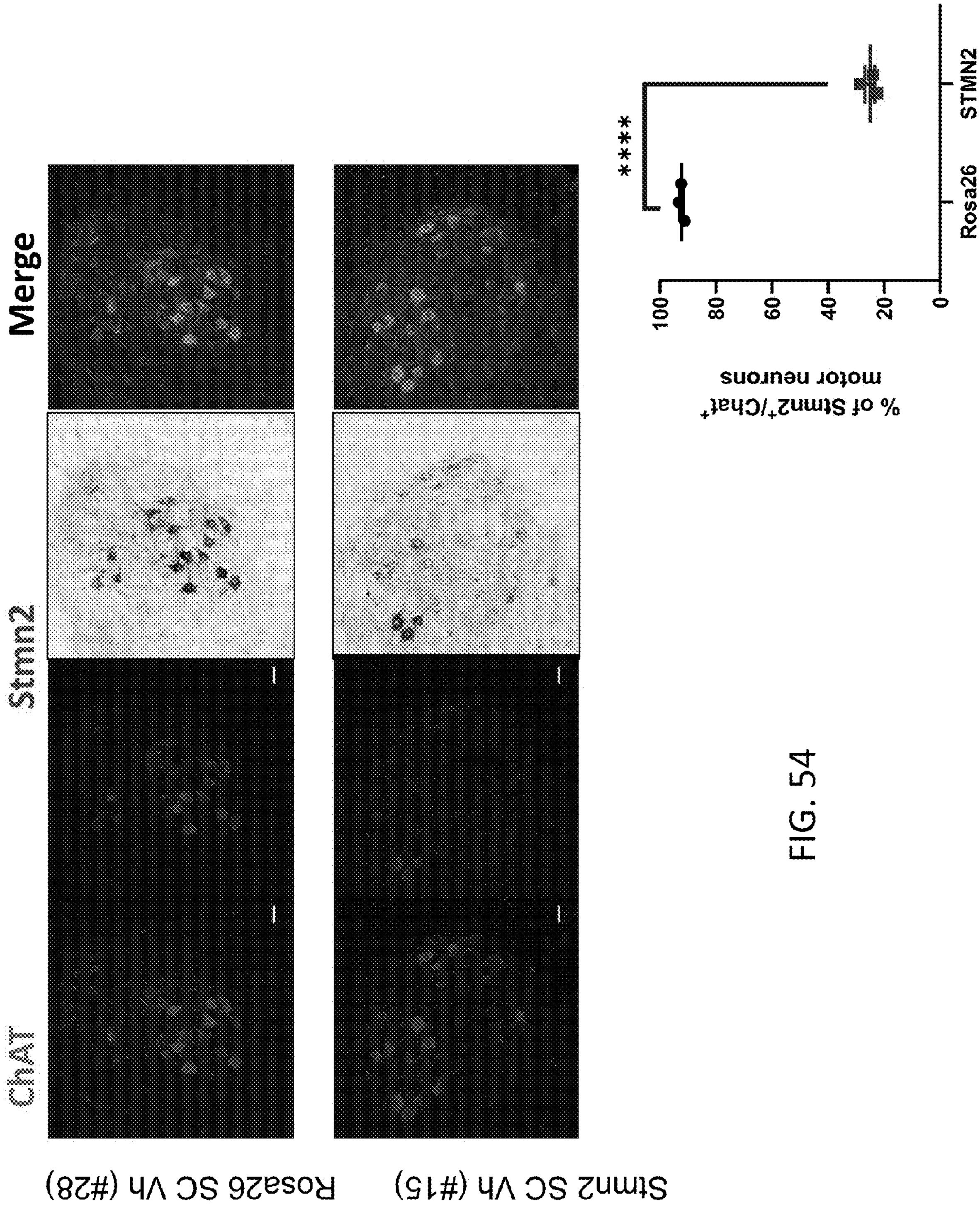

FIG. 54 demonstrates a STMN2 cohort exhibits a significant decrease in the number of STMN2+/ChAT+ motor neurons on the ventral horn of the spinal cord.

Figure 55:
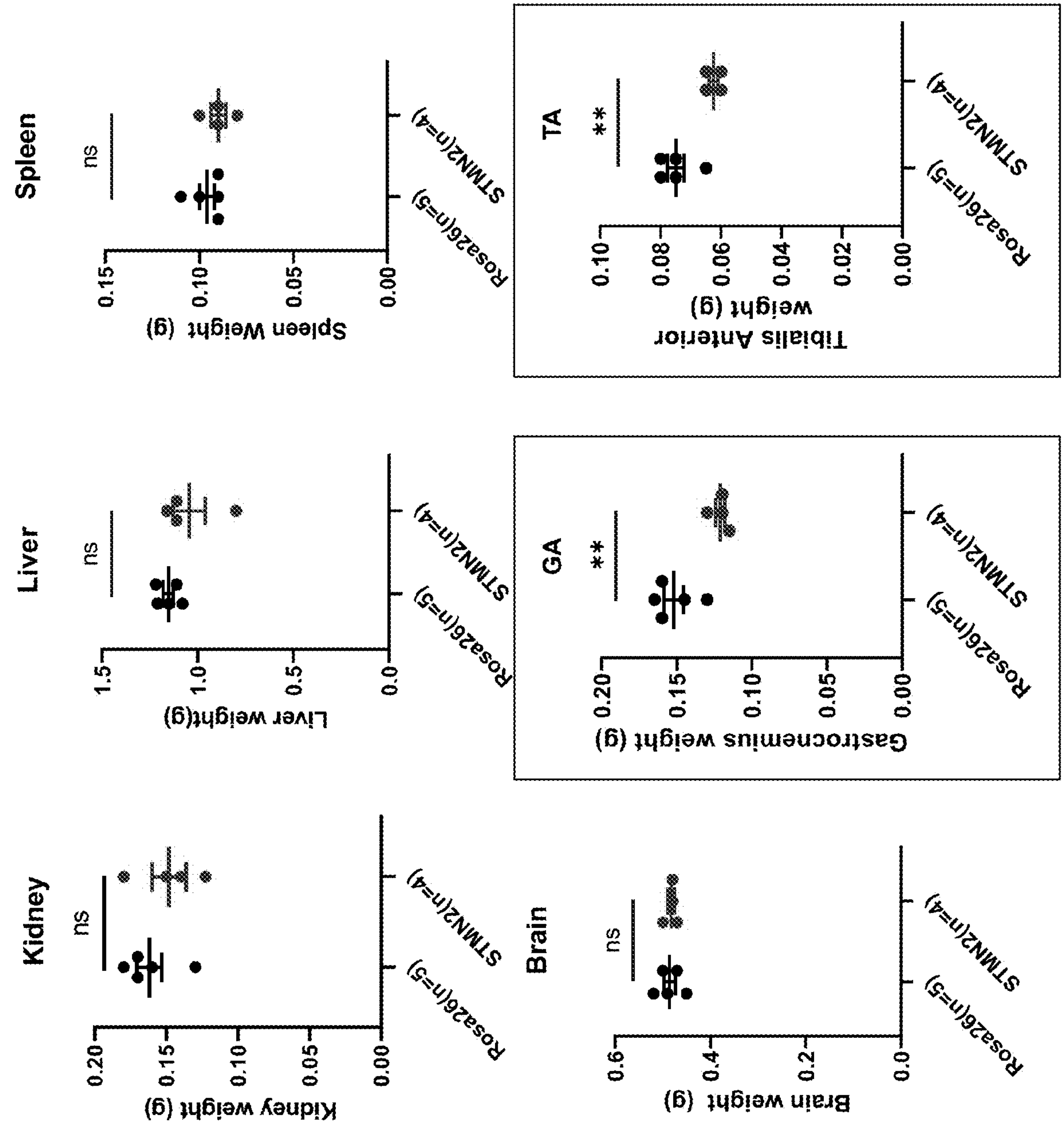

FIG. 55 provides graphs showing the difference in organ or muscle weight between control and STMN2 mice. It is demonstrated that lower limb muscles are lighter in STMN2 mice (see two boxed graphs).

Figure 56:
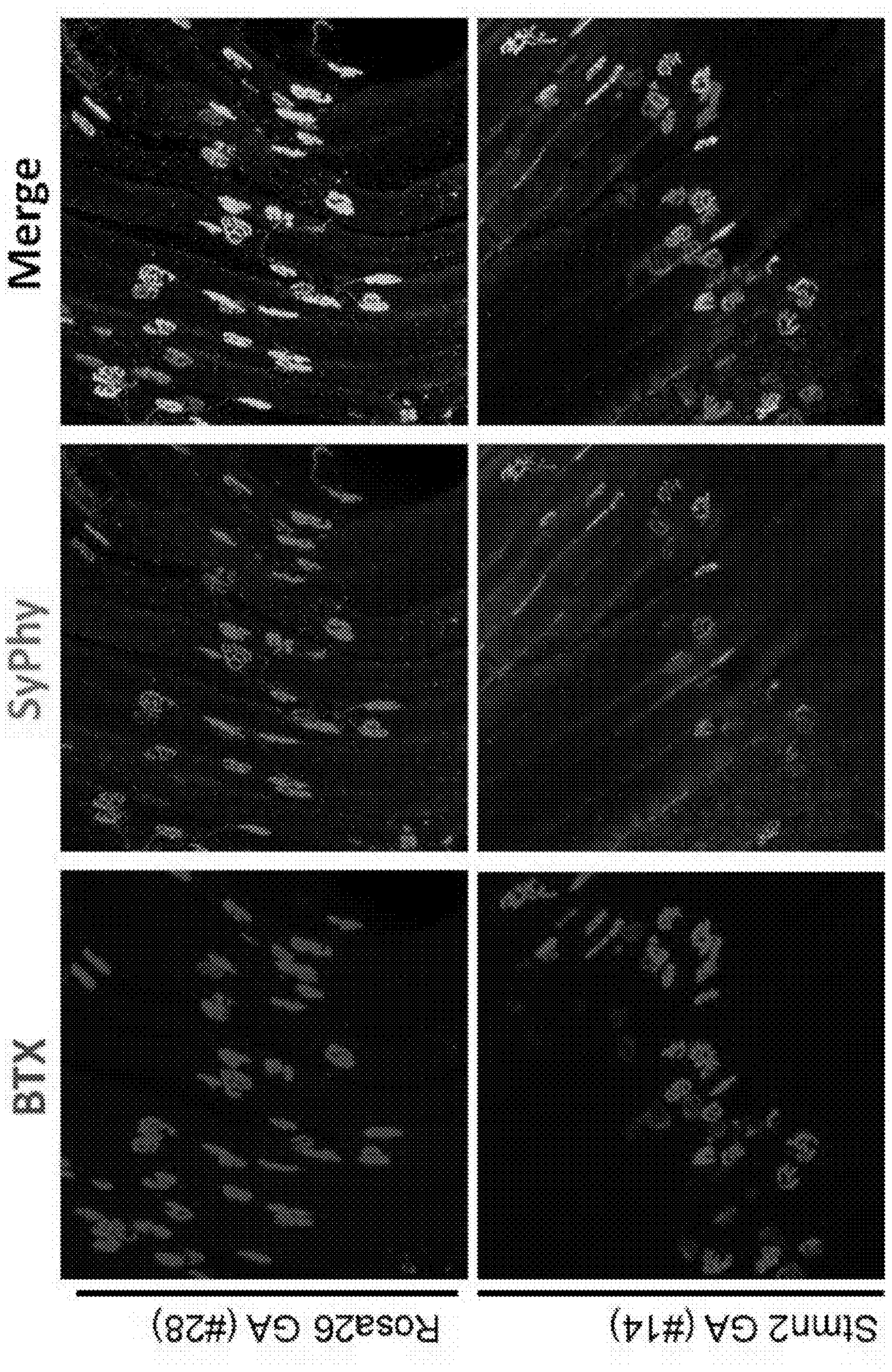

FIG. 56 provides pre- and post-synaptic staining of STMN2 gastrocnemius (GA) muscle and Rosa26 control gastrocnemius (GA) muscle. The staining suggests de-innervation in STMN2−/− animals.

Figure 57:
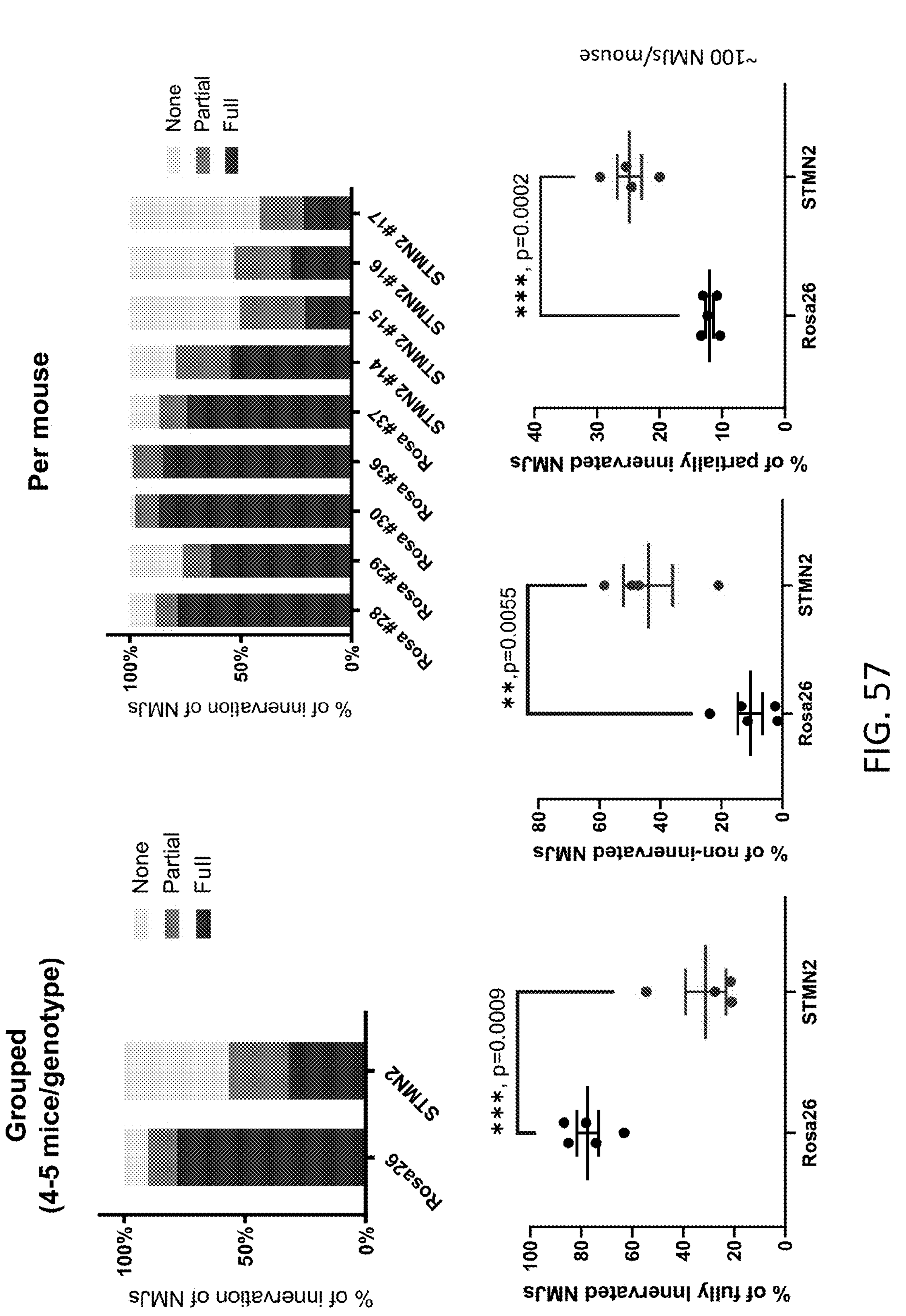

FIG. 57 demonstrates pre- and post-synaptic staining of STMN2 gastrocnemius (GA) muscle and Rosa26 control gastrocnemius (GA) muscle suggests de-innervation in STMN2−/− animals.

Figure 58:
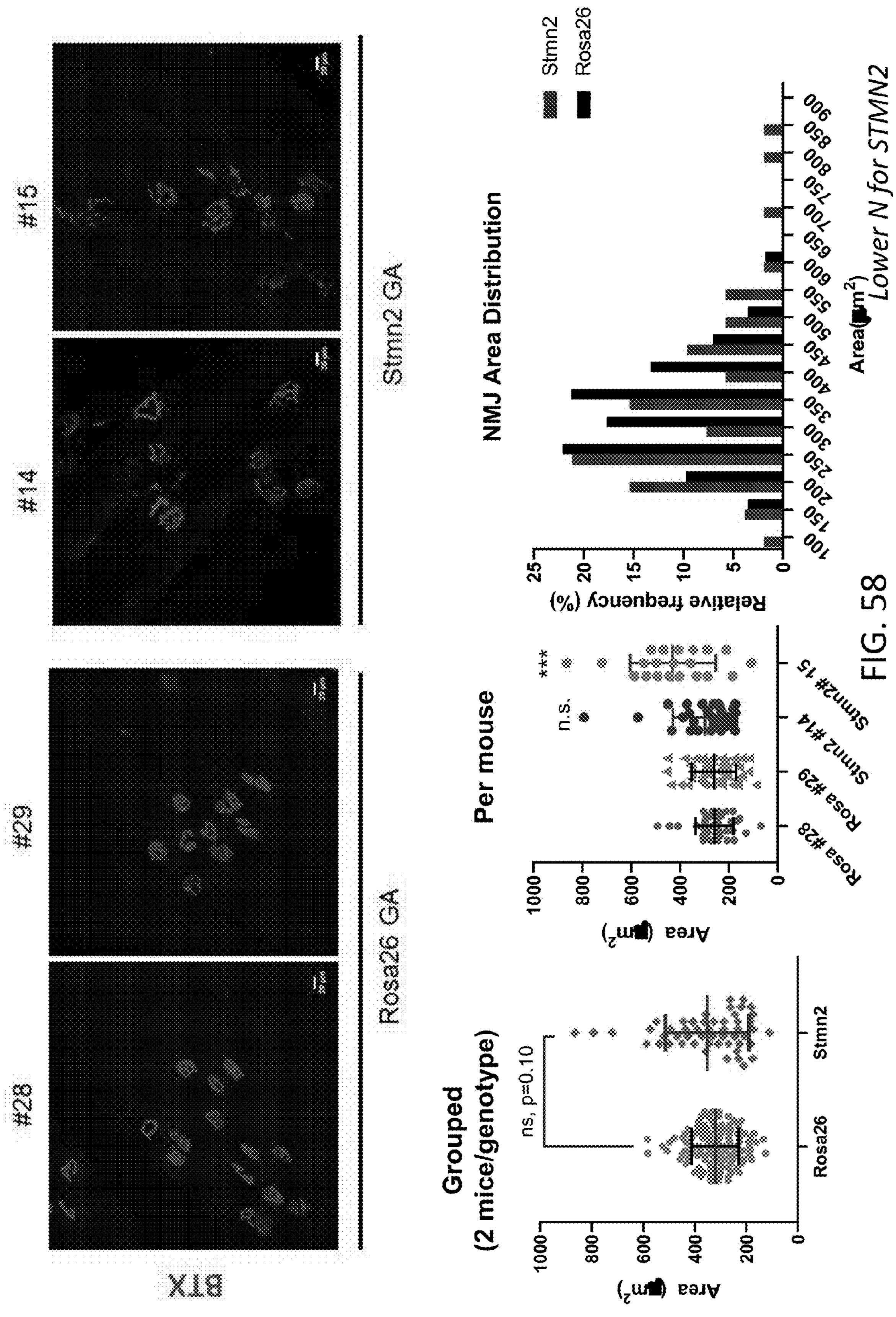

FIG. 58 demonstrates neuromuscular junction (NMJ) morphology supports active de-innervation in gastrocnemius muscle of STMN2 mutants.

Figure 59:
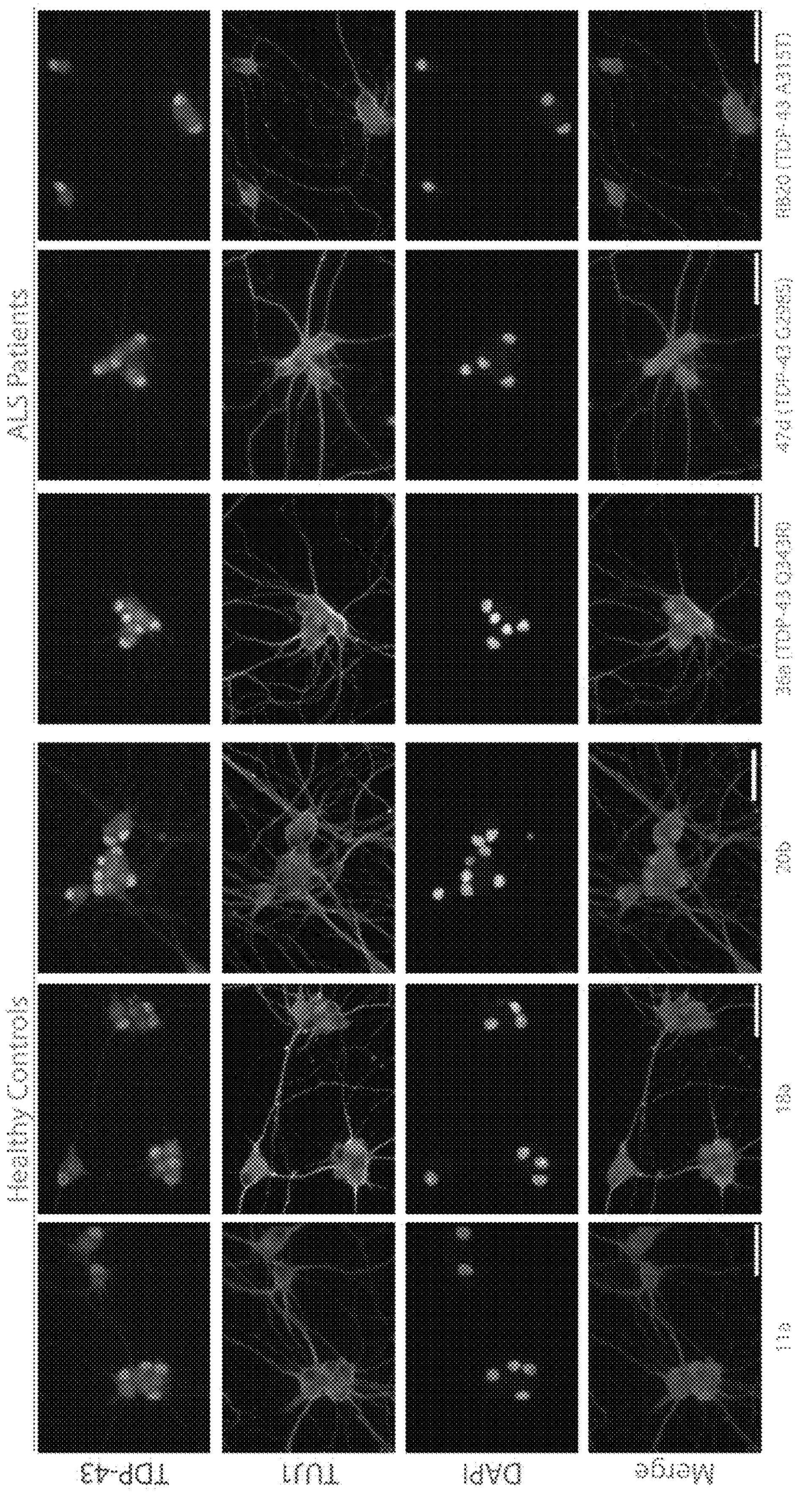

FIG. 59 demonstrates mutant TDP-43 does not display pathological mislocalization. Stains of control and ALS patient neurons for TDP-43 show that for both the control and ALS patient neurons TDP-43 was primarily nuclear.

Figure 60:
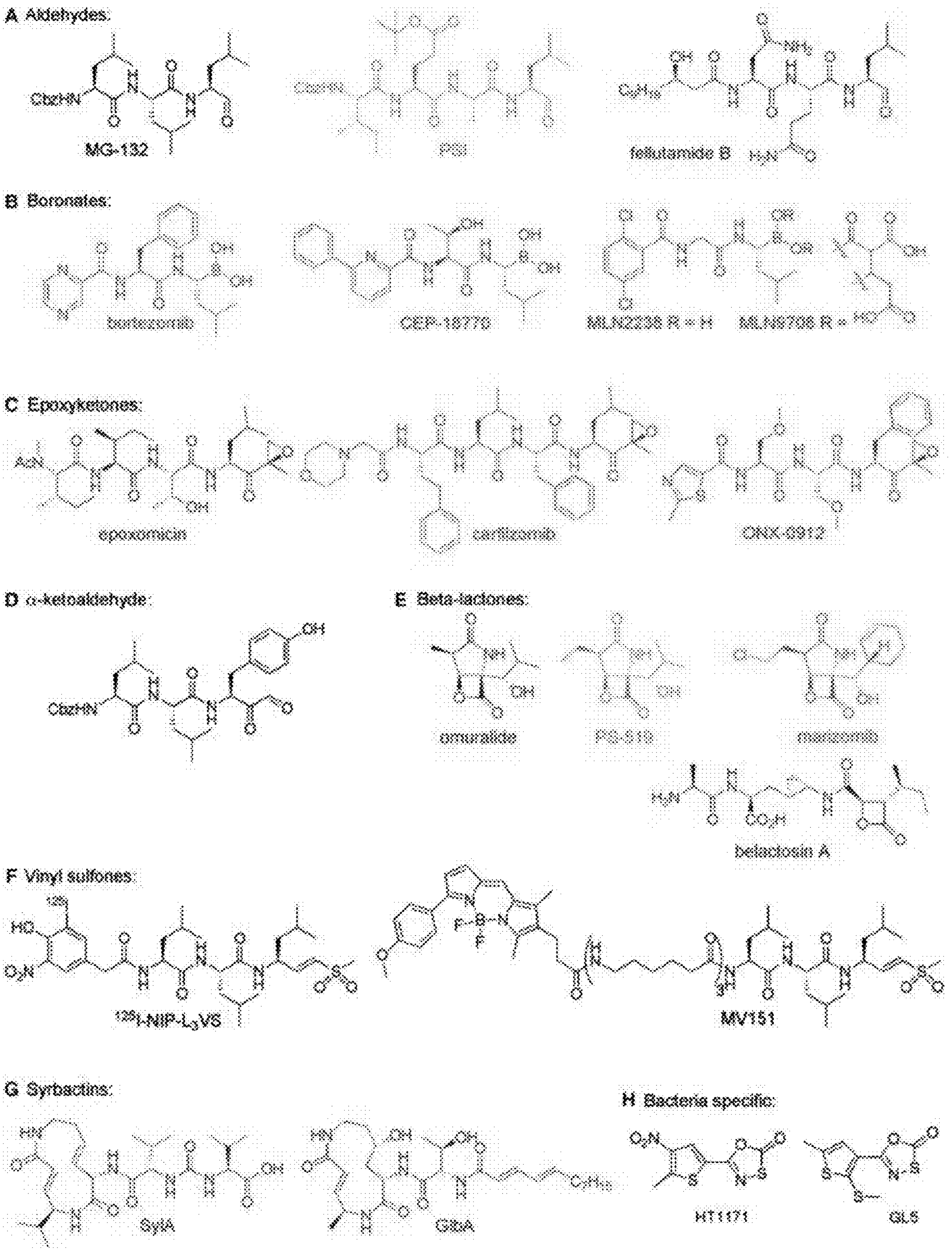

FIG. 60 identifies different classes of proteasome inhibitors and provides their chemical structures.

Figure 61:
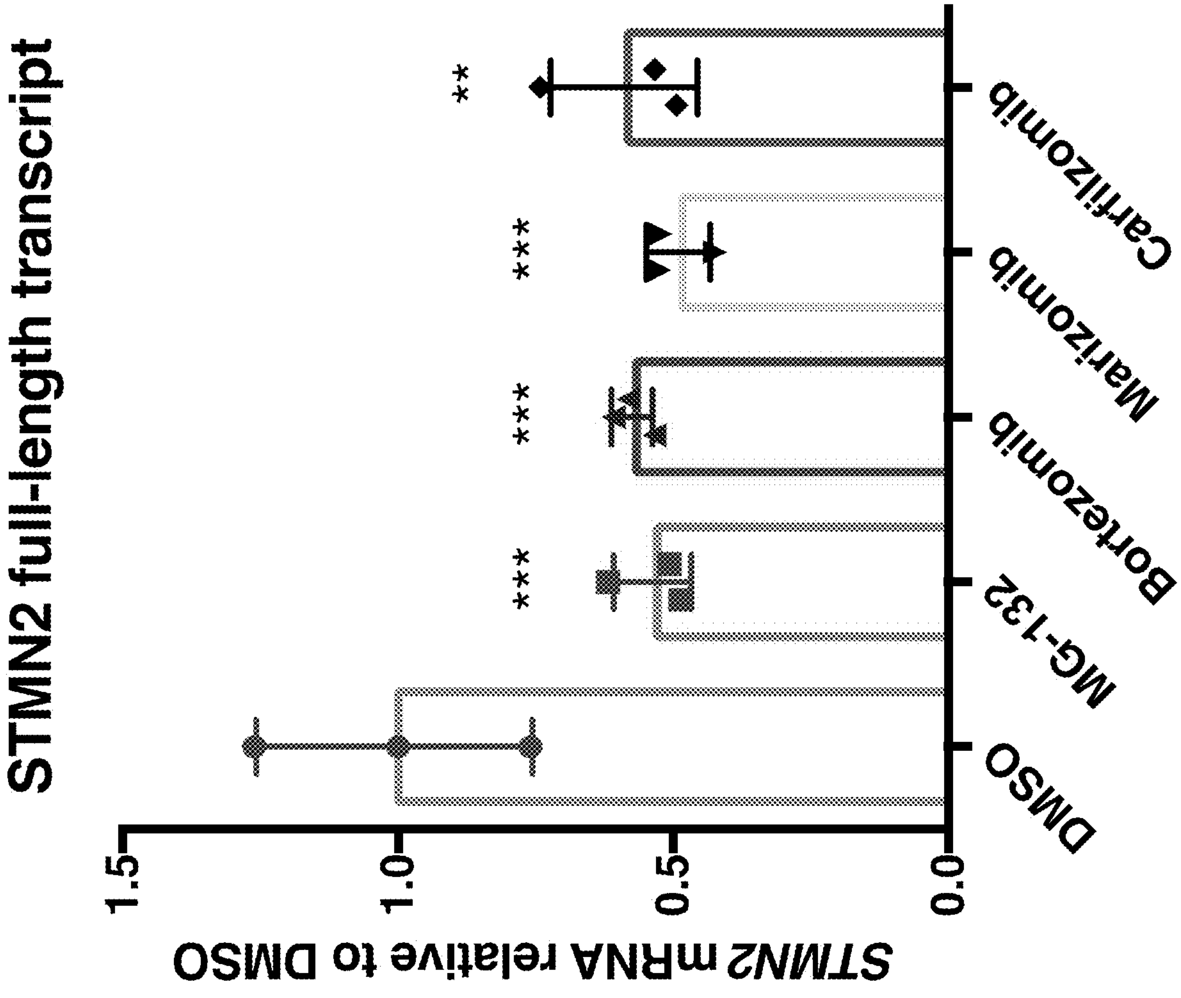

FIG. 61 shows decreased expression of full length STMN2 in hMNs upon treatment with structurally distinct proteasome inhibitors.

Figure 62:
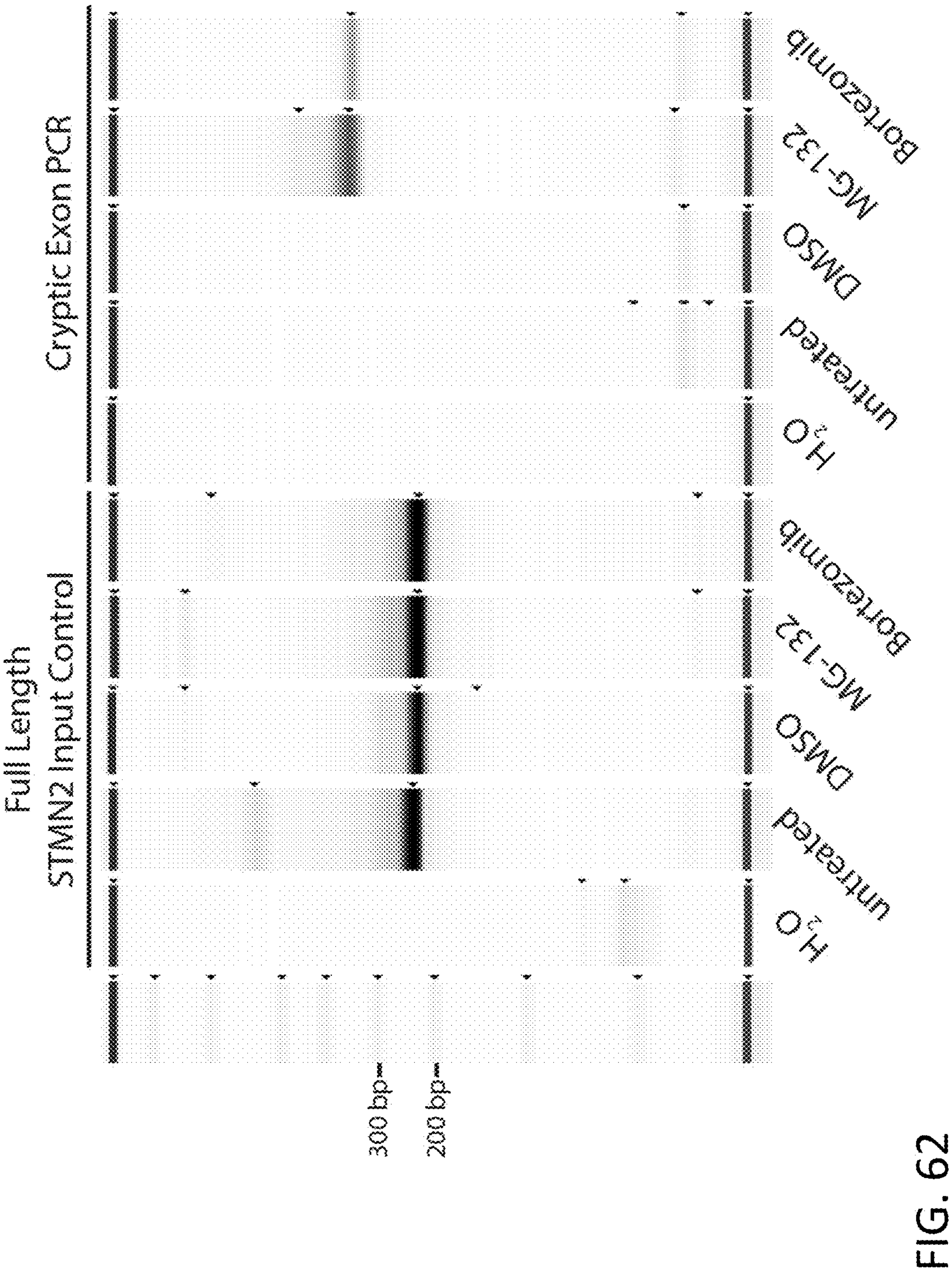

FIG. 62 shows a PCR assay of hMNs treated with MG-132 or Bortezomib. Full length STMN2 was detected in all samples as a control. The presence of transcripts containing the STMN2 cryptic exon were specific to those cells treated with the proteasome inhibitors.

Figure 63A:
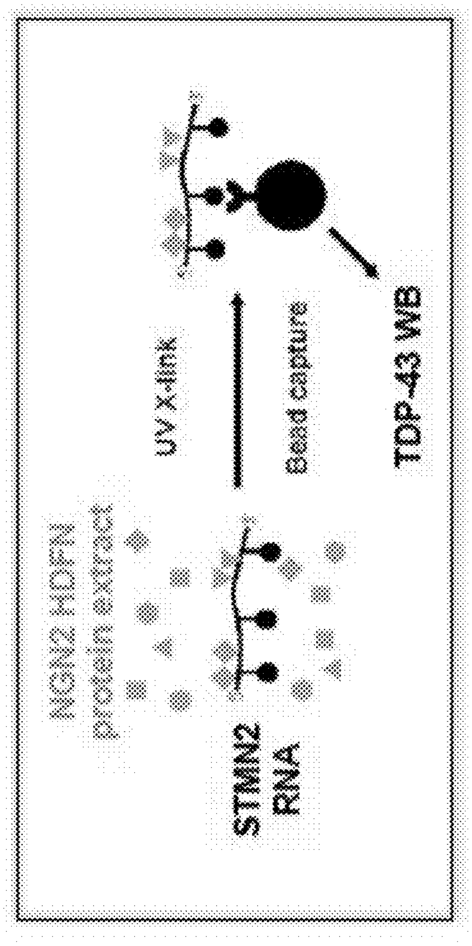
Figure 63B:
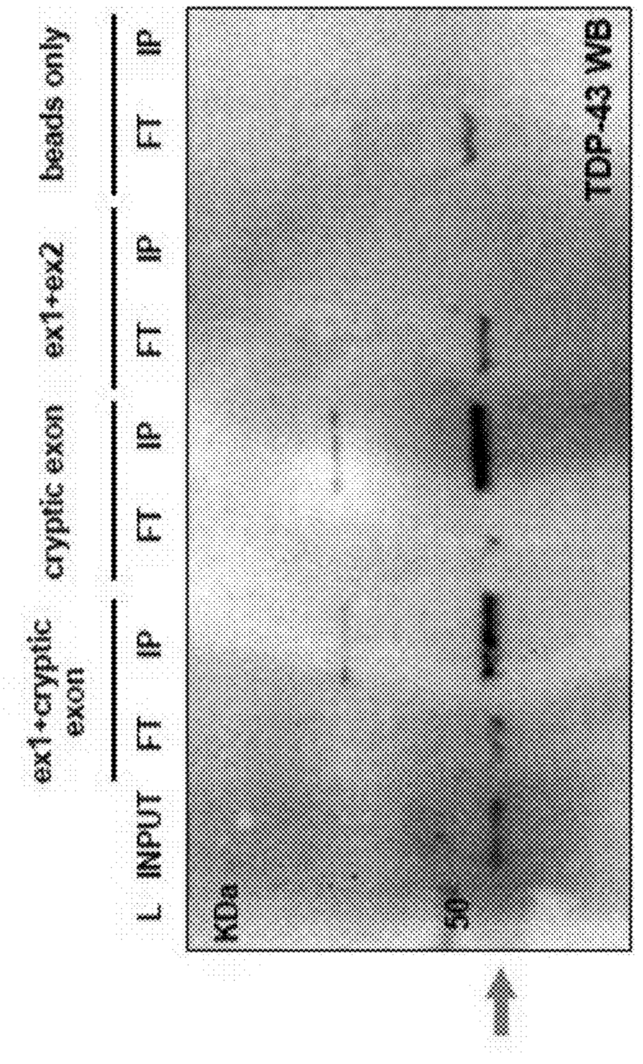

FIGS. 63A-63B demonstrate in vitro assay for TDP-43 binding to STMN2 RNA. Using genomic DNA, RNA containing the TDP-43 binding sites from the cryptic exon region of STMN2 was in vitro transcribed (FIG. 63A). The RNA was used to assess whether it could pull down IP TDP-43 protein from human neuronal protein lysates. The in vitro assay shows transcripts containing the cryptic exon region pulled down TDP-43 (FIG. 63B).

Figure 64:
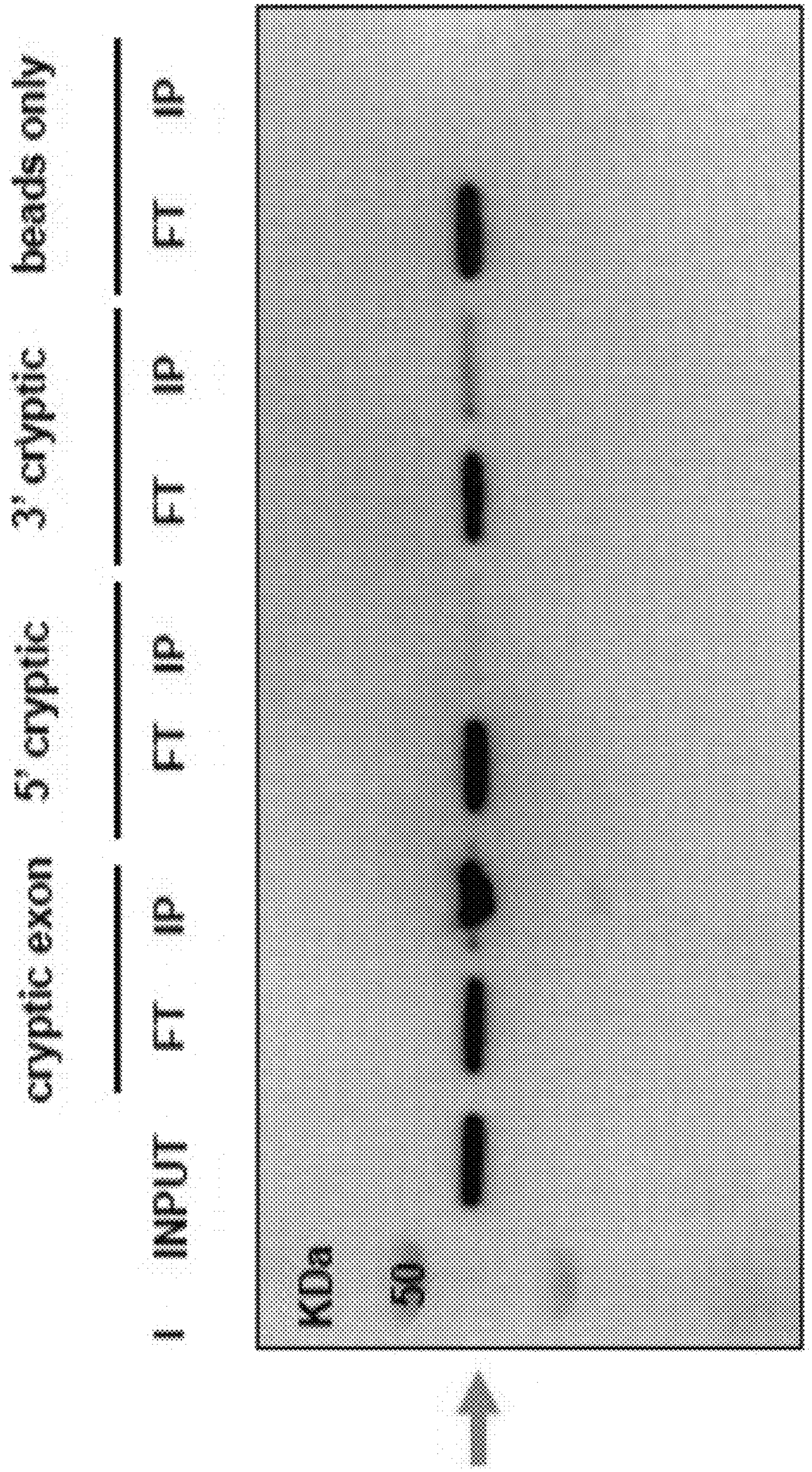

FIG. 64 shows an in vitro assay for TDP-43 binding to STMN2 RNA. RNA containing the 5' and 3' TDP-43 binding regions were in vitro transcribed similar that described in FIG. 63. Although both 5' and 3' transcripts can pull down some TDP-43, the enrichment is not as strong as the full cryptic exon.

Figure 65:
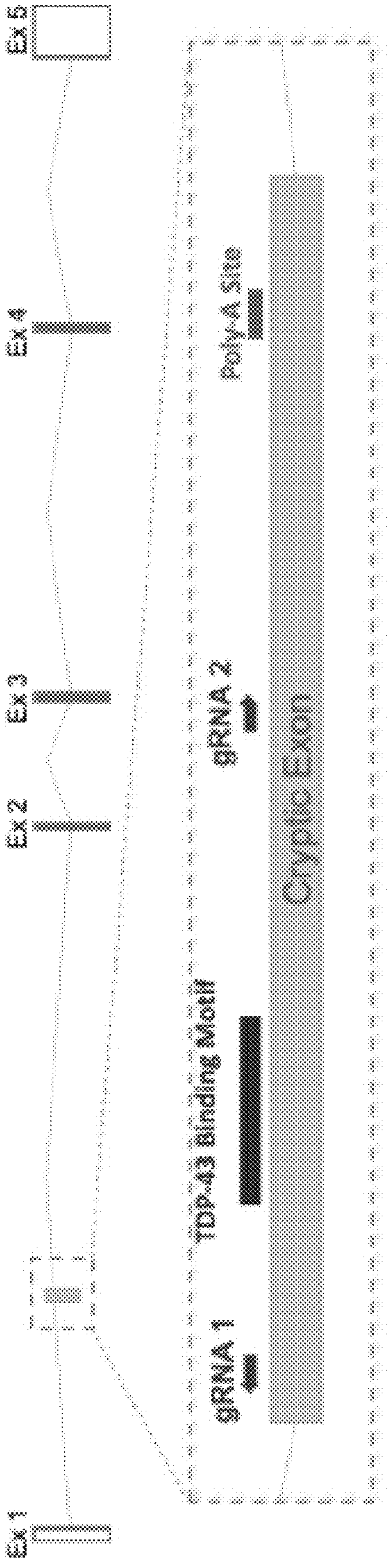

FIG. 65 shows design of gRNAs for generation of targeted mutant cell line with no cryptic exon. A strategy was prepared to delete 105 nucleotides within the cryptic exon within STMN2 intron between exons 1 and 2. The deletion will eliminate the TDP-43 binding motif, but not affect the predicted poly-adenylation site.

Figure 66:
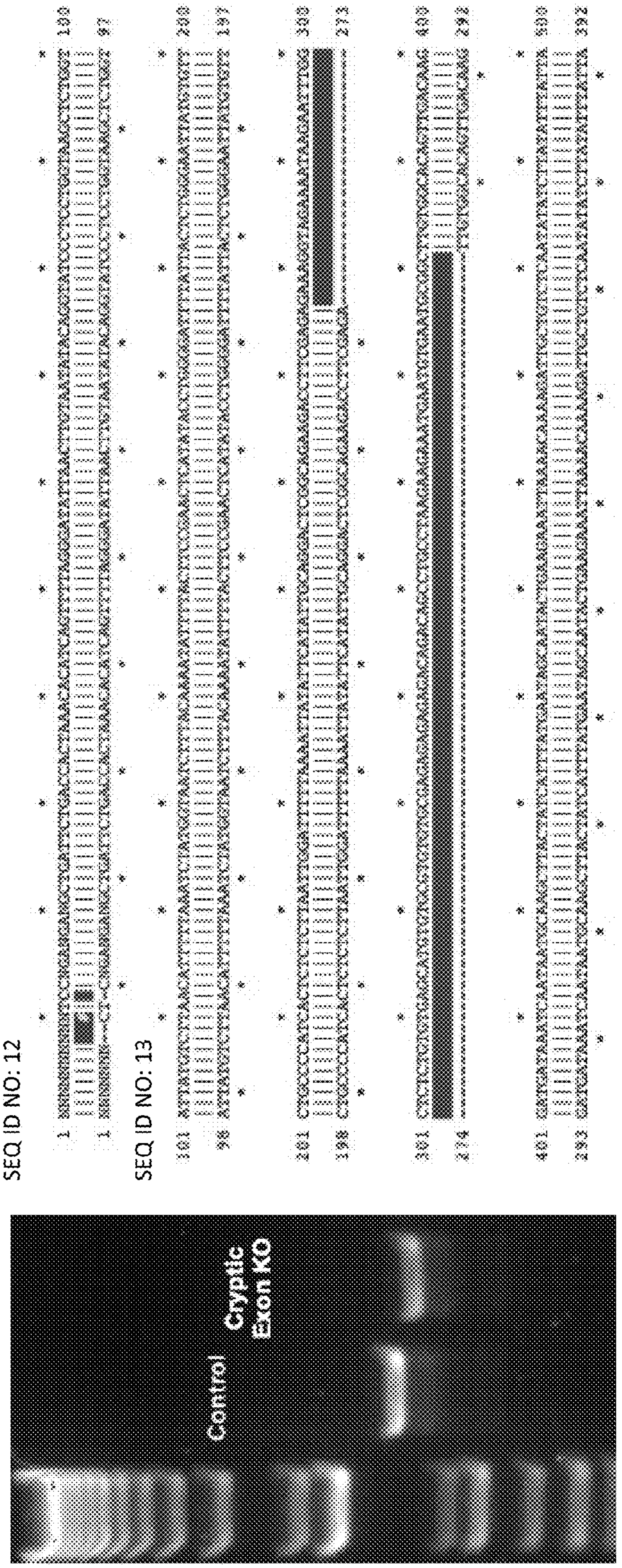

FIG. 66 provides a confirmation of mutational status. TIDE analysis was used to analyze the mutational status of the clones and checked the sequence alignment to control cells to obtain a more precise view of the size and location of the deletions. One cell line contained a homozygous 105 nt deletion, which was consistent with the gel electrophoresis. The deletion eliminated the TDP-43 binding motif, but did not affect the predicted poly-adenylation site.

Figure 67:
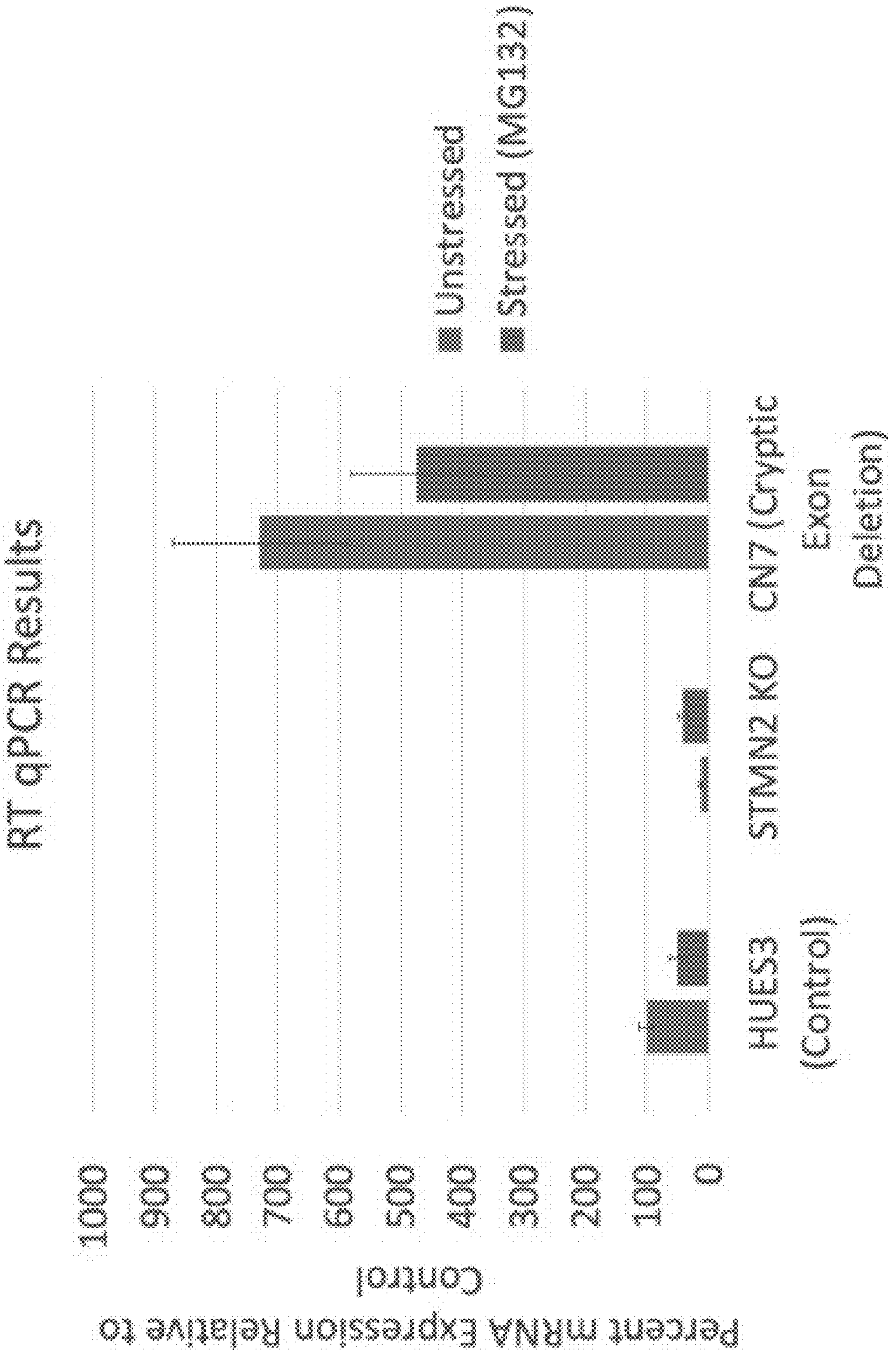

FIG. 67 shows TDP-43 binding site is a potential negative regulator of STMN2 expression. Three cell lines, HUES3, IG2 (Stmn2 KO), and CN7 (cryptic exon deletion) were treated with normal media or media+1 uM MG132 for 24 hours to stress the cells. In HUES3 cells, the stressed condition had 52% STMN2 mRNA expression compared to the unstressed condition. In IG2 (Stmn2 KO) condition, unstressed cells had 13% expression, and when stressed, expression increased to 42%. The expression levels in the CN7 (Cryptic Exon Deletion) cell line were significantly higher than the other two cell lines, with unstressed having 729% and stressed having 473% expression. It was shown that if several exons are knocked out the expression goes down, but if the TDP-43 binding site is removed, expression goes way up.

Figure 68A:
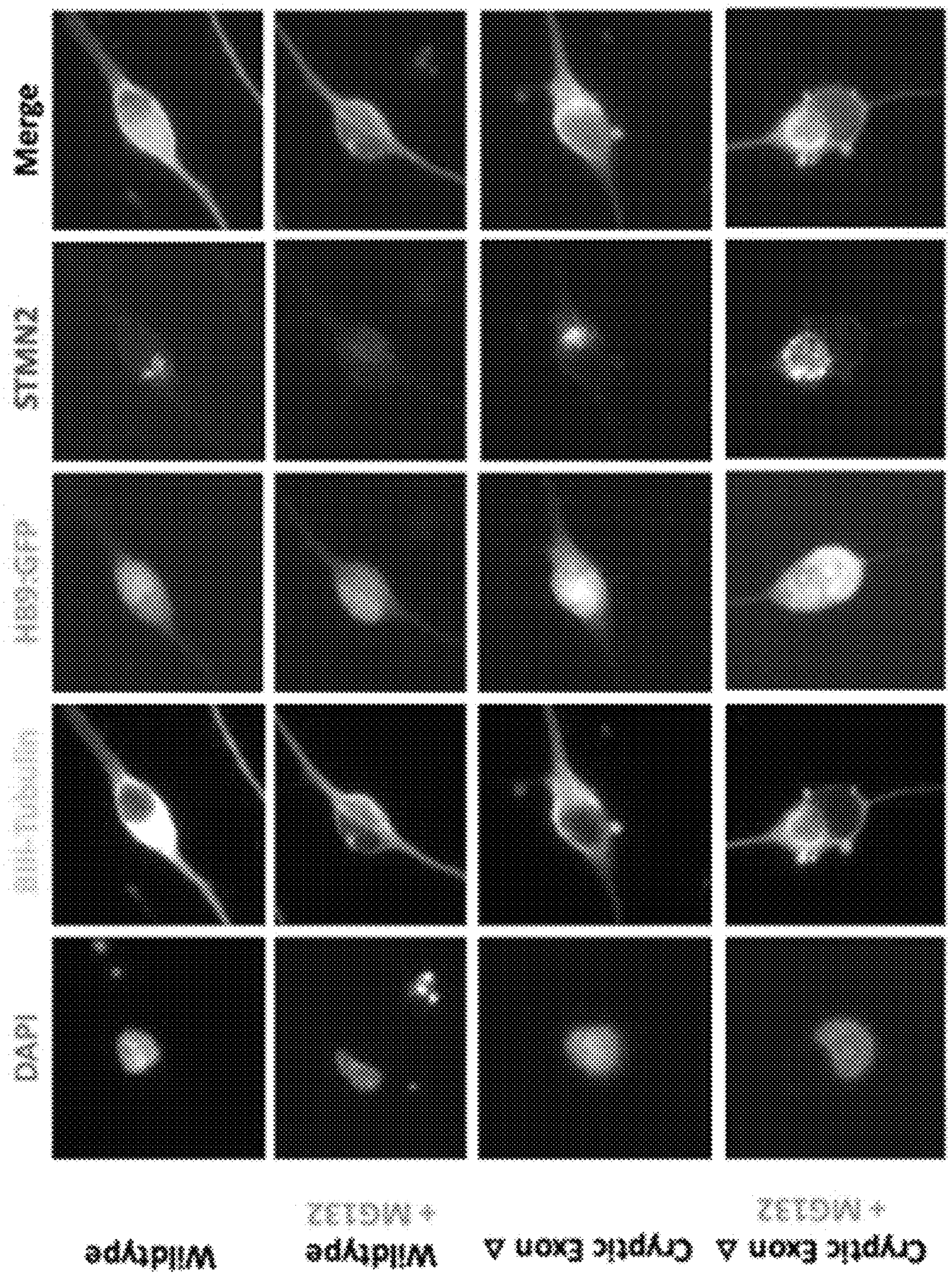
Figure 68B:
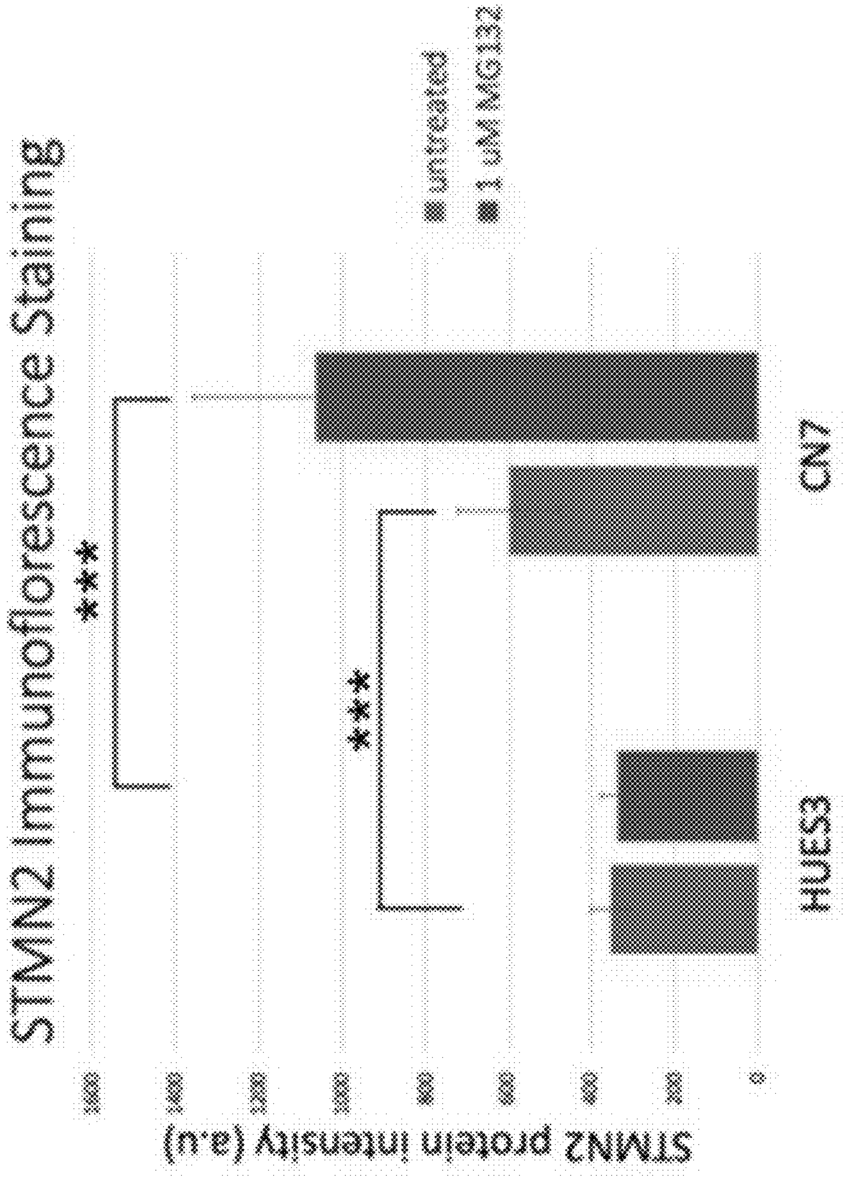

FIGS. 68A-68B demonstrate deletion of putative TDP-43 binding site leads to increased STMN2 protein levels. Consistent with the gene expression data, deletion of the TDP-43 binding region within the STMN2 cryptic exon causes increased protein expression.

Figure 69A:
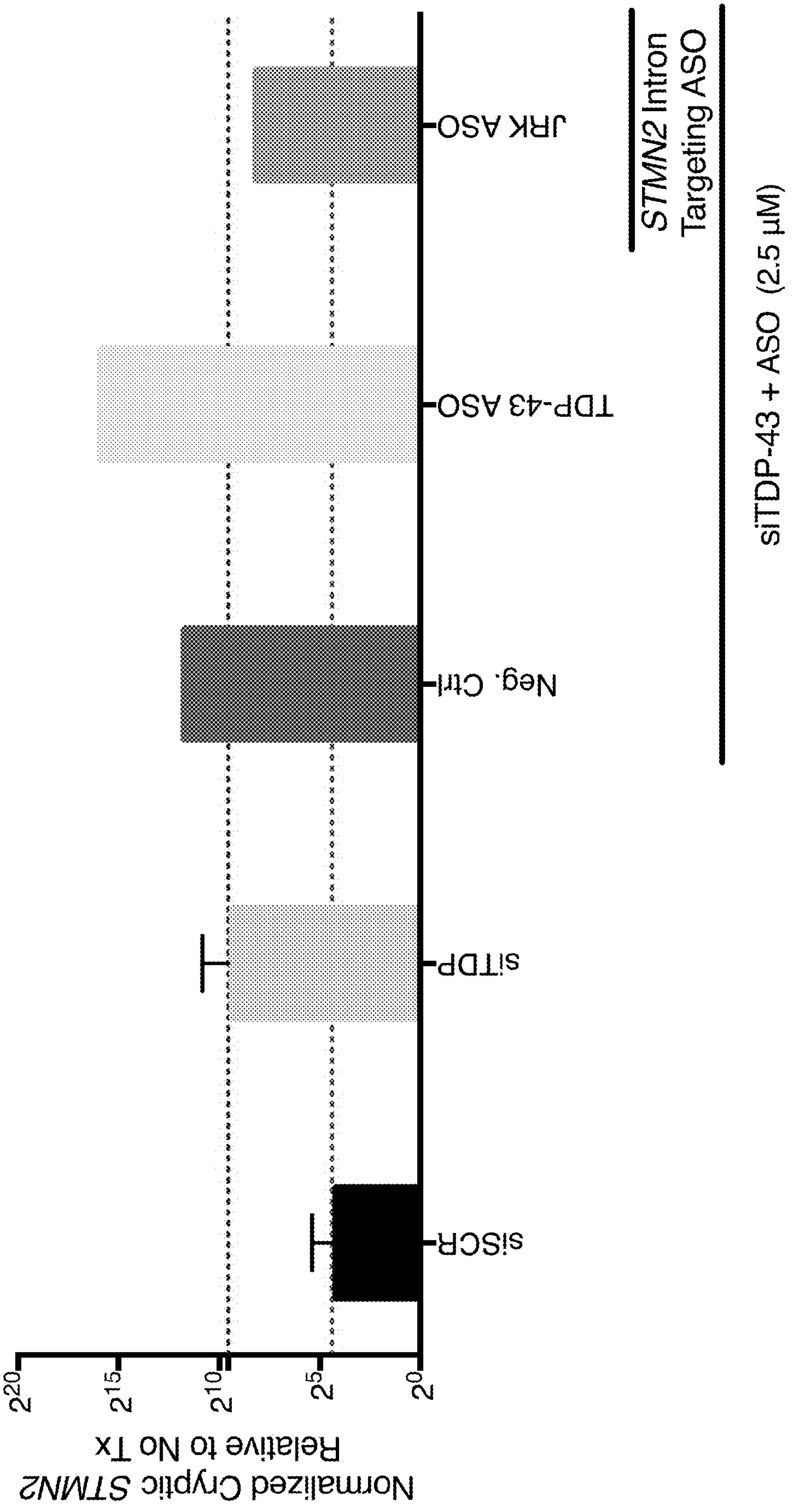
Figure 69B:
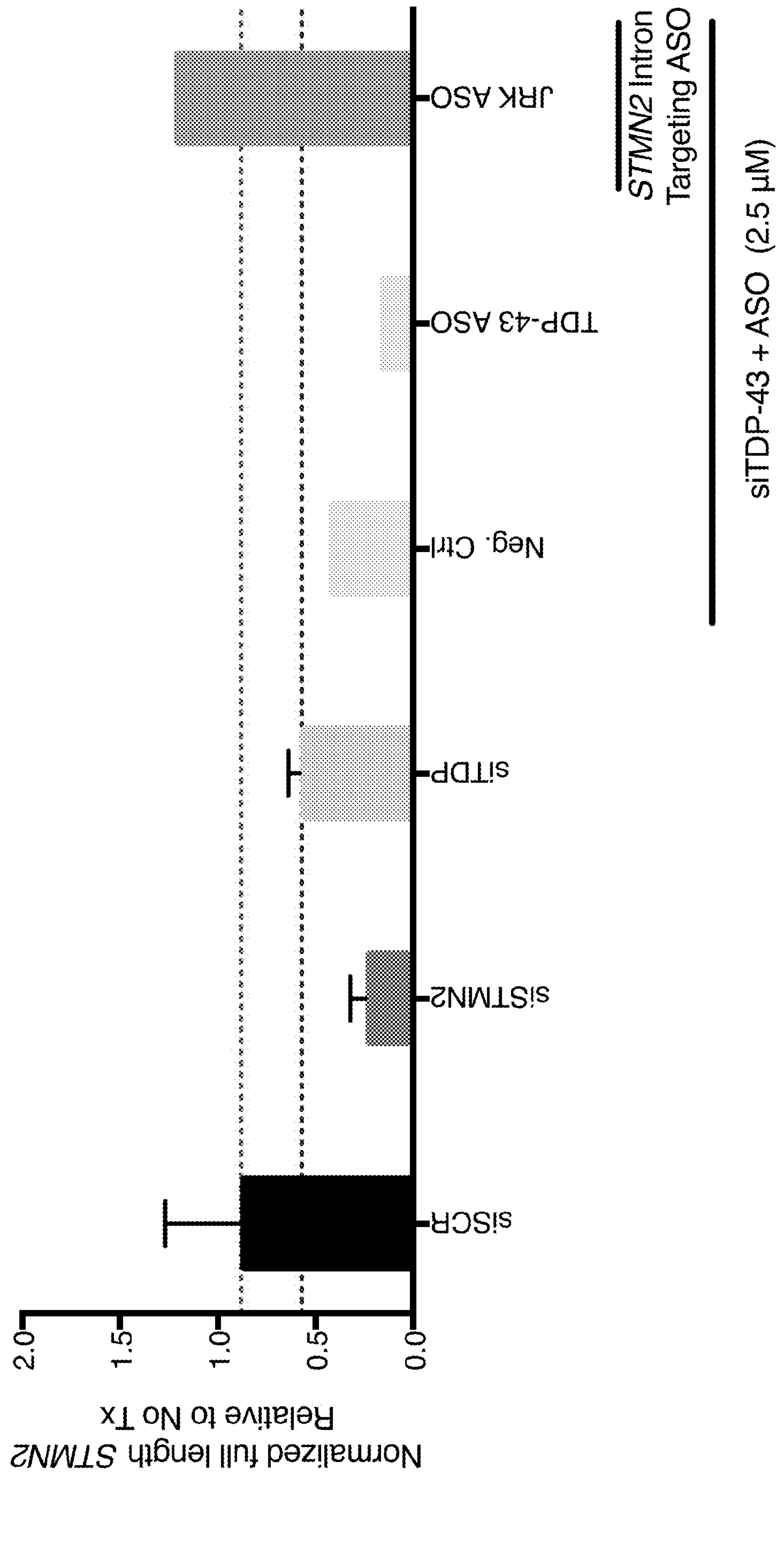

FIGS. 69A-69B demonstrate the effectiveness of an antisense oligonucleotide (ASO) (SEQ ID NO: 11). FIG. 69A shows applying the ASO at 2.5 μM and assessing its ability to decrease the abundance of cryptic exon containing transcripts.

FIG. 69B shows applying the ASO at 2.5 μM and assessing its ability to increase the abundance of full length STMN2 transcripts during TDP-43 depletion.

Figure 70A:
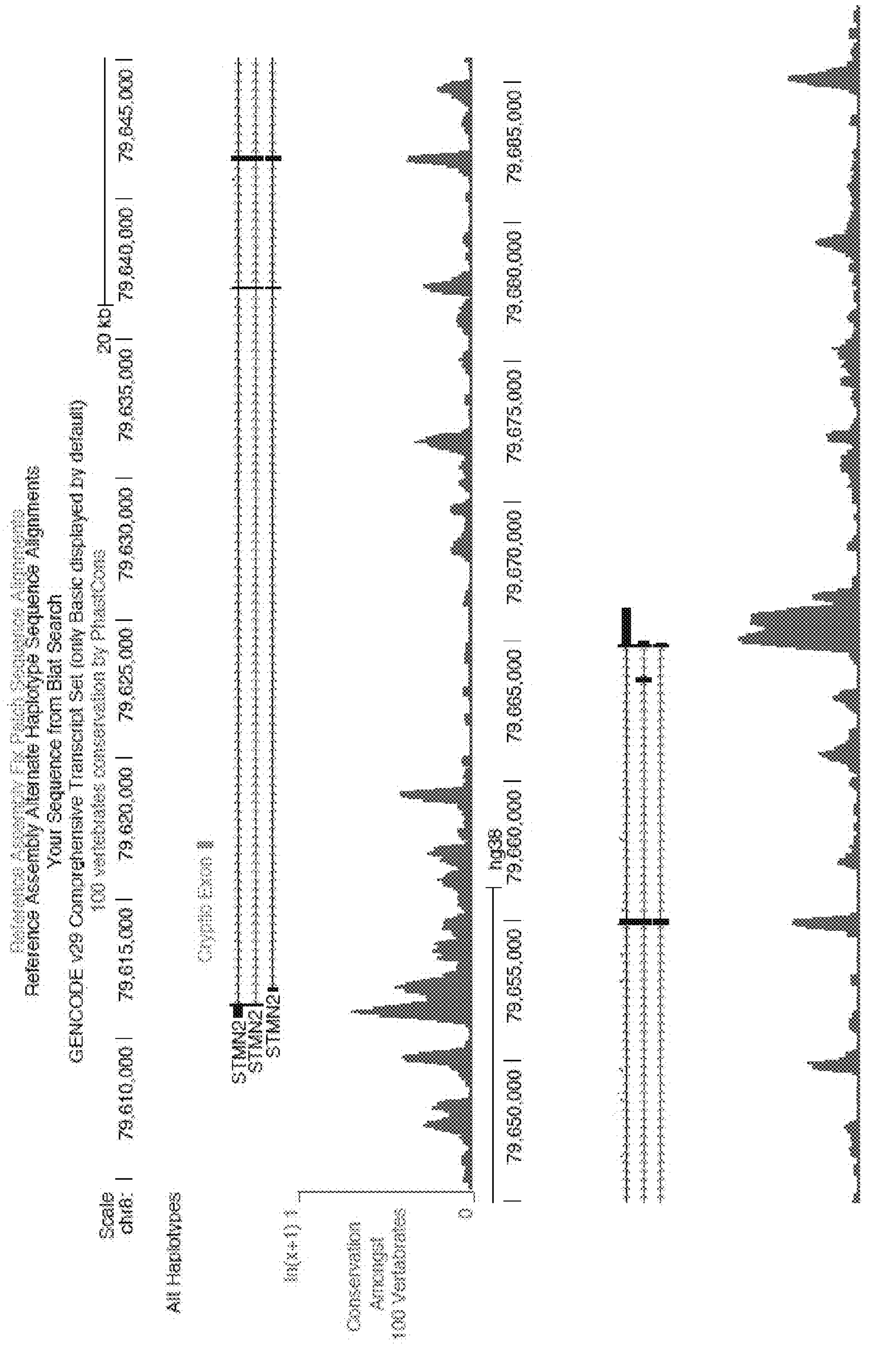
Figure 70B:
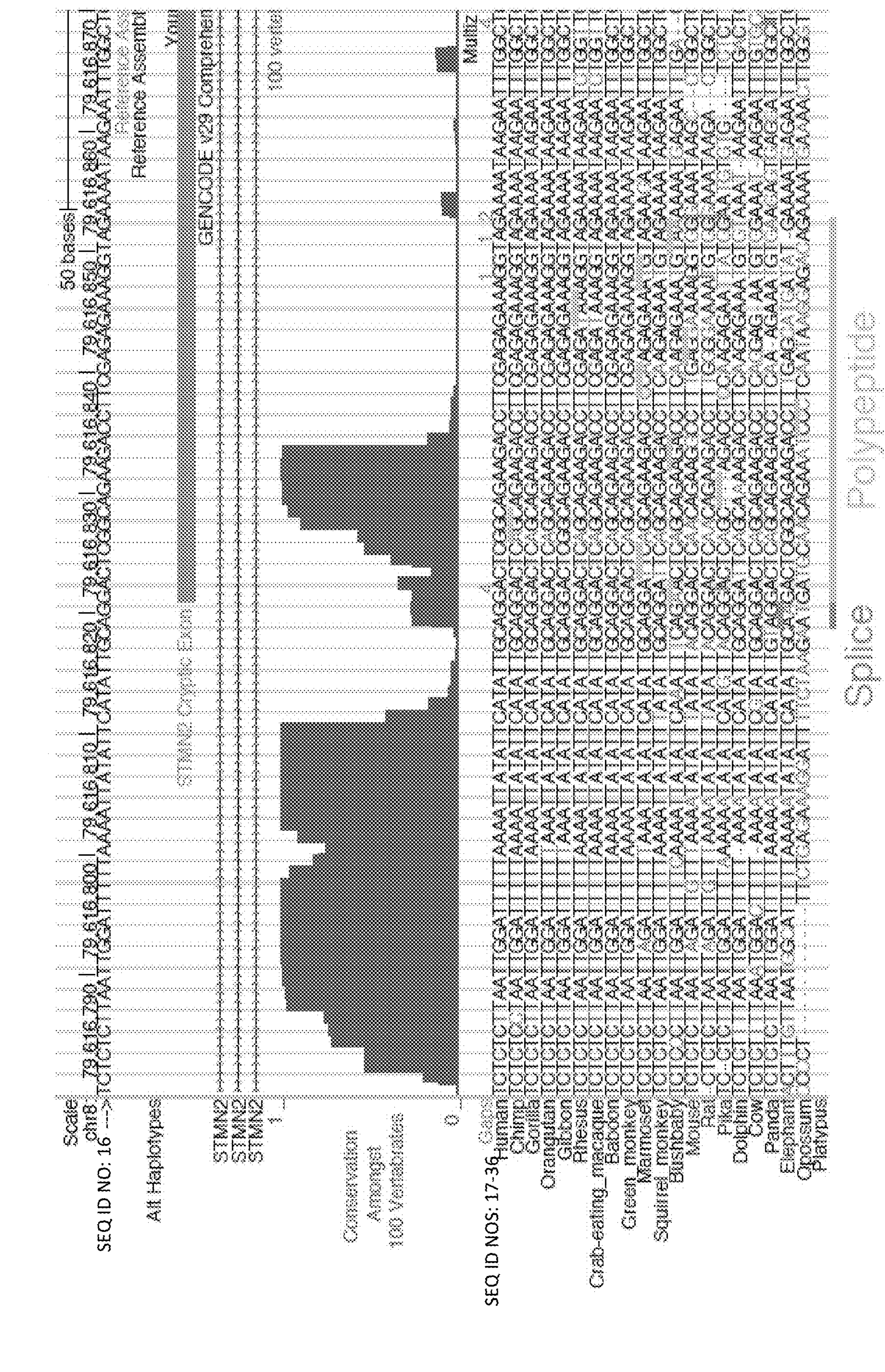
Figure 70B:
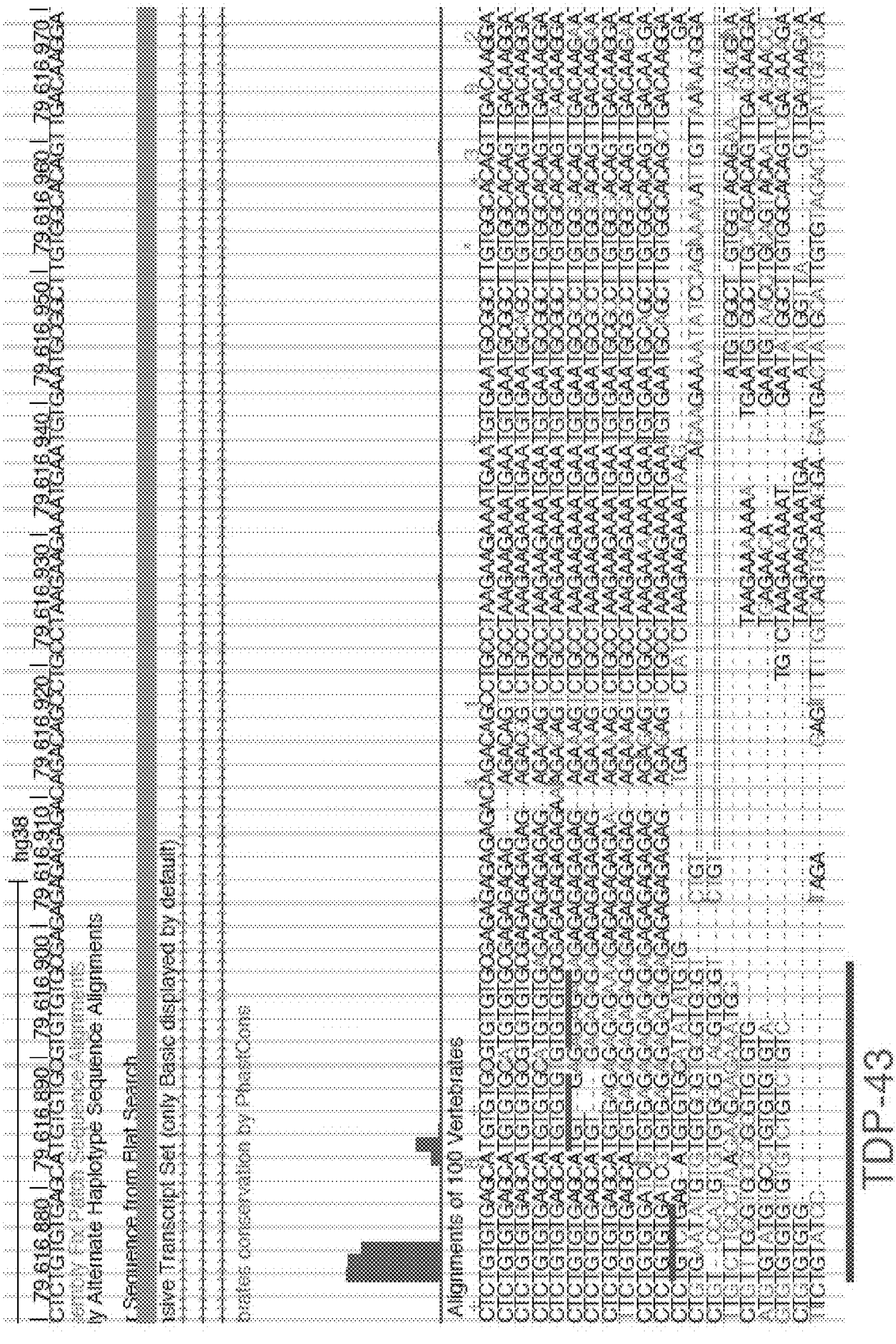
Figure 70B:
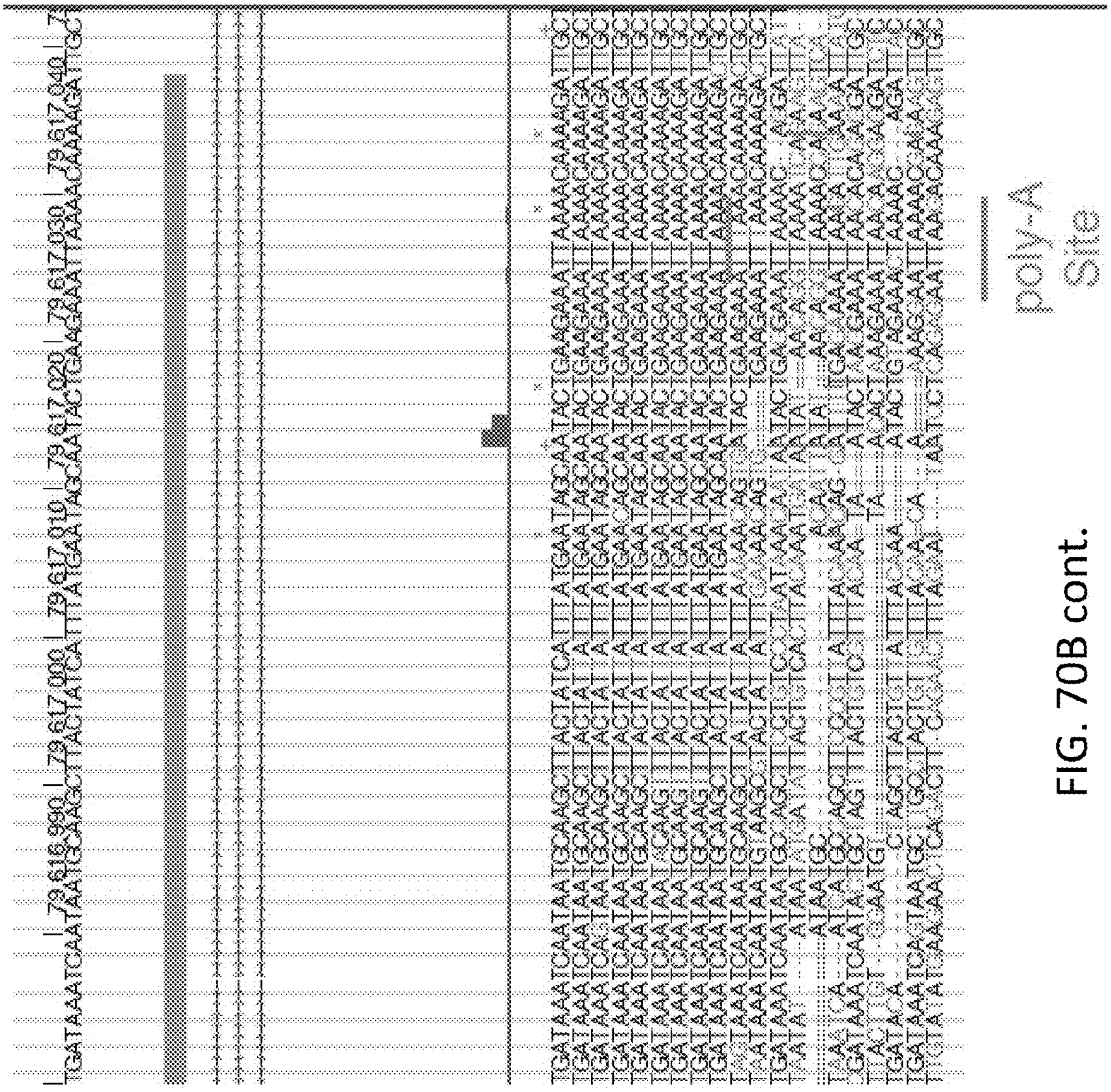

FIGS. 70A-70B demonstrate the conservation of the STMN2 locus across different species. The full triplet of TDP-43 binding motifs (red) is conserved amongst great apes.

DETAILED DESCRIPTION OF THE INVENTION

Mislocalization or depletion of the RNA-binding protein TDP-43 results in decreased expression of STMN2, which encodes a microtubule regulator. STMN2 is essential for normal axonal outgrowth and regeneration. Decreased TDP-43 function causes an abortive or altered STMN2 RNA sequence which results in reduced STMN2 protein expression. STMN2 may be a promising therapeutic target and biomarker of disease risk (e.g., neurodegenerative diseases).

Work described herein relates to compositions and methods for suppressing or preventing the inclusion of a cryptic exon in STMN2 mRNA. The inclusion of a cryptic exon in STMN2 mRNA may lead to a truncated transcript and protein. In some aspects the inclusion of the cryptic exon leads to early polyadenylation. STMN2 expression may be restored through suppression of a cryptic splicing form of STMN2 that occurs when TDP-43 becomes sequestered or is reduced in functionality, such as by blocking the occurrence or accumulation of the cryptic form and converting it back to or restoring functional STMN2 RNA (e.g., by administration of an agent).

Agents and Pharmaceutical Compositions

The disclosure contemplates agents that bind to an abortive or altered STMN2 RNA sequence that occurs and increases in abundance when TDP-43 function declines or TDP-pathology occurs, thereby restoring expression of a normal full-length or protein coding STMN2 RNA. In some aspects agents prevent degradation of STMN2 protein. In some aspects agents restore STMN2 protein levels. In some aspects an agent suppresses or prevents inclusion of a cryptic exon in STMN2 RNA. In certain aspects an agent specifically binds an STMN2 mRNA, pre-mRNA, or nascent RNA sequence coding for a cryptic exon.

In some embodiments, the agent binds to an STMN2 RNA sequence (e.g., an abortive or altered STMN2 RNA sequence). In some aspects the binding of an agent to a short abortive or altered STMN2 RNA sequence results in continued production by the RNA polymerase. For example, the agent may directly suppress premature transcriptional termination at the polyadenylation site of the cryptic exon or may mimic the activity of TDP-43 binding at its target site, thereby altering transcriptional termination at the cryptic exon. In some aspects, the agent suppresses or prevents inclusion of a cryptic exon in STMN2 RNA. In some aspects the agent prevents degradation of STMN2 protein. In some aspects the agent increases STMN2 levels (e.g., through exon skipping). In some aspects the agent restores normal length or protein coding STMN2 RNA (e.g., pre-mRNA or mRNA). In some aspects the agent increases the amount or activity of STMN2 RNA.

In some embodiments an agent targets one or more sites, for example, a 5' splice site, a 3' splice site, a normal binding site, and/or a polyadenylation site of the STMN2 transcript. In certain embodiments an agent targets one or more sites including a 5' TDP-43 splice site, a TDP-43 normal binding site, and/or a cryptic polyadenylation site. In some embodiments the agent does not target or bind to the polyadenylation site. In some embodiments the agent does not target or bind to the polyadenylation site of the STMN2 transcript. In some embodiments the agent does not target or bind to the cryptic polyadenylation site. In some aspects an agent targets and promotes the splicing of STMN2 Exon 2 to Exon 1.

STMN2 Exon 1 may have a sequence of:

```
                                        (SEQ ID NO: 1)
AGCTCCTAGGAAGCTTCAGGGCTTAAAGCTCCACTCTACTTGGACTGTAC

TATCAGGCCCCCAAAATGGGGGGAGCCGACAGGGAAGGACTGATTTCCAT

TTCAAACTGCATTCTGGTACTTTGTACTCCAGCACCATTGGCCGATCAAT

ATTTAATGCTTGGAGATTCTGACTCTGCGGGAGTCATGTCAGGGGACCTT

GGGAGCCAATCTGCTTGAGCTTCTGAGTGATAATTATTCATGGGCTCCTG

CCTCTTGCTCTTTCTCTAGCACGGTCCCACTCTGCAGACTCAGTGCCTTA

TTCAGTCTTCTCTCTCGCTCTCTCCGCTGCTGTAGCCGGACCCTTTGCCT

TCGCCACTGCTCAGCGTCTGCACATCCCTACAATGGCTAAAACAGCAATG

GGACTCGGCAGAAGACCTTCGAGAGAAAGGTAGAAAATAAGAATTTGGCT

CTCTGTGTGAGCATGTGTGCGTGTGTGCGAGAGAGAGAGACAGACAGCCT

GCCTAAGAAGAAATGAATGTGAATGCGGCTTGTGGCACAGTTGACAAGGA

TGATAAATCAATAATGCAAGCTTACTATCATTTATGAATAGC.
```

STMN2 Exon 2 may have a sequence of:

```
                                        (SEQ ID NO: 2)
CCTACAAGGAAAAAATGAAGGAGCTGTCCATGCTGTCACTGATCTGCTCT

TGCTTTTACCCGGAACCTCGCAACATCAACATCTATACTTACGATGG.
```

A cryptic exon may have a sequence of:

```
                                        (SEQ ID NO: 3)
GACTCGGCAGAAGACCTTCGAGAGAAAGGTAGAAAATAAGAATTTGGCTC

TCTGTGTGAGCATGTGTGCGTGTGTGCGAGAGAGAGAGACAGACAGCCTG

CCTAAGAAGAAATGAATGTGAATGCGGCTTGTGGCACAGTTGACAAGGAT

GATAAATCAATAATGCAAGCTTACTATCATTTATGAATAGC.
```

Exemplary types of agents that can be used include small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; antibodies; and any combination thereof.

In some embodiments the agent is an oligonucleotide, protein, or a small molecule. In some embodiments the agent comprises one or more oligonucleotides. In some aspects the oligonucleotide is a splice-switching oligonucleotide. In certain aspects the oligonucleotide is an antisense oligonucleotide (ASO). In some embodiments the agent is not an antisense oligonucleotide. In some embodiments the agent is a small molecule (e.g., Branaplam (Novartis) or Risdiplam (Roche)) capable of binding to the target site (e.g., the STMN2 transcript) and shifting the metabolism of the target.

An agent may target one or more of a 5' splice site, a 3' splice site, a normal binding site, or a polyadenylation site. In some aspects the polyadenylation site is the polyadenylation site of the STMN2 transcript. In some aspects the polyadenylation site is the polyadenylation site of the cryptic exon (e.g., is a cryptic polyadenylation site). In some embodiments an agent does not target a 5' splice site (e.g., a TDP-43 5' splice site). In some embodiments an agent does not target a normal binding site (e.g., a normal TDP-43 binding site). In some embodiments an agent does not target a polyadenylation site (e.g., a cryptic polyadenylation site). In certain embodiments an antisense oligonucleotide may target one or more of a 5' splice site, a 3' splice site, a normal binding site, or a polyadenylation site. In some embodiments an antisense oligonucleotide does not target a 5' splice site (e.g., a TDP-43 5' splice site). In some embodiments an antisense oligonucleotide does not target a normal binding site (e.g., a normal TDP-43 binding site). In some embodiments an antisense oligonucleotide does not target a polyadenylation site (e.g., a cryptic polyadenylation site). In certain embodiments, an antisense oligonucleotide comprises a sequence of TCTTCAGTATTGCTATTCAT (SEQ ID NO: 11).

Oligonucleotides (e.g., antisense oligonucleotides) may be designed to bind mRNA regions that prevent ribosomal assembly at the 5' cap, prevent polyadenylation during mRNA maturation, or affect splicing events (Bennett and Swayze, *Annu. Rev. Phamacol. Toxicol.,* 2010; Watts and Corey, *J. Pathol.,* 2012; Kole et al., *Nat. Rev. Drug Discov.,* 2012; Saleh et al, In *Exon Skipping: Methods and Protocols,* 2012, each incorporated herein by reference). In some aspects an oligonucleotide (e.g., an antisense oligonucleotide) is designed to target one or more sites including, for example, the 5' splice site, the 3' splice site, the normal binding site, and/or the polyadenylation site. In some aspects, the oligonucleotide targets one or more splice sites. In some aspects, the oligonucleotide targets one or more of the 5' TDP-43 splice site, the TDP-43 normal binding site, and/or the cryptic polyadenylation site. In some aspects an oligonucleotide is designed to target one or more sites between STMN2 Exon 2 and Exon 1 (e.g., an intron between Exon 2 and Exon 1). In some aspects an oligonucleotide is designed to not target a cryptic polyadenylation site. In some aspects an oligonucleotide is designed to not target a TDP-43 normal binding site. In some aspects an oligonucleotide is designed to not target a 5' TDP-43 splice site.

Antisense oligonucleotides are small sequences of DNA (e.g., about 8-50 base pairs in length) able to target RNA transcripts by Watson-Crick base pairing, resulting in reduced or modified protein expression. Oligonucleotides are composed of a phosphate backbone and sugar rings. In some embodiments oligonucleotides are unmodified. In other embodiments oligonucleotides include one or more modifications, e.g., to improve solubility, binding, potency, and/or stability of the antisense oligonucleotide. Modified oligonucleotides may comprise at least one modification relative to unmodified RNA or DNA. In some embodiments, oligonucleotides are modified to include internucleoside linkage modifications, sugar modifications, and/or nucleobase modifications. Examples of such modifications are known to those of skill in the art.

In some embodiments the oligonucleotide is modified by the substitution of at least one nucleotide with a modified nucleotide, such that in vivo stability is enhanced as compared to a corresponding unmodified oligonucleotide. In some aspects, the modified nucleotide is a sugar-modified nucleotide. In another aspect, the modified nucleotide is a nucleobase-modified nucleotide.

In some embodiments, oligonucleotides, may contain at least one modified nucleotide analogue. The nucleotide analogues may be located at positions where the target-specific activity, e.g., the splice site selection modulating activity is not substantially effected, e.g., in a region at the 5'-end and/or the 3'-end of the oligonucleotide molecule. In some aspects, the ends may be stabilized by incorporating modified nucleotide analogues.

In some aspects preferred nucleotide analogues include sugar- and/or backbone-modified ribonucleotides (i.e., include modifications to the phosphate-sugar backbone). For example, the phosphodiester linkages of a ribonucleotide may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

In some embodiments, modified oligonucleotides comprise one or more modified nucleosides comprising a modified sugar moiety. In some embodiments, modified oligonucleotides comprise one or more modified nucleosides comprising a modified nucleobase. In some embodiments, modified oligonucleotides comprise one or more modified internucleoside linkages. In certain embodiments, modified oligonucleotides comprise at least two of: one or more modified nucleosides comprising a modified sugar moiety, one or more modified nucleosides comprise a modified nucleobase, and one or more modified internucleoside linkages. In certain embodiments, modified oligonucleotides comprise one or more modified nucleosides comprising a modified sugar moiety, one or more modified nucleosides comprise a modified nucleobase, and one or more modified internucleoside linkages.

Sugar Modifications

In some embodiments, modified sugar moieties are non-bicyclic modified sugar moieties. In some embodiments, modified sugar moieties are bicyclic or tricyclic sugar moieties. In some embodiments, modified sugar moieties are sugar surrogates. Such sugar surrogates may comprise one or more substitutions corresponding to those of other types of modified sugar moieties.

In some embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched.

In some embodiments, modified sugar moieties comprise a substituent that bridges two atoms of the furanosyl ring to form a second ring, resulting in a bicyclic sugar moiety. In some aspects the bicyclic sugar moiety comprises a bridge between the 4' and 2' furanose ring atoms.

In some aspects bicyclic sugar moieties and nucleosides incorporating such bicyclic sugar moieties are further defined by isomeric configurations. In some embodiments, an LNA nucleoside is in the α-L configuration. In some embodiments, an LNA nucleoside is in the β-D configuration.

In some embodiments an oligonucleotide modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH2-)n group bridging the 2' oxygen atom and the 4' carbon atom wherein n is 1 or 2. LNAs and preparation thereof are described in WO 98/39352 and WO 99/14226, the entire contents of which are incorporated by reference herein.

In some embodiments, modified sugar moieties comprise one or more non-bridging sugar substituent and one or more bridging sugar substituent (e.g., 5'-substituted and 4'-2' bridged sugars).

In some embodiments, modified sugar moieties are sugar surrogates. In some aspects the oxygen atom of the sugar moiety is replaced, e.g., with a sulfur, carbon, or nitrogen atom. In some aspects such modified sugar moieties also comprise bridging and/or non-bridging substituents as described herein. In some aspects sugar surrogates comprise rings having other than 5 atoms. In certain aspects a sugar surrogate comprises a six-membered tetrahydropyran (THP). In some aspects sugar surrogates comprise acyclic moieties.

Nucleobase Modifications

Modified oligonucleotides may comprise one or more nucleosides comprising an unmodified nucleobase. In some embodiments modified oligonucleotides comprise one or more nucleosides comprising a modified nucleobase. In some embodiments, modified oligonucleotides comprise one or more nucleosides that does not comprise a nucleobase.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C°C—C]¾) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fhiorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone.

Also preferred are nucleobase-modified ribonucleotides, i.e., ribonucleotides, containing at least one non-naturally occurring nucleobase instead of a naturally occurring nucleobase. Examples of modified nucleobases include, but are not limited to, uridine and/or cytidine modifications at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine. Oligonucleotide reagents of the invention also may be modified with chemical moieties that improve the in vivo pharmacological properties of the oligonucleotide reagents.

Internucleoside Modifications

In some embodiments, nucleosides of modified oligonucleotides are linked together using any internucleoside linkage. The two main classes of internucleoside linking groups are defined by the presence or absence of a phosphorous atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include but are not limited to methylenemethylimino ($—CH_2—N(CH_3)—O—CH_2—$), thiodiester, thionocarbamate (—O—C(=O)(NH)—S—); siloxane ($—O—SiH_2—O—$); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Additional modifications are known by those of skill in the art and examples can be found in WO 2019/241648, U.S. Pat. Nos. 10,307,434, 9,045,518, and 10,266,822, each of which is incorporated herein by reference.

Oligonucleotides may be of any size and/or chemical composition sufficient to target the abortive or altered STMN2 RNA. In some embodiments, an oligonucleotide is between about 5-300 nucleotides or modified nucleotides. In some aspects an oligonucleotide is between about 10-100, 15-85, 20-70, 25-55, or 30-40 nucleotides or modified nucleotides. In certain aspects an oligonucleotide is between about 15-35, 15-20, 20-25, 25-30, or 30-35 nucleotides or modified nucleotides.

In some embodiments, an oligonucleotide and the target RNA sequence (e.g., the abortive or altered STMN2 RNA) have 100% sequence complementarity. In some aspects an oligonucleotide may comprise sequence variations, e.g., insertions, deletions, and single point mutations, relative to the target sequence. In some embodiments, an oligonucleotide has at least 70% sequence identity or complementarity to the target RNA (e.g., STMN2 mRNA, pre-mRNA, or nascent RNA). In certain embodiments, an oligonucleotide has at least 70%, 75%, 80%, 85%, 90%, 95%, 97%, 99%, or 100% sequence identity to the target sequence.

An antisense oligonucleotide targeting the abortive or altered STMN2 RNA sequence may be designed by any methods known to those of skill in the art. For example, an antisense oligonucleotide may be synthesized as follows: /52MOErT/*/i2MOErC/*/i2MOErT/*/i2MOErT/*/ i2MOErC/*/i2MOErA/*/i2MOEr G/*/i2MOErT/*/ i2MOErA/*/i2MOErT/*/i2MOErT/*/i2MOErG/*/ i2MOErC/*/i2MO ErT/*/i2MOErA/*/i2MOErT/*/ i2MOErT/*/i2MOErC/*/i2MOErA/*/32MOErT/. In certain embodiments an antisense oligonucleotide is synthesized as follows: 5'-/52MOErT/*/i2MOErC/*/i2MOErT/*/ i2MOErT/*/i2MOErC/*/i2MOErA/*/i2MOEr G/*/ i2MOErT/*/i2MOErA/*/i2MOErT/*/i2MOErT/*/ i2MOErG/*/i2MOErC/*/i2MO ErT/*/i2MOErA/*/ i2MOErT/*/i2MOErT/*/i2MOErC/*/i2MOErA/*/ i2MOErT/*/32 MOErT/-3'. One or more oligonucleotides may be synthesized.

In some embodiments, STMN2 is administered as a gene therapy. In some embodiments STMN2 is administered in combination with an agent described herein.

In some embodiments an agent is an inhibitor of c-Jun N-terminal kinase (JNK). In some aspects a JNK inhibitor is selected from the group consisting of small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; antibodies; and any combination thereof. In certain aspects the agent is a small molecule inhibitor, an oligonucleotide (e.g., designed to reduce expression of JNK), or a gene therapy (e.g., designed to inhibit JNK). In some aspects inhibition of JNK restores or increases STMN2 protein levels. In certain embodiments the agent is an oligonucleotide (e.g., an antisense oligonucleotide) targeting JNK.

The disclosure further contemplates pharmaceutical compositions comprising the agent that binds an abortive or altered STMN2 RNA sequence. In some embodiments, the pharmaceutical composition comprises the agent that binds an STMN2 mRNA, pre-mRNA, or nascent RNA sequence coding for a cryptic exon. In some embodiments pharmaceutical compositions comprise the agent that prevents degradation of an STMN2 protein. In some aspects the composition comprises an oligonucleotide, protein, or small molecule. In some embodiments the composition comprises an oligonucleotide (e.g., an antisense oligonucleotide), wherein the oligonucleotide specifically binds an STMN2 mRNA, pre-mRNA, or nascent RNA sequence coding for a cryptic exon. In some aspects the agent (e.g., the oligonucleotide) suppresses or prevents inclusion of a cryptic exon in STMN2 RNA. In some aspects the agent suppresses cryptic splicing.

In some embodiments, a pharmaceutical composition comprises an agent that targets one or more sites, e.g., one or more splice sites, binding sites, or polyadenylation sites. In some embodiments, a pharmaceutical composition comprises an agent that targets one or more splice sites (e.g., 5' TDP-43 splice site). In some embodiments, a pharmaceutical composition comprises an agent that targets a normal binding site (e.g., a TDP-43 normal binding site). In some embodiments, a pharmaceutical composition comprises an agent that targets a polyadenylation site (e.g., a cryptic polyadenylation site). In some embodiments, a pharmaceutical composition comprises an agent that does not target one or more splice sites (e.g., 5' TDP-43 splice site). In some embodiments, a pharmaceutical composition comprises an agent that does not target a normal binding site (e.g., a TDP-43 normal binding site). In some embodiments, a pharmaceutical composition comprises an agent that does not target a polyadenylation site (e.g., a cryptic polyadenylation site).

In some embodiments a pharmaceutical composition comprises an effective amount of an agent that binds an STMN2 mRNA sequence coding for a cryptic exon and an effective amount of a second agent. In some aspects the second agent is an agent that treats or inhibits a neurodegenerative disorder. In some aspects the second agent is an agent that treats or inhibits a traumatic brain injury. In some aspects the second agent is an agent that treats or inhibits a proteasome inhibitor induced neuropathy.

In some embodiments a pharmaceutical composition comprises an effective amount of an agent that binds to an abortive or altered STMN2 RNA sequence and an effective amount of STMN2 (e.g., administered as a gene therapy).

In some embodiments a pharmaceutical composition comprises an effective amount of a first agent that binds to an abortive or altered STMN2 RNA sequence and a second agent that inhibits JNK.

In some embodiments a pharmaceutical composition comprises an effective amount of an agent that binds an STMN2 mRNA, pre-mRNA, or nascent RNA sequence coding for a cryptic exon, an effective amount of a second agent, and a pharmaceutically acceptable carrier, diluent, or excipient.

The compositions comprising the agent that binds to an abortive or altered STMN2 RNA sequence can be used for treating a disease or condition associated with a decline in TDP-43 function or a TDP-pathology. In some aspects the compositions comprising the agent that binds to an abortive or altered STMN2 RNA sequence can be used for treating a disease or condition associated with mutant or reduced levels of STMN2 protein (e.g., in neuronal cells) as described herein.

Methods of Treatment

The disclosure contemplates various methods of treatment utilizing compositions comprising an agent that restores normal length or protein coding STMN2 RNA. In some aspects an agent binds to an abortive or altered STMN2 RNA sequence that occurs and increases in abundance when TDP-43 function declines or TDP-pathology occurs, thereby restoring expression of a normal full-length or protein coding STMN2 RNA. In some aspects an agent suppresses or prevents inclusion of a cryptic exon in STMN2 RNA.

In some aspects, the disclosure contemplates the treatment of any disease or condition in which the disease is associated with a decline in TDP-43 function or a TDP-pathology. In some embodiments, the inventions disclosed herein relate to methods of treating mutant or reduced levels of TDP-43 in neuronal cells (e.g., a disease or condition having a TDP-43 associated pathology). In some embodiments, the inventions disclosed herein relate to methods of treating TDP-43 associated dementias (e.g., ALS, FTD, Alzheimer's, Parkinson's, or TBI).

In some embodiments, the inventions disclosed herein relate to methods of treating a disease or condition associated with mutant, increased, or reduced levels of TDP-43. In some embodiments, the inventions disclosed herein relate to methods of treating a disease or condition associated with mislocalized TDP-43. In some embodiments the inventions disclosed herein relate to methods of treating a disease or condition associated with mutant or reduced levels of STMN2 protein and/or mislocalization of STMN2 protein. In some embodiments, the inventions disclosed herein relate to methods of treating a disease or condition associated with proteasome-inhibitor induced neuropathies (e.g., neuropathies occurring as a result of reduced amounts of functional nuclear TDP-43). In some embodiments, the inventions disclosed herein relate to methods of treating neurodegenerative disorders. In some embodiments, the inventions disclosed herein relate to methods of treating disorders or conditions associated with or occurring as a result of a traumatic brain injury (TBI) (e.g., a concussion).

In some aspects mutant or reduced levels of TDP-43 (e.g., nuclear TDP-43) or mislocalization of TDP-43 results in mutant or reduced levels of STMN2 protein. Mislocalization of TDP-43 may result in increased levels of TDP-43 in the cytosol, but decreased levels of nuclear TDP-43. In addition, STMN2 levels may be decreased as a result of mutations in TDP-43. In some aspects mutant or increased levels of TDP-43 (e.g., nuclear TDP-43) or mislocalization of TDP-43 results in mutant or reduced levels of STMN2 protein.

In some aspects methods of treatment comprise increasing levels of and/or preventing degradation or retardation of STMN2 protein. In some aspects methods of treatment comprise correcting mutant or reduced levels of STMN2 protein and/or correcting mislocalization of STMN2 protein. In some aspects methods of treating comprise increasing the amount or activity of STMN2 RNA. In some aspects methods of treatment comprise suppressing or preventing inclusion of a cryptic exon in STMN2 RNA (e.g., STMN2 mRNA). In some aspects methods of treatment comprise rescuing neurite outgrowth and axon regeneration.

In some embodiments methods of treatment comprise administering an effective amount of an agent to a subject, wherein the agent prevents degradation of STMN2 protein. In some embodiments methods of treatment comprise administering an effective amount of an agent to a subject, wherein the agent restores normal length or protein coding STMN2 RNA. In some embodiments methods of treatment comprise administering an effective amount of an agent to a subject, wherein the agent binds to an abortive or altered STMN2 RNA sequence. In some embodiments methods of treatment comprise administering an effective amount of an agent to a subject, wherein the agent suppresses or prevents inclusion of a cryptic exon in STMN2 RNA (e.g., in neuronal cells). In some aspects the agent increases STMN2 levels through exon skipping. In some aspects the agent is an oligonucleotide, protein, or small molecule. For example, the agent may be an oligonucleotide (e.g., an antisense oligonucleotide) that specifically binds an STMN2 mRNA, pre-mRNA or nascent RNA sequence coding for the cryptic exon.

In some embodiments an agent (e.g., an antisense oligonucleotide) is administered (e.g., in vitro or in vivo) in an amount effective for increasing and/or restoring STMN2 protein levels.

In some aspects the agent suppresses cryptic splicing. In some embodiments a subject treated with an agent that suppresses or prevents inclusion of a cryptic exon in STMN2 RNA exhibits improved neuronal (e.g., motor axon) outgrowth and/or repair. In some aspects the agent prevents degradation of STMN2 protein. In some aspects an agent improves symptoms of a neurodegenerative disease including ataxia, neuropathy, synaptic dysfunction, deficit in cognition, and/or decreased longevity.

In some embodiments inclusion of a cryptic exon in STMN2 RNA is suppressed or prevented using genome editing (e.g., CRISPR/Cas).

As used herein, "treat," "treatment," "treating," or "amelioration" when used in reference to a disease, disorder or medical condition, refers to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of, for example, a neurodegenerative disorder, delay or slowing progression of a neurodegenerative disorder, and an increased lifespan as compared to that expected in the absence of treatment.

"Neurodegenerative disorder" refers to a disease condition involving neural loss mediated or characterized at least partially by at least one of deterioration of neural stem cells and/or progenitor cells. Non-limiting examples of neurodegenerative disorders include polyglutamine expansion disorders (e.g., HD, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer disease, amyotrophic lateral sclerosis (ALS), ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, Guillain-Barré syndrome, ischemia stroke, Krabbe disease, kuru, Lewy body dementia, multiple sclerosis, multiple system atrophy, non-Huntingtonian type of Chorea, Parkinson's disease, Pelizaeus-Merzbacher disease, Pick's disease, primary lateral sclerosis, progressive supranuclear palsy, Refsum's disease, Sandhoff disease, Schilder's disease, spinal cord injury, spinal muscular atrophy (SMA), SteeleRichardson-Olszewski disease, frontotempéral dementia (FTD), and Tabes *dorsalis*. In some contexts neurodegenerative disorders encompass neurological injuries or damages to the CNS or PNS associated with physical injury (e.g., head trauma, mild to severe traumatic brain injury (TBI), diffuse axonal injury, cerebral contusion, acute brain swelling, and the like).

In some embodiments the neurodegenerative disorder is a disorder that is associated with mutant or reduced levels of TDP-43 in neuronal cells. In some embodiments the neurodegenerative disorder is a disorder that is associated with mutant or reduced levels of STMN2 protein and/or mislocalization of STMN2 protein. In some embodiments the neurodegenerative disorder is selected from the group consisting of amyotrophic lateral sclerosis (ALS), frontotemporal dementia (FTD), frontotemporal lobar degeneration (FTLD), Alzheimer's disease, Parkinson's disease, Inclusion Body Myositis (IBM) and combinations thereof. In some aspects the neurodegenerative disorder is ALS. In some aspects the neurodegenerative disorder is ALS in combination with FTD and/or FTLD. In some aspects the neurodegenerative disorder is Alzheimer's. In some aspects the neurodegenerative disorder is Parkinson's.

"Proteasome-inhibitor induced neuropathy" is used herein to refer to a disorder or condition that occurs as a result of a reduced amount of functional nuclear TDP-43. The nuclear TDP-43 may be decreased in overall levels, or the decreased levels may occur as a result of an increase in cytoplasmic aggregation of TDP-43, which induces evacuation of nuclear TDP-43. In some aspects, proteasome inhibition leads to decreased expression of STMN2.

"Traumatic brain injury" or "TBI" refers to an intracranial injury that occurs when an external force injures the brain. TBIs may be classified based on their severity (e.g., mild, moderate, or severe), mechanism (e.g., closed or penetrating head injury), or other features (e.g., location). A TBI can result in physical, cognitive, social, emotional, and behavioral symptoms. Conditions associated with TBI include concussions. TBIs and conditions associated with a TBI have been associated with TDP-43 pathology. In some aspects, alterations in STMN2 occur in a TBI or a condition associated therewith.

In some embodiments the traumatic brain injury is, or results in, a disorder that is associated with mutant levels of TDP-43 in neuronal cells. In some embodiments the traumatic brain injury is, or results in, a disorder that is associated with mutant or reduced levels of STMN2 protein and/or mislocalization of STMN2 protein. In some embodiments the severity of a traumatic brain injury is measured based on the decrease of functional TDP-43 in neuronal cells. In some embodiments the severity of a concussion is measured based on the decrease of functional TDP-43 in neuronal cells.

For administration to a subject, the agents disclosed herein can be provided in pharmaceutically acceptable compositions. These pharmaceutically acceptable compositions comprise a therapeutically-effective amount of one or more of the agents, formulated together with one or more pharmaceutically acceptable carriers (additives) and/or diluents. The pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intrathecal, intercranially, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, agents can be implanted into a patient or injected using a drug delivery system. (See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.)

As used herein, the term "pharmaceutically acceptable" refers to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of an agent, material, or composition comprising an agent described herein which is effective for producing some desired therapeutic effect in at least a sub-population of cells in an animal at a reasonable benefit/risk ratio applicable to any medical treatment. For example, an amount of an agent administered to a subject that is sufficient to produce a statistically significant, measurable increase in TDP-43 function.

The determination of a therapeutically effective amount of the agents and compositions disclosed herein is well within the capability of those skilled in the art. Generally, a therapeutically effective amount can vary with the subject's history, age, condition, sex, and the administration of other pharmaceutically active agents.

As used herein, the term "administer" refers to the placement of an agent or composition into a subject (e.g., a subject in need) by a method or route which results in at least partial localization of the agent or composition at a desired site such that desired effect is produced. Routes of administration suitable for the methods of the invention include both local and systemic routes of administration. Generally, local administration results in more of the administered agents being delivered to a specific location as compared to the entire body of the subject, whereas, systemic administration results in delivery of the agents to essentially the entire body of the subject.

The compositions and agents disclosed herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. Exemplary modes of administration include, but are not limited to, injection, infusion, instillation, inhalation, or ingestion. “Injection” includes, without limitation, intravenous, intramuscular, intraarterial, intrathecal, intraventricular, intracranial, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

As used herein, a “subject” means a human or animal (e.g., a mammal). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, “patient” and “subject” are used interchangeably herein. A subject can be male or female. In some embodiments the subject suffers from a disease or condition associated with mutant or reduced levels of TDP-43 (e.g., in neuronal cells).

Screening Methods

The disclosure contemplates methods of screening one or more test agents to identify candidate agents for treating or reducing the likelihood of a disease or condition associated with a TDP-pathology. In some aspects, a disease or condition is associated with mutant or reduced levels of TDP-43 (e.g., in neuronal cells). The disclosure further contemplates methods of screening one or more test agents to identify candidate agents for treating or reducing the likelihood of a disease or condition associated with either mutant or reduced levels of STMN2 protein.

In some embodiments the method comprises providing a neuronal cell having reduced TDP-43 levels; contacting the cell with the one or more test agents; determining if the contacted cell has an increased level of STMN2 protein; and identifying the test agent as a candidate agent if the contacted cell has an increased level of STMN2 protein. In some aspects the step of determining if the contacted cell has increased level of STMN2 protein comprises measuring STMN2 protein levels in the contacted cell. In some aspects STMN2 protein level is measured using an ELISA (e.g., a sandwich ELISA), dot blot, and/or Western blot. In some aspects the step of determining if the contacted cell has increased level of STMN2 protein comprises assessing the morphology or function of the contacted cell. For example, neurons lacking STMN2 may have an altered morphology from that of neurons having STMN2. In some aspects the morphology or function of the contacted cell is assessed using immunoblotting and/or immunocytochemistry. In some aspects the contacted cell may further be assessed to determine if it expresses full-length STMN2 RNA. STMN2 RNA expression may be measured using qRT-PCR.

In some embodiments the method comprises providing a neuronal cell having mutant TDP-43 levels; contacting the cell with the one or more test agents; determining if the contacted cell has an increased level of STMN2 protein; and identifying the test agent as a candidate agent if the contacted cell has an increased level of STMN2 protein. In some aspects the step of determining if the contacted cell has increased level of STMN2 protein comprises measuring STMN2 protein levels in the contacted cell. In some aspects STMN2 protein level is measured using an ELISA, dot blot, and/or Western blot. In some aspects the step of determining if the contacted cell has increased level of STMN2 protein comprises assessing the morphology or function of the contacted cell. For example, neurons lacking STMN2 or having a reduced amount of STMN2 may have an altered morphology from that of neurons having normal levels of STMN2 (i.e., levels of STMN2 from a control sample). In some aspects the morphology or function of the contacted cell is assessed using immunoblotting and/or immunocytochemistry. In some aspects the contacted cell may further be assessed to determine if it expresses full-length STMN2 RNA. STMN2 RNA expression may be measured using qRT-PCR.

In some embodiments the method comprises providing a neuronal cell having reduced TDP-43 levels; contacting the cell with the one or more test agents; and determining if the contacted cell has cryptic exons in STMN2 RNA. The contacted cell may be assessed using FISH RNA, or RT-PCT, qPCR, qRT-PCR, or RNA sequencing to identify whether there is a cryptic exon in the STMN2 RNA. In some embodiments the method comprises providing a neuronal cell having reduced TDP-43 levels; contacting the cell with the one or more test agents; and determining if the contacted cell expresses full length STMN2 RNA. The contacted cell may be assessed using RNA FISH or RT-PCT, qPCR, qRT-PCR, or RNA sequencing.

In some embodiments the method comprises providing a neuronal cell having mutant TDP-43 levels; contacting the cell with the one or more test agents; and determining if the contacted cell has cryptic exons in STMN2 RNA. The contacted cell may be assessed using FISH RNA or RT-PCT, qPCR or RNA sequencing to identify whether there is a cryptic exon in the STMN2 RNA. In some embodiments the method comprises providing a neuronal cell having mutant TDP-43 levels; contacting the cell with the one or more test agents; and determining if the contacted cell expresses full length STMN2 RNA. The contacted cell may be assessed using RNA FISH or RT-PCT, qPCR, qRT-PCR, or RNA sequencing.

Biomarkers

In some aspects the disclosure contemplates the use of STMN2 as a biomarker for a disease or condition associated with a decline in TDP-43 functionality (e.g., a disease or condition having a substantial TDP-43-associated pathology). In some aspects STMN2 may act as a biomarker for the presence of a disease or condition. In other aspects STMN2 may act as a biomarker for monitoring the progression of a disease or condition. In some aspects STMN2 protein levels are assessed. In some aspects STMN2 transcript levels are assessed. In some aspects the presence of an STMN2 abortive transcript or STMN2 cryptic exon is assessed. In some aspects a 17 amino acid peptide that an STMN2 cryptic exon encodes for is assessed. The putative peptide may act as a biomarker for the detection of the abortive STMN2 transcript. In some aspects the downstream protein coding exons of the STMN2 RNA or components of the pre-mRNA, nascent RNA, or mRNA that are downstream of the site where the STMN2 cryptic exon terminates are assessed. In some aspects the specific RNA originating from the 5' end of the gene that terminates in the cryptic exon is assessed.

In some embodiments, a disease or condition is associated with mutant or reduced levels of TDP-43 in neuronal cells. In some embodiments, a disease or condition is associated with mutant or increased levels of TDP-43 in neuronal cells. In some embodiments the disease or condition is a neurodegenerative disease (e.g., amyotrophic lateral sclerosis (ALS), Alzheimer's disease, Parkinson's disease, or frontotemperal dementia (FTD)). In some embodiments the disease or condition is associated with or occurs as a result of a traumatic brain injury.

In some aspects a method for detecting a disease or condition associated with a decline in TDP-43 functionality comprises obtaining a sample from a subject, and assessing the sample to determine if it exhibits either mutant or reduced levels of STMN2 protein. In some embodiments the STMN2 protein levels are measured using any method known to those of skill in the art, including immunoblot, immunocytochemistry, dot blot, and/or ELISA. In certain aspects STMN2 protein levels are measured using ELISA. In some aspects a method for detecting a disease or condition associated with a decline in TDP-43 functionality comprises obtaining a sample from a subject, and assessing the sample to determine if it exhibits reduced levels of STMN2 transcript. In some embodiments the STMN2 transcript levels are measured using any method known to those of skill in the art, including RNA FISH, RT-PCR, qPCR, or RNA sequencing. In certain aspects STMN2 transcript levels are measured using qRT-PCR. Reduced levels of STMN2 protein and/or transcript may be an indication of a decline in TDP-43 functionality as a result of a disease or disorder. In some aspects the progression of a disease or condition associated with a decline in TDP-43 functionality is assessed by analyzing multiple samples from a subject over an extended period of time to monitor the levels of STMN2 protein and/or transcript (e.g., in response to a treatment protocol).

In some aspects a method for detecting a neurodegenerative disease (e.g., ALS, FTD, Parkinson's, Alzheimer's) in a subject comprises obtaining a sample (e.g., a biofluid sample) from the subject suffering, and determining if the sample contains altered levels of STMN2 protein. In certain aspects the determination is made using ELISA. In some aspects a method for detecting a neurodegenerative disease (e.g., ALS, FTD, Parkinson's, Alzheimer's) in a subject comprises obtaining a sample (e.g., a biofluid sample) from the subject suffering, and determining if the sample contains reduced levels of STMN2 transcript. The screening of the sample may be performed using RNA FISH, RT-PCR, qPCR, or RNA sequencing. In certain aspects STMN2 transcript levels are measured using qRT-PCR. Reduced levels of STMN2 protein and/or transcript may be an indication of a decline in TDP-43 functionality as a result of a neurodegenerative disease or disorder.

In some aspects a method for detecting a traumatic brain injury (TBI) in a subject comprises obtaining a sample (e.g., a biofluid sample) from the subject, and determining if the sample contains altered levels of STMN2 protein. In certain aspects the determination is made using ELISA. In some aspects a method for detecting a traumatic brain injury (TBI) in a subject comprises obtaining a sample (e.g., a biofluid sample) from the subject, and screening the sample for reduced levels of STMN2 transcript. The screening of the sample may be performed using RNA FISH, RT-PCR, qPCR, or RNA sequencing. In certain aspects STMN2 transcript levels are measured using qRT-PCR. Reduced levels of STMN2 protein and/or transcript may be an indication of a decline in TDP-43 functionality as a result of a TBI.

In some aspects a method for detecting a disease or condition associated with the death of motor neurons comprises obtaining a sample (e.g., cerebral spinal fluid) from a subject, and assessing the sample to determine if it exhibits mutant or increased levels of STMN2 transcript. In some embodiments the STMN2 transcript levels are measured using RNA FISH, RT-PCR, qPCR, or RNA sequencing. In certain aspects STMN2 transcript levels are measured using qRT-PCR. The release of STMN2, i.e., the increase of STMN2 in the CSF, may occur as a result of dying motor neurons.

In some aspects the disclosure contemplates the use of the STMN2 cryptic exon as a biomarker for a disease or condition associated with a decline in TDP-43 functionality (e.g., a disease or condition having a substantial TDP-43-associated pathology). In some embodiments the disease or condition is a neurodegenerative disease (e.g., ALS, FTD, Alzheimer's, Parkinson's). In some embodiments the disease or condition is associated with or is a result of a traumatic brain injury.

In some aspects a method for detecting a disease or condition associated with a decline in TDP-43 functionality comprises obtaining a sample from a subject, and assessing the sample to determine if it includes an SMNT2 abortive transcript. In some aspects a method for detecting a disease or condition associated with a decline in TDP-43 functionality comprises obtaining a sample from a subject, and assessing the sample to determine if it includes an SMNT2 cryptic exon. In some embodiments the STMN2 transcript is assessed using RNA FISH, RT-PCR, qPCR, or RNA sequencing. In certain aspects an STMN2 transcript is measured using qRT-PCR. The presence of an abortive STMN2 transcript or an STMN2 cryptic exon may be an indication of a decline in TDP-43 functionality.

In some aspects a method for detecting a neurodegenerative disease comprises obtaining a sample (e.g., a biofluid sample) from the subject, and screening the sample for an abortive STMN2 transcript. In some aspects a method for detecting a neurodegenerative disease in a subject comprises obtaining a sample (e.g., a biofluid sample) from the subject, and screening the sample for a STMN2 cryptic exon. The screening of the sample may be performed using PCR. The presence of an abortive STMN2 transcript or an STMN2 cryptic exon may be an indication of a decline in TDP-43 functionality as a result of a neurodegenerative disease or disorder.

In some aspects a method for detecting a TBI comprises obtaining a sample (e.g., a biofluid sample) from the subject, and screening the sample for an abortive STMN2 transcript. In some aspects a method for detecting a TBI in a subject comprises obtaining a sample (e.g., a biofluid sample) from the subject, and screening the sample for a STMN2 cryptic exon. The screening of the sample may be performed using PCR. The presence of an abortive STMN2 transcript or an STMN2 cryptic exon may be an indication of a decline in TDP-43 functionality as a result of a traumatic brain injury.

In some aspects a method for detecting a disease or condition associated with a decline in TDP-43 functionality comprises obtaining a sample from a subject, and assessing the sample to determine if it includes a putative peptide (e.g., a 17 amino acid peptide). In some embodiments the peptide is detected using any methods known to those of skill in the art. The STMN2 transcript containing the cryptic exon (e.g., the abortive STMN2 transcript) encodes for the putative peptide (e.g., the 17 amino acid peptide). The presence of the peptide may indicate a decline in TDP-43 functionality.

In some aspects a method for detecting a neurodegenerative disease comprises obtaining a sample (e.g., a biofluid sample) from the subject, and assessing the sample to determine if it includes an SMNT2 cryptic exon peptide (e.g., a 17 amino acid peptide). In some embodiments the peptide is detected using any methods known to those of skill in the art. The presence of the peptide may indicate a decline in TDP-43 functionality as a result of a neurodegenerative disease or disorder.

In some aspects a method for detecting a TBI comprises obtaining a sample (e.g., a biofluid sample) from the subject, and assessing the sample to determine if it includes an SMNT2 cryptic exon peptide (e.g., a 17 amino acid peptide). In some embodiments the peptide is detected using any methods known to those of skill in the art. The presence of the peptide may indicate a decline in TDP-43 functionality as a result of a traumatic brain injury.

In some aspects STMN2 and/or TDP-43 is used as a biomarker for measuring the severity of a traumatic brain injury. In some aspects the disclosure contemplates the use of STMN2 as a biomarker for measuring the severity of a traumatic brain injury. In some embodiments the amount of accumulated TDP-43 in neuronal cells is an indicator of the severity of a traumatic brain injury.

In some aspects the disclosure contemplates the use of STMN2 as a biomarker for confirming the diagnosis of Alzheimer's in a subject. For example, a subject diagnosed as having Alzheimer's may in fact have FTD. In some aspects, a sample (e.g., a biofluid sample) is obtained from a subject diagnosed as having Alzheimer's, and the sample is assessed (e.g., using an assay) to determine if it contains altered levels of STMN2 protein. If the levels of STMN2 protein are altered in the sample, the subject may have been misdiagnosed as having Alzheimer's and may be diagnosed as having FTD.

In some aspects the disclosure contemplates the use of STMN2 as a biomarker for confirming the diagnosis of Parkinson's in a subject. For example, a subject diagnosed as having Parkinson's may in fact have FTD. In some aspects, a sample (e.g., a biofluid sample) is obtained from a subject diagnosed as having Parkinsons's, and the sample is assessed (e.g., using an assay) to determine if it contains altered levels of STMN2 protein. If the levels of STMN2 protein are altered in the sample, the subject may have been misdiagnosed as having Parkinson's and may be diagnosed as having FTD.

Assay

In some aspects the disclosure contemplates an assay for measuring STMN2 normal transcripts, STMN2 abortive transcripts, and/or STMN2 transcripts containing a cryptic exon in biofluid samples. In some embodiments the sample is a CSF sample. In some embodiments, the CSF sample is processed to isolate RNA from CSF-derived exosomes. The isolated RNA may be converted into cDNA. In some embodiments the assay is a Q-RT-PCR assay. In some embodiments a method of using the assay comprises obtaining a biofluid sample (e.g., a CSF biofluid sample); extracting exosome RNA; converting the extracted RNA into cDNA; and assaying the cDNA, e.g., using qPCR, to detect cryptic STMN2 and normal STMN2 transcripts in the sample. In some embodiments the STMN2 transcripts are normalized to the house keeping ribosomal subunit RNA18S5.

In some aspects the disclosure contemplates processing a sample for an assay. In some embodiments the processing of the sample includes obtaining a biofluid sample (e.g., from a subject), extracting exosome RNA from the biofluid sample, and converting the extracted exosome RNA into cDNA. In some embodiments the cDNA is used in an assay, e.g., a qPCR assay. In some embodiments the biofluid sample is a cerebral spinal fluid sample.

In some aspects the disclosure contemplates an assay for measuring STMN2 protein levels in biofluid samples. In some embodiments the sample is a CSF sample. In some embodiments the assay is an ELISA sandwich assay. In some embodiments a method of using the assay comprises obtaining a biofluid sample (e.g., a CSF biofluid sample); probing the biofluid sample; and quantitating the level of STMN2 protein in the sample, e.g., using an ELISA sandwich assay, to detect reduced levels of STMN2 protein in the sample.

In some aspects the disclosure contemplates an assay for measuring levels of a putative peptide (e.g., a 17 amino acid peptide) in biofluid samples. In some embodiments the sample is a CSF sample. In some embodiments a method of using the assay comprises obtaining a biofluid sample (e.g., a CSF biofluid sample); and assessing the sample to determine if it includes the putative peptide. In some aspects the amount of putative peptide is quantified. The presence of the putative peptide may act as a biomarker for the presence of the STMN2 abortive transcript. The presence of the peptide may further indicate a decline in TDP-43 functionality.

EXAMPLES

Example 1

In a landmark finding, TDP-43 (TAR DNA-binding protein 43) was discovered to be a major constituent of ubiquitin-positive inclusions in many sporadic cases of ALS and a substantial subset of FTD (7). TDP-43 is a predominantly nuclear DNA/RNA binding protein (8) with functional roles in transcriptional regulation (9), splicing (10, 11), pre-miRNA processing (12), stress granule formation (13, 14), and mRNA transport and stability (15, 16). Subsequently, autosomal-dominant, apparently causative mutations in TARDBP were identified in both ALS and FTD families, linking genetics and pathology with neurodegeneration (17-21). Thus, elucidating the role that TDP-43 mislocalization and mutation play in disease is essential to understanding both sporadic and familial ALS.

Whether neurodegeneration associated with TDP-43 pathology is the result of loss-of-function mechanisms, toxic gain-of-function mechanisms, or a combination of both, remains unclear (22). Early studies showed that overexpression of both wildtype and mutant TDP-43 led to its aggregation and loss of nuclear localization (22). While these studies along with the autosomal dominant inheritance pattern of TARDBP mutations would seemingly support a gain-of-function view, the loss of nuclear TDP-43, generally associated with its aggregation, suggests its normal functions might also be impaired. Subsequent findings revealed that TDP-43 depletion in the developing embryo or post-mitotic motor neurons can have profound consequences (23-27).

Given the myriad roles TDP-43 plays in neuronal RNA metabolism, a key question has become: what are the RNA substrates that are misregulated upon TDP-43 mislocalization, and how do they contribute to motor neuropathy? Early efforts to answer this question utilized cross-linking and immunoprecipitation with RNA sequencing (RNA-seq) of whole brain homogenates from either patients or mice subjected to TARDBP knockdown (11, 28). These resulting discoveries led to a general understanding that many transcripts are regulated by TDP-43 with a preference towards lengthy RNAs containing UG repeats and long introns; however, the prominence of glial RNAs in the brain homogenates sequenced in these experiments limited insights into the specific neuronal targets of TDP-43. As a result, few clear connections between the TDP-43 target RNAs and mechanisms of motor neuron degeneration could be forged.

To identify substrates that when misregulated contribute to neuronal degeneration, the identity of RNAs regulated by TDP-43 in purified human motor neurons was sought. Because the vulnerable motor neurons in living ALS patients are fundamentally inaccessible for isolation and experimental perturbation, directed differentiation approaches have been developed for guiding human pluripotent stem cells into motor neurons (hMNs) to study ALS and other neurodegenerative conditions in vitro (29-31). Here, RNA-seq of hMNs was performed after TDP-43 knockdown to identify transcripts whose abundance are positively or negatively regulated by TDP-43's deficit. In total, 885 transcripts were identified for which TDP-43 is needed to maintain normal RNA levels. Although misregulation of any number of these targets may play subtle roles in motor neuron degeneration, it was noted that one of the most abundant transcripts in motor neurons, encoding STMN2, was particularly sensitive to a decline in TARDBP, but not FUS or C9ORF72 activities. Additionally, it was determined that STMN2 levels were also decreased in hMNs expressing mutant TDP-43 and in hMNs whose proteasomes were pharmacologically inhibited, which has been shown to induce cytoplasmic accumulation and aggregation of TDP-43 in rodent neurons (32). It was further shown that STMN2, a known regulator of microtubule stability, encodes a protein that is necessary for normal human motor neuron outgrowth and repair. Importantly, loss of STMN2 function as a result of loss of TDP-43 activity is likely to be of functional relevance to people with ALS as its expression was also found to be reproducibly decreased in the motor neurons of ALS patients.

Results

Differentiation and Purification of Human Motor Neurons (hMNs)

Figure 7A:
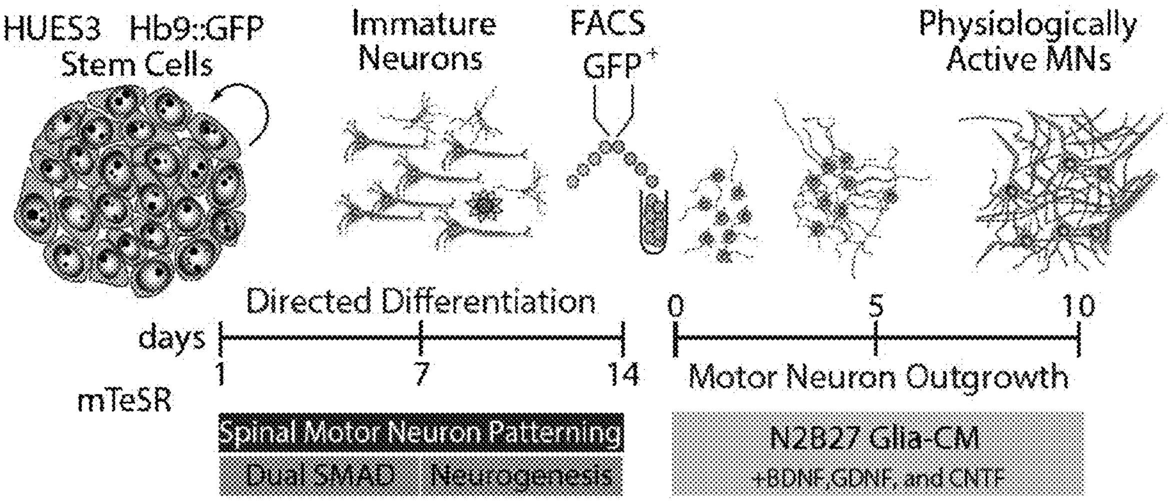
FIGS. 7A-7I demonstrate production of differentiated human motor neurons.
Figure 7B:
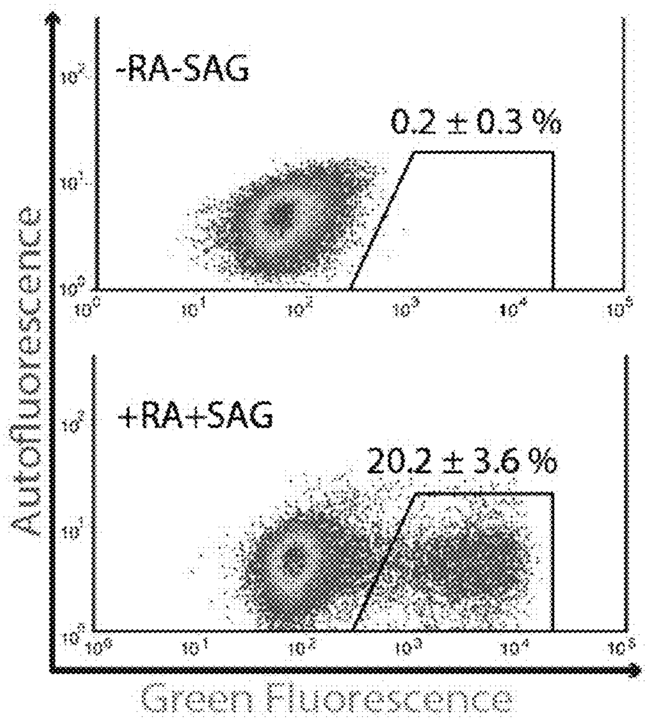
Figure 7E:
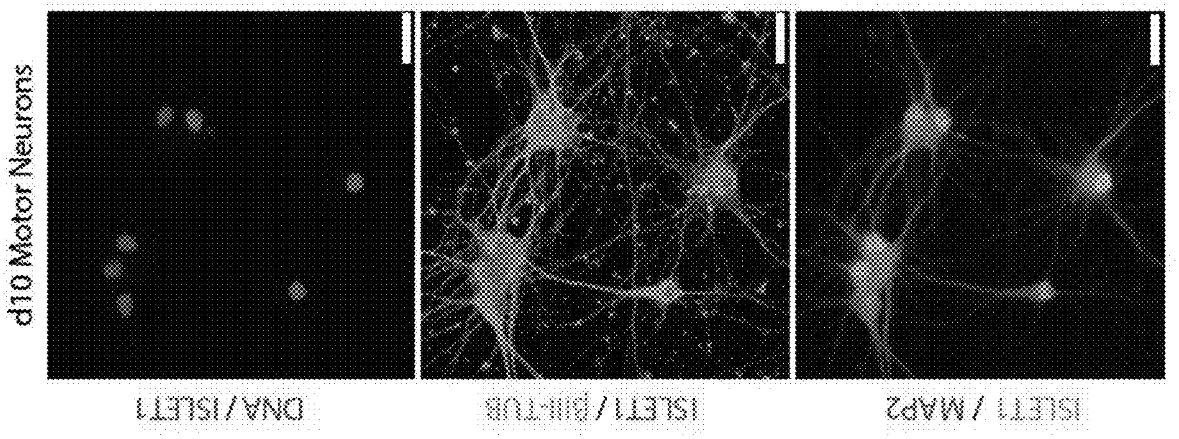
Figure 7D:
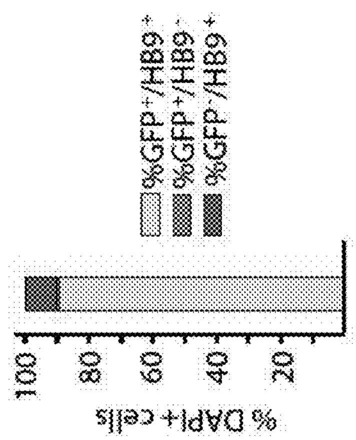
Figure 7F:
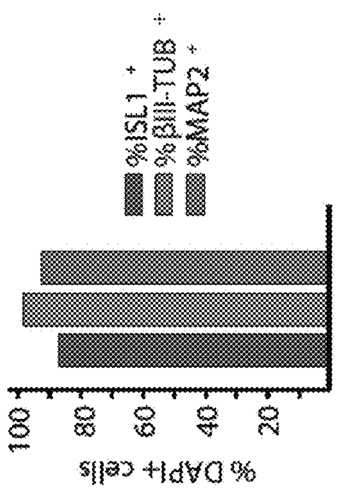
Figure 7C:
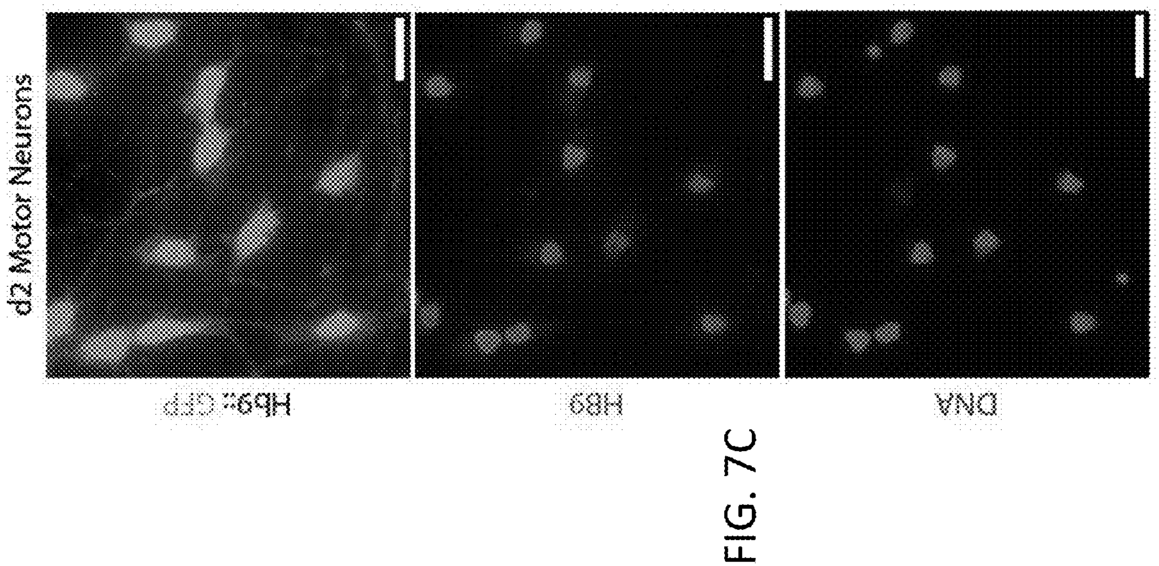
Figure 7I:
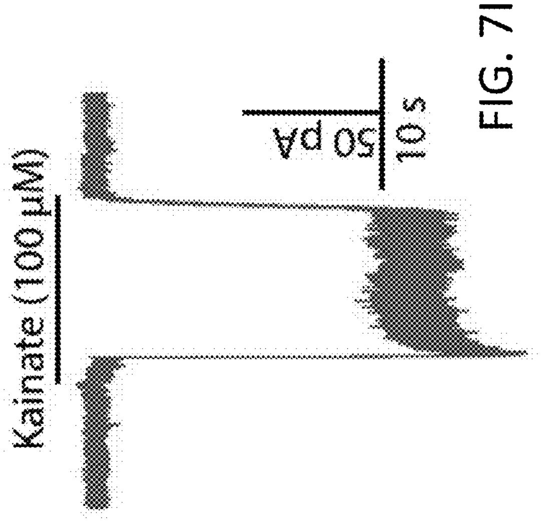
Figure 7G:
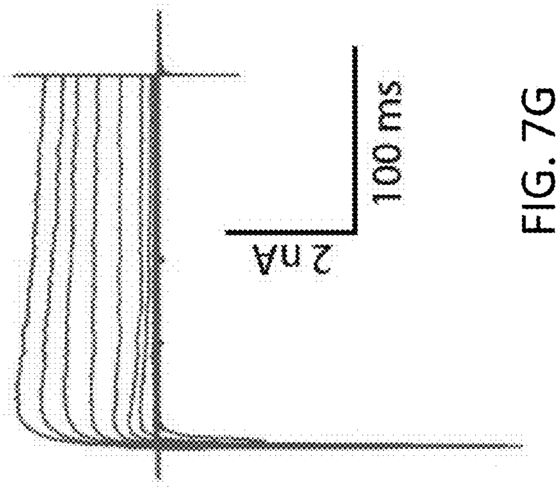
Figure 7H:
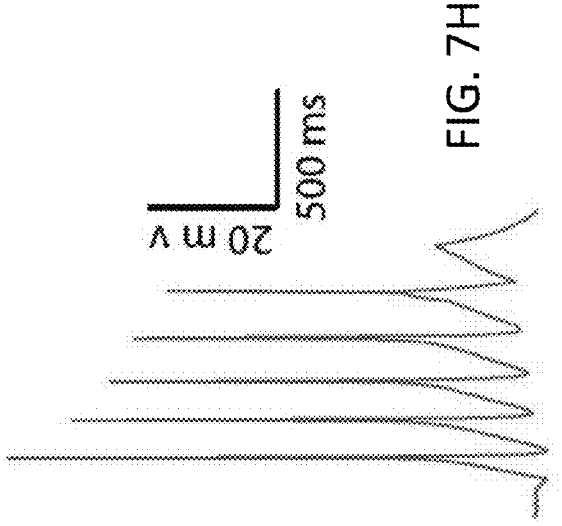

In order to produce hMNs, the human embryonic stem cell line HUES3 Hb9::GFP (33, 34) was differentiated into GFP+ hMNs under adherent culture conditions (35, 36) using a modified 14-day strategy (FIG. 7A). This approach relies on neural induction through small molecule inhibition of SMAD signaling, accelerated neural differentiation through FGF and NOTCH signaling inhibition, and MN patterning through the activation of retinoic acid (RA) and Sonic Hedgehog signaling pathways (FIG. 7A). On day 14 of differentiation, cultures comprising ~18-20% GFP+ cells were routinely obtained (FIG. 7B). 2 days following fluorescent activated cell sorting (FACS), >95% of the resulting cells expressed the transcription factors HB9 (FIGS. 7C-7D). After another 8 days, cultures were composed of neurons expressing the transcription factor Islet-1(80%) as well as the pan-neuronal cytoskeletal proteins b-III tubulin (97%) and microtubule associated protein 2 (MAP2) (90%) (FIGS. 7E-7F). Whole-cell patch-clamp recordings following FACS and 10 days of culture in glia-conditioned medium supplemented with neurotrophic factors revealed that these purified hMNs were electrophysiologically active (FIGS. 7G-7I). Upon depolarization, hMNs exhibited initial fast inward currents followed by slow outward currents, consistent with the expression of functional voltage-activated sodium and potassium channels, respectively (FIG. 7G). In addition, hMNs fired repetitive action potentials (FIG. 7H), and responded to Kainate, an excitatory neurotransmitter (FIG. 7I). Taken together, these data demonstrated these purified hMN cultures had expected functional properties.

RNA-Seq of hMNs with Reduced Levels of TDP-43

Figure 8A:
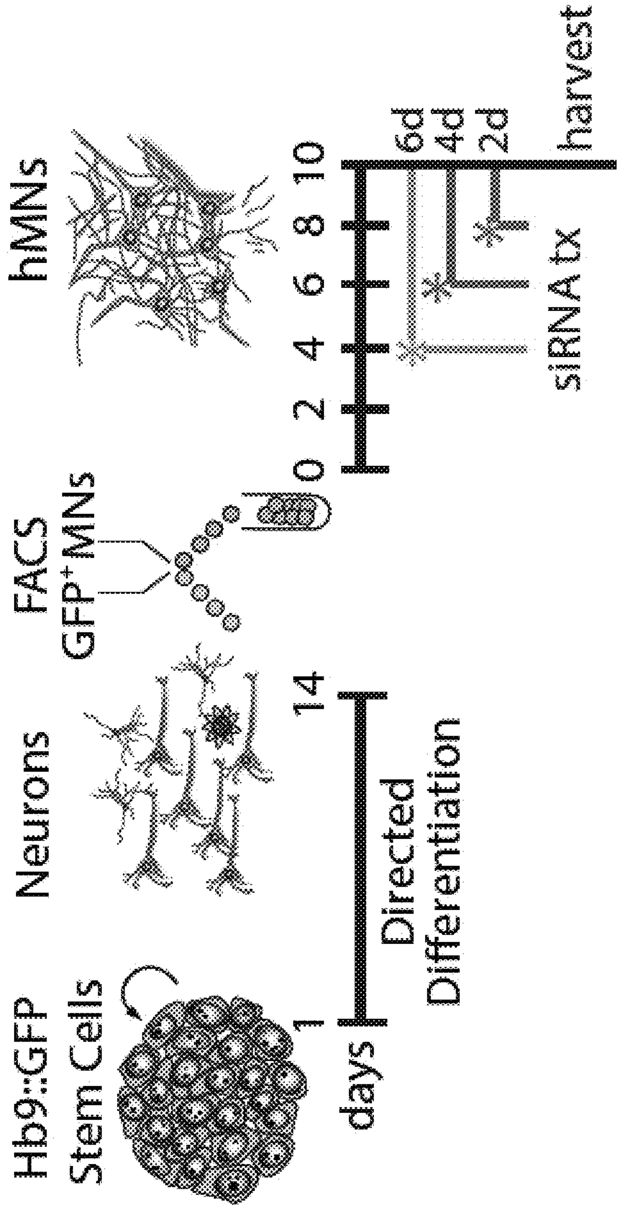
FIGS. 8A-8E demonstrate TDP-43 knockdown in cultured hMNs.
Figure 8B:
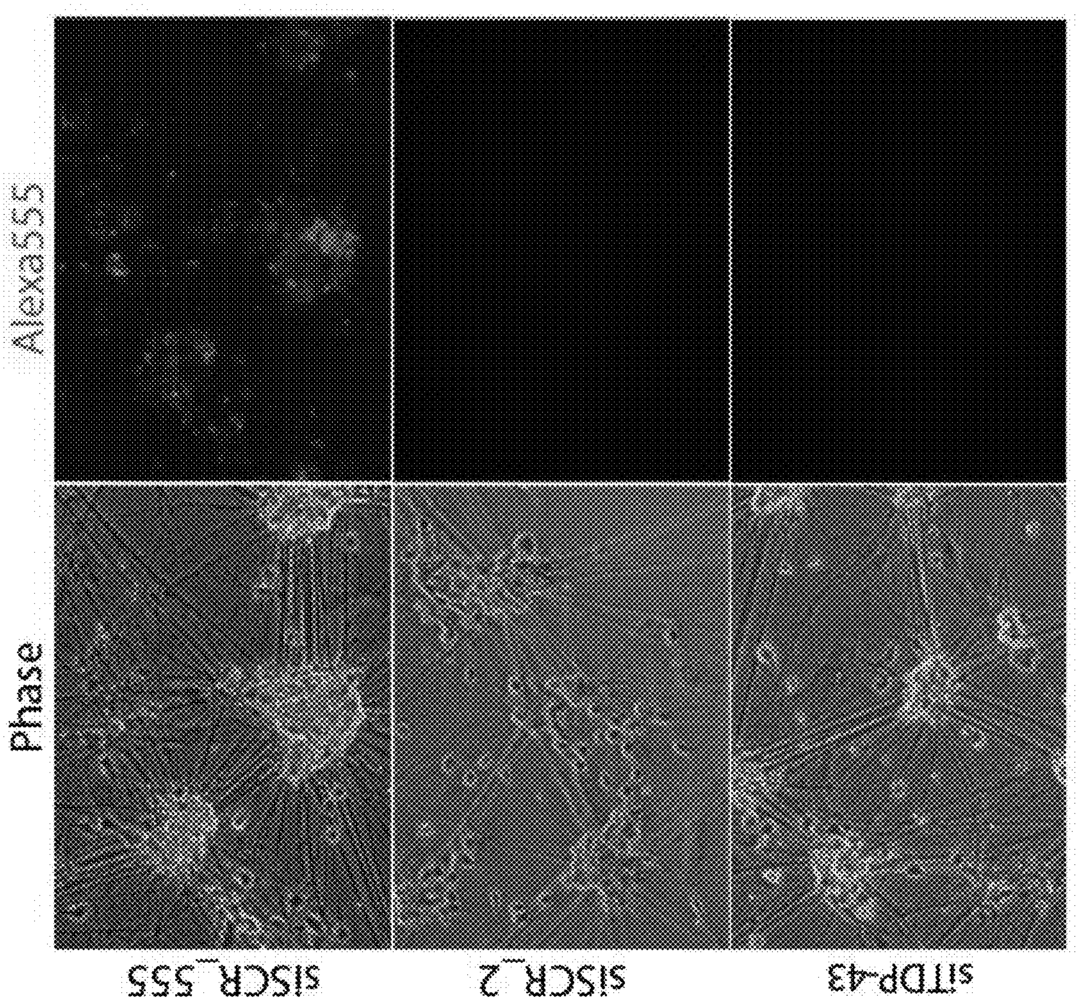
Figure 8C:
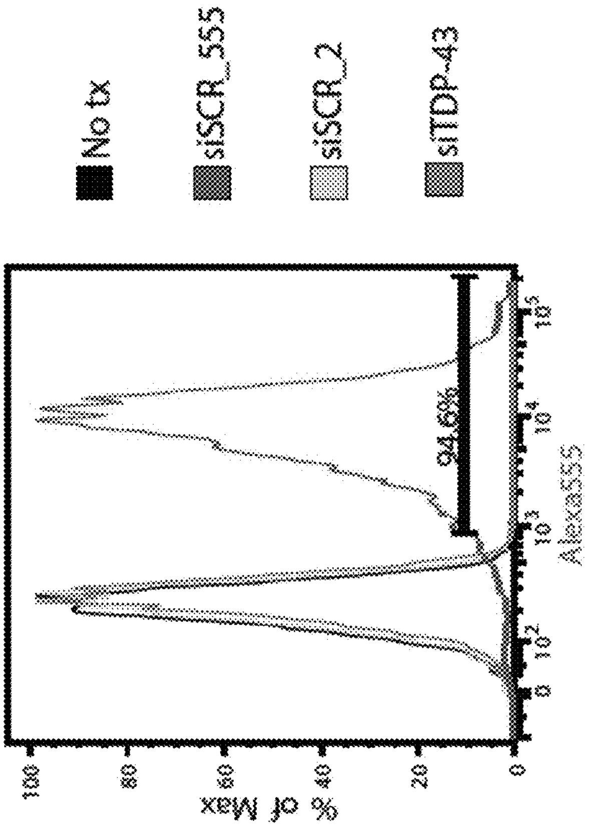
Figure 8D:
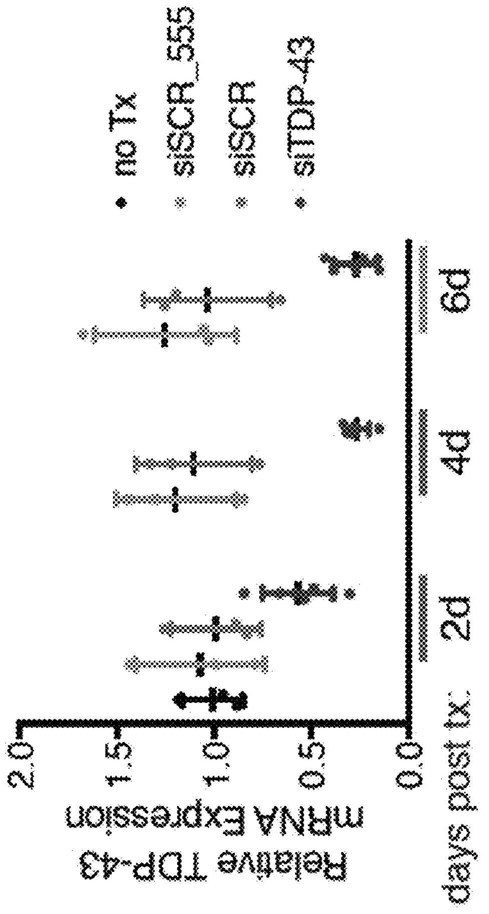
Figure 8E:
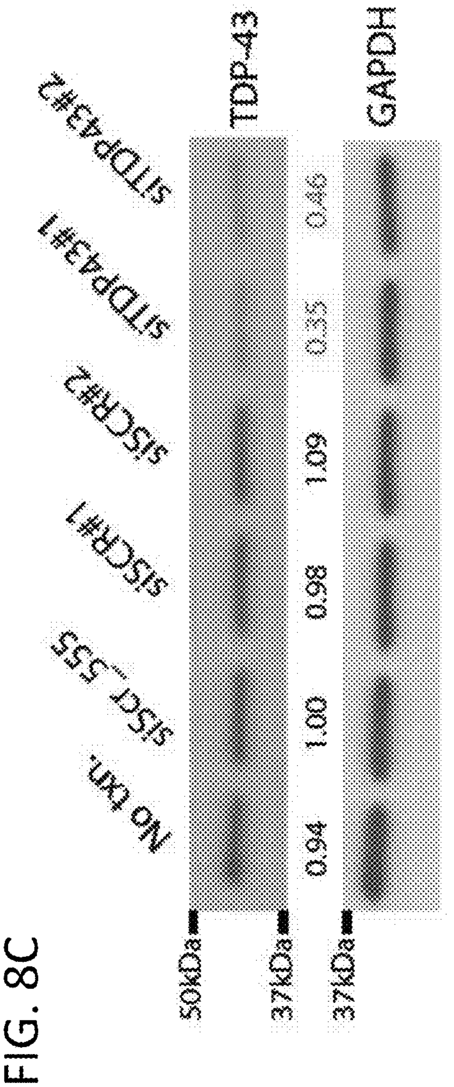

Reduced nuclear TDP-43 observed in ALS is emerging as potential cellular mechanism that may contribute to downstream neurodegenerative events (7, 37). It was therefore desired to identify the specific RNAs regulated by TDP-43 in purified hMN populations through a combination of knock-down and RNA-Seq approaches. Using a short interfering RNA conjugated to Alexa Fluor 555, transfection conditions were first validated to achieve high levels of siRNA delivery (~94.6%) into the hMNs (FIGS. 8A-8C). TDP-43 RNAi was then carried out in purified hMNs using two distinct siRNAs targeting the TDP-43 transcript (siTDP43), two control siRNAs with scrambled sequences that do not target any specific gene (siSCR and siSCR_555), and at three different time points after siRNA delivery (2, 4 and 6 days) (FIG. 8A). After siRNA transfection, total RNA and protein were isolated from the neurons. qRT-PCR assays validated the downregulation of TDP-43 mRNA levels at all the time points for MNs treated with siTDP43s, but not in those with the scrambled controls, with maximum knockdown occurring 4 days after siRNA transfection (FIG. 8D). Furthermore, depletion of TDP-43 was also confirmed at the protein level by immunoblot assays, with siTDP43-treated MNs showing a 54-65% reduction in TDP-43 levels (FIG. 8E).

Figure 1A:
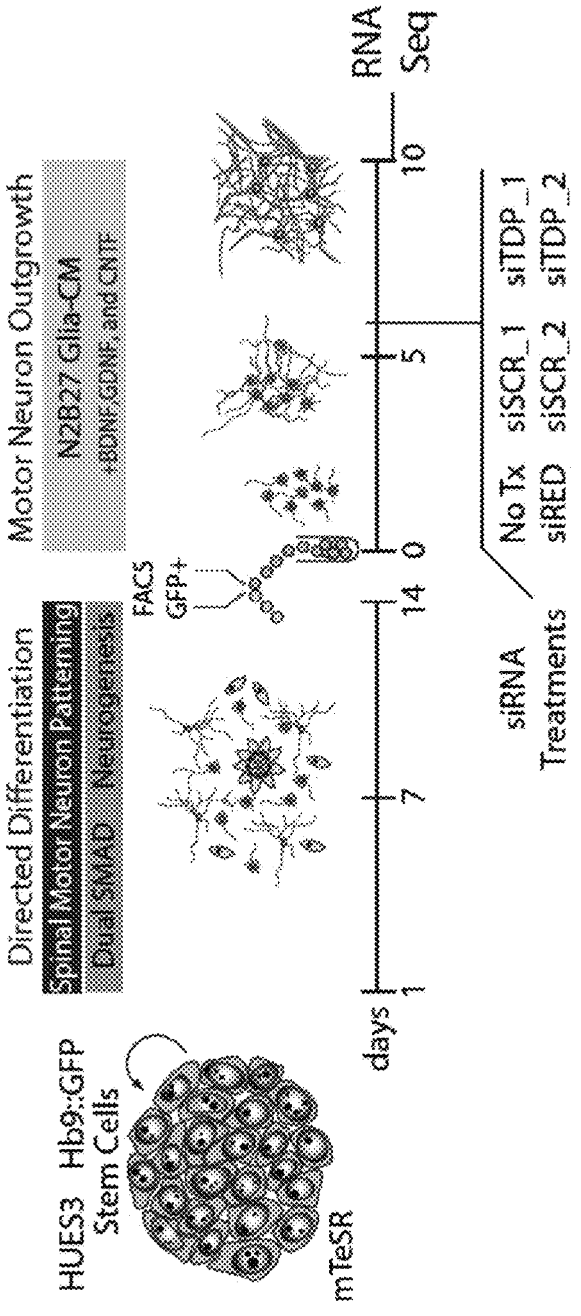
FIGS. 1A-1F demonstrate RNA Sequencing of TDP-43 knockdown in hMNs.
Figure 1B:
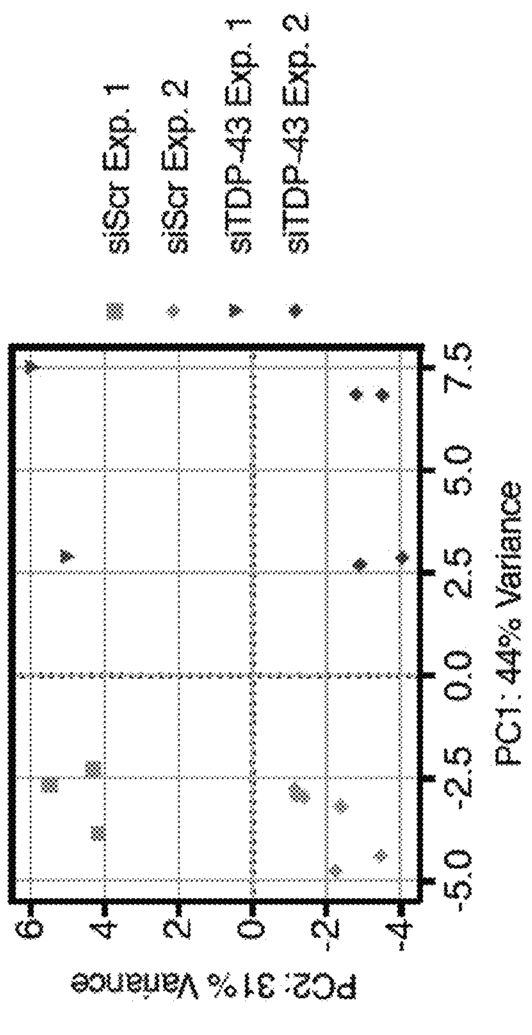
Figure 1C:
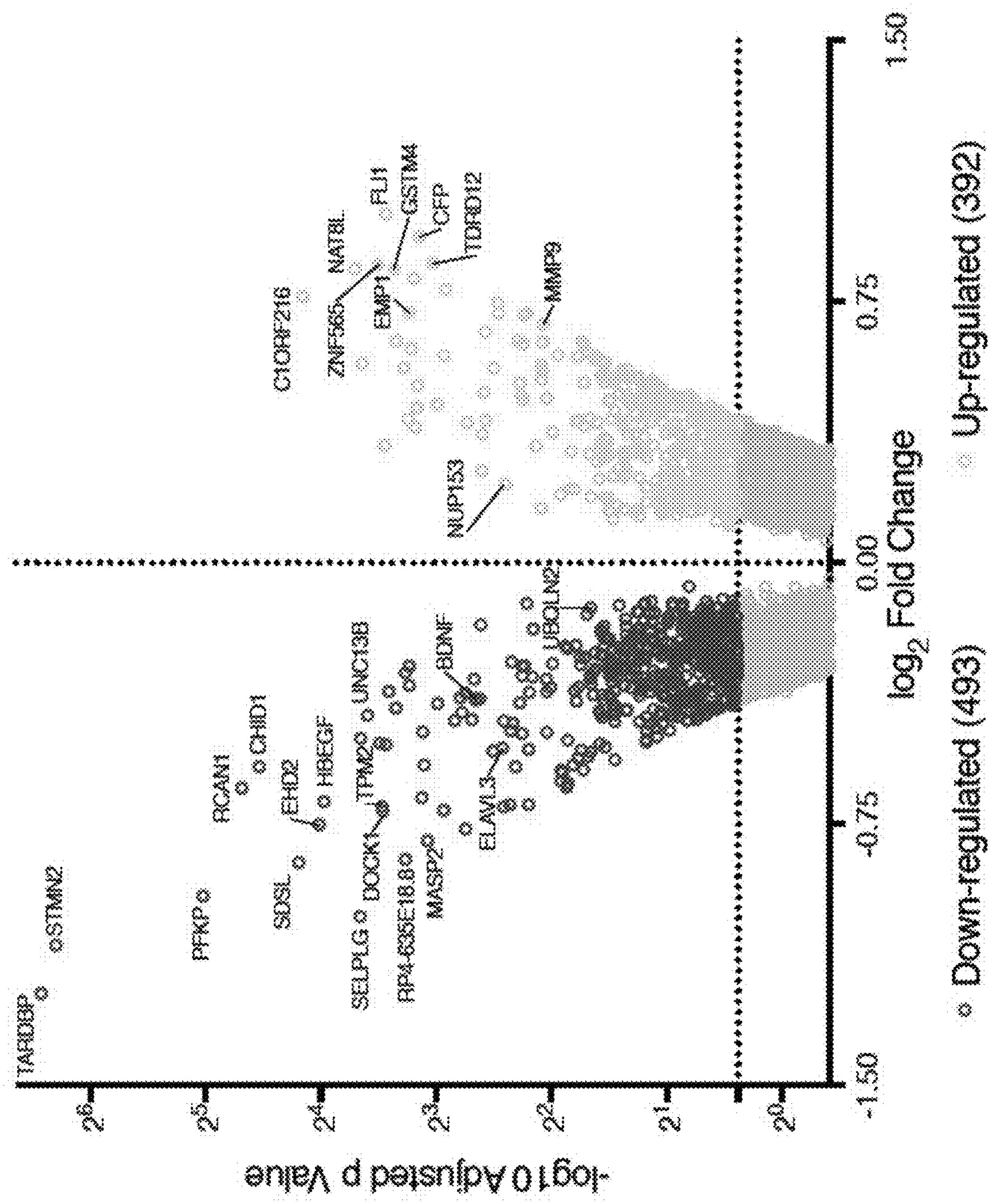
Figure 1D:
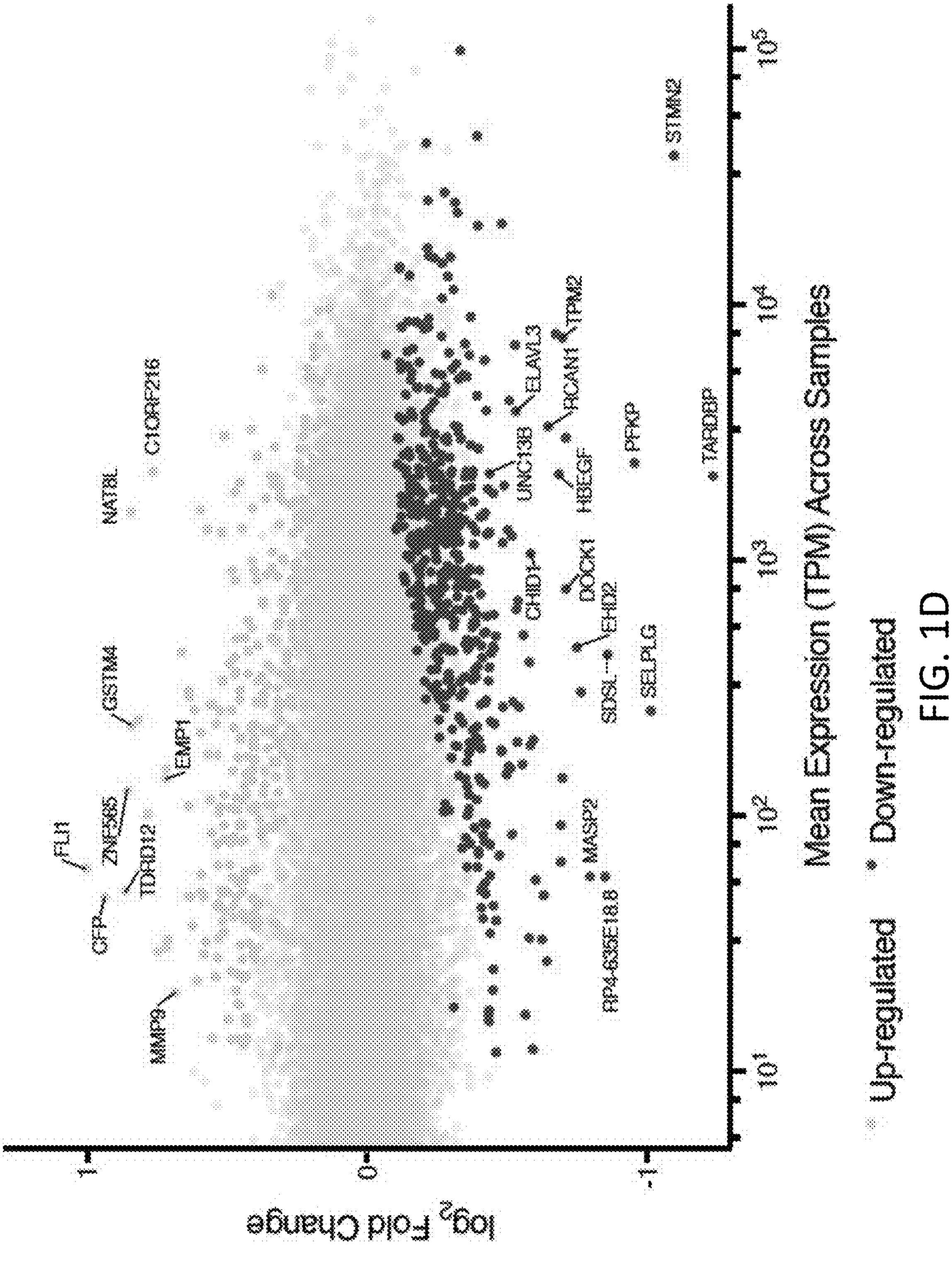
Figure 9A:
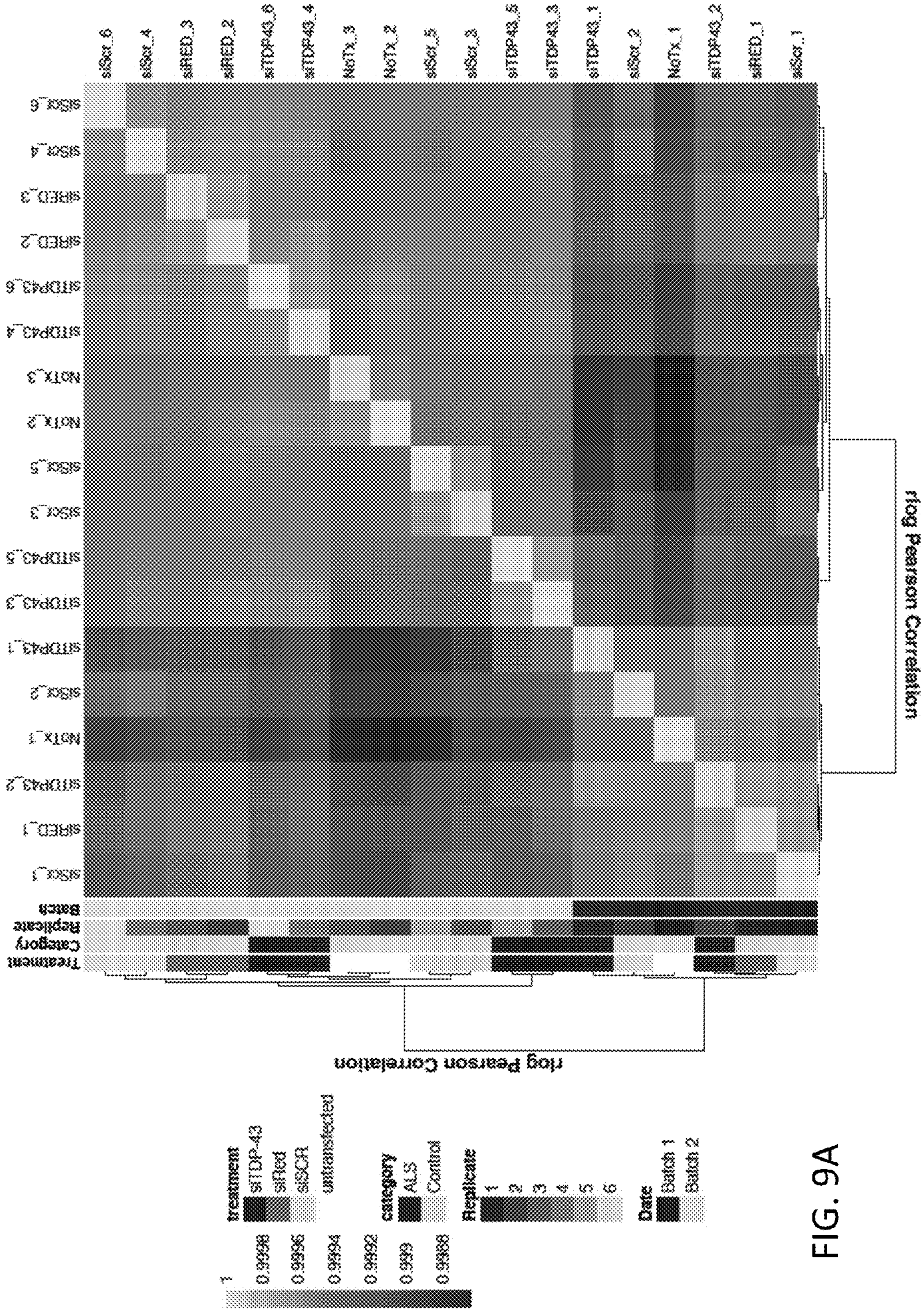
FIGS. 9A-9C demonstrate motor neuron RNA-Seq.
Figure 9C:
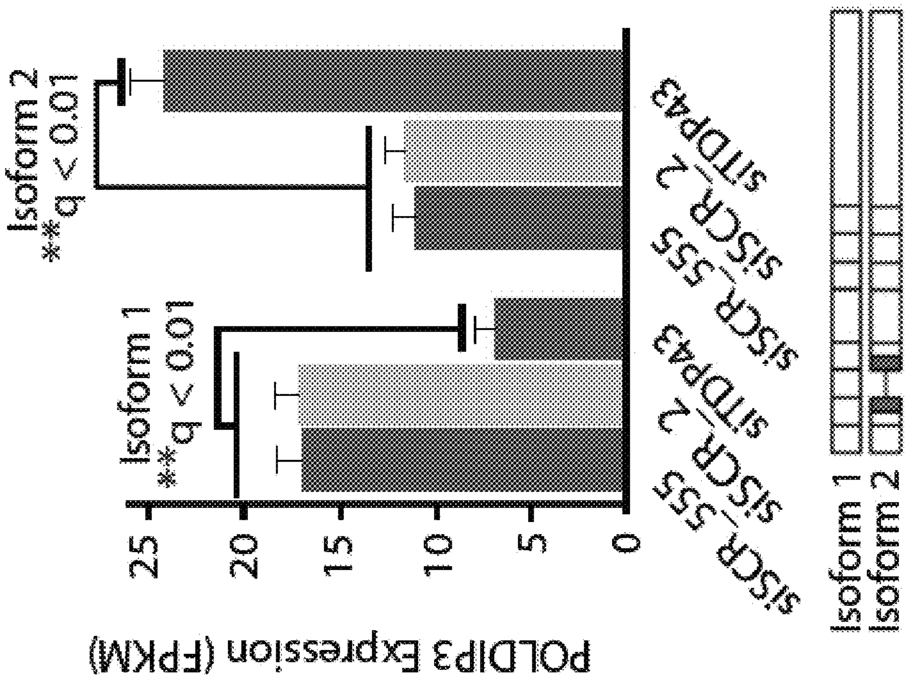
Figure 9B:
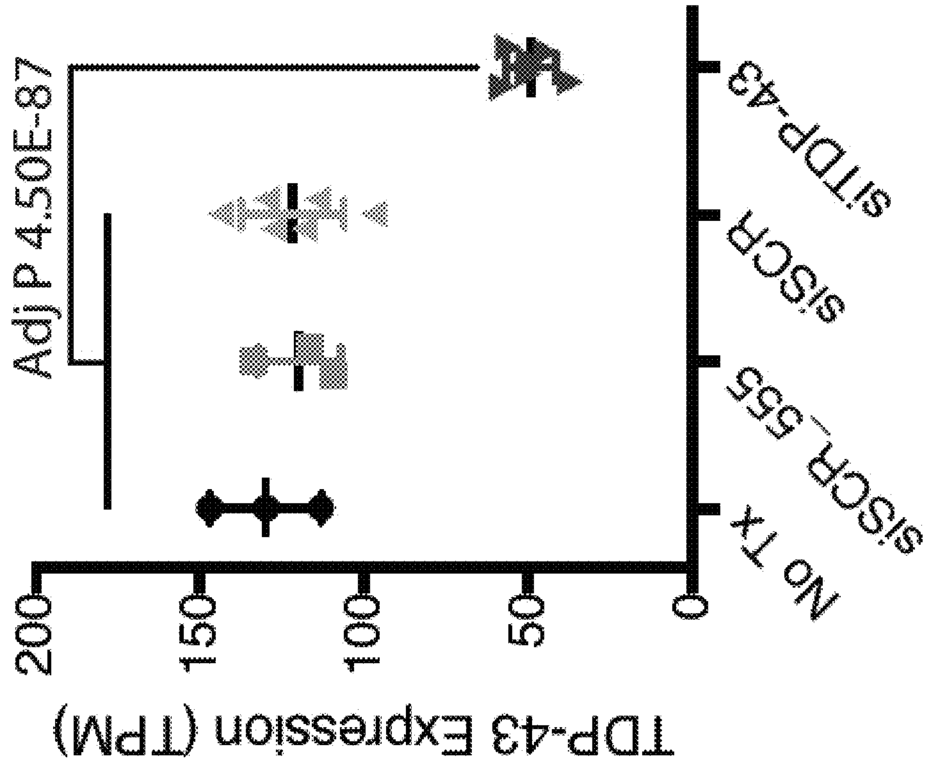

To capture global changes in gene expression in response to partial loss of TDP-43 in hMNs, RNA-Seq libraries were prepared from siRNA treated cells (FIG. 1A). After next-generation sequencing, expression data was obtained for each gene annotated as the number of transcripts per million (TPMs). Initial unsupervised hierarchical clustering revealed a transcriptional effect based on the batch of MN production (Experiment 1 vs. Experiment 2). (FIG. 9A) Subsequent principle component analyses of the RNA-Seq samples focused on the 500 most differentially expressed genes then segregated the samples based on siTDP-43 treatment (pcl), indicating that reduction of TDP-43 levels resulted in reliable transcriptional differences, followed by the batch of MN production (pc2) (FIG. 1B) Inspection of TPM values for TDP-43 transcripts confirmed that its abundance was significantly reduced only in MNs treated with siTDP43 (FIG. 9B). Differential gene expression analysis was then performed using DESeq2 suite of bioinformatics tools (38), which at a false discovery rate (FDR) of 5%, identified a total of 885 statistically differentially expressed genes in hMNs after TDP-43 knockdown (FIGS. 1C-1D). In these cells, TPM values were significantly higher for 392 genes ('upregulated'), and significantly lower for 493 genes ('downregulated') compared to those values in MNs treated with the scrambled sequence siRNA controls (FIGS. 1C-1D).

In addition to altering total transcriptional levels of hundreds of genes in the mammalian CNS (11), reduced levels of TDP-43 can also influence gene splicing (11, 39-42). Although global analysis of splicing variants traditionally involves splicing-sensitive exon arrays (11, 39), the development of computational approaches for isoform deconvolution of RNA-Seq reads is rapidly evolving (43-45). A limited examination of the data with the bioinformatics algorithm 'Cuffdiff 2' (45) was indeed able to detect the POLDIP3 gene as the top candidate for differential splicing with two significant isoform-switching events (FIG. 9C), which has previously been associated with deficits in TDP-43 function both in vitro and in vivo (42,46).

Figure 1F:
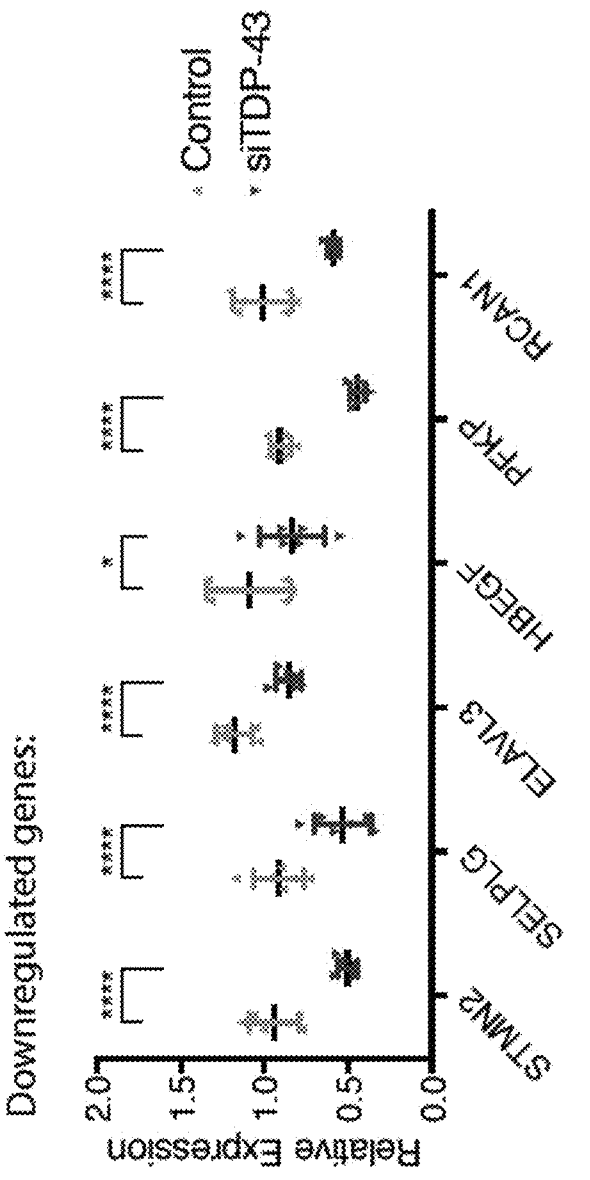
Figure 1E:
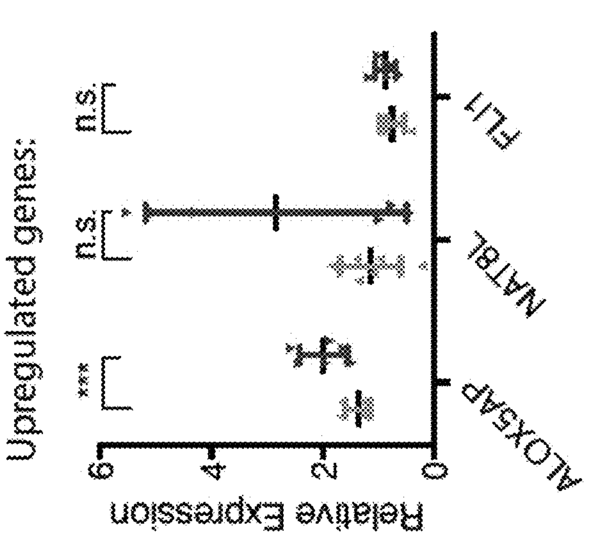

Of the 885 genes identified as significantly misregulated after TDP-43 knockdown, a candidate subset was selected for further validation. First, genes with enriched neuronal expression (STMN2 (47,48), ELAVL3 (49)), and association with neurodevelopment and neurological disorders (RCAN1 (50), NAT8L (51)) were considered. In addition, genes with reasonable expression levels (TPM≥5) and high fold changes as 'positive controls' (SELPLG, NAT8L) were considered, as it was hypothesized that these candidates would be more robust and likely to validate. RNA was then obtained from independent biological replicates after TDP-43 knockdown and the relative expression levels for 11 candidate genes, including TARDBP, was determined by qRT-PCR. Notably, differential gene expression for 9/11 of these genes was confirmed in cells treated with either siTDP-43 relative to those treated with scrambled control (FIGS. 1E-1F). These results indicate reproducible expression differences among the genes selected and validate the findings from RNA-Seq analysis.

STMN2 Levels are Downregulated in hMNs Expressing Mutant TDP-43

Figure 2A:
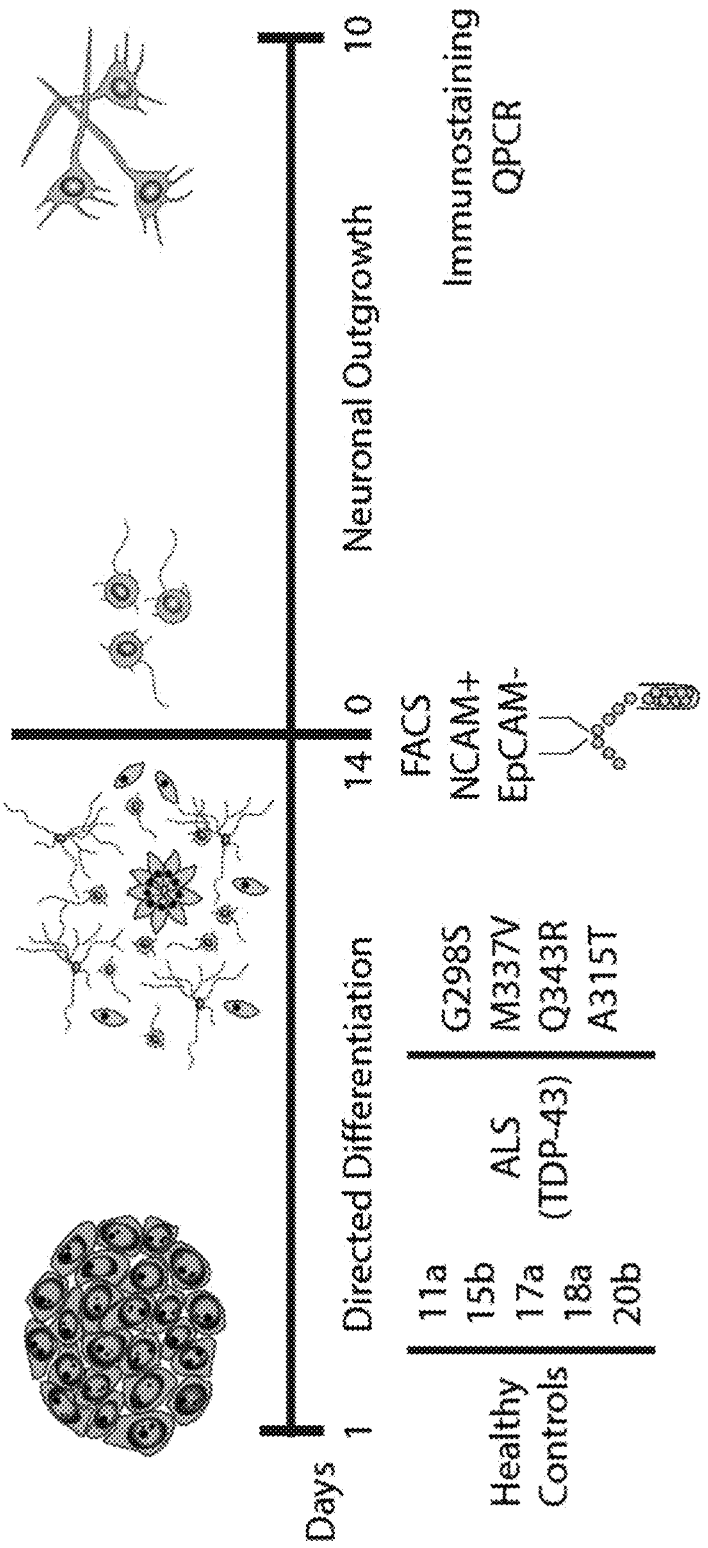
FIGS. 2A-2J Demonstrate a familial ALS model.
Figure 2B:
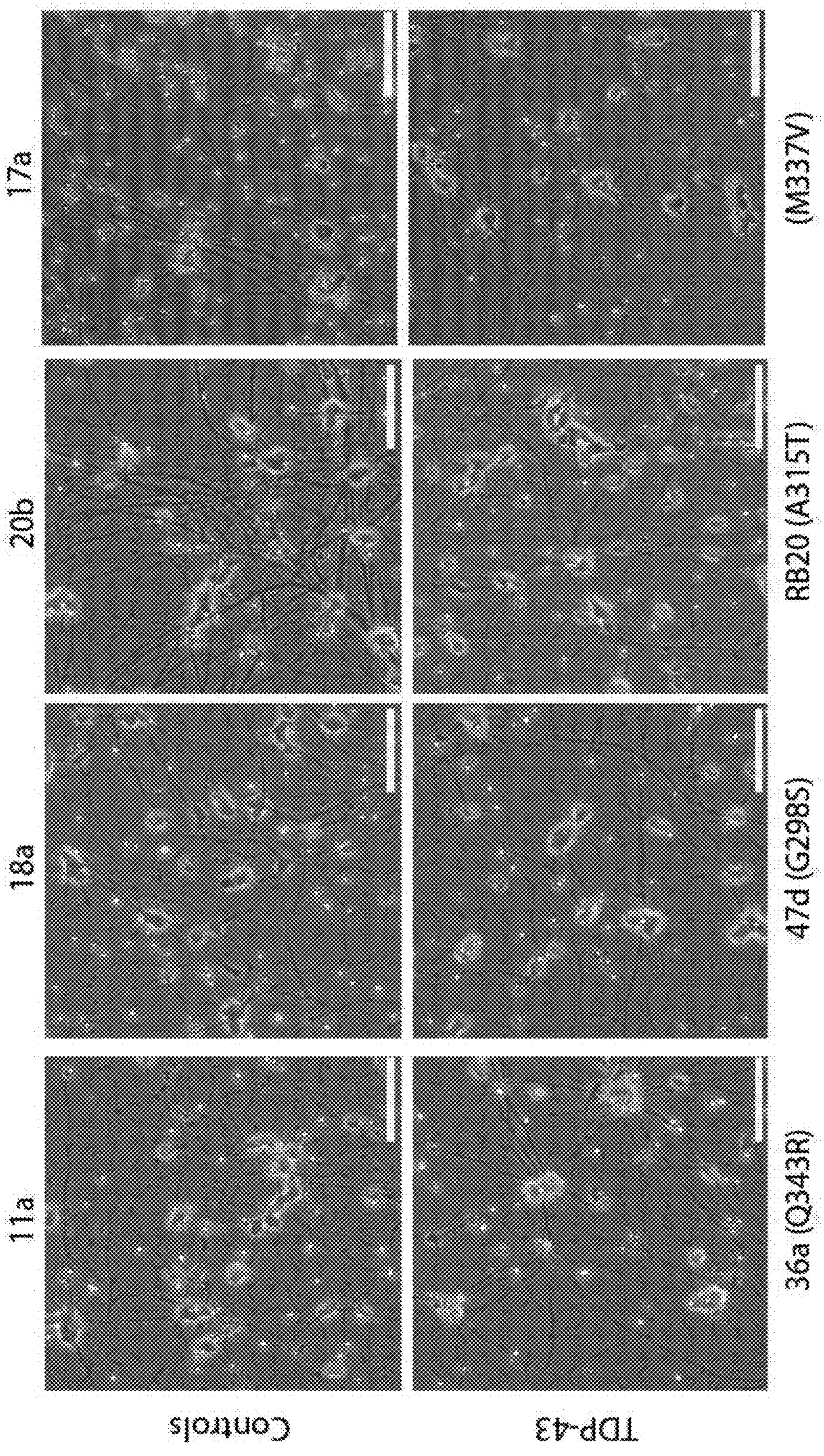
Figure 2C:
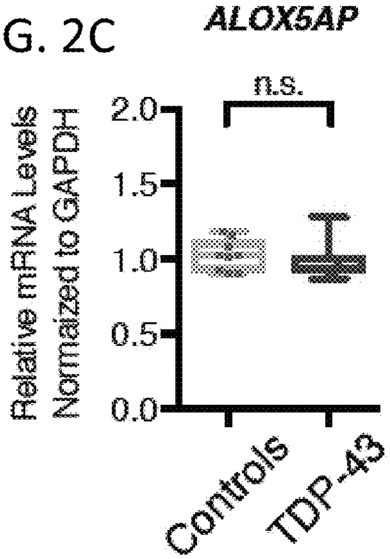
Figure 2D:
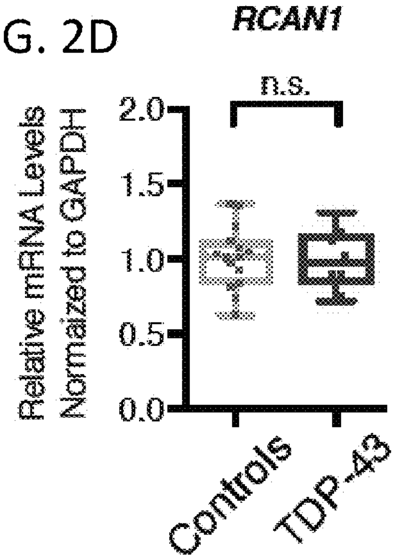
Figure 2E:
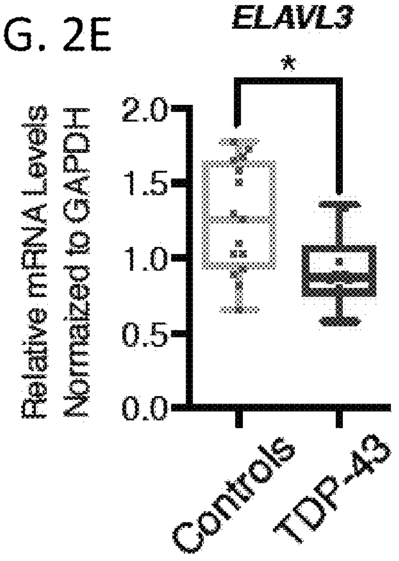
Figure 2F:
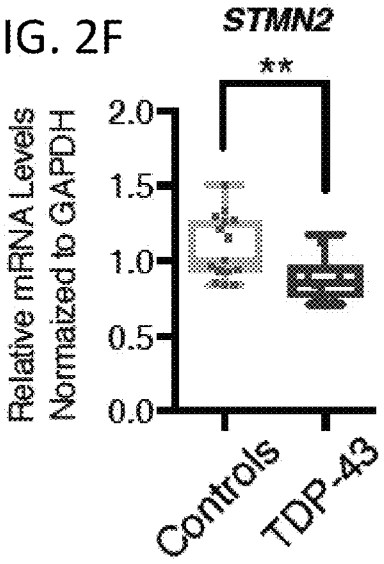
Figure 10:
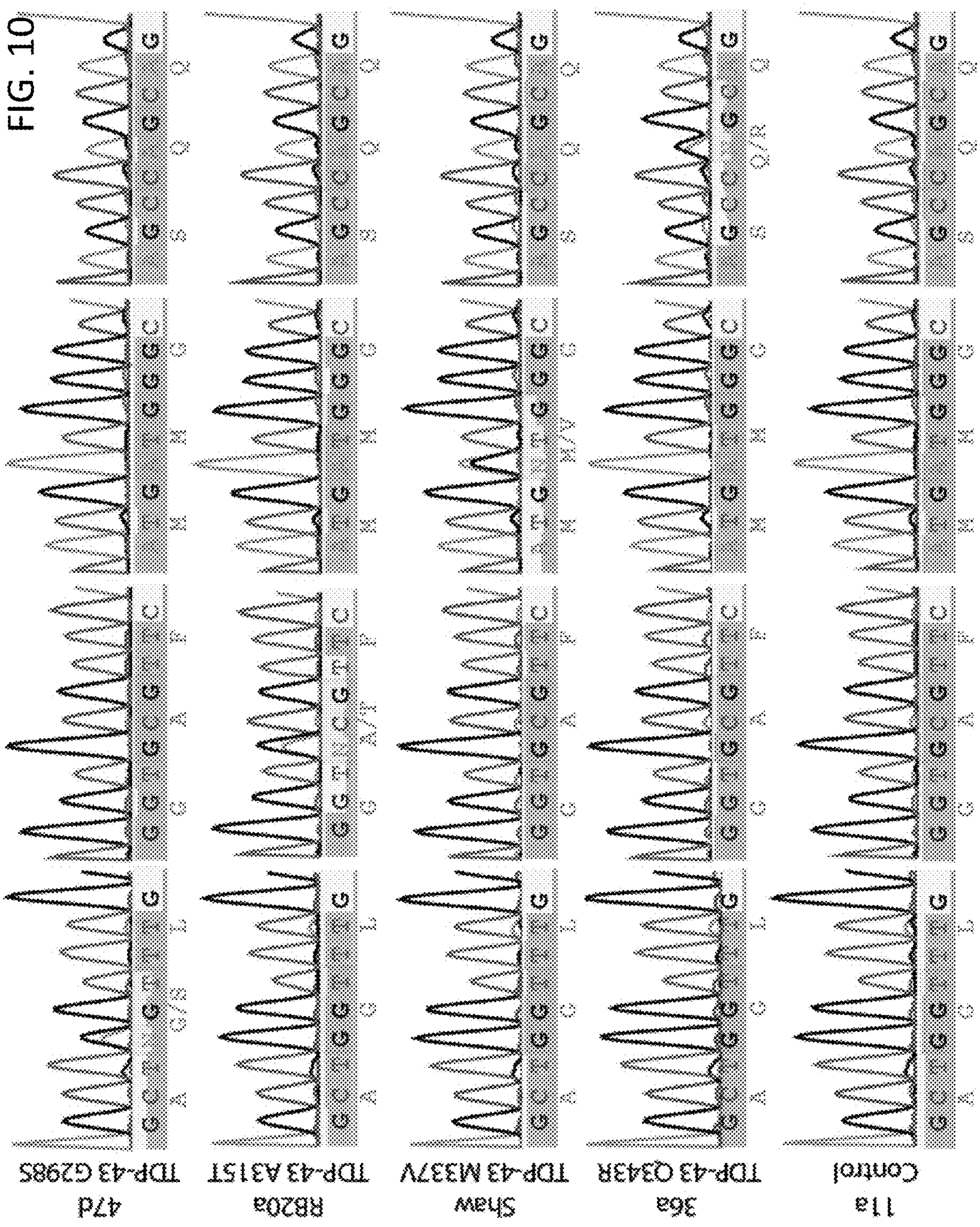
FIG. 10 demonstrates pluripotent stem cell genotyping sequencing chromatograms of Exon6 of TARDBP in the indicated iPS cell lines to confirm the heterozygous mutations in the patient lines.
Figure 10:
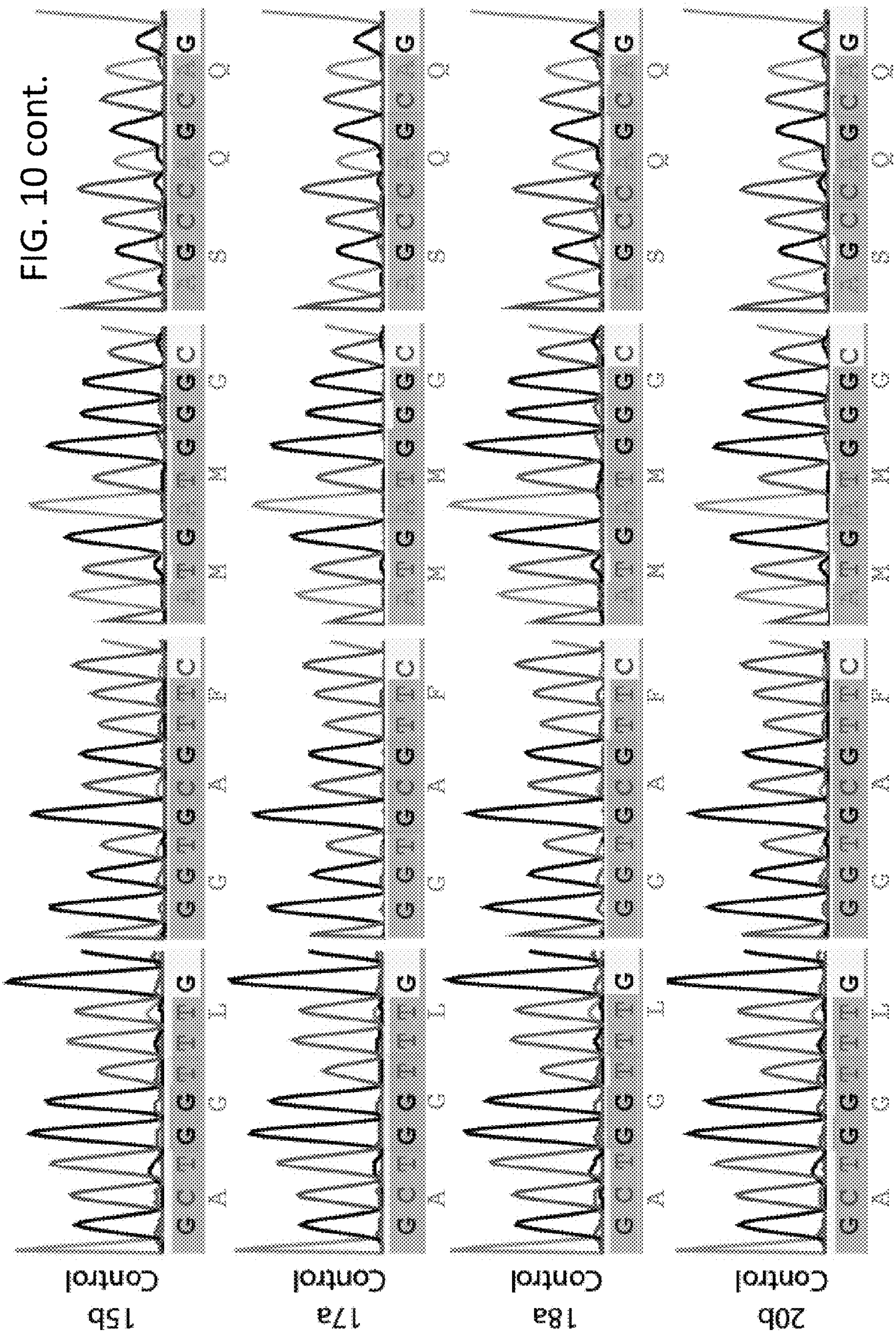
Figure 11A:
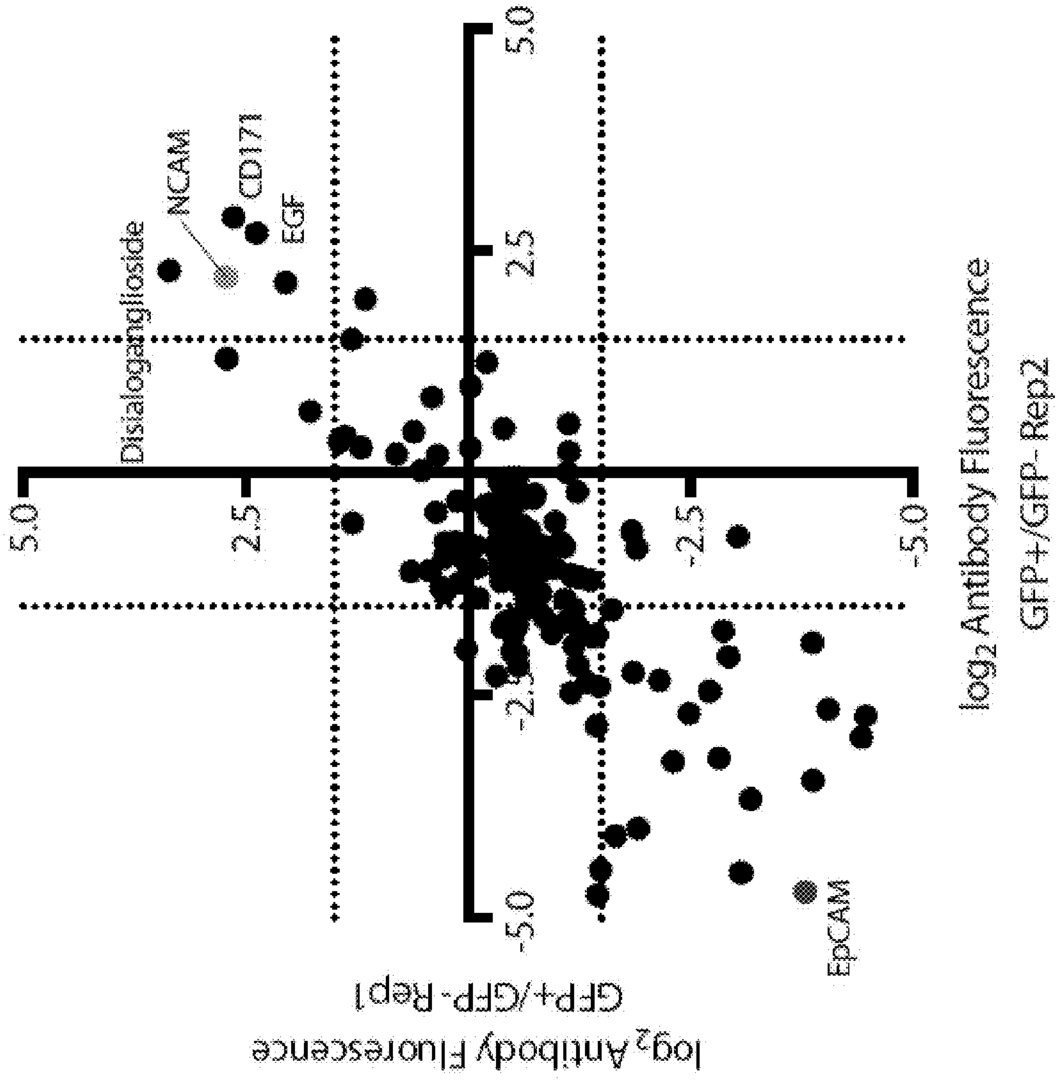
FIGS. 11A-11F demonstrate neuronal cell sorting.
Figure 11B:
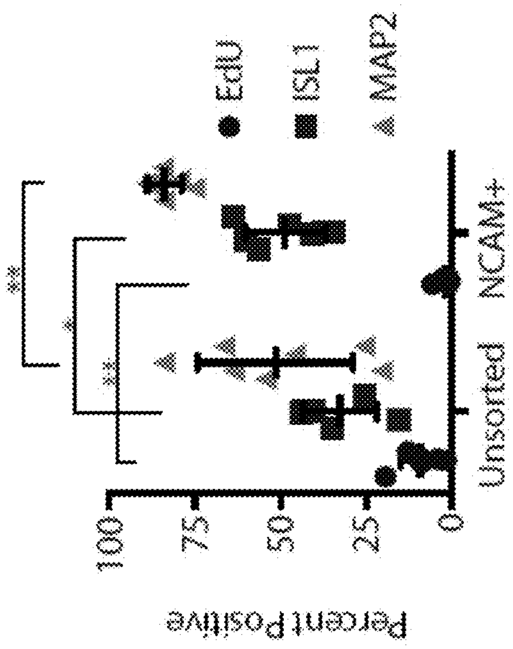
Figure 11C:
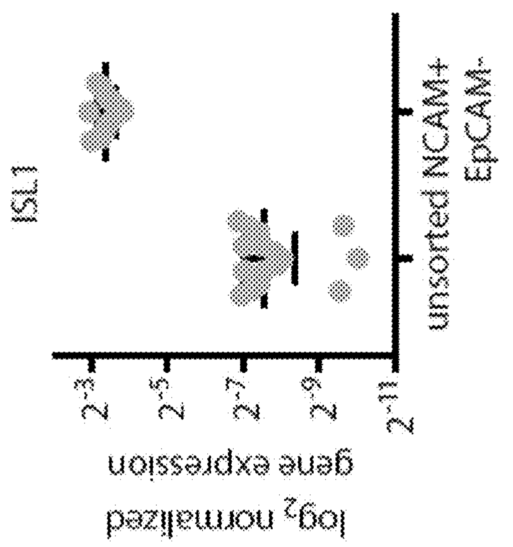
Figure 11D:
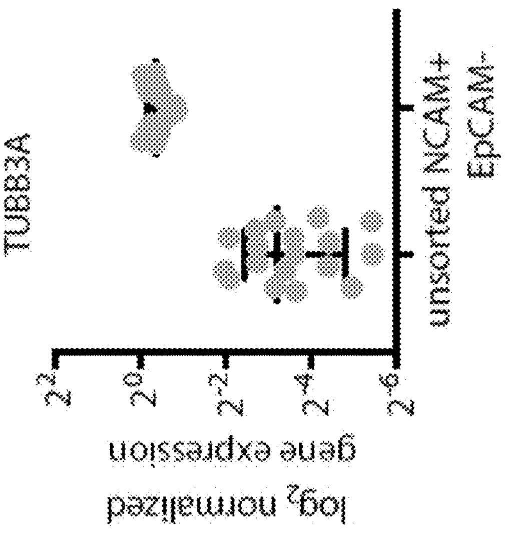
Figure 11E:
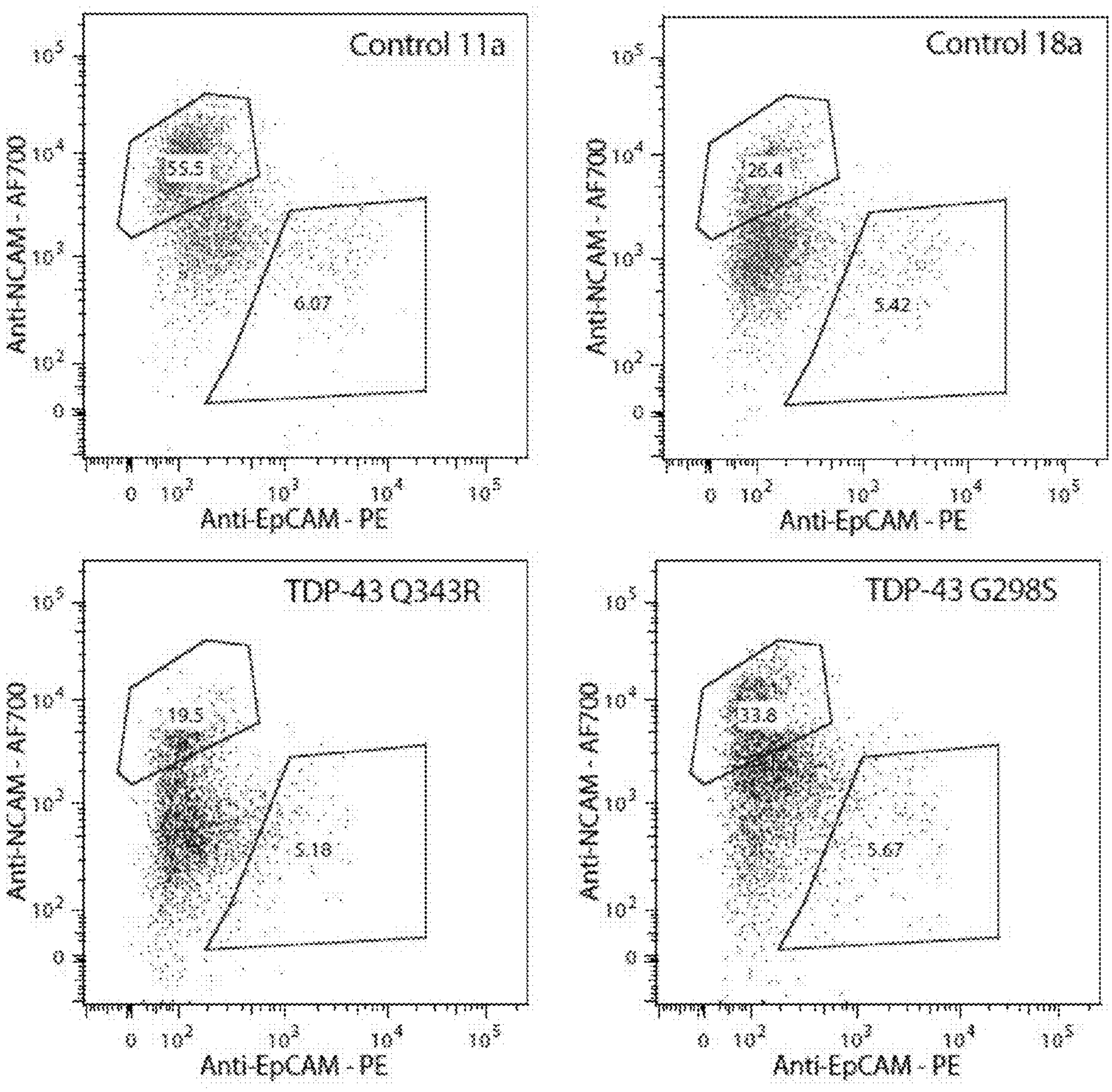
Figure 11E:
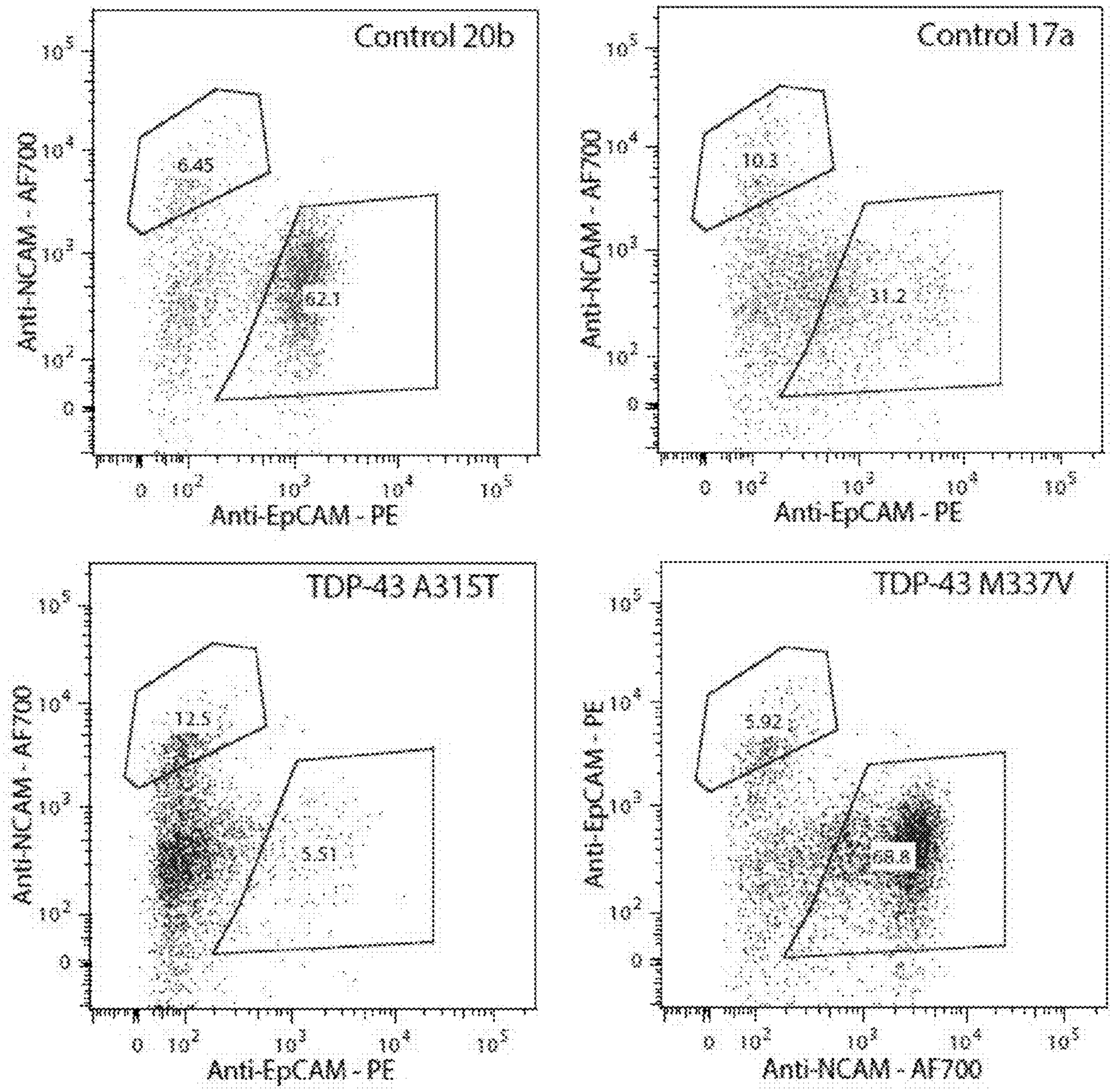
Figure 11F:
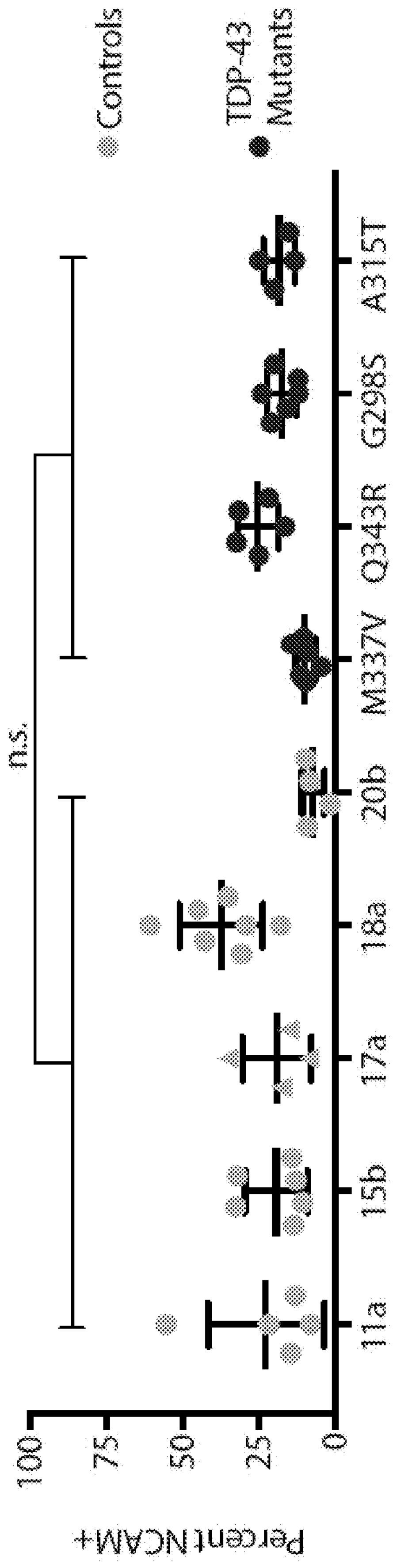

It was next asked if any of the RNAs with altered abundances after TDP-43 depletion were also perturbed by expression of mutant forms of TDP-43 that cause ALS. To this end, the putative TDP-43 target RNAs that displayed reproducibly altered expression after TDP-43 knockdown in patient iPS cell-derived motor neurons harboring pathogenic mutations in TARDBP were investigated (FIG. 10). Based on previous experience with pluripotent stem cells, it was known that directed differentiation approaches tend to yield heterogeneous cultures making quantitative, comparative analyses challenging (52). Furthermore, the presence of mitotic progenitor cells is especially troublesome because they can overtake the cultures and skew results. To overcome these barriers, an unbiased FACS-based immunoprofiling analysis was performed (53) on the differentiated HUES3 Hb9::GFP cell line using 242 antibodies against cell surface markers to identify signatures enriched on the GFP+ and GFPcells (FIG. 11A). By sorting for NCAM+/EpCAM− cells, it was determined that the cultures could be rid of proliferating, Edu+ cells and normalize the number of MAP2+/Islet-1+ neurons across a large number of induced pluripotent stem cell differentiations (FIGS. 11B-11D). Using this cell surface signature, 5 control iPSC lines (11a, 15b, 17a, 18a, and 20b) and 4 iPSC lines with distinct TDP-43 mutations (36a (Q343R), 47d (G298S), CS (M337V), and RB20 (A325T)) were differentiated and the resulting MNs were FACS purified. As anticipated, each iPS cell line exhibited its own propensity to differentiate into NCAM+MNs (FIGS. 11E-11F). After sorting, however, homogenous neuronal cultures for all iPSC lines were obtained (FIG. 2B).

Figure 2G:
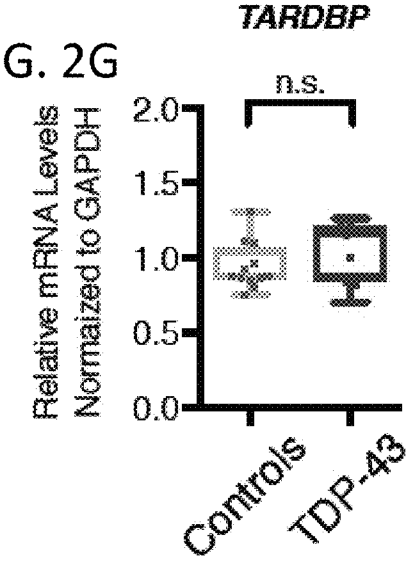
Figure 2H:
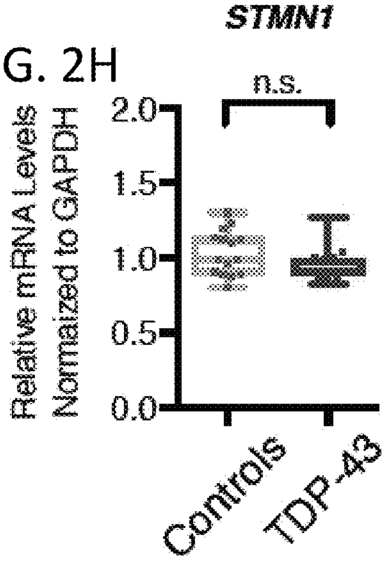
Figure 12A:
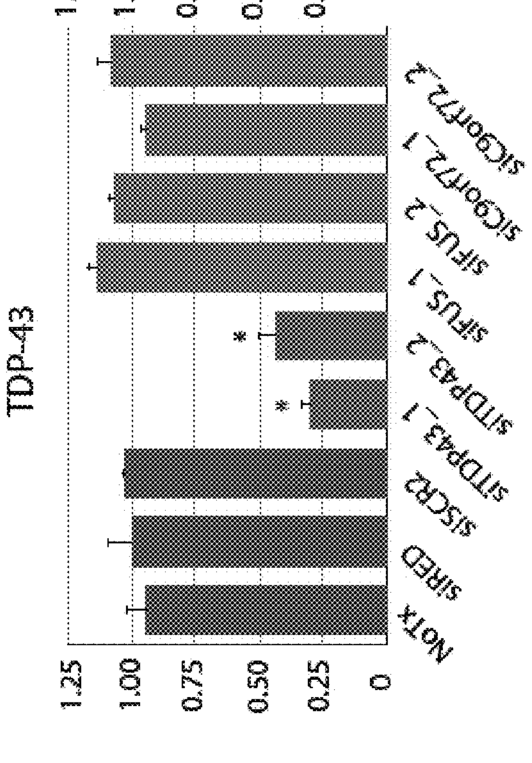
FIGS. 12A-12G demonstrate TDP-43 and STMN2 connections.
Figure 12B:
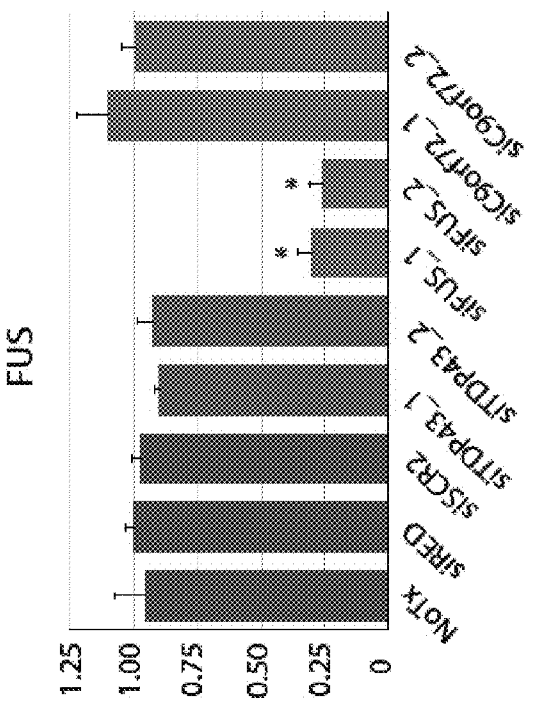
Figure 12C:
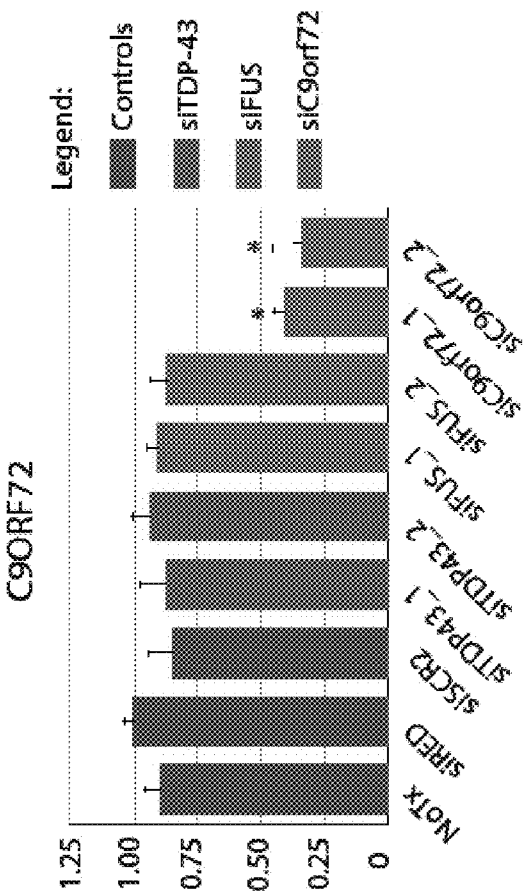
Figure 12D:
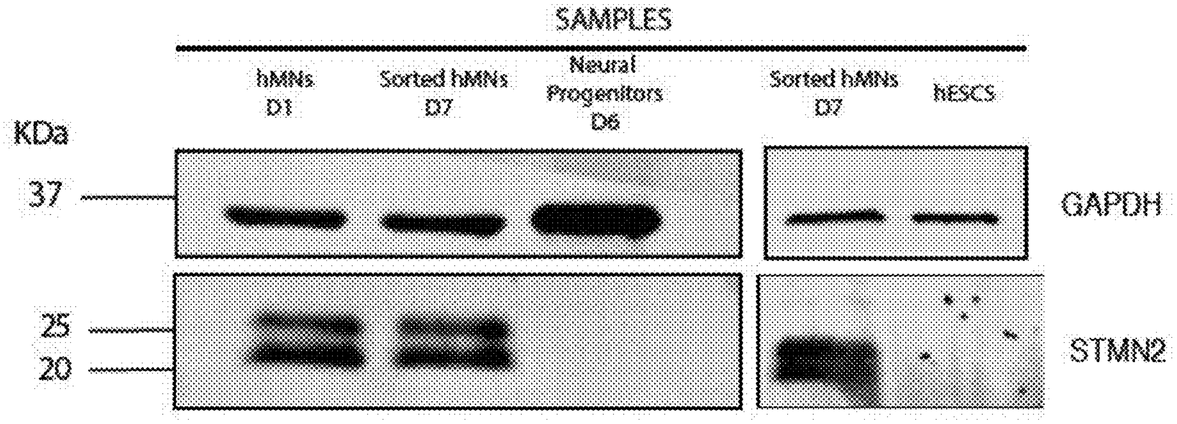
Figure 12E:
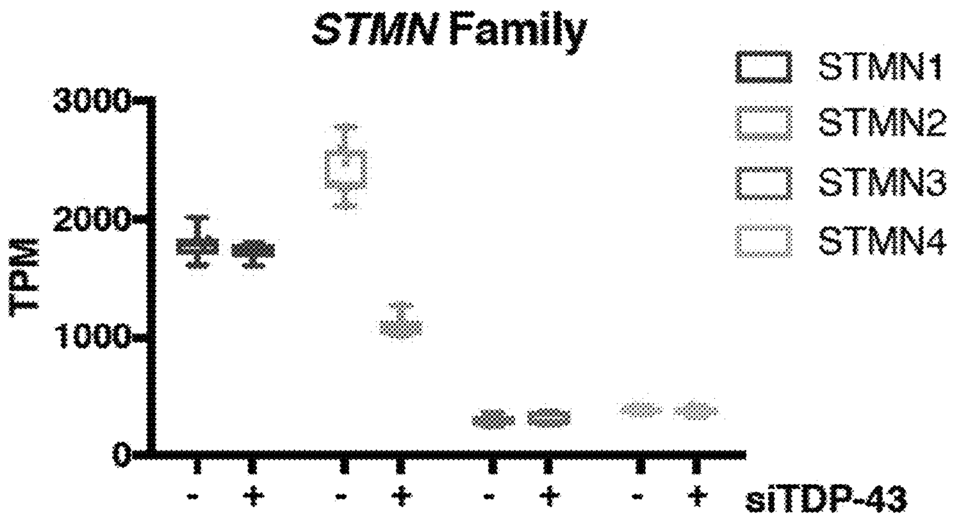

After 10 days of further neuronal culture, total RNA from these FACS-purified MNs were collected and qRT-PCR was performed to investigate levels of the gene products most reproducibly impacted by TDP-43 depletion (ALOX5AP, STMN2, ELAVL3, and RCAN1). For two of the genes (STMN2 and ELAVL3), a significant decrease in transcript levels was observed (FIGS. 2C-2F). Consistent with the TDP-43 depletion experiments, significant changes to the abundance of the closely related STMN1 RNA were not observed, suggesting a specific relationship between TDP-43 and STMN2 (FIG. 2H, FIG. 12E). Additionally, significant differences in TDP-43 transcript levels between mutant and control neurons were not observed (FIG. 2G). Together, these data imply that the presence of pathogenic point mutations in TDP-43 can alter STMN2 and ELAVL3 mRNA levels without affecting its own levels.

Figure 2I:
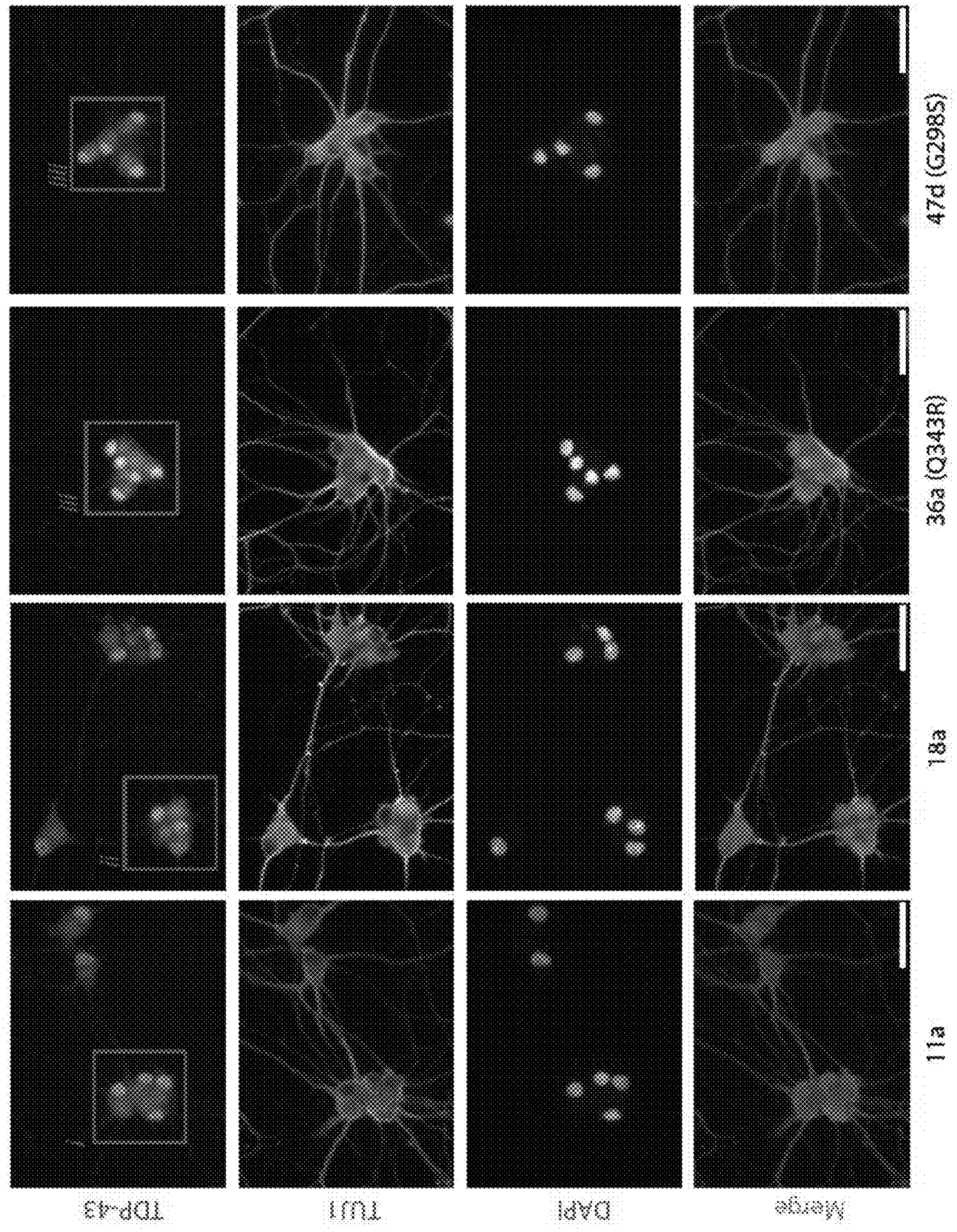
Figure 2I:
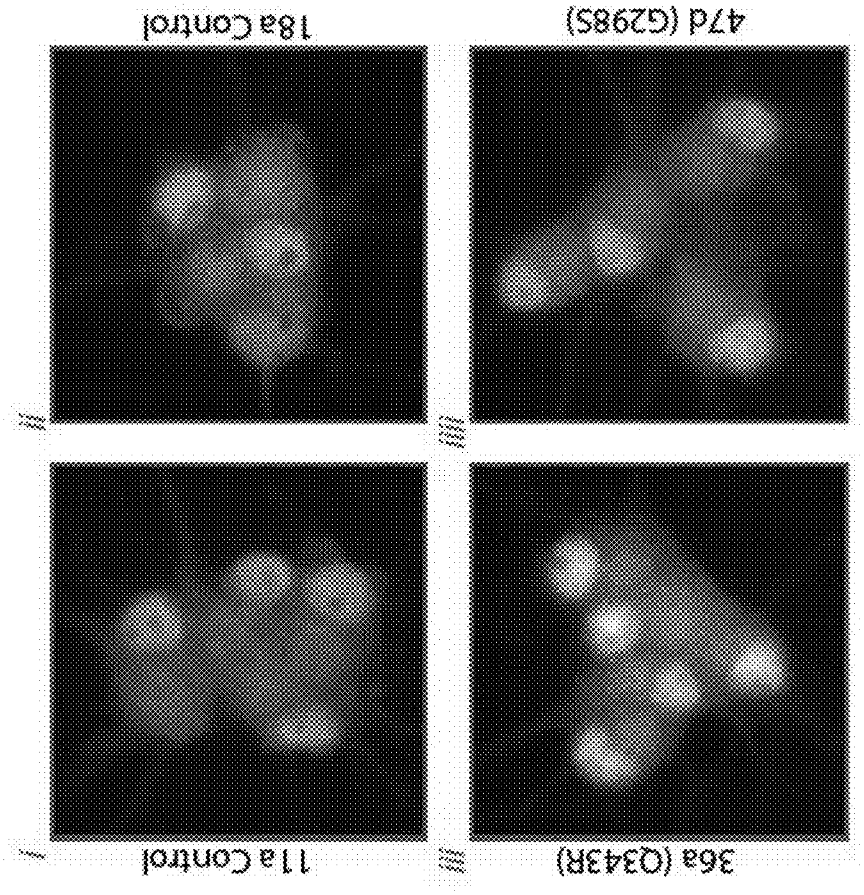
Figure 2J:
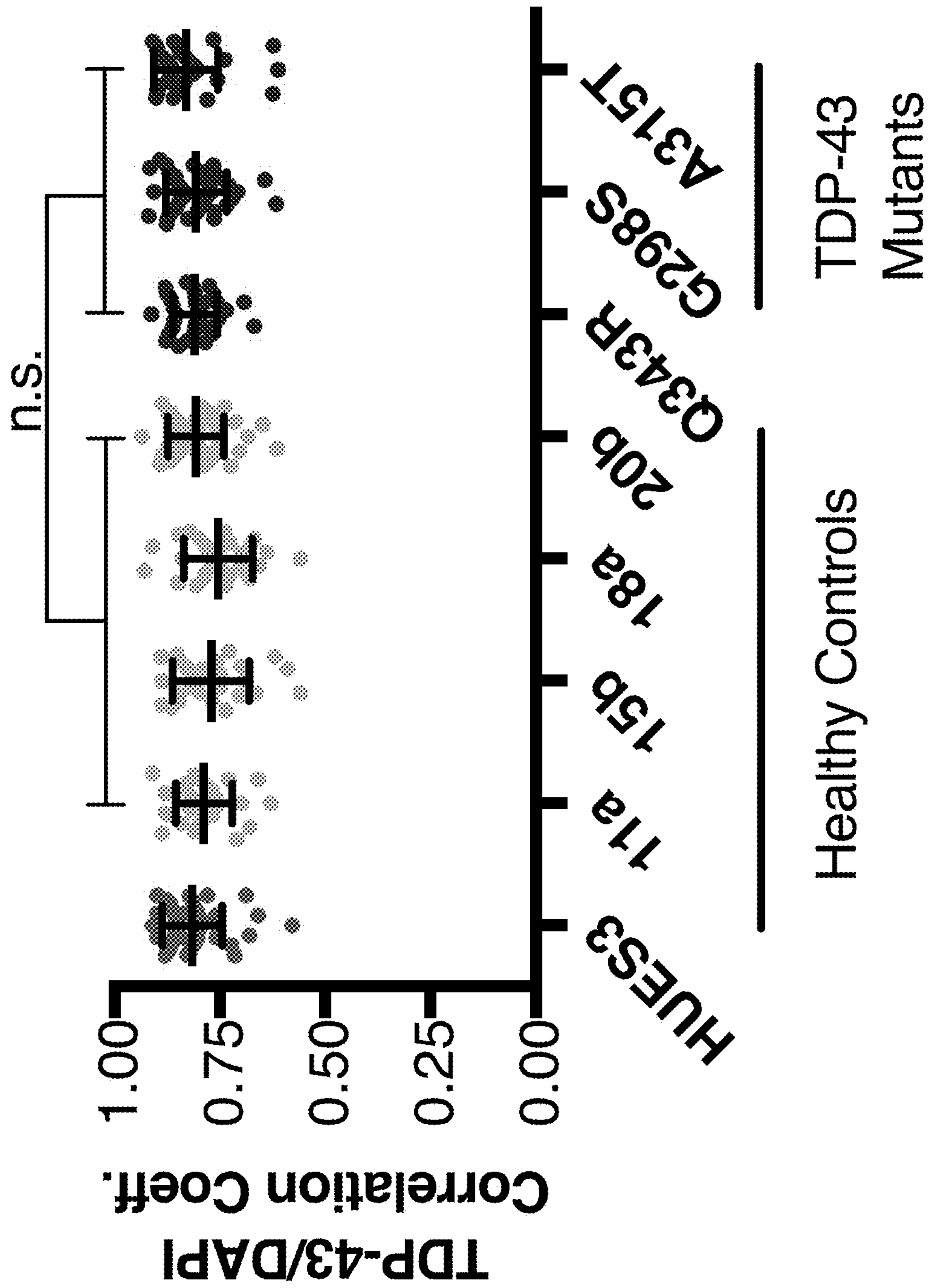

How ALS-associated mutations might hamper TDP-43's ability to regulate target transcripts was subsequently explored. Previous studies have reported that hMNs derived from iPSC lines expressing mutant TDP-43 recapitulate some aspects of TDP-43 pathology including its accumulation in both soluble and insoluble cell protein extracts (54, 55) as well as cytoplasmic mislocalization (56). Because decreased nuclear TDP-43 in mutant neurons could mimic the partial loss induced by the siRNAs, signs of TDP-43 mislocalization were tested for using immunofluorescence. In both control and mutant neurons, however, primarily nuclear staining for TDP-43 was observed (FIG. 2I). Pearson's correlation coefficient analysis supported these observations and revealed a strong correlation between TDP-43 immunostaining and DNA counterstain for both mutant and control neurons (FIG. 2J). These results are consistent with some TDP-43 iPS disease modeling studies (56), yet inconsistent with others (54), and raises the possibility that additional cellular perturbations could be required to induce TDP-43 mislocalization (57). Collectively, the data suggest that a subset of genes affected after TDP-43 depletion are also altered in neurons expressing mutant TDP-43, and that these changes precede the hallmark cytoplasmic aggregation of TDP-43. Thus, at least through the lens of these limited number of transcripts, the data suggest that mutations in TDP-43 can contribute in part to a loss-of-function transcriptional phenotype.

STMN2 Levels are Regulated by TDP-43 in hMNs

It was intriguing to see that transcripts for Stathmin-like 2 (STMN2) were decreased in both neurons expressing mutant TDP-43 and after TDP-43 depletion. STMN2 is one of four proteins (STMN1, STMN2, SCLIP/STMN3, and RB3/STMN4) belonging to the Stathmin family of microtubule-binding proteins with functional roles in neuronal cytoskeletal regulation and axonal regeneration pathways (47,48,58-62). In humans, STMN1 and STMN3 genes exhibit ubiquitous expression, whereas STMN2 and STMN4 are enriched in CNS tissues (63). Considering the growing evidence for the relevance of cytoskeletal pathways in ALS (64-66) and its enrichment within the CNS, it was decided to focus on further characterizing the relationship between STMN2 and TDP-43.

Figure 3A:
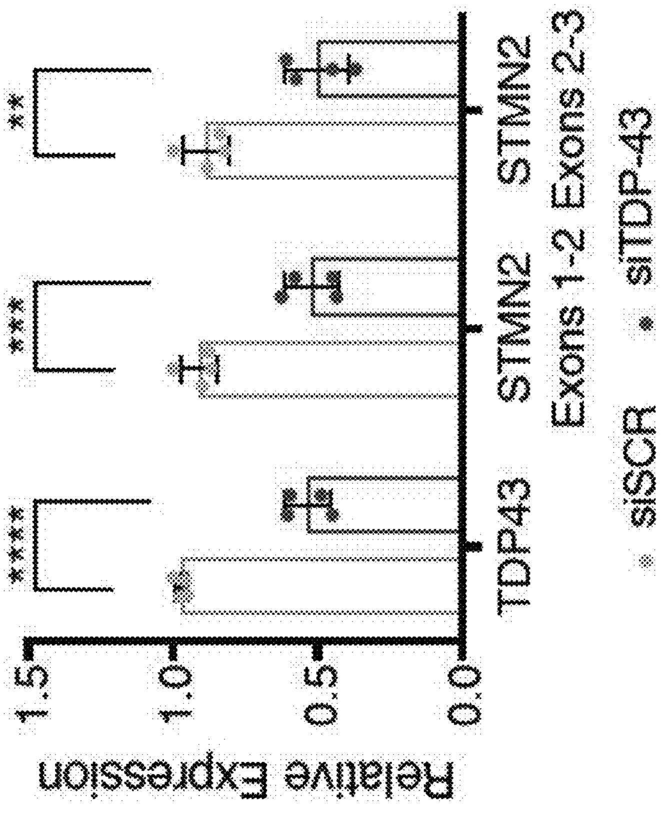
FIGS. 3A-3I demonstrate STMN2 regulation and localization.
Figure 3B:
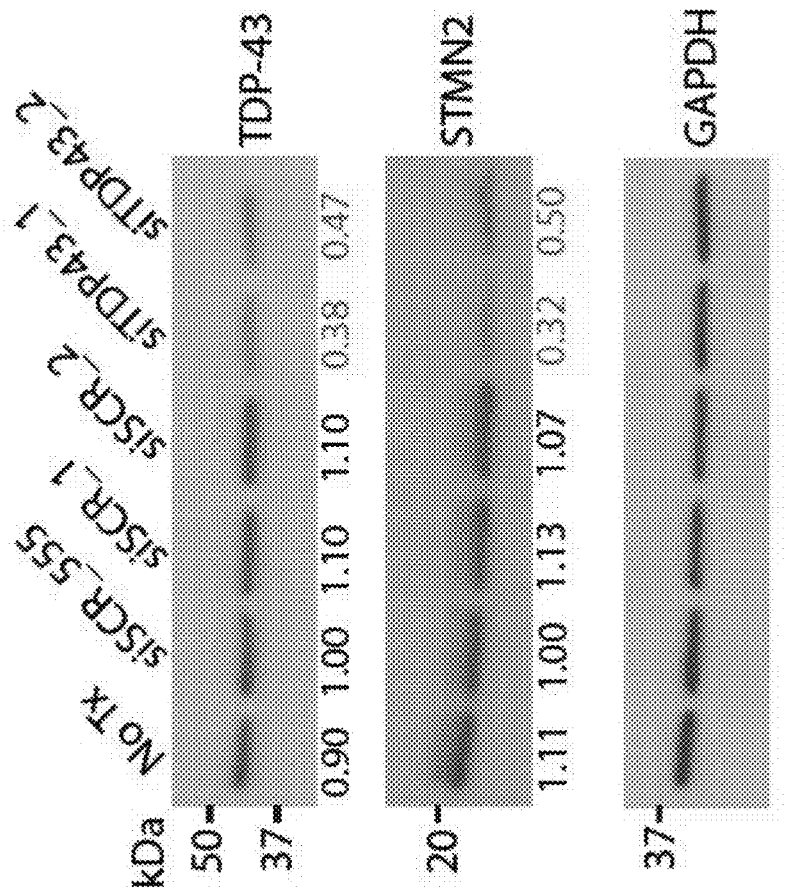

First, it was examined if the significant downregulation of the STMN2 transcripts also resulted in reduced levels of STMN2 protein. In independent RNAi experiments, qRT-PCR was performed with two different sets of primer pairs binding the STMN2 mRNA and found significant downregulation (~50-60%) in siTDP43-treated hMNs relative to controls (FIG. 3A). Immunoblot assays were then carried out on hMN protein lysates and found that STMN2 protein levels were also reduced in siTDP-43-treated hMNs (FIG. 3B).

Figure 3C:
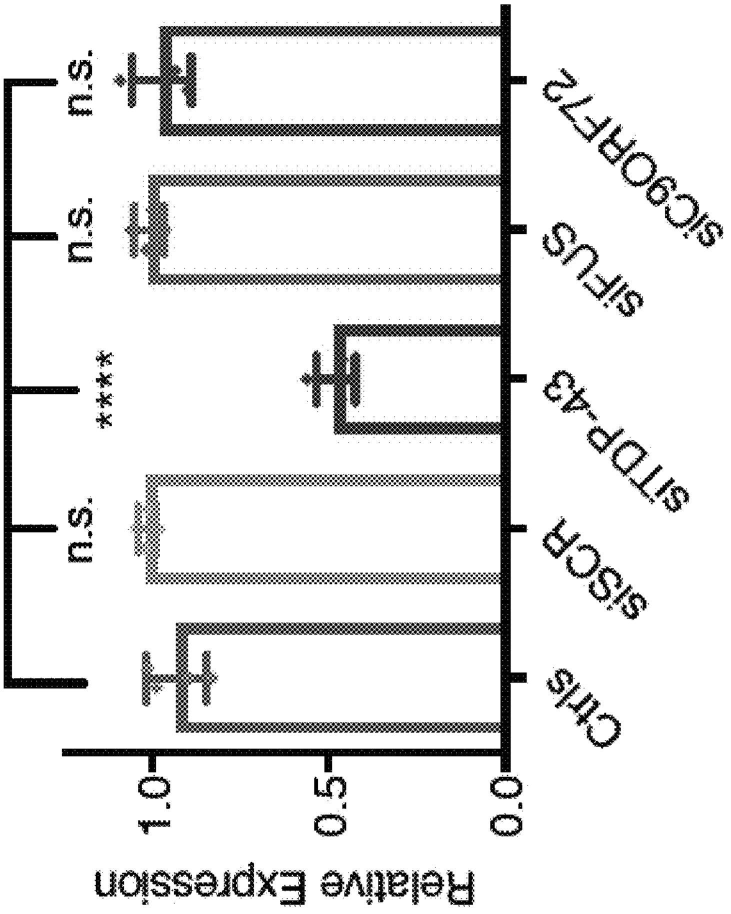

It was then considered whether downregulation of two other ALS-linked genes, FUS or C9ORF72 (5,67), would also change STMN2 levels in hMNs. FUS protein, structurally similar to TDP-43, is also involved in RNA metabolism (68), and FUS variants have been detected in familial ALS and FTD cases (69). The function of C9ORF72 is an active area of research, but large repeat expansions in the intronic regions of C9ORF72 are responsible for a substantial number of familial and sporadic ALS and FTD cases (70-72). Following induction of RNAi targeting TDP-43, FUS, or C9ORF72, significant downregulation of the respective siRNA-targeted genes by qRT-PCR was found. (FIGS. 12A-12C). Downregulation of TDP-43 did not alter expression levels of FUS or C9ORF72, and reduced expression of either FUS or C9ORF72 showed no effect on the other ALS-linked genes (FIGS. 12A-12C). Although knockdown of TDP-43 again reduced levels of STMN2, it was not the case for FUS or C9ORF72 (FIG. 3C). Importantly, these results demonstrate that STMN2 downregulation is not a consequence of RNAi induction, but instead a specific molecular mechanism in response to partial loss of TDP-43.

Figure 3D:
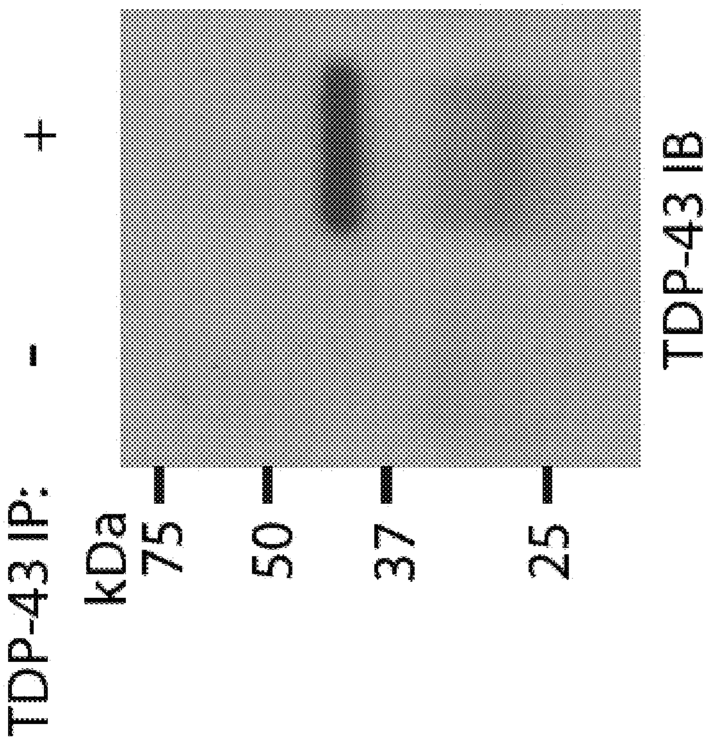
Figure 3F:
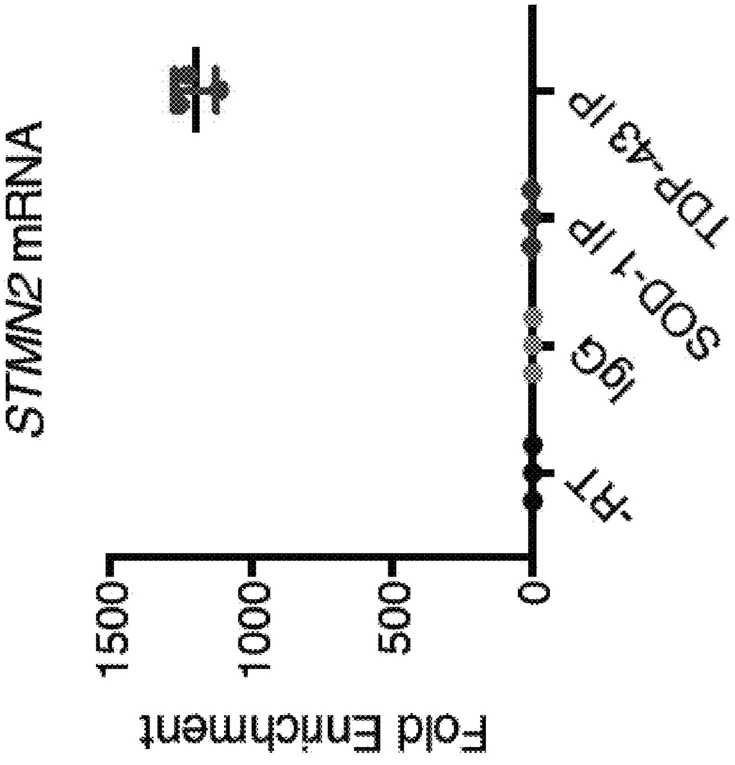
Figure 3E:
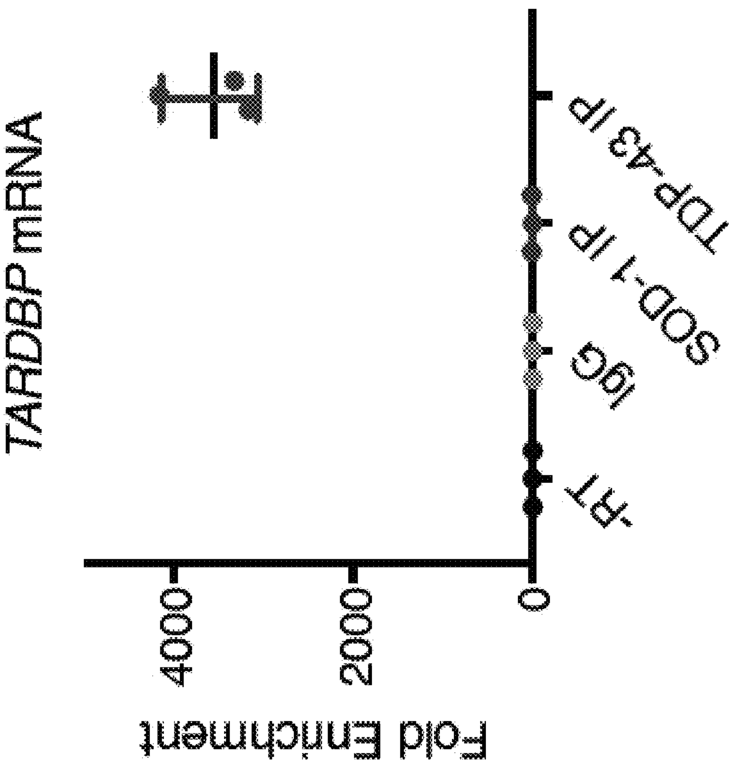
Figure 12F:
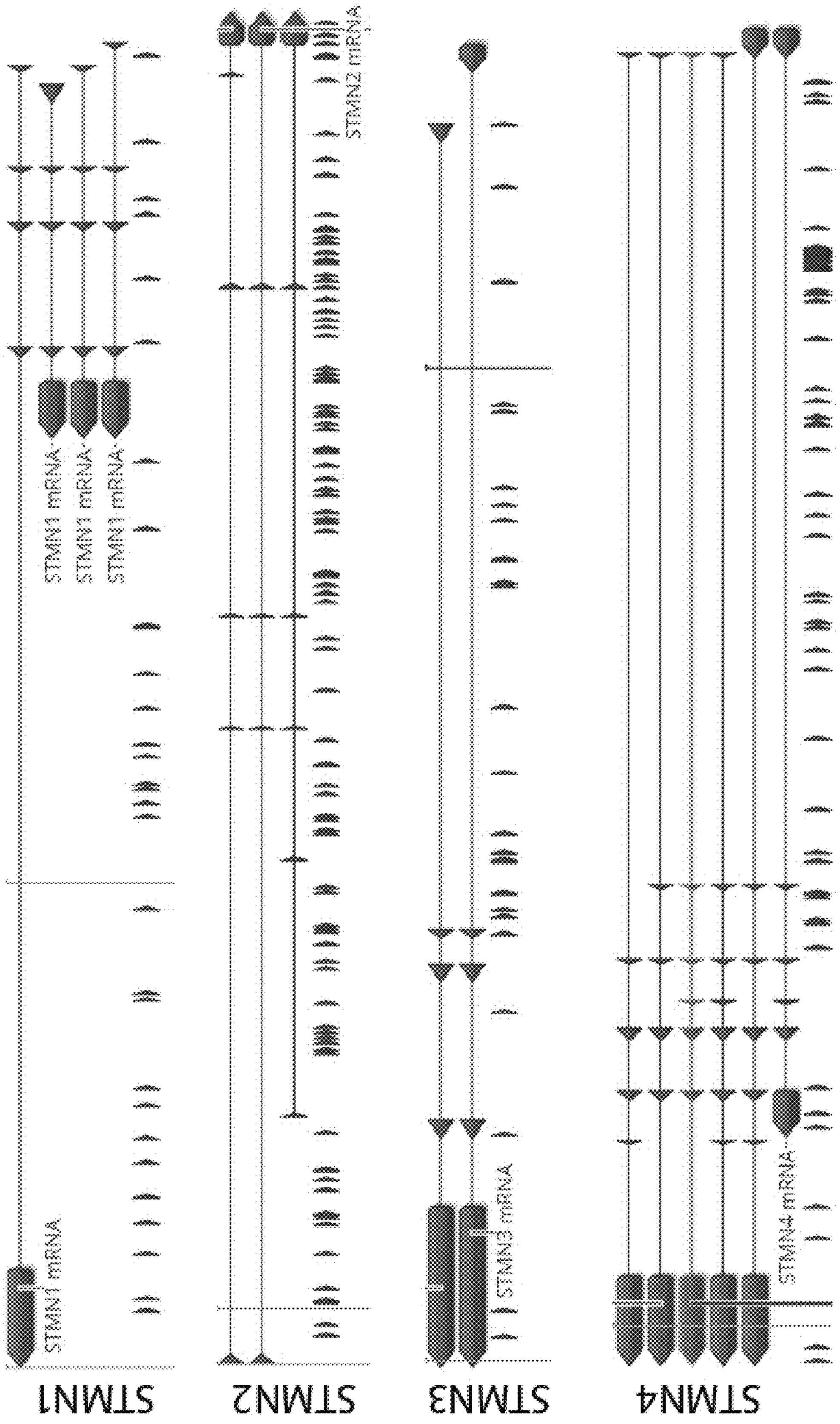
Figure 12G:
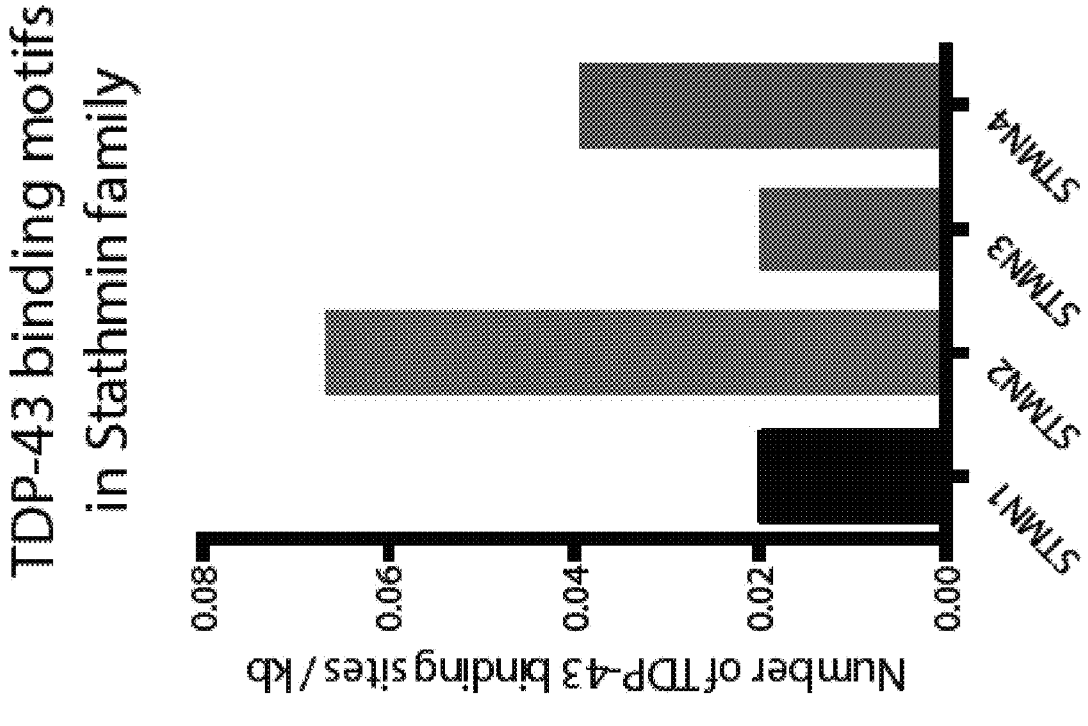
Figure 13A:
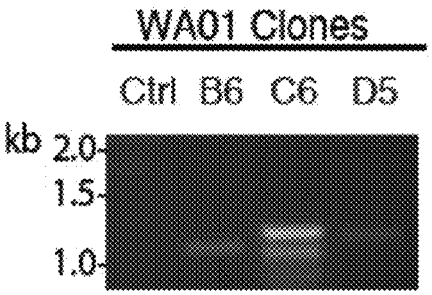
Figure 13B:
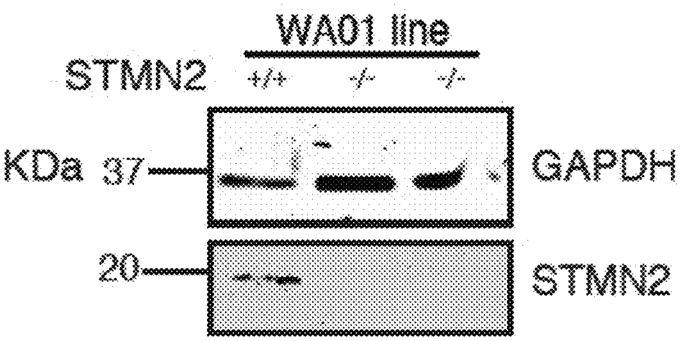
Figure 13C:
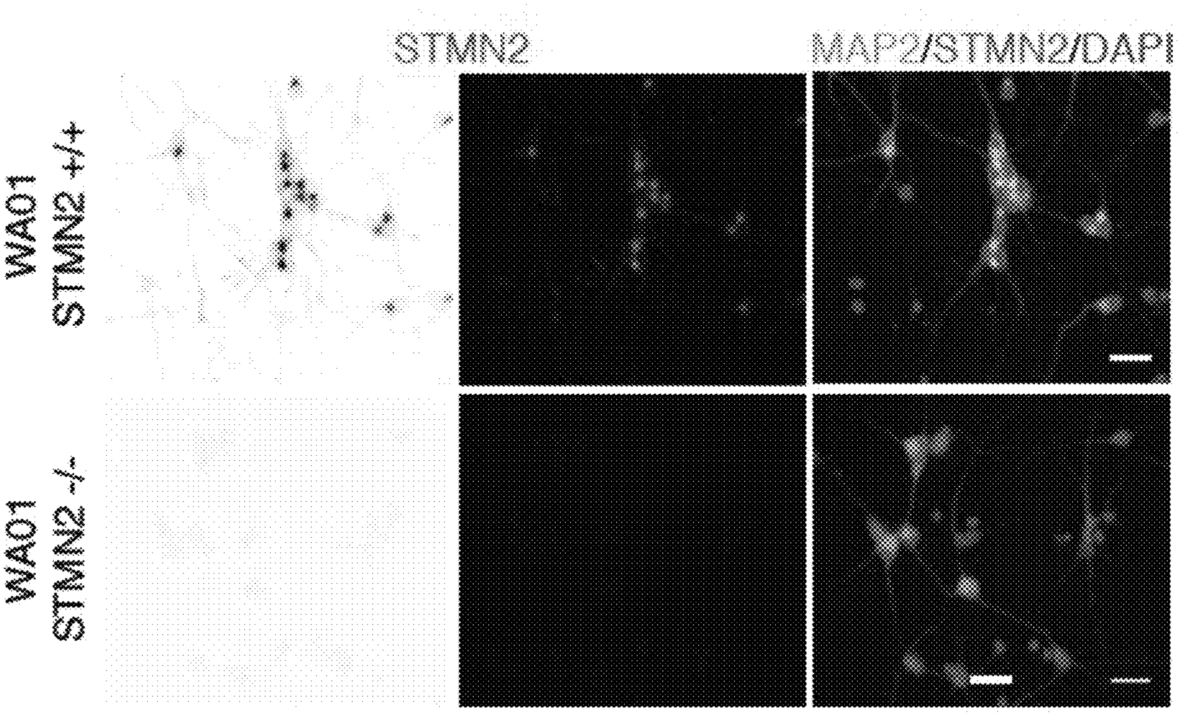
Figure 13G:
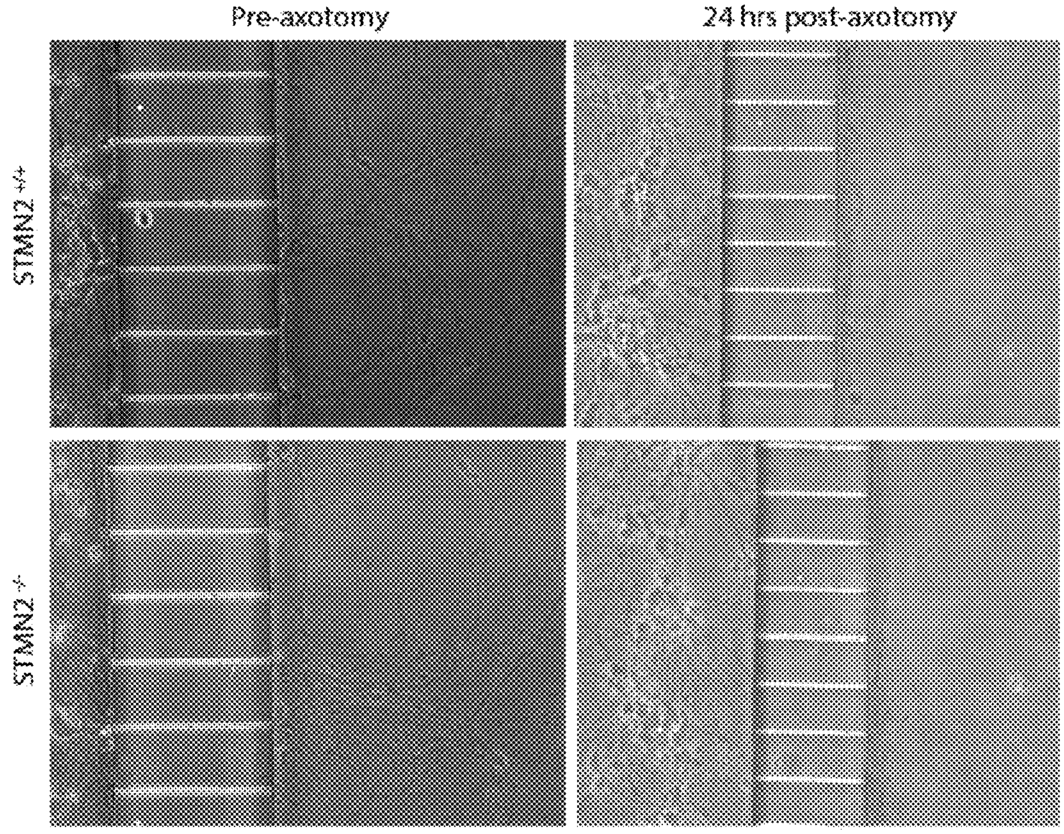
Figure 13H:
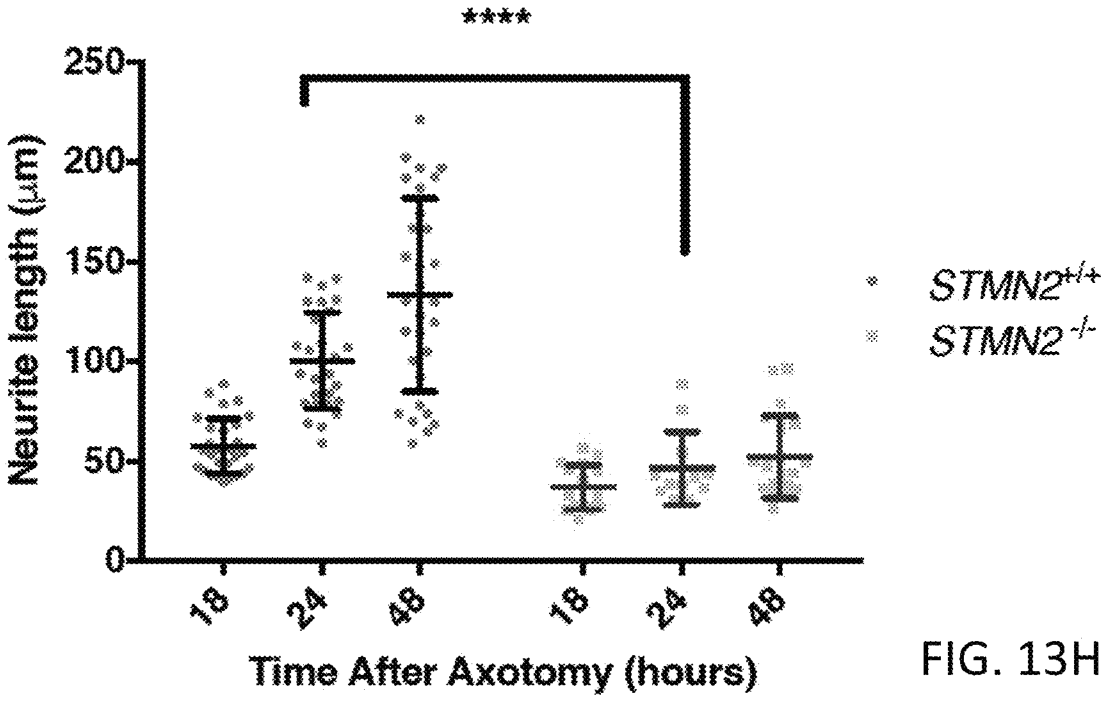

Through highly conserved RNA recognition motifs (73), TDP-43 can bind to RNA molecules to regulate them. To determine whether TDP-43 associates directly with STMN2 RNA, which has many canonical TDP-43 binding motifs (FIGS. 12F-12G), conditions for TDP-43 immunoprecipitation were developed (FIG. 3D) and subsequently formaldehyde RNA immunoprecipitation (fRIP) was performed. After reversing the cross-linking, quantitative qRT-PCR was performed to detect bound RNA molecules. Amplification from TDP-43 RNA transcripts was looked for, because this auto-regulation is well established (11), as well as STMN2 transcripts. In both cases, enrichment after TDP-43 pull down was observed, but not for an IgG control or when a different ALS-associated protein, SOD-1, was pulled down (FIGS. 3E-3F). Together, the results indicate that TDP-43 associates directly with STMN2 mRNA, and that reduced TDP-43 levels lead to reduced STMN2 levels.

STMN2 Function in hMNs

Figure 3G:
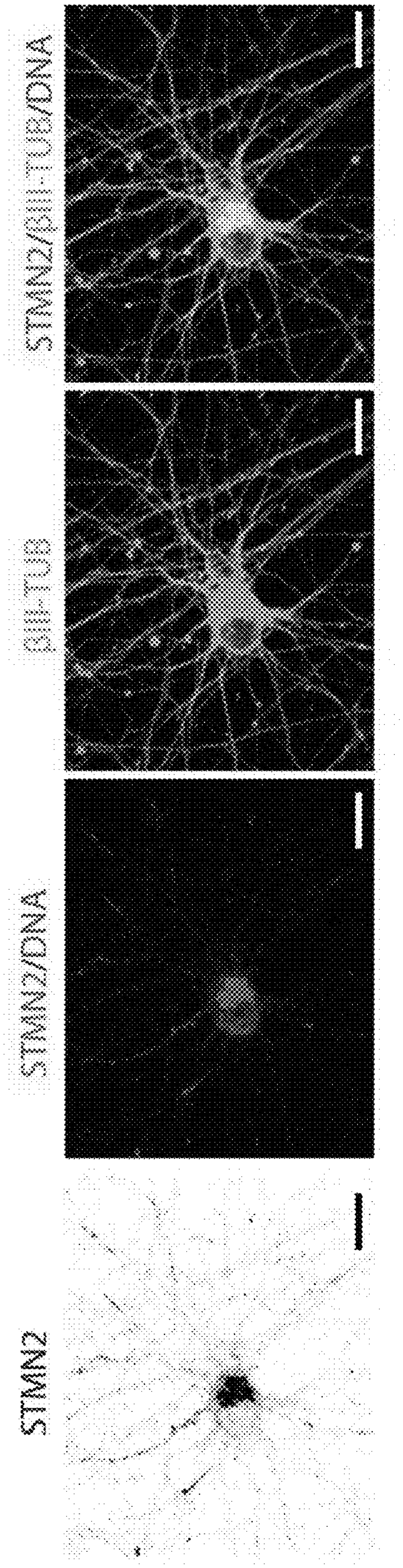
Figure 3H:
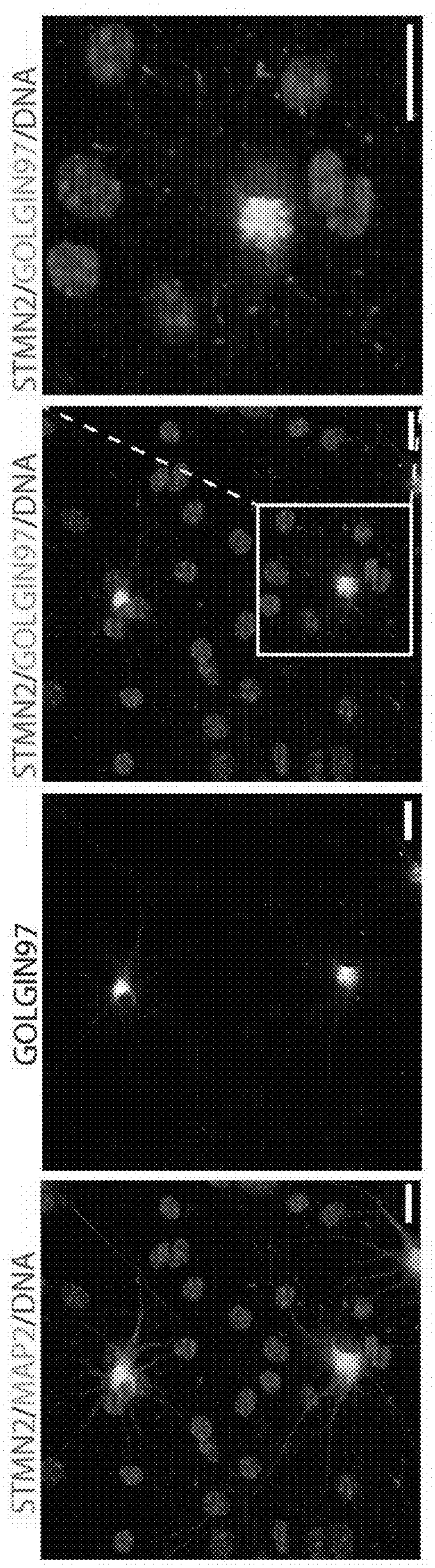
Figure 3I:
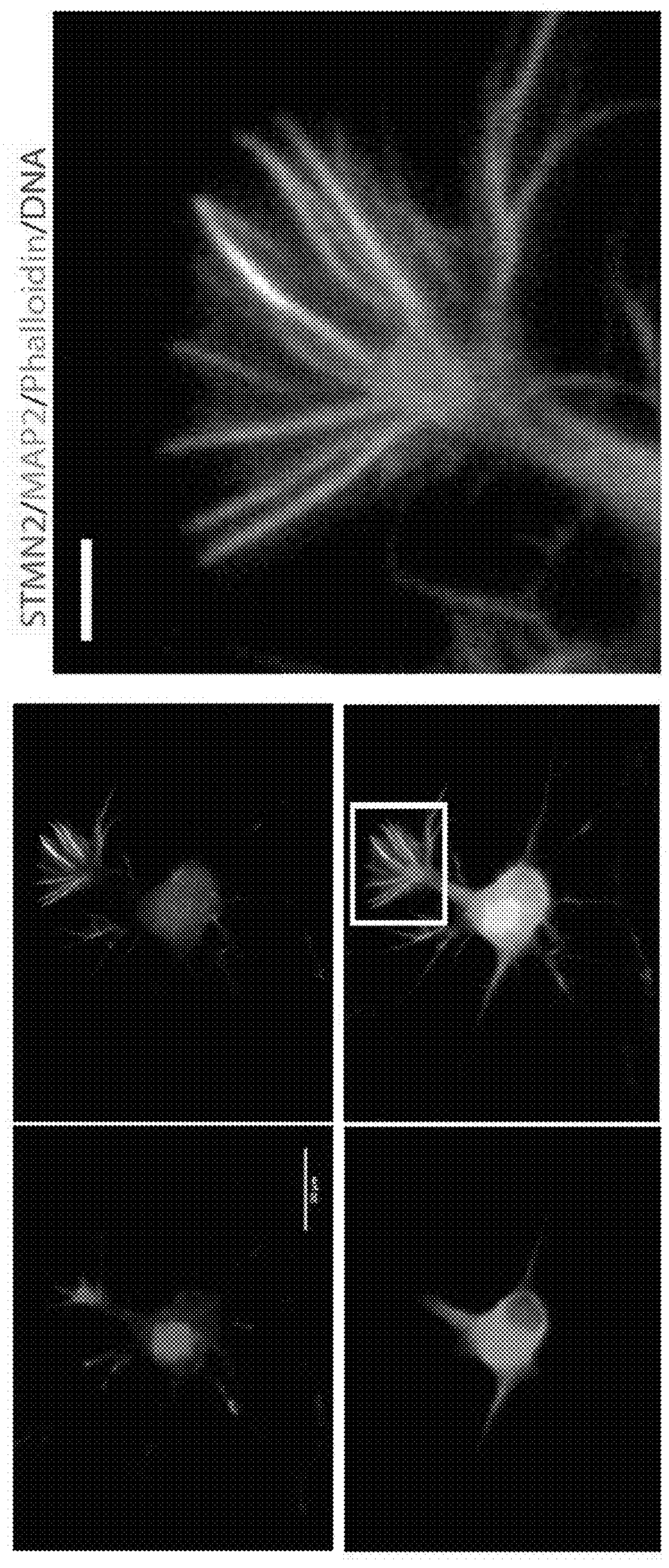

The function of STMN2 in hMNs was explored next. First, expression of STMN2 was examined across the differentiation process that yields MNs (FIG. 12D). Supporting previous expression studies (62, 63, 74), it was found that STMN2 protein is selectively expressed in differentiated neurons, as it could not be detected in stem cells or in neuronal progenitors (FIG. 12D). Immunocytochemistry was then used to probe the subcellular localization of STMN2 and found that it localized to discrete cytoplasmic puncta present at neurite tips with particular enrichment in the perinuclear region (FIG. 3G). It was determined that this region corresponds to the Golgi apparatus using a human-specific antibody against the Golgi-associated protein GOLGIN97, (FIG. 3H), substantiating the prediction of STMN2 N-terminus as the target of palmitoylation for vesicle trafficking and membrane binding (75). STMN2 is also predicted to function at the growth cone during neurite extension and injury (47). When hMNs were stained just after differentiation and sorting, strong staining of STMN2 was observed at the interface between microtubules and F-actin bundles, components defining the growth cone (FIG. 3I). These findings support a role for STMN2 microtubule dynamics at the growth cone. Together, the data indicate that STMN2 could function in cytoskeletal defects and altered axonal transport pathways implicated in ALS pathogenesis (76).

Figure 4A:
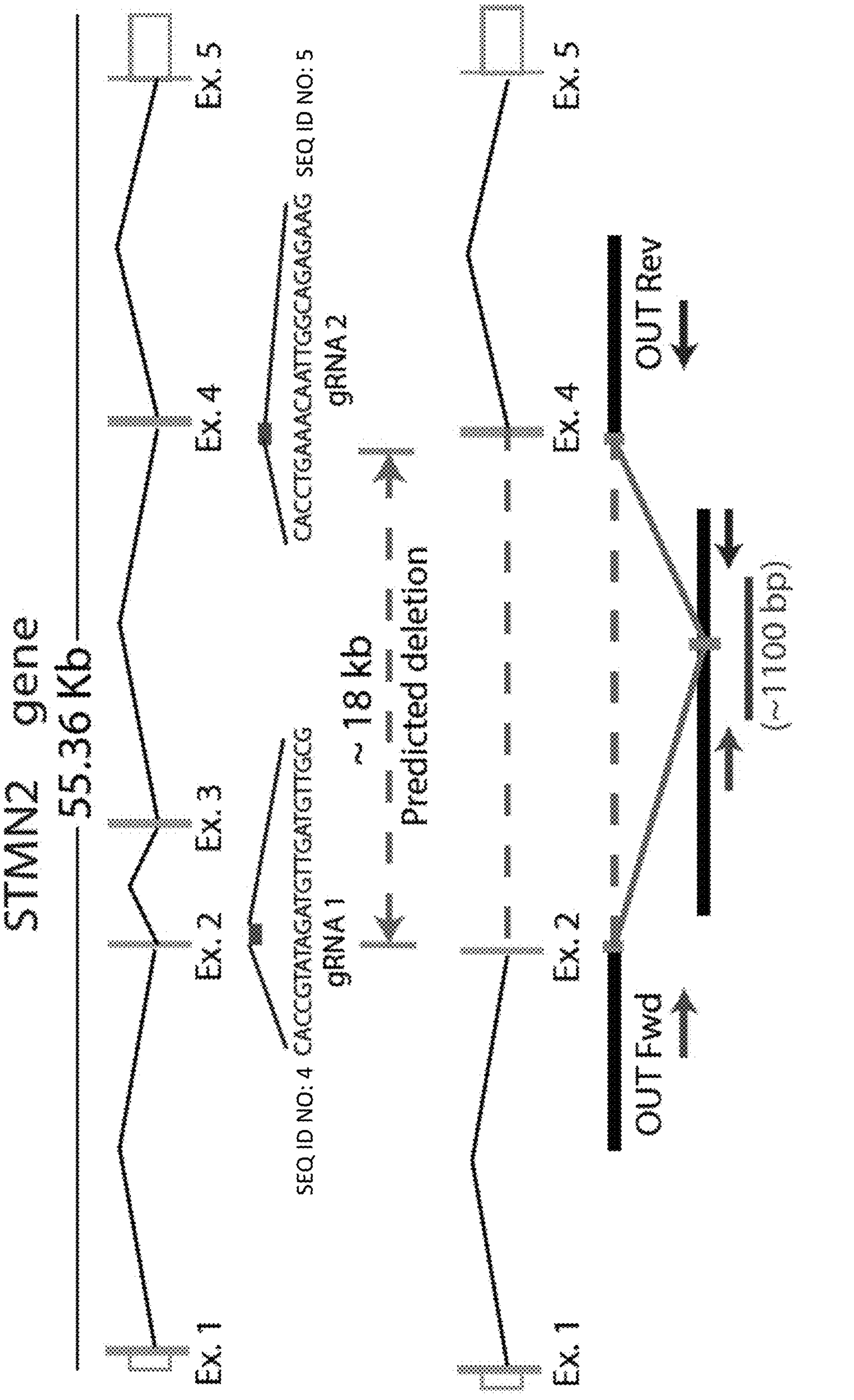
Figure 4B:
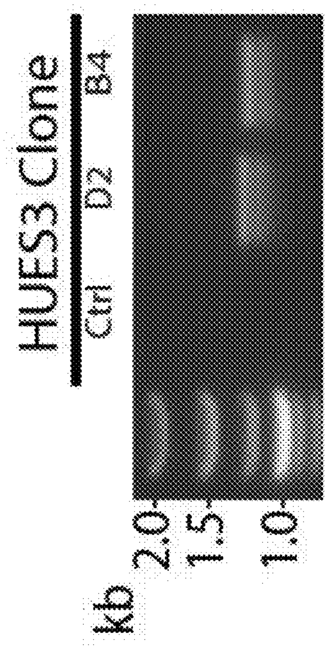
Figure 4C:
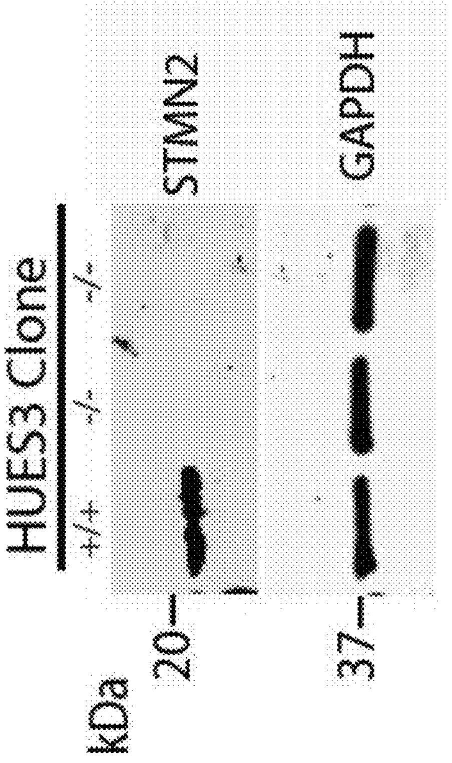
Figure 4D:
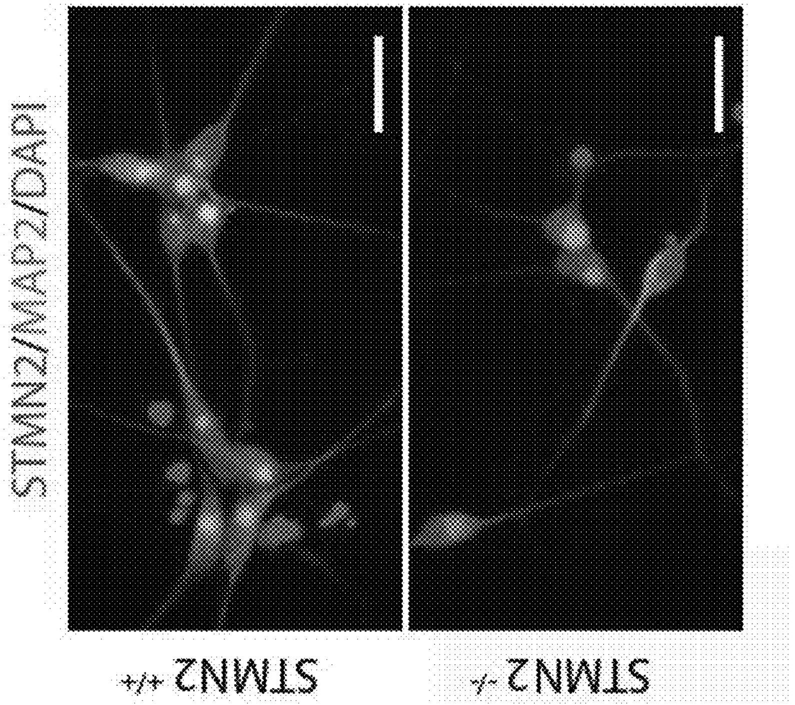

To explore the cellular consequences of decreased STMN2 levels in hMNs, STMN2 knock-out stem cells were generated. Specifically, a CRISPR/Cas9-mediated genome editing strategy was used (FIG. 4A) to generate a large deletion in the human STMN2 locus in two hES cell lines (WA01 and HUES3 Hb9::GFP). After carrying out a primary PCR screen to identify clones harboring the 18 kb deletion in the STMN2 gene (FIG. 4B), protein knockout in differentiated hMNs was confirmed by both immunoblotting and immunocytochemistry (FIGS. 4C-4D). As expected, it was found that when compared to the parental STMN2+/+ lines, the hMNs derived from the candidate deletion clones exhibited the complete absence of STMN2 staining.

Given the reported role of STMN2 in regulating axonal growth by promoting the dynamic instability of microtubules (77), phenotypic assays were carried out characterizing neurite outgrowth in the STMN2−/− hMNs. After 7 days in culture, sorted hMNs were fixed and stained for β-III-tubulin to label the neuronal processes (FIG. 4E). Sholl analysis, which quantifies the number of intersections at a given interval from the center of the soma (78), revealed significantly reduced neurite extension in the STMN2$^{-/-}$ lines compared to the STMN2$^{+/+}$ (FIGS. 4F-4G). Separately, neurons were cultured in the presence of a ROCK inhibitor, Y-27632, which has been shown to increase neurite extension. The difference in neurite outgrowth was even more striking in these experiments with the molecule enhancing the outgrowth of the STMN$^{+/+}$ line but not the STMN$^{-/-}$ line, which suggests a role for STMN2 in this signaling cascade (FIG. 4H). Similar results were observed for the WA01 cell line (FIG. 13).

Figure 4K:
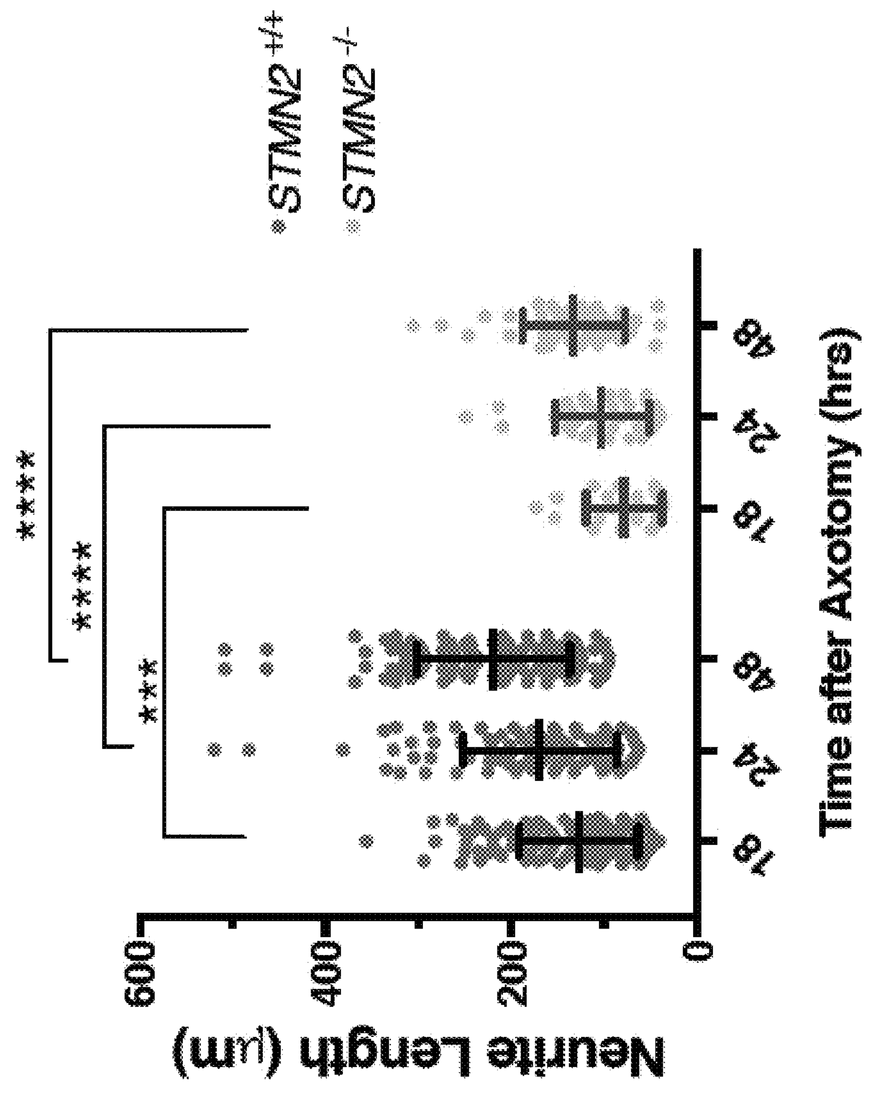

It was next asked if STMN2 functions not only in neuronal outgrowth, but also in neuronal repair after injury. To test these hypothesis, sorted hMNs were plated into a microfluidic device that permits the independent culture of axons from neuronal cell bodies (79) (FIG. 4I). Cells cultured for 7 days in the soma compartment of the device extended axons through the microchannels into the axon chamber (FIG. 4J). Repeated vacuum aspiration and reperfusion of the axon chamber was performed until axons were cut effectively without disturbing cell bodies in the soma compartment. Neurite length was then measured from the microchannel across a time course to assess axonal repair after injury. The analysis revealed significantly reduced regrowth in the STMN2$^{-/-}$ lines compared to the STMN2$^{+/+}$ for all time points measured (FIG. 4K). Similar results were observed for the WA01 cell line (FIG. 13). Together, these data indicate that reducing levels of STMN2 can have measurable phenotypic effects on the growth and complexity of neuronal processes in hMNs as well as repair after axotomy.

Proteasome Function Regulates TDP-43 Localization and STMN2 Levels

Figure 5A:
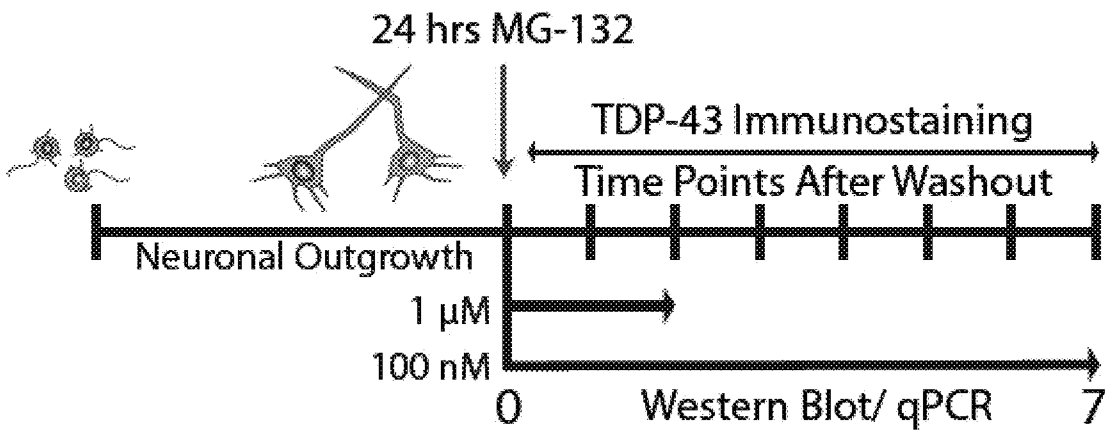
FIGS. 5A-5G demonstrate a sporadic ALS model.
Figure 5B:
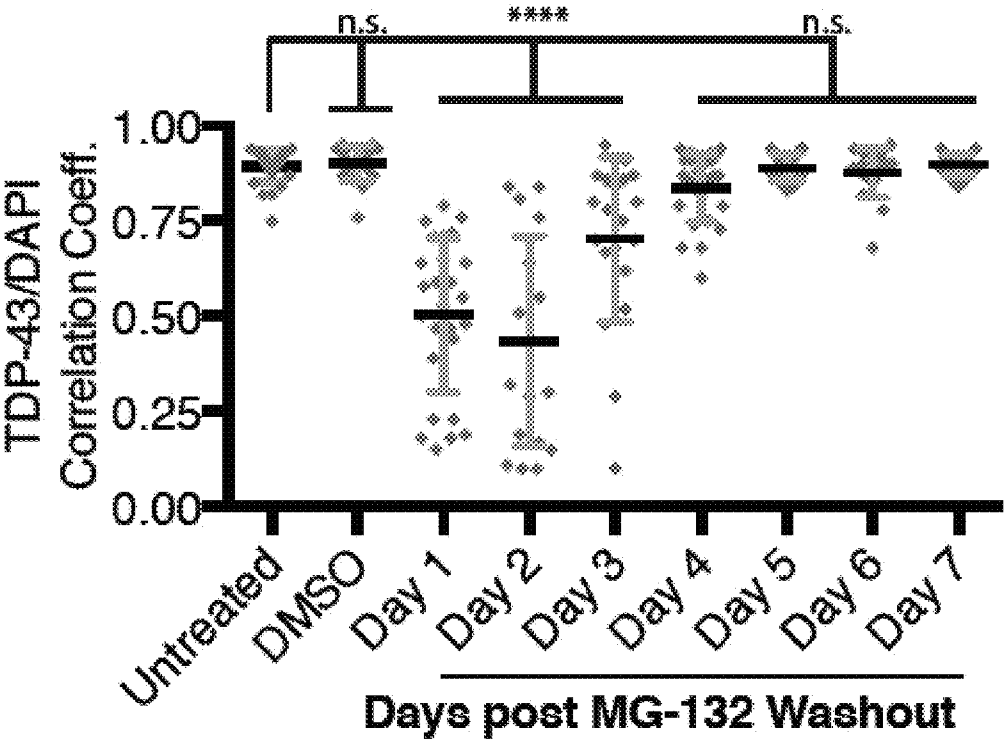
Figure 5C:
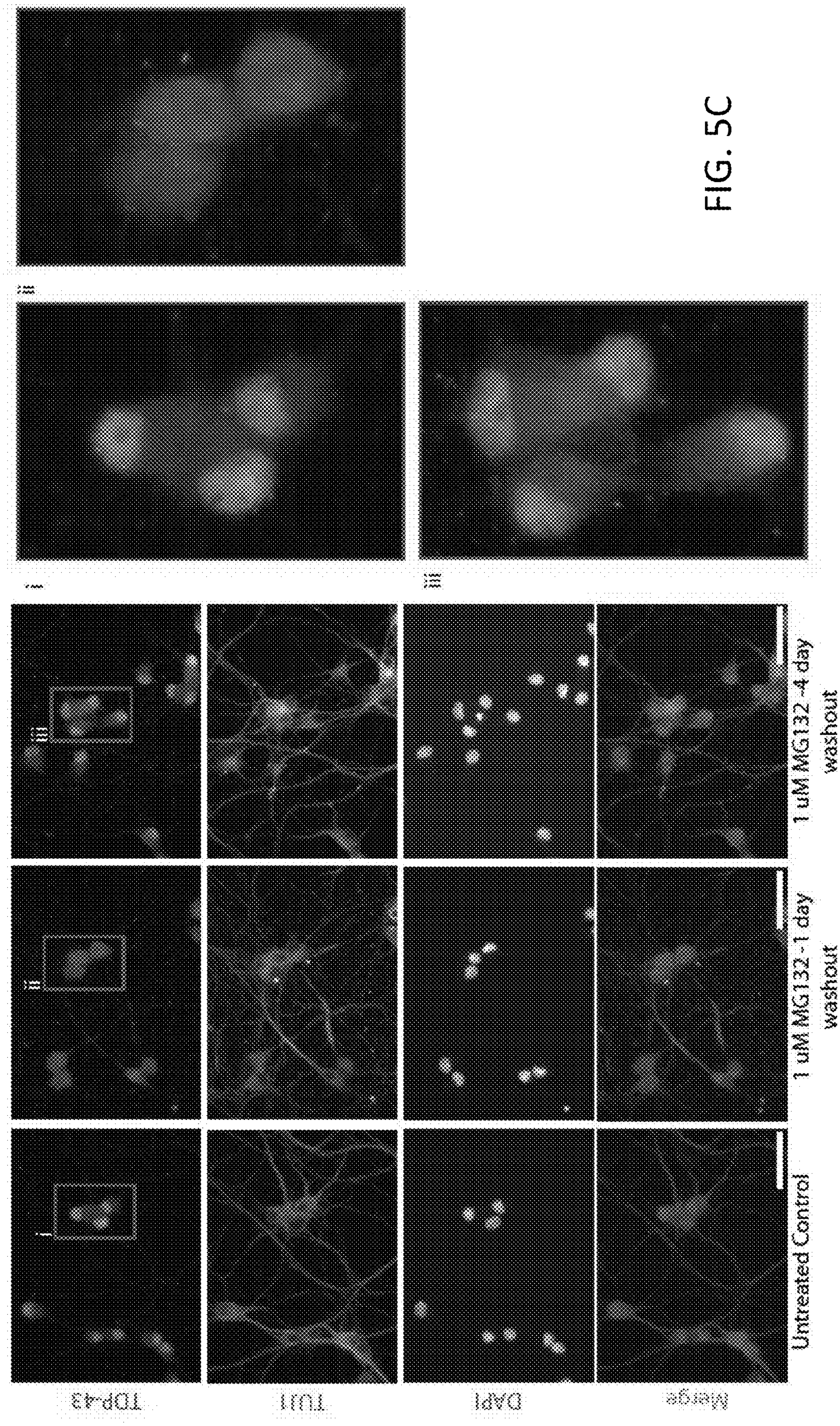
Figure 14C:
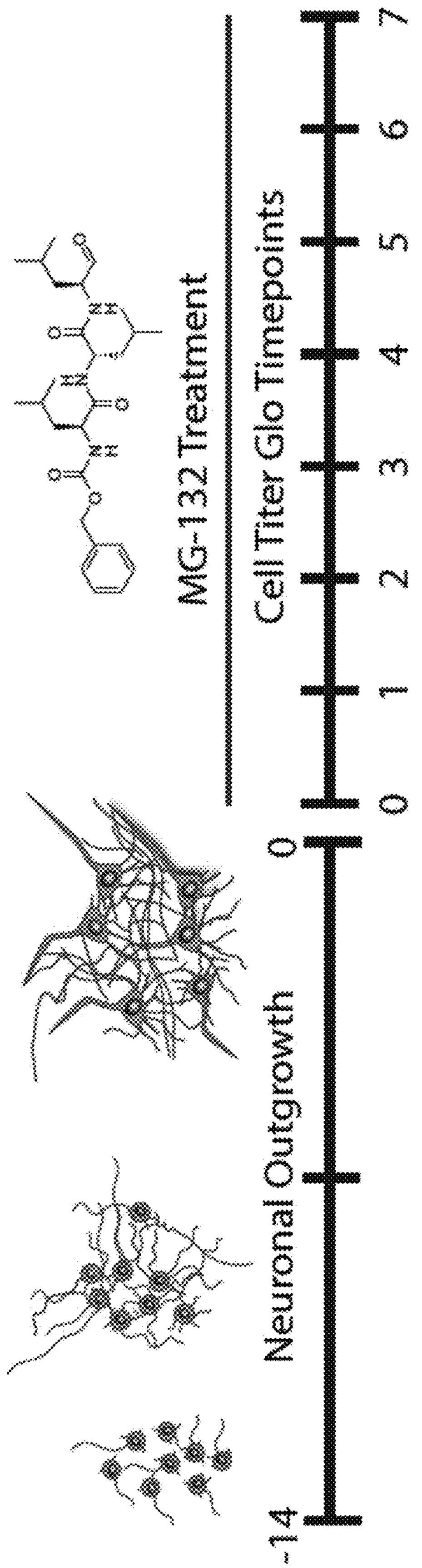
Figure 14D:
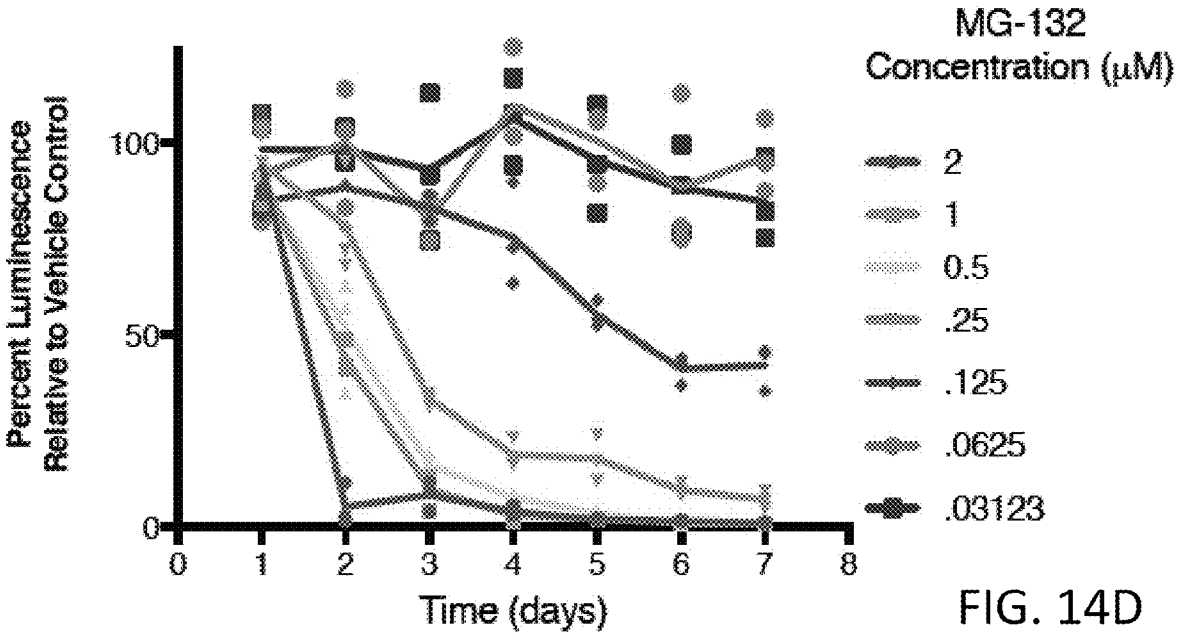
Figure 14E:
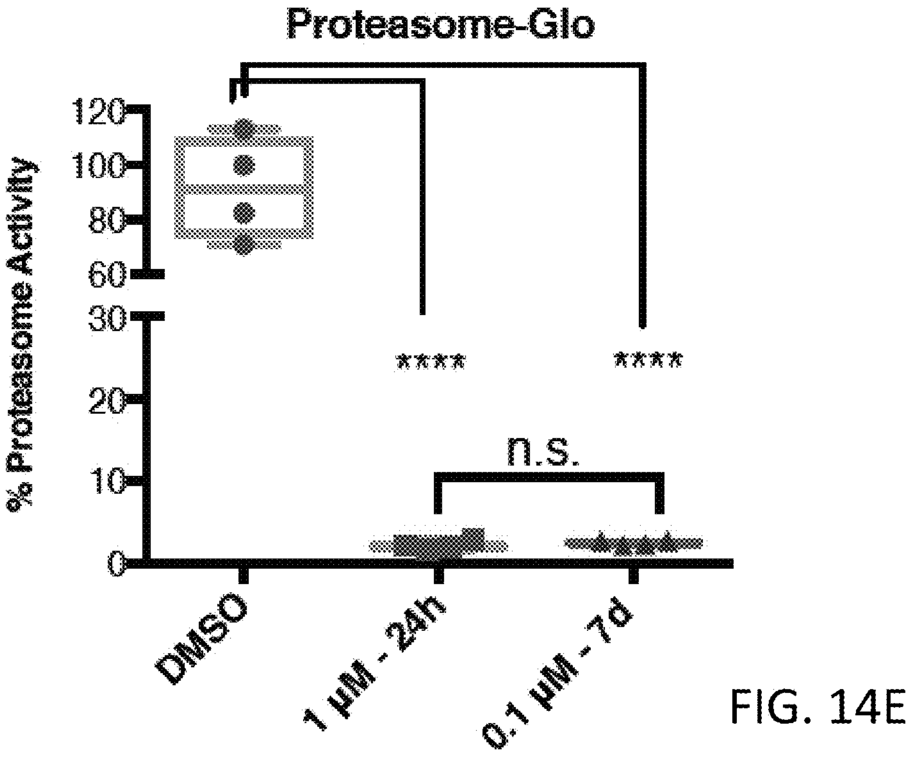

A previous study established that proteasome inhibition in hMNs could trigger accumulation of mutant SOD-1 (31). It was, therefore, examined whether MG-132-mediated proteasome inhibition affected TDP-43 localization in hMNs as a potential model of sporadic ALS. First, the range and timing of small molecule treatment that could inhibit the proteasome without inducing overt cellular toxicity was established (FIGS. 14A-14D). It was determined that neurons could withstand an overnight 1 μM treatment, which decreases proteasome activity to less than 10% of normal activity (FIG. 14E). Then a pulse-chase experiment was performed to determine the consequences of proteasome inhibition on TDP-43 localization (FIG. 5A). Strikingly, using the Pearson's correlation coefficient analysis as described above, it was observed that TDP-43 staining in the nucleus was greatly diminished after 24 hour 1 μM pulse of MG-132 (FIGS. 5B-5C). Notably, following washout, it was found that TDP-43 staining became indistinguishable to unchallenged neurons after 4 days (FIGS. 5B-5C). Thus, proteasome inhibition in hMNs induces a TDP-43 mislocalization that is reversible. These findings are analogous with stress condition studies on primary cortical and hippocampal neurons, where proteasome inhibition also caused loss of TDP-43 nuclear staining (32).

Figures 5D, 5E, 5F, 5G:
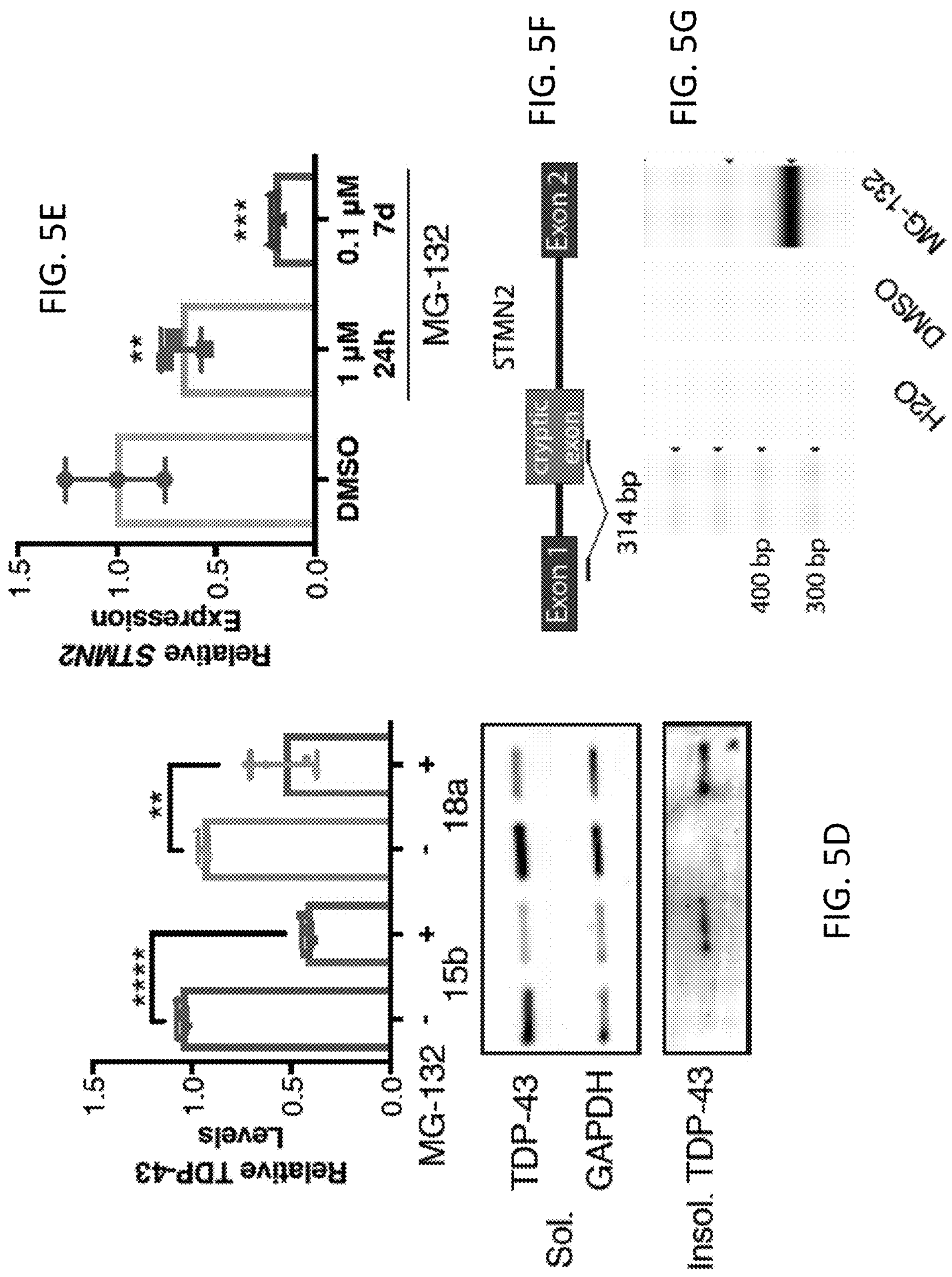

To determine what happened to TDP-43 after proteasome inhibition, TDP-43 levels were examined by immunoblot analysis in both the detergent-soluble and detergent-insoluble fractions. In the soluble lysates obtained from control neurons treated with a low dose of MG-132 (FIG. 5A), significantly decreased TDP-43 levels (FIG. 5D) were found. The UREA, or insoluble, fraction was probed and it was discovered that proteasome inhibition triggers TDP-43 to become insoluble (FIG. 5D). Finally, STMN2 levels in neurons treated with either a short-term high dose or a long-term low dose of MG-132 were probed. In both cases, significant decreases were observed in STMN2 mRNA levels (FIG. 5E). Together, these data connect protein homeostasis with TDP-43 localization and STMN2 levels.

TDP-43 Suppresses Appearance of Cryptic Exons in hMNs

TDP-43 plays an important role in the nucleus regulating RNA splicing, and recent studies highlight its ability to suppress non-conserved or cryptic exons to maintain intron integrity (80). When cryptic exons are included in RNA transcripts, in many cases, their inclusion can affect normal levels of the gene product by disrupting its translation or by promoting nonsense-mediated decay (80). Interestingly, no overlap in the genes regulated by TDP-43 cryptic exon suppression has been observed between mouse and man (80). The sequencing data was examined for evidence of cryptic exons in genes observed to be reproducibly regulated by TDP-43 in human cancer cells (81). Reads mapping to cryptic exons in 9 of these 95 genes were found, including PFKP, which was consistently down-regulated in the RNA-Seq experiment (FIG. 15A, FIG. 3C). Based on this observation, the RNA-Seq reads mapping to the other genes consistently misregulated in hMNs after TDP-43 depletion were also scrutinized. Strong evidence was found for the inclusion of cryptic exons in both ELAVL3 and STMN2 (FIGS. 15B-15C). It was then asked if cryptic exon inclusion could be contributing to decreased STMN2 levels in hMNs after proteasome inhibition. To accomplish this goal, an RT-PCR assay was developed to detect transcripts containing the cryptic exon (FIG. 5F). Only hMNs treated with the proteasome inhibitor had detectable levels of the expected PCR product (FIG. 5G), and Sanger sequencing of the PCR product confirmed the anticipated splice junction (FIGS. 15D-15E). Together the data suggest that the mechanism for STMN2 down-regulation is similar for both TDP-43 depletion and mislocalization.

STMN2 is Expressed in Human Adult Primary Spinal MNs and is Altered in ALS

Figure 6A:
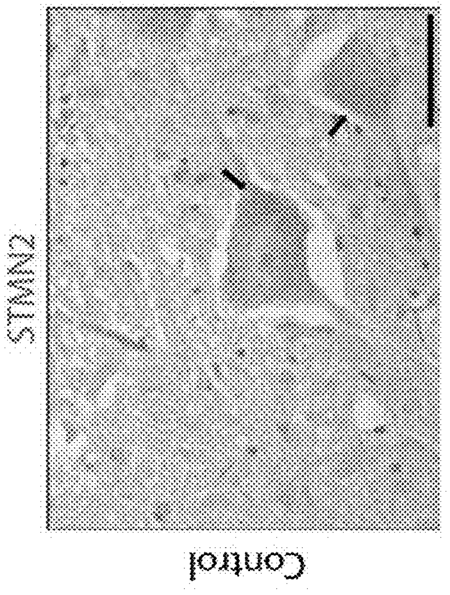
FIGS. 6A-6H demonstrates ALS patient data.
Figure 6B:
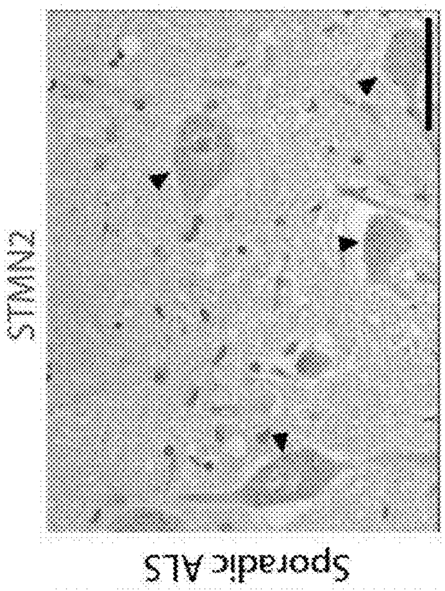
Figure 6C:
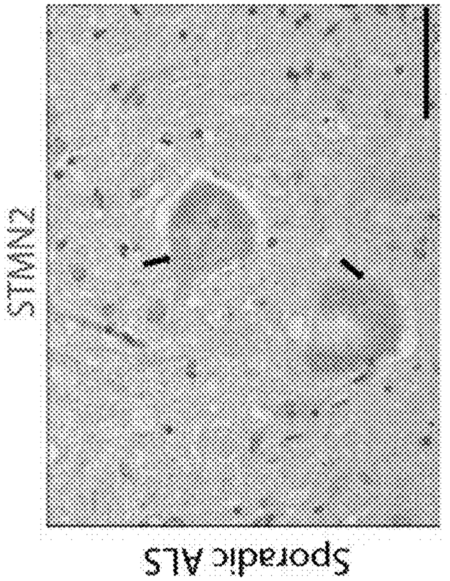
Figure 6D:
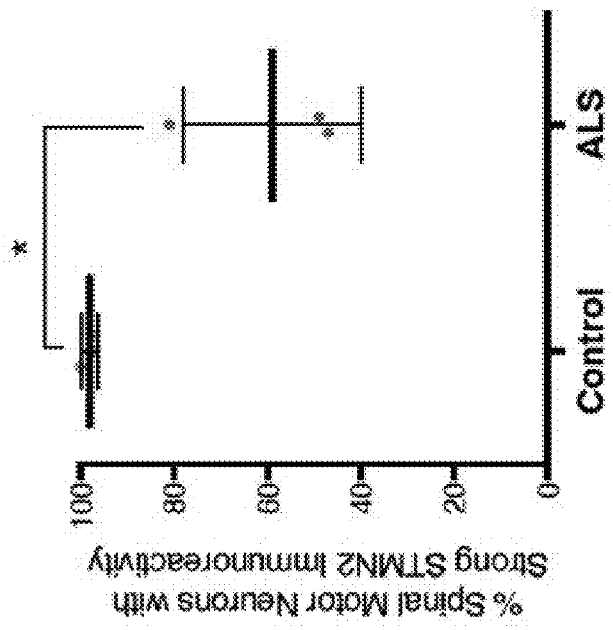
Figure 6E:
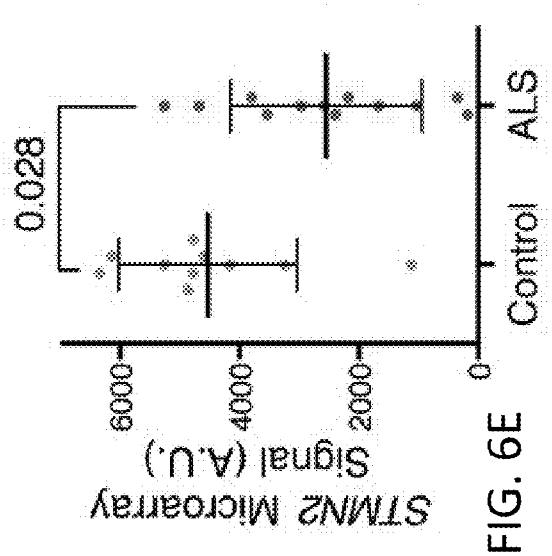
Figure 6F:
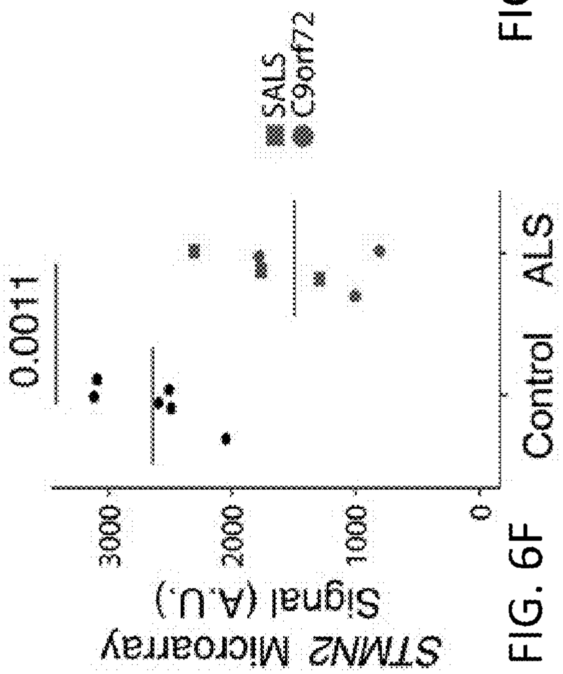
Figure 6G:
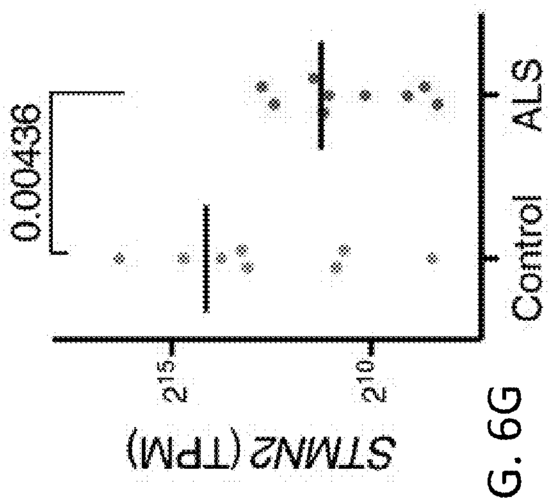
Figure 6H:
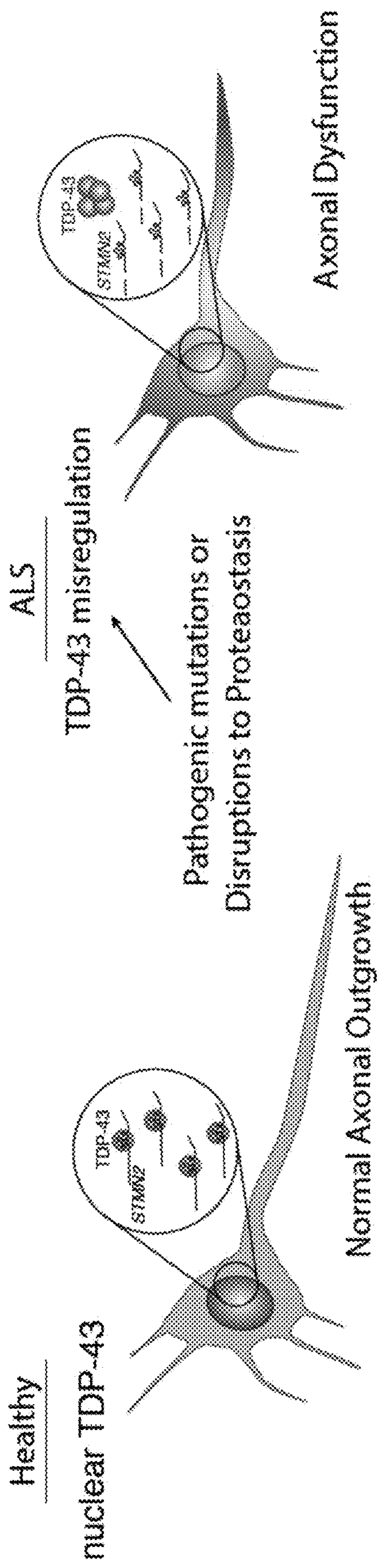

Finally, it was sought to test if the in vitro findings were relevant to ALS patient motor neurons in vivo. To this end, immunohistochemistry was used of human adult spinal cord tissues to investigate STMN2 expression in control and ALS patients. It was predicted that levels of STMN2 protein would be altered in post-mortem spinal MNs from sporadic ALS cases, which typically manifest pathological loss of nuclear TDP-43 staining and accumulation of cytoplasmic TDP-43 immunoreactive inclusions (7, 37). Similar to what was observed in stem cell derived hMNs, strong STMN2 immunoreactivity was present in the cytoplasmic region of human adult lumbar spinal MNs, but absent in the surrounding glial cells (FIGS. 6A-6C). The percentage of MNs exhibiting strong STMN2 immunoreactivity in lumbar spinal cord tissue sections in 3 control cases (no evidence of spinal cord disease) and in 3 ALS cases was determined. Consistent with the hypothesis, it was found that the percentage of lumbar MNs with clear immunoreactivity to the STMN2 antibody was significantly reduced in tissue samples collected from sporadic ALS cases (FIG. 6D). The results are further supported by several independent expression studies of ALS postmortem samples. Three studies have performed laser dissection of motor neuron from ALS patients to perform expression studies (82-84). This data was interrogated and decreased STMN2 transcript levels were observed for the ALS patient samples relative to control samples (FIGS. 6E-6F).

DISCUSSION

The studies suggest that the abundance of hundreds of transcripts is likely regulated by TDP-43 in human motor neurons, including several RNAs that have surfaced previously in the context of studying ALS. For instance, the findings suggest that BDNF expression could in part be regulated by TDP-43, which is of note given that decreased expression of this neurotrophin has been observed previously (85). MMP9 has previously been shown in the SOD1 ALS mouse model to define populations of motor neurons most sensitive to degeneration (86). The studies suggest that reduced TDP-43 function might more widely induce expression of this factor, which could sensitize motor neurons to degeneration. Further interrogation of the transcripts that were identified here may provide insights into how perturbations to TDP-43 lead to motor neuron dysfunction.

An important outstanding question has been, what are the mechanistic consequences of familial mutations in TDP-43 and how do their effects relate to the events that occur when TDP-43 becomes pathologically relocalized in patients with sporadic disease. The identification of motor neuron transcripts regulated by TDP-43 provided an opportunity to explore the potential impact of differing manipulations to TDP-43 relevant to both familial and sporadic disease. First, it was asked whether a subset of the target RNAs identified as reduced after TDP-43 depletion displayed significant expression changes in motor neurons produced from patients with TDP-43 mutations. Interestingly, modest but significant changes were found in the expression of the RNA binding protein ELAVL3 and the microtubule regulator STMN2, but not other putative targets identified. Thus, reduced expression of target RNAs is considered as a TDP-43 phenotype, patient mutations displayed partial loss-of-function effects.

Upon over-expression, it has previously been shown that mutant TDP-43 is prone to aggregation (22). Some studies have also suggested that mutant TDP-43 is similarly prone to aggregation when expressed at native levels in patient specific motor neurons (54, 56, 57). To determine whether aggregation or loss of nuclear mutant TDP-43 could be contributing to decreased expression of STMN2 and ELAVL3 in the experiments, TDP-43 was carefully monitored in these patient motor neurons, but no such defect was identified. Although it cannot be ruled out that modest nuclear TDP-43 loss or insolubility that were below the range of detection are responsible for the observed decline in STMN2 and ELAVL3 expression, the findings are consistent with the notion that mutant protein might simply have reduced affinity or ability to process certain substrates. Further biochemical experiments beyond the scope of this study will likely be required to discern these potential hypotheses.

It is believed that if larger scale aggregation, or nuclear loss of mutant TDP-43 were occurring in familial patient motor neurons it would be detectable. It was found that proteasome inhibition induced dramatic nuclear loss of TDP-43, along with its insoluble accumulation. The inspiration to perform this manipulation occurred after discovering that proteasome inhibition led to an accumulation of insoluble SOD1 in motor neurons from SOD1 ALS patient-specific stem cells but not in control motor neurons harboring only normal SOD1 (31). Interestingly, and as apparently observed by others in distinct contexts (32), proteasome inhibition caused loss of nuclear TDP-43 and its insoluble accumulation regardless of whether in a control of disease genotype. This result was captivating as it suggested that disrupted proteostasis induced by any number of ALS implicated mutations or events could be upstream of the most common histopathological finding in sporadic ALS. The findings further the thought that TDP-43 re-localization to the cytoplasm may initially provide a protective and adaptive response to disrupted proteostasis (87). However, it may be that the biochemical nature of this response and the liquid crystal conversion that these complexes can undergo causes a transient response to become a pathological state that chronically depletes motor neurons of important RNAs regulated by TDP-43 (88). The finding that TDP-43 targets are depleted from motor neurons following proteasome inhibition is consistent with that model.

Although it was found that hundreds of RNAs were impacted by TDP-43 depletion, it was noted that not all transcripts seemed to be equally affected by alterations in TDP-43, with a modest number, including those encoding STMN2, ELAVL3 being particularly sensitive. This observation raises an important question with substantial therapeutic implications: Are the primary effects of TDP-43 pathology in patients and the role that it might play in motor neuropathy and degeneration propagated through a small number of target RNAs? If so, understanding the functions of these key TDP-43 targets, the mechanisms by which they become disrupted and whether they can be restored could be significant as it might spotlight a pathway downstream of TDP-43 pathology for restoring motor neuron functionality. Given the established functions of STMN orthologs and the magnitude of the effect of TDP-43 depletion on STMN2 levels, it was wondered if it might be such a target.

The Stathmin family of proteins are recognized regulators of microtubule stability and have been demonstrated to regulate motor axon biology in the fly (77). Gene editing was used to determine if STMN2 has an important function in human stem cell derived motor neurons and it was found that both motor axon outgrowth and repair were significantly impaired in the absence of this protein. Although hMNs generated in vitro share many molecular and functional properties with bona fide MNs (29), the in vivo validation of discoveries from stem cell-based models of ALS is a critical test of their relevance to disease mechanisms and therapeutic strategies (89). Human adult spinal cord tissues were therefore used to provide in vivo evidence corroborating the finding that STMN2 levels are altered in ALS. Given that it was found the likely mechanism for reduced expression of STMN2 was the emergence of a cryptic exon, in the future it will be of interest to determine whether a properly targeted antisense oligonucleotides might suppress this splicing event and restore STMN2 expression.

Materials and Methods

Cell Culture and Differentiation of hESCs and hiPSCs into MNs

Pluripotent stem cells were grown with mTeSR1 medium (Stem Cell Technologies) on tissue culture dishes coated with Matrigel™ (BD Biosciences), and maintained in 5% CO2 incubators at 37° C. Stem cells were passaged as small aggregates of cells after 1 mM EDTA treatment. 10 μM ROCK inhibitor (Sigma, Y-27632) was added to the cultures for 16-24 hours after dissociation to prevent cell death. MN differentiation was carried out using a modified protocol based on adherent culture conditions in combination with dual inhibition of SMAD signaling, inhibition of NOTCH and FGF signaling, and patterning by retinoic acid and SHH signaling. In brief, ES cells were dissociated to single cells using Accutase™ (Stem Cell Technologies) and plated at a density of 80,000 cells/cm$^2$ on matrigel-coated culture plates with mTeSR1 medium (Stem Cell Technologies) supplemented with ROCK inhibitor (10 μM Y-27632, Sigma). When cells reached 100% confluency, medium was changed to differentiation medium (1/2 Neurobasal (Life Technologies™) 1/2 DMEM-F12 (Life Technologies™) supplemented with 1×B-27 supplement (Gibed)), 1×N-2 supplement (Gibed)), 1× Gibco® GlutaMAX™ (Life Technologies™) and 100 μM non-essential amino-acids (NEAA)). This time point was defined as day 0 (d0) of motor neuron differentiation. Treatment with small molecules was carried out as follows: 10 μM SB431542 (Custom Synthesis), 100 nM LDN-193189 (Custom Synthesis), 1 μM retinoic acid (Sigma) and 1 μM Smoothend agonist (Custom Synthesis) on d0-d5; 5 μM DAPT (Custom Synthesis), 4 μM SU-5402 (Custom Synthesis), 1 μM retinoic acid (Sigma) and 1 μM Smoothend agonist (Custom Synthesis) on d6-d14.

Fluorescent Activated Cell Sorting (FACS) of GFP+MNs

On d14, differentiated cultures were dissociated to single cells using Accutase™ treatment for 1 hour inside a 5% CO2/37° C. incubator. Repeated (10-20 times) but gentle pipetting with a 1000 μL Pipetman® was used to achieve a single cell preparation. Cells were spun down, washed 1× with PBS and resuspended in sorting buffer (1× cation-free PBS 15 mM HEPES at pH 7 (Gibco®), 1% BSA (Gibco®, 1× penicillin-streptomycin (Gibco®), 1 mM EDTA, and DAPI (1 μg/mL). Cells were passed through a 45 μm filter immediately before FACS analysis and purification. The BD FACS Aria II cell sorter was routinely used to purify Hb9::GFP$^+$ cells into collection tubes containing MN medium (Neurobasal (Life Technologies™), 1×N-2 supplement (Gibco®, B-27 supplement (Gibco®), GlutaMax and NEAA) with 10 μM ROCK inhibitor (Sigma, Y-27632) and 10 ng/mL of neurotrophic factors GDNF, BDNF and CNTF (R&D). DAPI signal was used to resolve cell viability, and differentiated cells not exposed to MN patterning molecules (RA and SAG) were used as negative controls to gate for green fluorescence. For lines not containing the Hb9::GFP reporter, single cell sunspensions were incubated with antibodies against NCAM (BD Bioscience, BDB557919, 1:200) and EpCAM (BD Bioscience, BDB347198, 1:50) for 25 minutes in sorting buffer, then washed once with PBS 1× and resuspended in sorting buffer. For RNA-Seq experiments, 200,000 GFP$^+$ cells per well were plated in 24-well tissue culture dishes precoated with matrigel. MN medium supplemented with 10 ng/mL of each GDNF, BDNF and CNTF (R&D Systems) was used to feed and mature the purified MNs. RNA-Seq experiments and most downstream assays were carried with d10 purified MNs (10 days in culture after FACS) grown plates coated with 0.1 mg/ml poly-Dlysine (Invitrogen) and 5 μg/ml laminin (Sigma-Aldrich) at a concentration of around 130000 cells/$cm^2$.

RNAi

RNAi in cultures of purified $GFP^+$ MNs was induced with Silencer® Select siRNAs (Life Technologies™) targeting the TDP-43 mRNA or with a non-targeting siRNA control with scrambled sequence that is not predicted to bind to any human transcripts. Lyophilized siRNAs were resuspended in nuclease-free water and stored at −20° C. as 20 μM stocks until ready to use. For transfection, siRNAs were diluted in Optimem (Gibco®) and mixed with RNAiMAX (Invitrogen) according to manufacturer's instructions. After 30 min incubation, the mix was added drop-wise to the MN cultures, so that the final siRNA concentration in each well was 60 nM in 1:1 Optimem:MN medium (Neurobasal (Life Technologies™, N2 supplement (Gibco®), B-27 supplement (Gibco®), GlutaMax and NEAA) and 10 ng/mL of each GDNF, BDNF and CNTF (R&D). 12-16 hours post-transfection media was changed. RNA-Seq experiments and validation assays were carried with material collected 4 days after transfection.

Immunocytochemistry

For immunofluorescence, cells were fixed with ice-cold 4% PFA for 15 minutes at 4° C., permeabilized with 0.2% Triton-X in 1×PBS for 45 minutes and blocked with 10% donkey serum in 1×PBS-T (0.1% Tween-20) for 1 hour. Cells were then incubated overnight at 4° C. with primary antibody (diluted in blocking solution). At least 4 washes (5 min incubation each) with 1×PBS-T were carried out, before incubating the cells with secondary antibodies for 1 hour at room temperature (diluted in blocking solution). Nuclei were stained with DAPI. The following antibodies were used in this study: Hb9 (1:100, DSHB, MNR2 81.5C10-c), TUJ1 (1:1000, Sigma, T2200), MAP2 (1:10000, Abcam ab5392), Ki67 (1:400, Abcam, ab833), GFP (1:500, Life Technologies™, A10262), Isletl (1:500, Abcam ab20670), TDP-43 (1:500, ProteinTech Group), STMN2 (1:4000, Novus), AlexaFluor™ 647-Phalloidin (1:200). Secondary antibodies used (488, 555, 594, and 647) were AlexaFluor™ (1:1000, Life Technologies™) and DyLight (1:500, Jackson ImmunoResearch Laboratories). Micrographs were analyzed using FIJI software to determine the correlation coefficient.

Immunoblot Assays

For analysis of TDP-43 and STMN2 protein expression levels, d10 MNs were lysed in RIPA buffer (150 mM Sodium Chloride; 1% Triton X-100; 0.5% sodium deoxycholate; 0.1% SDS; 50 mM Tris pH 8.0) containing protease and phosphatase inhibitors (Roche) for 20 min on ice, and centrifuged at high speed. 200 μL of RIPA buffer per well of 24-well culture were routinely used, which yielded ~20 μg of total protein as determined by BCA (Thermo Scientific). After two washes with RIPA buffer, insoluble pellets were resuspended in 200 μl of UREA buffer (Bio-Rad). For immunoblot assays 2-3 μg of total protein were separated by SDS-PAGE (BioRad), transferred to PDVF membranes (BioRad) and probed with antibodies against TDP-43 (1:1000, ProteinTech Group), GAPDH (1:1000, Millipore) and STMN2 (1:3000, Novus). Insoluble pellets were loaded based on protein concentration of correspondent RIPA-soluble counterparts. The same PDVF membrane was immunoassayed 2-3 times using Restore™ PLUS Western Blot Stripping Buffer (Thermo Scientific). GAPDH levels were used to normalized each sample, and LiCor software was used to quantitate protein band signal.

RNA Preparation, qRT-PCR and RNA Sequencing

Total RNA was isolated from d10 MNs for RNA-Seq experiments and validation assays using Trizol LS (Invitrogen) according to manufacturer's instructions. 500 μL were added per well of the 24-well cultures. A total of 300-1000 ng of total RNA was used to synthesize cDNA by reverse transcription according to the iSCRIPT kit (Bio-rad). Quantitative RT-PCR (qRT-PCR) was then performed using SYBR green (Bio-Rad) and the iCycler system (Bio-rad). Quantitative levels for all genes assayed were normalized using GAPDH expression. Normalized expression was displayed relative to the relevant control sample (mostly siREDtreated MNs or cells with 1×TDP-43 levels). For comparison between patient line, normalized expression was displayed relative to the average of pooled data points. All primer sequences are available upon request. For next-generation RNA sequencing (RNA-Seq), at least two technical replicas per siRNA sample or AAVS1-TDP43 genotype were included in the analyses. After RNA extraction, samples with RNA integrity numbers (RIN) above 7.5, determined by a bioAnalyzer, were used for library preparation. In brief, RNA sequencing libraries were generated from ~250 ng of total RNA using the illumina TruSeq RNA kit v2, according to the manufacturer's directions. Libraries were sequenced at the Harvard Bauer Core Sequencing facility on a HiSeq 2000 platform. All FASTQ files were analyzed using the bcbioRNASeq workflow and toolchain (90). The FASTQ files were aligned to the GRCh37/hg19 reference genome. Differential expression testing was performed using DESeq2 suite of bioinformatics tools (38). The Cuffdiff module of Cufflinks was used to identify differential splicing. Salmon was used to generate the counts and tximport to load them at gene level (91,92). All p-values are then corrected for multiple comparisons using the method of Benjamini and Hochberg (93).

Electrophysiology Recordings $GFP^+$ MNs were plated at a density of 5,000 cells/$cm^2$ on poly-D-lysine/laminin-coated coverslips and cultured for 10 days in MN medium, conditioned for 2-3 days by mouse glial cells and supplemented with 10 ng/mL of each GDNF, BDNF and CNTF (R&D Systems). Electrophysiology recordings were carried out as previously reported (31,94). Briefly, whole-cell voltage-clamp or current-clamp recordings were made using a Multiclamp 700B (Molecular Devices) at room temperature (21-23C). Data were digitized with a Digidata 1440A A/D interface and recorded using pCLAMP 10_software (Molecular Devices). Data were sampled at 20 kHz and low-pass filtered at 2 kHz. Patch pipettes were pulled from borosilicate glass capillaries on a Sutter Instruments P-97 puller and had resistances of 2-4 MW. The pipette capacitance was reduced by wrapping the shank with Parafilm and compensated for using the amplifier circuitry. Series resistance was typically 5-10 MW, always less than 15 MW, and compensated by at least 80%. Linear leakage currents were digitally subtracted using a P/4 protocol. Voltages were elicited from a holding potential of −80 mV to test potentials ranging from −80 mV to 30 mV in 10 mV increments. The intracellular solution was a potassium-based solution and contained K gluconate, 135; $MgCl_2$, 2; KCl, 6; HEPES, 10; Mg ATP, 5; 0.5 (pH 7.4 with KOH). The extracellular was sodium-based and contained NaCl, 135; KCl, 5; $CaCl_2$), 2; $MgCl_2$, 1; glucose, 10; HEPES, 10, pH 7.4 with NaOH). Kainate was purchased from Sigma.

Formaldehyde RNA Immunoprecipitation 1 well of a 6 well plate of hMNs (2 million cells) were crosslinked and processed according to the MagnaRlP instructions (Millipore). The following antibodies were used in this study: SOD1 (Cell Signaling Technologies), TDP-43 (FL9, gift of D. Cleveland), and mouse IgG, (cell signaling technology). Each RIP RNA fractions' Ct value was normalized to the Input RNA fraction Ct value for the same qPCR Assay to account for RNA sample preparation differences. To calculate the dCt [normalized RIP], Ct[RIP]−(Ct [Input]−log 2 (Input Dilution Factor)) was determined, where the dilution factor was 100 or 1%. To determine the fold enrichment, the ddCt by dCt[normalized RIP]−dCt [normalized IgG] then fold enrichment=2^-ddCt was calculated.

STMN2 Knockout Generation

STMN2 guide RNAs were designed using the following web resources: CHOPCHOP (chopchop.rc.fas.harvard.edu) from the Schier Lab (95). Guides were cloned into a vector containing the human U6 promotor (custom synthesis Broad Institute, Cambridge) followed by the cloning site available by cleavage with BbsI, as well as ampicillin resistance. To perform the cloning, all the gRNAs were modified before ordering. The following modifications were used in order to generate overhangs compatible with a BbsI sticky end: if the 5' nucleotide of the sense strand was not a G, this nucleotide was removed and substituted with a G; for the reverse complement strand, the most 3' nucleotide was removed and substituted with a C, while AAAC was added to the 5' end. The resulting modified STMN2 gRNA sequences were used for Cas9 nuclease genome editing: guide 1: 5' CACCGTATAGATGTTGATGTTGCG 3' (Exon 2) (SEQ ID NO: 4), guide 2: 5' CACCTGAAACAAT-TGGCAGAGAAG 3' (Exon 3) (SEQ ID NO: 5), guide 3: 5' CACCAGTCCTTCAGAAGGCTTTGG 3' (Exon 4) (SEQ ID NO: 6). Cloning was performed by first annealing and phosphorylating both the gRNAs in PCR tubes. 1 μL of both the strands at a concentration of 100 μM was added to 1 μL of T4 PNK (New England Biolabs), 1 μL of T4 ligation buffer and 6 μL of H2O. The tubes were placed in the thermocycler and incubated at 37° C. for 30 mins, followed by 5 mins at 95° C. and a slow ramp down to 25° C. at a rate of 5° C./minute. The annealed oligos were subsequently diluted 1:100 and 2 μL was added to the ligation reaction containing 2 μL of the 100 μM pUC6 vector, 2 μL of NEB buffer 2.1, 1 μL of 10 mM DTT, 1 μL of 10 mM ATP, 1 μL of BbsI (New England Biolabs), 0.5 μL of T7 ligase (New England Biolabs) and 10.5 μL of H2O. This solution was incubated in a thermocycler with the following cycle, 37° C. for 5 minutes followed by 21° C. for 5 minutes, repeated a total of 6 times. The vectors were subsequently cloned in OneShot Top10 (ThermoFisher Scientific) cells and plated on LB-ampicilin agar plates and incubated overnight on 37° C. The vectors were isolated using the Qiagen MIDIprep kit (Qiagen) and measured DNA concentration using the nanodrop. Proper cloning was verified by sequencing the vectors by Genewiz using the M13F(−21) primer.

Stem cell transfection was performed using the Neon Transfection System (ThermoFisher Scientific) with the 100 μL kit (ThermoFisher Scientific). Prior to the transfection, stem cells were incubated in mTeSR1 containing 10 μM Rock inhibitor for 1 hour. Cells were subsequently dissociated by adding accutase and incubating for 5 min at 37° C. Cells were counted using the Countess and resuspended in R medium at a concentration of $2.5*10^6$ cells/mL. The cell solution was then added to a tube containing 1 μg of each vector containing the guide and 1.5 μg of the pSpCas9n (BB)-2A-Puro (PX462) V2.0, a gift from Feng Zhang (Addgene). The electroporated cells were immediately released in pre-incubated 37° C. mTeSR medium containing 10 μM of Rock inhibitor in a 10-cm dish when transfected with the puromycin resistant vector. 24 hours after transfection with the Puromycin resistant vector, selection was started. Medium was aspirated and replaced with mTESR1 medium containing different concentrations of Puromycin: 1 μg/μL, 2 μg/μL and 4 μg/μL. After an additional 24 hours, the medium was aspirated and replaced with mTeSR1 medium. Cells were cultured for 10 days before colony picking the cells into a 24-well plate for expansion.

Genomic DNA was extracted from puromycin-selected colonies using the Qiagen DNeasy Blood and Tissue kit (Qiagen) and PCR screened to confirm the presence of the intended deletion in the STMN2 gene. PCR products were analyzed after electrophoresis on a 1% Agarose Gel. In brief, the targeted sequence was PCR amplified by a pair of primers external to the deletion, designed to produce a 1100 bp deletion-band in order to detect deleted clones. Sequences of the primers used are as follows: OUT_FWD, 5' GCAAAGGAGTCTACCTGGCA 3' (SEQ ID NO: 7) and OUT_REV, 5' GGAAGGGTGACTGACTGCTC 3' (SEQ ID NO: 8). Knockout lines were further confirmed using immunoblot analysis.

Neurite Outgrowth Assay

Individual Tuj1-positive neurons used for Sholl analyses were randomly selected and imaged using a Nikon Eclipse TE300 with a 40× objective. The neurites were traced using the ImageJ (NIH) plugin NeuronJ (78), and Sholl analysis was performed using the Sholl tool of Fiji (96), quantifying the number of intersections at 10-μm intervals from the cell body. Statistical analysis was performed by comparing the number of intersections of KO clones with the parental WT line for each 10-μm interval using Prism 6 (Graph Pad, La Jolla, CA, USA). Significance was assessed by a standard Student's t-test, with a p value of $p<0.05$ considered as significant.

Axotomy

Sorted motor neurons were cultured in standard neuron microfluidic devices (SND150, XONA Microfluidics) mounted on glass coverslips coated with 0.1 mg/ml poly-D-lysine (Sigma-Aldrich) and 5 μg/ml laminin (Invitrogen) at a concentration of around 250,000 neurons/device. Axotomy was performed at day 7 of culture by repeated vacuum aspiration and reperfusion of the axon chamber until axons were cut effectively without disturbing cell bodies in the soma compartment.

TDP-43 and STMN2 Immunohistochemical Analyses

Post-mortem samples from 3 sporadic ALS cases and 3 controls (no evidence of spinal cord disease) were gathered from the Massachusetts Alzheimer's Disease Research Center (ADRC) in accordance with Partners and Harvard IRB protocols. Histologic analysis of TDP-43 immunoreactivity (rabbit polyclonal, ProteinTech Group) was performed to confirm the diagnosis. For STMN2 analyses, sections of formalin fixed lumbar spinal cord were stained using standard immunohistochemical procedure with the exception that citrate buffer antigen retrieval was performed before blocking. Briefly, samples were rehydrated, rinsed with water, blocked in 3% hydrogen peroxide then normal serum, incubated with primary STMN2 rabbit-derived antibody (1:100 dilution, Novus), followed by incubation with the appropriate secondary antibody (anti-rabbit IgG conjugated to horseradish peroxidase 1:200), and exposure to ABC Vectastain kit and DAB peroxidase substrate, and briefly counterstained with hematoxylin before mounting. Multiple levels were examined for each sample.

STMN2 Splicing Analysis

Total RNA was isolated from neurons using RNeasy Mini Kit (Qiagen) according to manufacturer's instructions. A total of 300-1000 ng of total RNA was used to synthesize cDNA by reverse transcription according to the iSCRIPT kit (Bio-rad). RT-PCR was then performed using one cryptic exon-specific primer and then analyzed using the Agilent 2200 Tapestation.

Statistical Analysis

Statistical significance for qRT-PCR assays and STMN2 immunohistochemical analyses was assessed using a 2-tail unpaired Student's t-test, with a p value of $^{*}p<0.05$ considered as significant. Type II Error was controlled at the customary level of 0.05.

REFERENCES

1. Pasinelli, P. & Brown, R. H. Molecular biology of amyotrophic lateral sclerosis: insights from genetics. *Nat. Rev. Neurosci.* 7, 710-723 (2006).
2. Rowland, L. P. & Shneider, N. A. Amyotrophic lateral sclerosis. *New England Journal of Medicine* 344, 1688-1700 (2001).
3. Ravits, J. et al. Deciphering amyotrophic lateral sclerosis: What phenotype, neuropathology and genetics are telling us about pathogenesis. *Amyotroph Lateral Scler Frontotemporal Degener* 14, 5-18 (2013).
4. Miller, R. G., Mitchell, J. D. & Moore, D. H. Riluzole for amyotrophic lateral sclerosis (ALS)/motor neuron disease (MND). *Cochrane Database Syst Rev* 3, CD001447 (2012).
5. Ling, S.-C., Polymenidou, M. & Cleveland, D. W. Converging mechanisms in ALS and FTD: disrupted RNA and protein homeostasis. *Neuron* 79, 416-438 (2013).
6. Dion, P. A., Daoud, H. & Rouleau, G. A. Genetics of motor neuron disorders: new insights into pathogenic mechanisms. *Nat. Rev. Genet.* 10, 769-782 (2009).
7. Neumann, M. et al. Ubiquitinated TDP-43 in frontotemporal lobar degeneration and amyotrophic lateral sclerosis. *Science* 314, 130-133 (2006).
8. Chen-Plotkin, A. S., Lee, V. M.-Y. & Trojanowski, J. Q. TAR DNA-binding protein 43 in neurodegenerative disease. *Nature Reviews Neurology* 6, 211-220 (2010).
9. Ignatius, S. H., Wu, F., Harrich, D., GarciaMartinez, L. F. & Gaynor, R. B. Cloning and Characterization of a Novel Cellular Protein, Tdp-43, That Binds to Human-Immunodeficiency-Virus Type-1 Tar Dna-Sequence Motifs. *J Virol* 69, 3584-3596 (1995).
10. Buratti, E. et al. Nuclear factor TDP-43 and SR proteins promote in vitro and in vivo CFTR exon 9 skipping. *EMBO J* 20, 1774-1784 (2001).
11. Polymenidou, M. et al. Long pre-mRNA depletion and RNA missplicing contribute to neuronal vulnerability from loss of TDP-43. *Nat Neurosci* 14, 459-468 (2011).
12. Kawahara, Y. & Mieda-Sato, A. TDP-43 promotes microRNA biogenesis as a component of the Drosha and Dicer complexes. *P Natl Acad Sci Usa* 109, 3347-3352 (2012).
13. Liu-Yesucevitz, L. et al. Tar DNA Binding Protein-43 (TDP-43) Associates with Stress Granules: Analysis of Cultured Cells and Pathological Brain Tissue. *PLoS ONE* 5, (2010).
14. Parker, S. J. et al. Endogenous TDP-43 localized to stress granules can subsequently form protein aggregates. *Neurochem. Int.* 60, 415-424 (2012).
15. Alami, N. H. et al. Axonal transport of TDP-43 mRNA granules is impaired by ALS-causing mutations. *Neuron* 81, 536-543 (2014).
16. Volkening, K., Leystra-Lantz, C., Yang, W., Jaffee, H. & Strong, M. J. Tar DNA binding protein of 43 kDa (TDP-43), 14-3-3 proteins and copper/zinc superoxide dismutase (SOD1) interact to modulate NFL mRNA stability. Implications for altered RNA processing in amyotrophic lateral sclerosis (ALS). *Brain Research* 1305, 168-182 (2009).
17. Benajiba, L. et al. TARDBP mutations in motoneuron disease with frontotemporal lobar degeneration. *Ann Neurol.* 65, 470-473 (2009).
18. Rutherford, N. J. et al. Novel Mutations in TARDBP (TDP-43) in Patients with Familial Amyotrophic Lateral Sclerosis. *PLoS Genet* 4, (2008).
19. Sreedharan, J. et al. TDP-43 mutations in familial and sporadic amyotrophic lateral sclerosis. *Science* 319, 1668-1672 (2008).
20. Van Deerlin, V. M. et al. TARDBP mutations in amyotrophic lateral sclerosis with TDP-43 neuropathology: a genetic and histopathological analysis. *The Lancet Neurology* 7, 409-416 (2008).
21. Yokoseki, A. et al. TDP-43 mutation in familial amyotrophic lateral sclerosis. *Ann Neurol.* 63, 538-542 (2008).
22. Lee, E. B., Lee, V. M.-Y. & Trojanowski, J. Q. Gains or losses: molecular mechanisms of TDP43-mediated neurodegeneration. *Nat. Rev. Neurosci.* 13, 38-50 (2012).
23. Kraemer, B. C. et al. Loss of murine TDP-43 disrupts motor function and plays an essential role in embryogenesis. *Acta Neuropathol* 119, 409-419 (2010).
24. Sephton, C. F. et al. TDP-43 is a developmentally regulated protein essential for early embryonic development. *J. Biol. Chem.* 285, 6826-6834 (2010).
25. Wu, L.-S., Cheng, W.-C. & Shen, C.-K. J. Targeted depletion of TDP-43 expression in the spinal cord motor neurons leads to the development of amyotrophic lateral sclerosis-like phenotypes in mice. *J. Biol. Chem.* 287, 27335-27344 (2012).
26. Yang, C. et al. Partial loss of TDP-43 function causes phenotypes of amyotrophic lateral sclerosis. *Proc. Natl. Acad. Sci. U.S.A.* 111, E1121-9 (2014).
27. Iguchi, Y. et al. Loss of TDP-43 causes age-dependent progressive motor neuron degeneration. *Brain* 136, 1371-1382 (2013).
28. Tollervey, J. R. et al. Characterizing the RNA targets and position-dependent splicing regulation by TDP-43. *Nat Neurosci* 14, 452-458 (2011).
29. Davis-Dusenbery, B. N., Williams, L. A., Klim, J. R. & Eggan, K. How to make spinal motor neurons. *Development* 141, 491-501 (2014).
30. Han, S. S. W., Williams, L. A. & Eggan, K. C. Constructing and deconstructing stem cell models of neurological disease. *Neuron* 70, 626-644 (2011).
31. Kiskinis, E. et al. Pathways disrupted in human ALS motor neurons identified through genetic correction of mutant SOD1. *Cell Stem Cell* 14, 781-795 (2014).
32. van Eersel, J. et al. Cytoplasmic accumulation and aggregation of TDP-43 upon proteasome inhibition in cultured neurons. *PLoS ONE* 6, e22850 (2011).
33. Di Giorgio, F. P., Boulting, G. L., Bobrowicz, S. & Eggan, K. C. Human Embryonic Stem Cell-Derived Motor Neurons Are Sensitive to the Toxic Effect of Glial Cells Carrying an ALS-Causing Mutation. *Stem Cell* 3, 637-648 (2008).

34. Amoroso, M. W. et al. Accelerated high-yield generation of limb-innervating motor neurons from human stem cells. *J Neurosci* 33, 574-586 (2013).
35. Chambers, S. M. et al. Highly efficient neural conversion of human ES and iPS cells by dual inhibition of SMAD signaling. *Nat Biotechnol* 27, 275-280 (2009).
36. Chambers, S. M. et al. Combined small-molecule inhibition accelerates developmental timing and converts human pluripotent stem cells into nociceptors. *Nat Biotechnol* 30, 715-720 (2012).
37. Mackenzie, I. R. A. et al. Pathological TDP-43 distinguishes sporadic amyotrophic lateral sclerosis from amyotrophic lateral sclerosis with SOD1 mutations. *Ann Neurol.* 61, 427-434 (2007).
38. Love, M. I., Huber, W. & Anders, S. Moderated estimation of fold change and dispersion for RNA-seq data with DESeq2. *Genome Biology* 15, 550 (2014).
39. Arnold, E. S. et al. ALS-linked TDP-43 mutations produce aberrant RNA splicing and adult-onset motor neuron disease without aggregation or loss of nuclear TDP-43. *Proc. Natl. Acad. Sci. U.S.A.* 110, E736-45 (2013).
40. Fiesel, F. C., Weber, S. S., Supper, J., Zell, A. & Kahle, P. J. TDP-43 regulates global translational yield by splicing of exon junction complex component SKAR. *Nucleic Acids Res* 40, 2668-2682 (2012).
41. Prudencio, M. et al. Misregulation of human sortilin splicing leads to the generation of a nonfunctional progranulin receptor. *P Natl Acad Sci Usa* 109, 21510-21515 (2012).
42. Yang, C. et al. Partial loss of TDP-43 function causes phenotypes of amyotrophic lateral sclerosis. *Proc. Natl. Acad. Sci. U.S.A.* 111, E1121-9 (2014).
43. Bernard, E., Jacob, L., Mairal, J. & Vert, J.-P. Efficient RNA isoform identification and quantification from RNA-Seq data with network flows. *Bioinformatics* 30, 2447-2455 (2014).
44. Bryant, D. W., Priest, H. D. & Mockler, T. C. Detection and quantification of alternative splicing variants using RNA-seq. *Methods Mol Biol* 883, 97-110 (2012).
45. Trapnell, C. et al. Differential analysis of gene regulation at transcript resolution with RNA-seq. *Nat Biotechnol* 31, 46-53 (2013).
46. Shiga, A. et al. Alteration of POLDIP3 Splicing Associated with Loss of Function of TDP-43 in Tissues Affected with ALS. *PLoS ONE* 7, (2012).
47. Grenningloh, G., Soehrman, S., Bondallaz, P., Ruchti, E. & Cadas, H. Role of the microtubule destabilizing proteins SCG10 and stathmin in neuronal growth. *J. Neurobiol.* 58, 60-69 (2004).
48. Shin, J. E., Geisler, S. & DiAntonio, A. Dynamic regulation of SCG10 in regenerating axons after injury. *Exp Neurol* 252, 1-11 (2014).
49. Kasashima, K., Sakashita, E., Saito, K. & Sakamoto, H. Complex formation of the neuron-specific ELAV-like hu RNA-binding proteins. *Nucleic Acids Res* 30, 4519-4526 (2002).
50. Martin, K. R. et al. Over-expression of RCAN1 causes Down syndrome-like hippocampal deficits that alter learning and memory. *Human Molecular Genetics* 21, 3025-3041 (2012).
51. Ariyannur, P. S. et al. Methamphetamine-induced neuronal protein NAT8L is the NAA biosynthetic enzyme: implications for specialized acetyl coenzyme A metabolism in the CNS. *Brain Research* 1335, 1-13 (2010).
52. Boulting, G. L. et al. A functionally characterized test set of human induced pluripotent stem cells. *Nat Biotechnol* 29, 279-286 (2011).
53. Yuan, S. H. et al. Cell-surface marker signatures for the isolation of neural stem cells, glia and neurons derived from human pluripotent stem cells. *PLoS ONE* 6, e17540 (2011).
54. Egawa, N. et al. Drug Screening for ALS Using Patient-Specific Induced Pluripotent Stem Cells. *Sci Transl Med* 4, 145ra104-145ra104 (2012).
55. Serio, A. et al. Astrocyte pathology and the absence of non-cell autonomy in an induced pluripotent stem cell model of TDP-43 proteinopathy. *Proc. Natl. Acad. Sci. U.S.A.* 110, 4697-4702 (2013).
56. Bilican, B. et al. Mutant induced pluripotent stem cell lines recapitulate aspects of TDP-43 proteinopathies and reveal cell-specific vulnerability. *Proc. Natl. Acad. Sci. U.S.A.* 109, 5803-5808 (2012).
57. Zhang, Z. et al. Downregulation of MicroRNA-9 in iPSC-Derived Neurons of FTD/ALS Patients with TDP-43 Mutations. *PLoS ONE* 8, e76055 (2013).
58. Mason, M., Lieberman, A. R., Grenningloh, G. & Anderson, P. N. Transcriptional upregulation of SCG10 and CAP-23 is correlated with regeneration of the axons of peripheral and central neurons in vivo. *Mol Cell Neurosci* 20, 595-615 (2002).
59. *Morii*, H., Shiraishi-Yamaguchi, Y. & Mori, N. SCG10, a microtubule destabilizing factor, stimulates the neurite outgrowth by modulating microtubule dynamics in rat hippocampal primary cultured neurons. *J. Neurobiol.* 66, 1101-1114 (2006).
60. Shin, J. E. et al. SCG10 is a JNK target in the axonal degeneration pathway. P *Natl Acad Sci* Usa 109, E3696-E3705 (2012).
61. Sobczak, A. et al. Calmyrinl binds to SCG10 protein (stathmin2) to modulate neurite outgrowth. *Biochim Biophys Acta* 1813, 1025-1037 (2011).
62. Stein, R., Mori, N., Matthews, K., Lo, L. C. & Anderson, D. J. The NGF-inducible SCG10 mRNA encodes a novel membrane-bound protein present in growth cones and abundant in developing neurons. *Neuron* 1, 463-476 (1988).
63. Bieche, I. et al. Expression of stathmin family genes in human tissues: non-neural-restricted expression for SCLIP. *Genomics* 81, 400-410 (2003).
64. Smith, B. N. et al. Exome-wide rare variant analysis identifies TUBA4A mutations associated with familial ALS. *Neuron* 84, 324-331 (2014).
65. Wu, C.-H. et al. Mutations in the profilin 1 gene cause familial amyotrophic lateral sclerosis. *Nature* 488, 499-503 (2012).
66. Nicolas, A. et al. Genome-wide Analyses Identify KIF5A as a Novel ALS Gene. *Neuron* 97, 1268-1283.e6 (2018).
67. Guerreiro, R., Bras, J. & Hardy, J. SnapShot: Genetics of ALS and FTD. *Cell* 160, 798-U485 (2015).
68. Lagier-Tourenne, C. et al. Divergent roles of ALS-linked proteins FUS/TLS and TDP-43 intersect in processing long pre-mRNAs. *Nat Neurosci* 15, 1488-1497 (2012).
69. Lattante, S., Rouleau, G. A. & Kabashi, E. TARDBP and FUS Mutations Associated with Amyotrophic Lateral Sclerosis: Summary and Update. *Hum. Mutat.* 34, 812-826 (2013).
70. DeJesus-Hernandez, M. et al. Expanded GGGGCC hexanucleotide repeat in noncoding region of C9ORF72 causes chromosome 9p-linked FTD and ALS. *Neuron* 72, 245-256 (2011).

71. Renton, A. E., Chia, A. & Traynor, B. J. State of play in amyotrophic lateral sclerosis genetics. *Nat Neurosci* 17, 17-23 (2014).

72. Renton, A. E. et al. A Hexanucleotide Repeat Expansion in C9ORF72 Is the Cause of Chromosome 9p21-Linked ALS-FTD. *Neuron* 72, 257-268 (2011).

73. Buratti, E. & Baralle, F. E. Multiple roles of TDP-43 in gene expression, splicing regulation, and human disease. *Front Biosci* 13, 867-878 (2008).

74. Sugiura, Y. & Mori, N. SCG10 expresses growth-associated manner in developing rat brain, but shows a different pattern to p19/stathmin or GAP-43. *Brain Res. Dev. Brain Res.* 90, 73-91 (1995).

75. Levy, A. D. et al. Subcellular Golgi localization of stathmin family proteins is promoted by a specific set of DHHC palmitoyl transferases. *Mol Biol Cell* 22, 1930-1942 (2011).

76. Taylor, J. P., Brown, R. H. & Cleveland, D. W. Decoding ALS: from genes to mechanism. *Nature* 539, 197-206 (2016).

77. Chauvin, S. & Sobel, A. Neuronal stathmins: A family of phosphoproteins cooperating for neuronal development, plasticity and regeneration. *Progress in Neurobiology* 126, 1-18 (2015).

78. Meijering, E. et al. Design and validation of a tool for neurite tracing and analysis in fluorescence microscopy images. *Cytometry Part A* 58*A*, 167-176 (2004).

79. Taylor, A. M. et al. A microfluidic culture platform for CNS axonal injury, regeneration and transport. *Nat Methods* 2, 599-605 (2005).

80. Ling, J. P., Pletnikova, O., Troncoso, J. C. & Wong, P. C. TDP-43 repression of nonconserved cryptic exons is compromised in ALS-FTD. *Science* 349, 650-655 (2015).

81. Humphrey, J., Emmett, W., Fratta, P., Isaacs, A. M. & Plagnol, V. Quantitative analysis of cryptic splicing associated with TDP-43 depletion. *BMC Med Genomics* 10, 38 (2017).

82. Rabin, S. J. et al. Sporadic ALS has compartment-specific aberrant exon splicing and altered cell-matrix adhesion biology. *Human Molecular Genetics* 19, 313-328 (2009).

83. Highley, J. R. et al. Loss of nuclear TDP-43 in amyotrophic lateral sclerosis (ALS) causes altered expression of splicing machinery and widespread dysregulation of RNA splicing in motor neurones. *Neuropathology and Applied Neurobiology* 40, 670-685 (2014).

84. D'Erchia, A. M. et al. Massive transcriptome sequencing of human spinal cord tissues provides new insights into motor neuron degeneration in ALS. *Sci Rep* 7, 10046 (2017).

85. Henriques, A., Pitzer, C. & Schneider, A. Neurotrophic growth factors for the treatment of amyotrophic lateral sclerosis: where do we stand? *Front Neurosci* 4, 32 (2010).

86. Kaplan, A. et al. Neuronal Matrix Metalloproteinase-9 Is a Determinant of Selective Neurodegeneration. Neuron 81, 333-348 (2014).

87. Markmiller, S. et al. Context-Dependent and Disease-Specific Diversity in Protein Interactions within Stress Granules. *Cell* 172, 590-604.e13 (2018).

88. Taylor, J. P., Brown, R. H. & Cleveland, D. W. Decoding ALS: from genes to mechanism. *Nature* 539, 197-206 (2016).

89. de Boer, A. S. et al. Genetic validation of a therapeutic target in a mouse model of ALS. *Sci Transl Med* 6, 248ra104-248ra104 (2014).

90. Steinbaugh, M. J. et al. bcbioRNASeq: R package for bcbio RNA-seq analysis. *F*1000*Research* 6, 1976 (2017).

91. Patro, R., Duggal, G., Love, M. I., Irizarry, R. A. & Kingsford, C. Salmon provides fast and bias-aware quantification of transcript expression. *Nat Methods* 14, 417-419 (2017).

92. Soneson, C., Love, M. I. & Robinson, M. D. Differential analyses for RNA-seq: transcript-level estimates improve gene-level inferences. *F*1000*Research* 4, 1521 (2016).

93. Benjamini, Y. & Hochberg, Y. Controlling the False Discovery Rate: A Practical and Powerful Approach to Multiple Testing. http://www.jstor.org/stable/2346101 1, 289-300 (1995).

94. Son, E. Y. et al. Conversion of mouse and human fibroblasts into functional spinal motor neurons. *Cell Stem Cell* 9, 205-218 (2011).

95. Labun, K., Montague, T. G., Gagnon, J. A., Thyme, S. B. & Valen, E. CHOPCHOP v2: a web tool for the next generation of CRISPR genome engineering. *Nucleic Acids Res* 44, W272-W276 (2016).

96. Ferreira, T. A. et al. Neuronal morphometry directly from bitmap images. *Nat Methods* 11, 982-984 (2014).

Example 2

Recently the identity of mRNA transcripts regulated by the RNA binding protein TDP-43 in human motor neurons was reported. See Klim, J. R., et al., ALS-implicated protein TDP-43 sustains levels of STMN2, a mediator of motor neuron growth and repair. *Nat Neurosci,* 2019. 22(2): p. 167-179. Although TDP-43 regulates hundreds of transcripts in human motor neurons, one of the transcripts most affected by TDP-43 depletion was STMN2. STMN2 is a protein involved in microtubule assembly and is one of the most abundant transcripts expressed by a neuron. In depth analysis of the data revealed that TDP-43 suppresses a cryptic exon in the STMN2 transcript. The inclusion of this cryptic exon prevents the full-length form from being expressed leading to drastically decreased levels of STMN2 protein. Knockdown of TDP-43 in cell culture, as well as post-mortem tissue from patients exhibiting TDP-43 pathology, display altered STMN2 splicing. The cryptic exon-containing transcript contains its own stop and start sites and therefore potentially encodes for a 17 amino acid peptide. This change in human models was validated in RNA sequencing data from post-mortem spinal cord. Therefore, it was considered whether the cryptic STMN2 transcript or the peptide it encodes could serve as a CSF/fluid biomarker for people developing or with ALS or other patients exhibiting TDP-43 proteinopathies (e.g., Parkinson's, traumatic brain injury, Alzheimer's).

FIGS. 17A-17C show RNA can be readily collected from CSF-derived exosomes and then converted into cDNA to assay for full and cryptic STMN2 transcripts as well as control RNAs for normalization (FIG. 17A). The TaqMan Q-RT-PCR assay was validated to show that it simultaneously detects both the full and cryptic STMN2 transcripts using TDP-43 knockdown approaches in human neurons. STMN2 transcripts are normalized to the house keeping ribosomal subunit RNA18S5. TDP-43 levels were reduced in cultured human neurons using either an antisense oligonucleotide (ASO) to deplete cells of TDP-43 or an siRNAs to induce TDP-43 knockdown. In both conditions, a strong induction of the cryptic exon relative to a control was identified (FIG. 17B). Using the validated multiplexed qPCR assay, next RNA was isolated from CSF-derived exosomes using 300 ul patient samples to determine the levels of cryptic STMN2 (n=7 healthy controls, n=2 disease mimics and n=9 ALS patients). Relative to control samples, most ALS samples demonstrated above average levels of the STMN2 cryptic exon, with several samples showing levels orders of magnitude higher (FIG. 17C). Note that even in this modest set of samples that the increase in cryptic exon expression in ALS patients was highly significant ($P<0.005$). It is further notable that the two individuals who had non-ALS motor neuron disease (mimics) showed control levels of splicing. Finally, there is an interesting "texture" to the patient data with some patients showing high levels of expression and others more normal levels. It is hypothesized that patients with lower levels may either be earlier in their disease or have non-TDP-43 disease.

The most common pathological hallmark in ALS is the cytoplasmic accumulation and nuclear clearance of TDP-43. Many groups and companies are interested in developing therapeutics that rescue these changes in TDP-43 localization and function. However, to date, there are no biomarkers that could be used in a living person to monitor TDP-43 dysfunction or its rescue. The assay described here could be used in exactly this way. Furthermore, there is interest in STMN2 and its cryptic splicing itself as a target in ALS. The assay will allow for target engagement to be directly measured in patients during clinical studies.

Additional CSF samples from controls and from patients will be used for replicating the association between ALS and changes in STMN2 splicing. In addition, samples from individual patients will be assessed over the course of their disease to determine how cryptic splicing changes with disease course. Additionally, samples from individuals that have mutation in FUS and SOD1, which would not be expected to have TDP-43 pathology, will be assessed. Generally, it would be expected that these individuals have control levels of STMN2 cryptic exon.

Finally, additional biofluid samples, including serum, plasma and urine will be assessed to determine if the cryptic exon of STMN2 can be detected in these fluids as well.

Those skilled in the art will recognize, or be able to ascertain using no more than routine experimentation, many equivalents to the specific embodiments described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" or "and/or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more element(s), feature(s), or limitation(s) found in any other claim, e.g., any other claim that is dependent on the same base claim. Any one or more claims can be modified to explicitly exclude any one or more embodiment(s), element(s), feature(s), etc. For example, any particular sideroflexin, sideroflexin modulator, cell type, cancer type, etc., can be excluded from any one or more claims.

It should be understood that (i) any method of classification, prediction, treatment selection, treatment, etc., can include a step of providing a sample, e.g., a sample obtained from a subject in need of classification, prediction, treatment selection, treatment, for cancer, e.g., a cancer sample obtained from the subject; (ii) any method of classification, prediction, treatment selection, treatment, etc., can include a step of providing a subject in need of such classification, prediction, treatment selection, treatment, or treatment for cancer.

Where the claims recite a method, certain aspects of the invention provide a product, e.g., a kit, agent, or composition, suitable for performing the method.

Where elements are presented as lists, e.g., in Markush group format, each subgroup of the elements is also disclosed, and any element(s) can be removed from the group. For purposes of conciseness only some of these embodiments have been specifically recited herein, but the present disclosure encompasses all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the disclosure encompasses embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. It should also be understood that unless otherwise indicated or evident from the context, any product or composition described herein may be considered "isolated". It should also be understood that, where applicable, unless otherwise indicated or evident from the context, any method or step of a method that may be amenable to being performed mentally or as a mental step or using a writing implement such as a pen or pencil, and a surface suitable for writing on, such as paper, may be expressly indicated as being performed at least in part, substantially, or entirely, by a machine, e.g., a computer, device (apparatus), or system, which may, in some embodiments, be specially adapted or designed to be capable of performing such method or step or a portion thereof.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

What is claimed is:

1. A method of screening one or more test agents to identify candidate agents for treating or reducing the likelihood of a disease or condition associated with a decline in TDP-43 functionality in neuronal cells in a subject, comprising:

providing a neuronal cell having decreased STMN2 protein levels as a result of a cryptic exon;

contacting the cell with the one or more test agents;

measuring the levels of STMN2 protein in the cell using an ELISA, dot blot, and/or Western Blot; and identifying the test agent as a candidate agent if the contacted cell has an increase in STMN2 protein levels as compared to the STMN2 protein levels in the cell in the absence of the test agent.

2. The method of claim 1, wherein the disease or condition is a neurodegenerative disease.

3. The method of claim 1, wherein the disease or condition is selected from the group consisting of amyotrophic lateral sclerosis (ALS), frontotemporal dementia (FTD), inclusion body myositis (IBM), Parkinson's disease, and Alzheimer's disease.

4. The method of claim 1, wherein the disease or condition is a traumatic brain injury.

5. The method of claim 1, wherein the disease or condition is a proteasome-inhibitor induced neuropathy.

6. The method of claim 1, wherein the candidate agent suppresses the cryptic exon.

7. The method of claim 1, wherein the candidate agent restores motor neuron functionality, motor axon outgrowth, and/or motor axon repair.

8. The method of claim 1, wherein the one or more test agents comprise antisense oligonucleotides.

9. A method of screening one or more test agents to identify candidate agents for restoring STMN2 protein levels in neuronal cells in a subject, comprising:

providing a neuronal cell having decreased STMN2 protein levels as a result of a cryptic exon;

contacting the cell with the one or more test agents;

measuring the levels of STMN2 protein in the cell using an ELISA, dot blot, and/or Western Blot; and identifying the test agent as a candidate agent if the contacted cell has an increase in STMN2 protein levels as compared to the STMN2 protein levels in the cell in the absence of the test agent.

10. The method of claim 9, wherein the subject has a neurodegenerative disease.

11. The method of claim 10, wherein the neurodegenerative disease is selected from the group consisting of amyotrophic lateral sclerosis (ALS), frontotemporal dementia (FTD), inclusion body myositis (IBM), Parkinson's disease, and Alzheimer's disease.

12. The method of claim 9, wherein the subject has a traumatic brain injury.

13. The method of claim 9, wherein the subject has a proteasome-inhibitor induced neuropathy.

14. The method of claim 9, wherein the one or more test agents comprise antisense oligonucleotides.

15. A method of screening one or more test agents to identify candidate agents for treating or reducing the likelihood of a neurodegenerative disease or disorder associated with reduced levels of STMN2 protein, comprising:

providing a neuronal cell comprising a STMN2 cryptic exon;

contacting the cell with the one or more test agents;

measuring the levels of STMN2 protein in the cell using an ELISA, dot blot, and/or Western Blot; and identifying the test agent as a candidate agent if the contacted cell has an increase in STMN2 protein levels as compared to the STMN2 protein levels in the cell in the absence of the test agent.

16. The method of claim 15, wherein the neurodegenerative disease or disorder is selected from the group consisting of amyotrophic lateral sclerosis (ALS), frontotemporal dementia (FTD), inclusion body myositis (IBM), Parkinson's disease, and Alzheimer's disease.

17. The method of claim 15, wherein the one or more test agents comprise antisense oligonucleotides.

* * * * *

SEQUENCE LISTING

```
<160> NUMBER OF SEQ ID NOS: 36

<210> SEQ ID NO 1
<211> LENGTH: 592
<212> TYPE: DNA
<213> ORGANISM: Homo sapiens

<400> SEQUENCE: 1

agctcctagg aagcttcagg gcttaaagct ccactctact tggactgtac tatcaggccc      60

ccaaaatggg gggagccgac agggaaggac tgatttccat ttcaaactgc attctggtac     120

tttgtactcc agcaccattg gccgatcaat atttaatgct tggagattct gactctgcgg     180

gagtcatgtc aggggacctt gggagccaat ctgcttgagc ttctgagtga taattattca     240

tgggctcctg cctcttgctc tttctctagc acggtcccac tctgcagact cagtgcctta     300

ttcagtcttc tctctcgctc tctccgctgc tgtagccgga ccctttgcct tcgccactgc     360

tcagcgtctg cacatcccta caatggctaa aacagcaatg ggactcggca gaagaccttc     420

gagagaaagg tagaaaataa gaatttggct ctctgtgtga gcatgtgtgc gtgtgtgcga     480

gagagagaga cagacagcct gcctaagaag aaatgaatgt gaatgcggct tgtggcacag     540

ttgacaagga tgataaatca ataatgcaag cttactatca tttatgaata gc             592


<210> SEQ ID NO 2
<211> LENGTH: 97
<212> TYPE: DNA
<213> ORGANISM: Homo sapiens

<400> SEQUENCE: 2

cctacaagga aaaaatgaag gagctgtcca tgctgtcact gatctgctct tgcttttacc      60

cggaacctcg caacatcaac atctatactt acgatgg                               97


<210> SEQ ID NO 3
<211> LENGTH: 191
<212> TYPE: DNA
<213> ORGANISM: Homo sapiens
```

<400> SEQUENCE: 3
gactcggcag aagaccttcg agagaaaggt agaaaataag aatttggctc tctgtgtgag 60
catgtgtgcg tgtgtgcgag agagagagac agacagcctg cctaagaaga aatgaatgtg 120
aatgcggctt gtggcacagt tgacaaggat gataaatcaa taatgcaagc ttactatcat 180
ttatgaatag c 191

<210> SEQ ID NO 4
<211> LENGTH: 24
<212> TYPE: DNA
<213> ORGANISM: Artificial
<220> FEATURE:
<223> OTHER INFORMATION: gRNA

<400> SEQUENCE: 4
caccgtatag atgttgatgt tgcg 24

<210> SEQ ID NO 5
<211> LENGTH: 24
<212> TYPE: DNA
<213> ORGANISM: Artificial
<220> FEATURE:
<223> OTHER INFORMATION: gRNA

<400> SEQUENCE: 5
cacctgaaac aattggcaga gaag 24

<210> SEQ ID NO 6
<211> LENGTH: 24
<212> TYPE: DNA
<213> ORGANISM: Artificial
<220> FEATURE:
<223> OTHER INFORMATION: gRNA

<400> SEQUENCE: 6
caccagtcct tcagaaggct ttgg 24

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gcaaaggagt ctacctggca 20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ggaagggtga ctgactgctc 20

<210> SEQ ID NO 9
<211> LENGTH: 51
<212> TYPE: DNA
<213> ORGANISM: Artificial
<220> FEATURE:
<223> OTHER INFORMATION: modified STMN2

<400> SEQUENCE: 9

```
atggctaaaa cagcaatggg actcggcaga agaccttcga gagaaaggta g              51


<210> SEQ ID NO 10
<211> LENGTH: 16
<212> TYPE: PRT
<213> ORGANISM: Artificial
<220> FEATURE:
<223> OTHER INFORMATION: modified STMN2

<400> SEQUENCE: 10

Met Ala Lys Thr Ala Met Gly Leu Gly Arg Arg Pro Ser Arg Glu Arg
1               5                   10                  15


<210> SEQ ID NO 11
<211> LENGTH: 20
<212> TYPE: DNA
<213> ORGANISM: Artificial
<220> FEATURE:
<223> OTHER INFORMATION: antisense oligonucleotide

<400> SEQUENCE: 11

tcttcagtat tgctattcat                                                 20


<210> SEQ ID NO 12
<211> LENGTH: 500
<212> TYPE: DNA
<213> ORGANISM: Artificial
<220> FEATURE:
<223> OTHER INFORMATION: STMN2/modified STMN2
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 12

nnnnnnnnnn tccngangan gctgattctg accactaaac acatcagttt tagggatatt     60

aacttgtaat atacaggtat ccctcctggt aagctctggt attatgtctt aacattttta    120

aatctatggt aatctttaca aaatatttta cttccgaact catatacctg ggattttat    180

tactctggga attatgtgtt ctgccccatc actctctctt aattggattt ttaaaattat    240

attcatattg caggactcgg cagaagacct tcgagagaaa ggtagaaaat aagaatttgg    300

ctctctgtgt gagcatgtgt gcgtgtgtgc gagagagaga gacagacagc ctgcctaaga    360

agaaatgaat gtgaatgcgg cttgtggcac agttgacaag gatgataaat caataatgca    420

agcttactat catttatgaa tagcaatact gaagaaatta aaacaaaaga ttgctgtctc    480

aatatatctt atatttatta                                                500


<210> SEQ ID NO 13
<211> LENGTH: 392
<212> TYPE: DNA
<213> ORGANISM: Artificial
<220> FEATURE:
<223> OTHER INFORMATION: STMN2/modified STMN2
```

<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 13
nnnnnnnctc ngangangct gattctgacc actaaacaca tcagttttag ggatattaac 60
ttgtaatata caggtatccc tcctggtaag ctctggtatt atgtcttaac atttttaaat 120
ctatggtaat ctttacaaaa tattttactt ccgaactcat atacctgggg attttattac 180
tctgggaatt atgtgttctg ccccatcact ctctcttaat tggattttta aaattatatt 240
catattgcag gactcggcag aagaccttcg agattgtggc acagttgaca aggatgataa 300
atcaataatg caagcttact atcatttatg aatagcaata ctgaagaaat taaaacaaaa 360
gattgctgtc tcaatatatc ttatatttat ta 392

<210> SEQ ID NO 14
<211> LENGTH: 20
<212> TYPE: DNA
<213> ORGANISM: Artificial
<220> FEATURE:
<223> OTHER INFORMATION: gRNA

<400> SEQUENCE: 14
cgcaacatca acatctacac 20

<210> SEQ ID NO 15
<211> LENGTH: 20
<212> TYPE: DNA
<213> ORGANISM: Artificial
<220> FEATURE:
<223> OTHER INFORMATION: gRNA

<400> SEQUENCE: 15
cgagcgagag gtgctccaga 20

<210> SEQ ID NO 16
<211> LENGTH: 262
<212> TYPE: DNA
<213> ORGANISM: Homo sapiens

<400> SEQUENCE: 16
tctctcttaa ttggattttt aaaattatat tcatattgca ggactcggca gaagaccttc 60
gagagaaagg tagaaaataa gaatttggct ctctgtgtga gcatgtgtgc gtgtgtgcga 120
gagagagaga cagacagcct gcctaagaag aaatgaatgt gaatgcggct tgtggcacag 180
ttgacaagga tgataaatca ataatgcaag cttactatca tttatgaata gcaatactga 240
agaaattaaa acaaaagatt gc 262

<210> SEQ ID NO 17
<211> LENGTH: 262
<212> TYPE: DNA

<213> ORGANISM: Homo sapiens

<400> SEQUENCE: 17

```
tctctcttaa ttggattttt aaaattatat tcatattgca ggactcggca gaagaccttc      60

gagagaaagg tagaaaataa gaatttggct ctctgtgtga gcatgtgtgc gtgtgtgcga     120

gagagagaga cagacagcct gcctaagaag aaatgaatgt gaatgcggct tgtggcacag     180

ttgacaagga tgataaatca ataatgcaag cttactatca tttatgaata gcaatactga     240

agaaattaaa acaaaagatt gc                                              262
```

<210> SEQ ID NO 18
<211> LENGTH: 258
<212> TYPE: DNA
<213> ORGANISM: Chimp

<400> SEQUENCE: 18

```
tctctcctaa ttggattttt aaaattatat tcatattgca ggactcagca gaagaccttc      60

gagagaaagg tagaaaataa gaatttggct ctctgtgtga gcatgtgtgc atgtgtgcga     120

gagagagaga cagtctgcct aagaagaaat gaatgtgaat gcggcttgtg gcacagttga     180

caaggatgat aaatcaataa tgcaagctta ctattattta tgaatagcaa tactgaagaa     240

attaaaacaa aagattgc                                                   258
```

<210> SEQ ID NO 19
<211> LENGTH: 260
<212> TYPE: DNA
<213> ORGANISM: Gorilla

<400> SEQUENCE: 19

```
tctctcttaa ttggattttt aaaattatat tcatattgca ggactcagca gaagaccttc      60

gagagaaagg tagaaaataa gaatttggct ctctgtgtga gcatgtgtgc gtgtgtgcga     120

gagagagaga gacggtctgc ctaagaagaa atgaatgtga atgcagcttg tggcacagtt     180

gacaaggatg ataaatcagt aatgcaagct tactattatt tatgaatagc aatactgaag     240

aaattaaaac aaaagattgc                                                 260
```

<210> SEQ ID NO 20
<211> LENGTH: 260
<212> TYPE: DNA
<213> ORGANISM: Orangutan

<400> SEQUENCE: 20

```
tctctcttaa ttggattttt taaattatat tcatattgca ggactcagca gaagaccttc      60

gagagaaagg tagaaaataa gaatttggct ctctgtgtga gcatgtgtgc atgtgtgaga     120

gagagagaga gagagtctgc ctaagaagaa atgaatgtga atgcggcttg tggcacagtt     180

gacaaggatg ataaatcaat aatgcaagct tactattatt tatgaacagc aatactgaag     240

aaattaaaac aaaagattgc                                                 260
```

<210> SEQ ID NO 21
<211> LENGTH: 262
<212> TYPE: DNA
<213> ORGANISM: Gibbon

<400> SEQUENCE: 21

```
tctctcttaa ttggattttt taaattatat tcatattgca ggactcggca gaagaccttc      60

gagagaaagg tagaaaataa gaatttggct ctctgtgtga gcatgtgtgt gtgtgtgcga     120
```

gagagagaga aagagagtct gcctaagaag aaatgaatgt gaatgcggct tgtggcacag 180
ttaacaagga tgataaatca ataatgcaag cttactatta tttatgaata gcaatactga 240
agaaattaaa acaaaagatt gc 262

<210> SEQ ID NO 22
<211> LENGTH: 258
<212> TYPE: DNA
<213> ORGANISM: Rhesus

<400> SEQUENCE: 22
tctctcttaa ttggattttt aaaattatat tcatattgca ggactcagca gaagaccttc 60
gagataaagg tagaaaataa gaatctggtt ctctgtgtga gcatgtgaga gagagagaga 120
gagagagaga aagtctgcct aagaagaaat gaatgtgaat gcgccttgtg ggacagttga 180
caagaatgat aaatcaataa tacaagttta ctattattta tgaatagcaa tactgaagaa 240
attaaaacaa aagattgc 258

<210> SEQ ID NO 23
<211> LENGTH: 256
<212> TYPE: DNA
<213> ORGANISM: Crab-eating macaque

<400> SEQUENCE: 23
tctctcttaa ttggattttt aaaattatat tcatattgca ggactcagca gaagaccttc 60
gagataaagg tagaaaataa gaatctggtt ctctgtgtga gcatgtgaga gagagagaga 120
gagagagaaa gtctgcctaa gaagaaatga atgtgaatgc gccttgtggg acagttgaca 180
agaatgataa atcaataatg caagtttact attatttatg aatagcaata ctgaagaaat 240
taaaacaaaa gattgc 256

<210> SEQ ID NO 24
<211> LENGTH: 260
<212> TYPE: DNA
<213> ORGANISM: Baboon

<400> SEQUENCE: 24
tctctcttaa ttggattttt aaaattatat tcatattgca ggactcagca gaagaccttc 60
gagagaaagg tagaaaataa gaatttggct ctctgtgtga gcatgtgaga gagagaaaga 120
gagagagaaa gaaagtctgc ctaagaagaa atgaatgtga atgcgccttg tgggacagtt 180
gacaaggatg ataaatcaat aatgcaagtt tactattatt tatgaatagc aatactgaag 240
aaattaaaac aaaagattgc 260

<210> SEQ ID NO 25
<211> LENGTH: 260
<212> TYPE: DNA
<213> ORGANISM: Green monkey

<400> SEQUENCE: 25
tctctcttaa ttggattttt aaaattatat tcatattgca ggactcagca gaagaccttc 60
gagagaaagg tagaaaataa gaatttggct ttctgtgtga gcatgtgaga gagagagaga 120
gagagagaga gaaagtctgc ctaagaagaa atgaatgtga atgcgccttg tgggacagtt 180
gacaagaatg ataaatcaat aatgcaagct tactattatt tatgaatagc aatactgaag 240
aaattaaaac aaaagactgc 260

<210> SEQ ID NO 26
<211> LENGTH: 259
<212> TYPE: DNA
<213> ORGANISM: Marmoset

<400> SEQUENCE: 26
tctctcttaa ttagattttt taaattatat tcatattgca ggattcagca gaagacctcc 60
aagagaaatg tagaagataa gaatttggct ctctgtgtga tcgtgtgaga gagagagaga 120
gagagagaga gagagtctgc ctaagaaaaa atgaatgtga atgcagcttg tggcacagtt 180
gacaagatag taaatcaata atgcaagctt attattattt aaaaacagtg atactgaaga 240
aatttaaaca aaagactgc 259

<210> SEQ ID NO 27
<211> LENGTH: 256
<212> TYPE: DNA
<213> ORGANISM: Squirrel monkey

<400> SEQUENCE: 27
tctctcttaa ttggattttt aaaattatat ttatattgca ggattcagca gaagaccttc 60
aagagaaatg tagaaaataa gaatttggct ctctgtgtga tcgtgtgaga gagagagaga 120
gagagagaga gagagtctgc ctaagaagaa atgaatgtga atgcagcttg tggcacagct 180
gacaaggata ataaatcaat aatgtaagcg tactattatt tgaaaacagt gtgaagaaat 240
ttaaacaaaa gactgc 256

<210> SEQ ID NO 28
<211> LENGTH: 210
<212> TYPE: DNA
<213> ORGANISM: Bushbaby

<400> SEQUENCE: 28
tctcccttaa ttggattttc aaaattatat tcaaatttca gaactcagca gaagaccttc 60
aagagaaatg taaaaaatga gaatttgact ctgtctgaga tgtgtgcata tatgtgtgac 120
tatctaagaa gaaataagga tgataaatca ataatgccag cttcctgtcc ctaataaaca 180
ataatactga ggaaattaaa acaggattat 210

<210> SEQ ID NO 29
<211> LENGTH: 219
<212> TYPE: DNA
<213> ORGANISM: Mouse

<400> SEQUENCE: 29
tctctcttaa ttagattgtt taaaatatat ttatattaca ggactcaaca gaaggccttt 60
gaggaaaagg tgggaaataa gcctggctct gtgaatatgt gtgtgggtgg gtgggtctgt 120
agaagaaaat atccagaaaa attgttaaaa gggataatat ataatatgat attactgtca 180
cttacaaatg ataatataac aggttaaaat cagaagtta 219

<210> SEQ ID NO 30
<211> LENGTH: 156
<212> TYPE: DNA
<213> ORGANISM: Rat

<400> SEQUENCE: 30
ctctcttaat tagattgttt aaaatatatt tatattacag gactcaacag aagacctttg 60
gggaaaatgt gggaaataag actggctctg tccatgtgtg tgggtaggtg ggtctgtata 120
atgcacaatt atataacagg ttaaaaccag aagtca 156

<210> SEQ ID NO 31
<211> LENGTH: 201
<212> TYPE: DNA
<213> ORGANISM: Pika

<400> SEQUENCE: 31
tcctcttaat tggattttaa aaaatatatt catgttacag gactcagcag acctccaaga 60
gaattatgga atgtgtgtct ctttgtcttg cctaagaaga agaaatggat gtggctgtgg 120
tacagaaaag gaataaatca atcatgccag cttcccgtta tttacaaaca ggattttgag 180
aaaattaaga ttgaaaatta t 201

<210> SEQ ID NO 32
<211> LENGTH: 221
<212> TYPE: DNA
<213> ORGANISM: Dolphin

<400> SEQUENCE: 32
tctcttttaa ttggattttt aaaatatatt catattgcag gattcagcaa aagaccttca 60
agagaaatgt gtaaataaga atttgactct gtttgggtgg gggggtgtgt gtaagaaaaa 120
aatgaatgtg gcttgcagca cagttgagaa ggacgataaa tcaatactgc tagtttactg 180
tcgtttacaa taatactaag gaaattaaca cagaggattg c 221

<210> SEQ ID NO 33
<211> LENGTH: 194
<212> TYPE: DNA
<213> ORGANISM: Cow

<400> SEQUENCE: 33
tctcttttaa atggactttt aaaatatatt cgtattgcag gactcagcag aagaccttca 60
ggagaatgtg gaaataagaa tttgtgcatg tgtatgtgcc tgtgtgtgta tgagaacaga 120
atgtaacctg cagtacaatt cagaaccttt acttgtggaa tgttaacact aaagaaatta 180
acaaggagga tctc 194

<210> SEQ ID NO 34
<211> LENGTH: 212
<212> TYPE: DNA
<213> ORGANISM: Panda

<400> SEQUENCE: 34
tctctcttaa ttggattttt aaaaatatat tcatattgta ggactcagca gaagaccttc 60
aaagaaatgt gaagagtgag gatttggctg tgtgtgtgtg tgtctgtctg tctgtctaag 120
aaaaaatgaa tatggcttgt ggcacagtcg agaaagatga tacactagct tactgttatt 180
tacaaaatac tgtagaaact aaaacagatt ac 212

<210> SEQ ID NO 35
<211> LENGTH: 195
<212> TYPE: DNA
<213> ORGANISM: Elephant

<400> SEQUENCE: 35
actttgttaa tggcattttt aaaaatatat tcatattgca agactcggca gaagaccttt 60
gagcatgata tgaaaatgag aatttggctc tgtgtgtgta agaagaaatg aatatggtta 120

-continued

```
gttgagaaga atgataaatc agtaatgctt gcctactgtt gtttacaaca aaaaggaatt    180

aaaacgagaa gttgc                                                     195


<210> SEQ ID NO 36
<211> LENGTH: 215
<212> TYPE: DNA
<213> ORGANISM: Opossum

<400> SEQUENCE: 36

cccctttctg agaaaggatt ttctaagaat gatgcaacag aaatccctca ataaggagac     60

agaaaatgaa aacttgggtt tctgtatcct agagagtttt tgtcagtgca aaggagatga    120

ctatgcattg tgtagactct attggtcatt gtatatgaag aactcagact tcagaacttt    180

agaataatcc tcagagaatt aagacaaaga gttgc                               215
```